(12) United States Patent
Hwang et al.

(10) Patent No.: US 10,003,035 B2
(45) Date of Patent: Jun. 19, 2018

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Kyuyoung Hwang, Anyang-si (KR); Kum Hee Lee, Suwon-si (KR); Whail Choi, Seoul (KR); Ohyun Kwon, Yongin-si (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 69 days.

(21) Appl. No.: 14/953,104

(22) Filed: Nov. 27, 2015

(65) Prior Publication Data

US 2016/0155963 A1   Jun. 2, 2016

(30) Foreign Application Priority Data

Nov. 28, 2014   (KR) .................. 10-2014-0169185
Jul. 21, 2015    (KR) .................. 10-2015-0103012

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| C09K 11/02 | (2006.01) | |
| H01L 51/50 | (2006.01) | |

(52) U.S. Cl.
CPC ...... *H01L 51/0094* (2013.01); *C07F 15/0033* (2013.01); *C09K 11/025* (2013.01); *C09K 11/06* (2013.01); *H01L 51/0058* (2013.01); *H01L 51/0072* (2013.01); *H01L 51/0085* (2013.01); *C09K 2211/1007* (2013.01); *C09K 2211/1029* (2013.01); *C09K 2211/1096* (2013.01); *C09K 2211/185* (2013.01); *H01L 51/5004* (2013.01); *H01L 51/5016* (2013.01); *H01L 2251/552* (2013.01); *H01L 2251/558* (2013.01)

(58) Field of Classification Search
CPC combination set(s) only.
See application file for complete search history.

(56) References Cited

U.S. PATENT DOCUMENTS

| | | |
|---|---|---|
| 2009/0123720 A1 | 5/2009 | Chen et al. |
| 2010/0109515 A1 | 5/2010 | Boerner et al. |
| | (Continued) | |

FOREIGN PATENT DOCUMENTS

| | | |
|---|---|---|
| KR | 1020130078591 A | 7/2013 |
| KR | 10-1344787 B1 | 12/2013 |

OTHER PUBLICATIONS

Chun Huang et al., "High-efficiency solution processable electrophosphorescent iridium complexes bearing polyphenylphenyl dendron ligands", Journal of Organometallic Chemistry 694 (2009) 1317-1324.

*Primary Examiner* — Golam Mowla
(74) *Attorney, Agent, or Firm* — Cantor Colburn LLP

(57) ABSTRACT

An organometallic compound represented by Formula 1:

$$M(L_1)_{n1}(L_2)_{n2} \qquad \text{Formula 1}$$

wherein in Formula 1, M, $L_1$, $L_2$, n1, and n2 are the same as described in the specification.

20 Claims, 1 Drawing Sheet

(56) References Cited

U.S. PATENT DOCUMENTS

| | | | |
|---|---|---|---|
| 2010/0127215 A1* | 5/2010 | Boerner | C07F 15/0033 252/301.16 |
| 2012/0264936 A1* | 10/2012 | Inoue | C07F 15/0033 544/225 |
| 2013/0026452 A1* | 1/2013 | Kottas | C09K 11/06 257/40 |
| 2014/0008617 A1* | 1/2014 | Beers | H01L 51/0085 257/40 |
| 2014/0158998 A1* | 6/2014 | Noh | H01L 51/0085 257/40 |
| 2015/0021585 A1* | 1/2015 | Yu | C09K 11/06 257/40 |
| 2015/0073142 A1* | 3/2015 | Ohsawa | H01L 51/0085 544/225 |
| 2015/0194614 A1* | 7/2015 | Kravchuk | H01L 51/0085 257/40 |
| 2016/0028024 A1* | 1/2016 | Das | H01L 51/0085 257/40 |
| 2016/0043330 A1* | 2/2016 | Kim | H01L 51/0085 257/40 |
| 2016/0093814 A1 | 3/2016 | Hwang et al. | |
| 2016/0118604 A1 | 4/2016 | Choi et al. | |
| 2016/0141526 A1 | 5/2016 | Lee et al. | |
| 2016/0155962 A1 | 6/2016 | Hwang et al. | |
| 2016/0190484 A1 | 6/2016 | Lee et al. | |
| 2016/0222044 A1 | 8/2016 | Lee et al. | |

\* cited by examiner

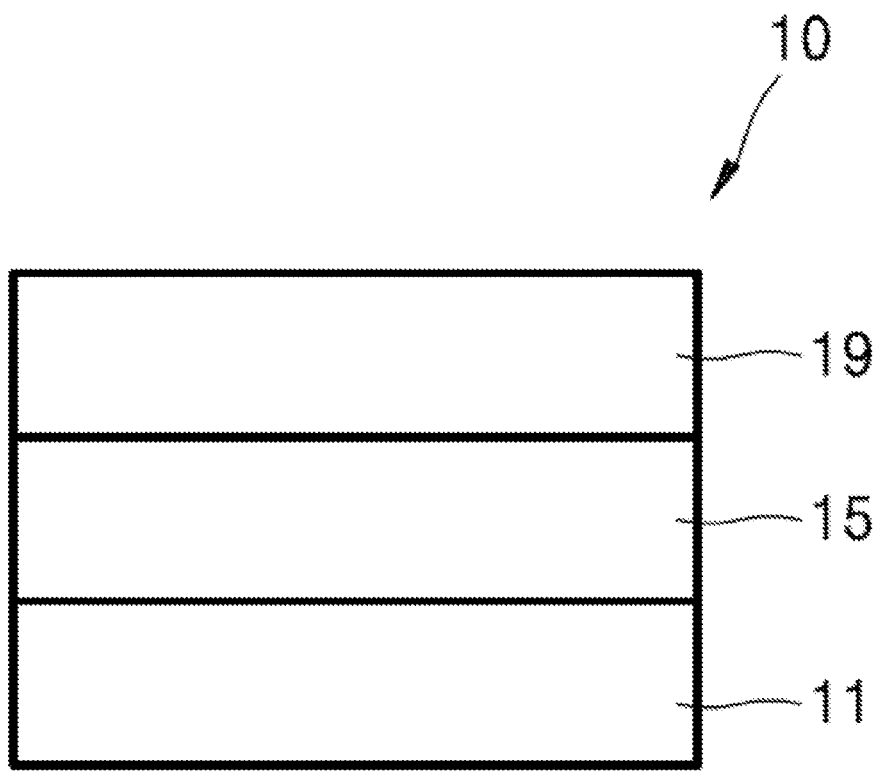

ORGANOMETALLIC COMPOUND AND ORGANIC LIGHT-EMITTING DEVICE INCLUDING THE SAME

CROSS-REFERENCE TO RELATED APPLICATION

This application claims priority to and the benefit of Korean Patent Applications No. 10-2014-0169185, filed on Nov. 28, 2014 and Korean Patent Applications No. 10-2015-0103012, filed on Jul. 21, 2015, in the Korean Intellectual Property Office, the contents of which are incorporated herein in their entirety by reference.

BACKGROUND

1. Field

The present disclosure relates to an organometallic compound and organic light-emitting device including the same.

2. Description of the Related Art

Organic light emitting devices (OLEDs) are self-emission devices that have wide viewing angles, high contrast ratios, and short response times. In addition, OLEDs exhibit excellent brightness, driving voltage, and response speed characteristics, and produce full-color images.

In an example, an organic light-emitting device includes an anode, a cathode, and an organic layer including an emission layer disposed between the anode and the cathode. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

Provided are a novel organometallic compound and an organic light-emitting device including the same.

Additional aspects will be set forth in part in the description which follows and, in part, will be apparent from the description, or may be learned by practice of the presented exemplary embodiments.

An aspect provides an organometallic compound represented by Formula 1:

$$M(L_1)_{n1}(L_2)_{n2} \quad \text{Formula 1}$$

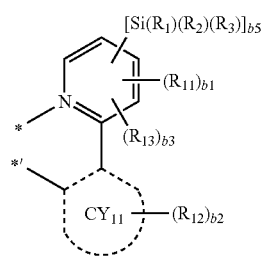

Formula 2 wherein

M in Formula 1 is selected from Ir, Pt, Os, Ti, Zr, Hf, Eu, Tb, Tm, and Rh, $L_1$ in Formula 1 is selected from ligands represented by Formula 2, n1 is 1, 2, or 3, provided that when n1 is 2 or greater, two or more groups $L_1$ are identical to or different from each other, $L_2$ in Formula 1 is selected from a monovalent organic ligand, a divalent organic ligand, a trivalent organic ligand, and a tetravalent organic ligand, n2 is 0, 1, 2, 3, or 4, provided that when n2 is 2 or greater, two or more groups $L_2$ are identical to or different from each other, $L_1$ and $L_2$ in Formula 1 are different from each other, $CY_{11}$ in Formula 2 is selected from a $C_5$-$C_{30}$ carbocyclic ring and a $C_2$-$C_{30}$ heterocyclic ring, $R_1$ to $R_3$ and $R_{11}$ to $R_{13}$ in Formula 2 are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), and —P(=O)($Q_8$)($Q_9$), b1 in Formula 2 is an integer selected from 0 to 3, b2 in Formula 2 is an integer selected from 0 to 4, b3 and b5 in Formula 2 is each independently an integer selected from 1 to 3, at least one $R_3$ in Formula 2 is connected to at least one $R_{13}$ to form a substituted or unsubstituted saturated or unsaturated $C_2$-$C_{30}$ cyclic ring, each of * and *' in Formula 2 indicates a binding site to M in Formula 1, and at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$), —B(Q$_{16}$)(Q$_{17}$), and —P(=O)(Q$_{18}$)(Q$_{19}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), —B(Q$_{26}$)(Q$_{27}$), and —P(=O)(Q$_{28}$)(Q$_{29}$); and —Si(Q$_{31}$)(Q$_{32}$)(Q$_{33}$), —N(Q$_{34}$)(Q$_{35}$), —B(Q$_{36}$)(Q$_{37}$), and —P(=O)(Q$_{38}$)(Q$_{39}$), wherein Q$_1$ to Q$_9$, Q$_{11}$ to Q$_{19}$, Q$_{21}$ to Q$_{29}$, and Q$_{31}$ to Q$_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

Another aspect provides an organic light-emitting device including:

a first electrode;

a second electrode; and an organic layer disposed between the first electrode and the second electrode, wherein the organic layer includes an emission layer and at least one organometallic compounds represented by Formula 1.

The emission layer may include the at least one organometallic compound.

The organometallic compound included in the emission layer may act as a dopant, and the emission layer may further include a host.

BRIEF DESCRIPTION OF THE DRAWING

These and/or other aspects will become apparent and more readily appreciated from the following description of the exemplary embodiments, taken in conjunction with FIG. 1 which is a schematic view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound according to an embodiment is represented by Formula 1 below:

$$M(L_1)_{n1}(L_2)_{n2} \quad \text{Formula 1}$$

M in Formula 1 may be selected from iridium (Ir), platinum (Pt), osmium (Os), titanium (Ti), zirconium (Zr), hafnium (Hf), europium (Eu), terbium (Tb), thulium (Tm), and rhodium (Rh).

For example, M in Formula 1 may be selected from iridium (Ir), platinum (Pt), osmium (Os), and rhodium (Rd).

In some embodiments, M in Formula 1 may be selected from iridium (Ir) and platinum (Pt), but is not limited thereto.

$L_1$ in Formula 1 may be selected from ligands represented by Formula 2, n1 is 1, 2, or 3, provided that when n1 is 2 or greater, two or more groups $L_1$ may be identical to or different from each other.

Formula 2

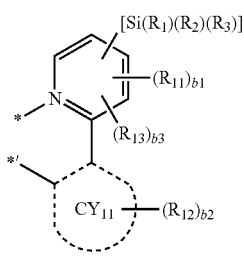

$L_2$ in Formula 1 is selected from a monovalent organic ligand, a divalent organic ligand, a trivalent organic ligand, and a tetravalent organic ligand, n2 is 0, 1, 2, 3, or 4, provided that when n2 is 2 or greater, two or more groups $L_2$ may be identical to or different from each other.

$L_1$ and $L_2$ in Formula 1 may be different from each other.

For example, n1 in Formula 1 may be 1 or 2, but is not limited thereto.

In some embodiments, the organometallic compound represented by Formula 1 may be neutral, not a salt consisting of an ionic pair.

In some embodiments, in Formula 1, M is Ir and the sum of n1 and n2 is 3; or M is Pt and the sum of n1 and n2 is 2, and the organometallic compound represented by Formula 1 may be neutral.

$CY_{11}$ in Formula 2 may be selected from a $C_5$-$C_{30}$ carbocyclic ring and a $C_2$-$C_{30}$ heterocyclic ring.

For example, $CY_{11}$ in Formula 2 may be selected from a benzene, an indene, a naphthalene, an azulene, a heptalene, an indacene, an acenaphthylene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentacene, a hexacene, a rubicene, a coronene, an ovalene, an isoindole, an indole, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, a benzofuran, a benzothiophene, a dibenzofuran, a dibenzothiophene, an isobenzothiazole, a benzoxazole, an isobenzoxazole, a carbazole, a benzocarbazole, a dibenzocarbazole, an imidazopyridine, and an imidazopyrimidine.

In some embodiments, $CY_{11}$ in Formula 2 may be selected from a benzene, a naphthalene, a fluorene, a spiro-bifluorene, a benzofluorene, a dibenzofluorene, a phenalene, a phenanthrene, an anthracene, a fluoranthene, a triphenylene, a pyrene, a chrysene, naphthacene, a picene, a perylene, a pentacene, a hexacene, a quinoline, an isoquinoline, a benzoquinoline, a phthalazine, a naphthyridine, a quinoxaline, a quinazoline, a cinnoline, a phenanthridine, an acridine, a phenanthroline, a phenazine, a dibenzofuran, a dibenzothiophene, a carbazole, a benzocarbazole, and a dibenzocarbazole.

In an embodiment, $CY_{11}$ in Formula 2 may be selected from a benzene, a naphthalene, a phenanthrene, a triphenylene, a pyrene, a fluorene, a spiro-bifluorene, a dibenzofuran, and a dibenzothiophene.

In some embodiments, $CY_{11}$ in Formula 2 may be a benzene or a naphthalene, but is not limited thereto.

$R_1$ to $R_3$ and $R_{11}$ to $R_{13}$ in Formula 2 may be each independently selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), and —P(=O)($Q_8$)($Q_9$).

For example, $R_{11}$ to $R_{13}$ in Formula 2 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl (adamantyl) group, a norbornanyl (norbornyl) group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_6$)($Q_7$) and —P(=O)($Q_8$)($Q_9$), wherein $Q_6$ to $Q_9$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, $R_{11}$ to $R_{13}$ in Formula 2 may be each independently selected from hydrogen, deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —B($Q_6$)($Q_7$) and —P(=O)($Q_8$)($Q_9$), wherein $Q_6$ to $Q_9$ are each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, $R_1$ to $R_3$ in Formula 2 may be each independently selected from a $C_1$-$C_{10}$ alkyl group, a phenyl group, and —Si($Q_1$)($Q_2$)($Q_3$); and a $C_1$-$C_{10}$ alkyl group and a phenyl group, each substituted with at least one selected from deuterium and a $C_1$-$C_{10}$ alkyl group, wherein $Q_1$ to $Q_3$ are each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

In an embodiment, $R_{11}$ to $R_{13}$ in Formula 2 may be each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, and $R_1$ to $R_3$ in Formula 2 may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and —Si($Q_1$)($Q_2$)($Q_3$); and an n-propyl group, an isopropyl group, an n-butyl group, an isobutyl group, a sec-butyl group, a tert-butyl group, an n-pentyl group, an isopentyl group, a sec-pentyl group, a tert-pentyl group, and a phenyl group, each substituted with at least one selected from a deuterium and a $C_1$-$C_{10}$ alkyl group, wherein $Q_1$ to $Q_3$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group, but they are not limited thereto:

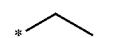

Formula 9-1

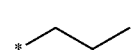

Formula 9-2

Formula 9-3

Formula 9-4

Formula 9-5

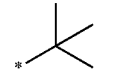

Formula 9-6

Formula 9-7

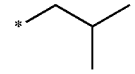

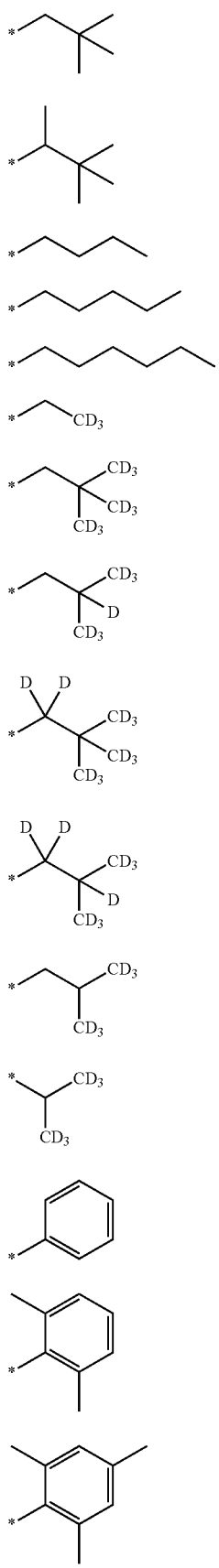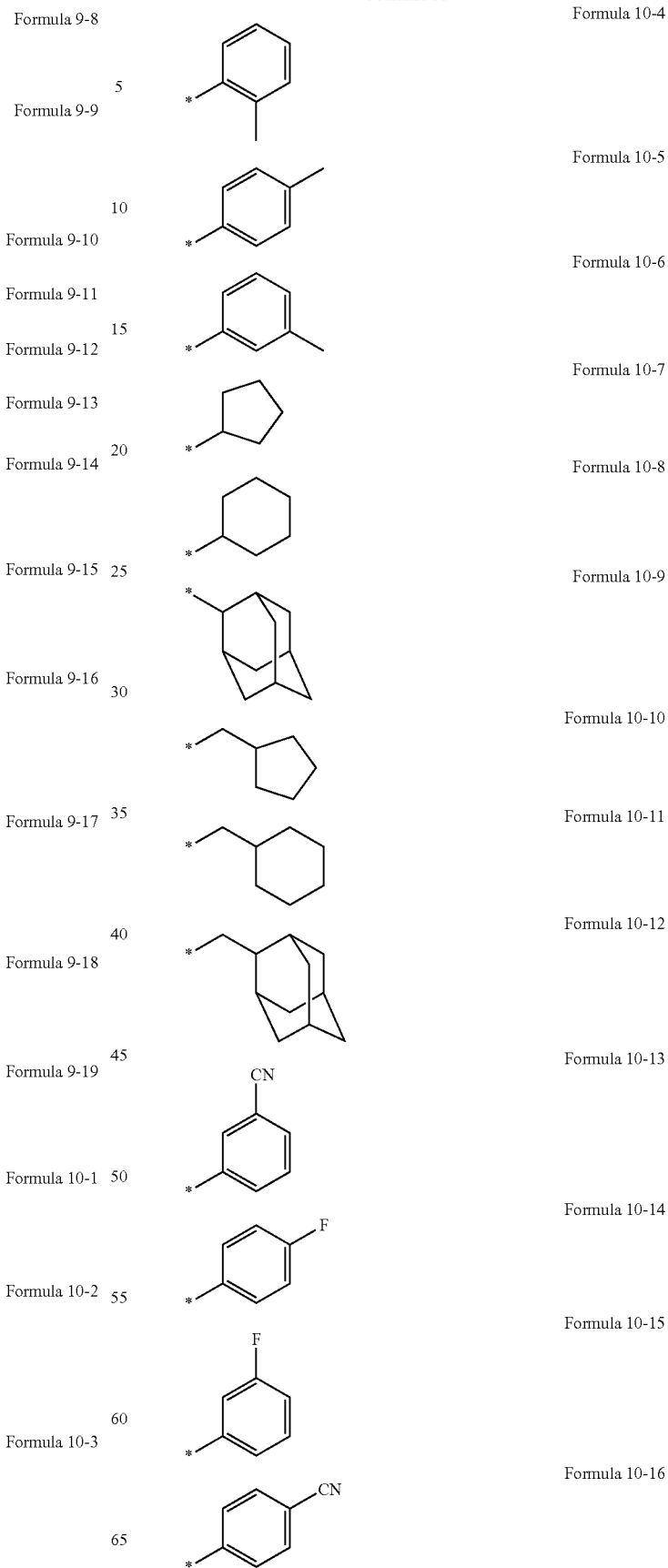

-continued

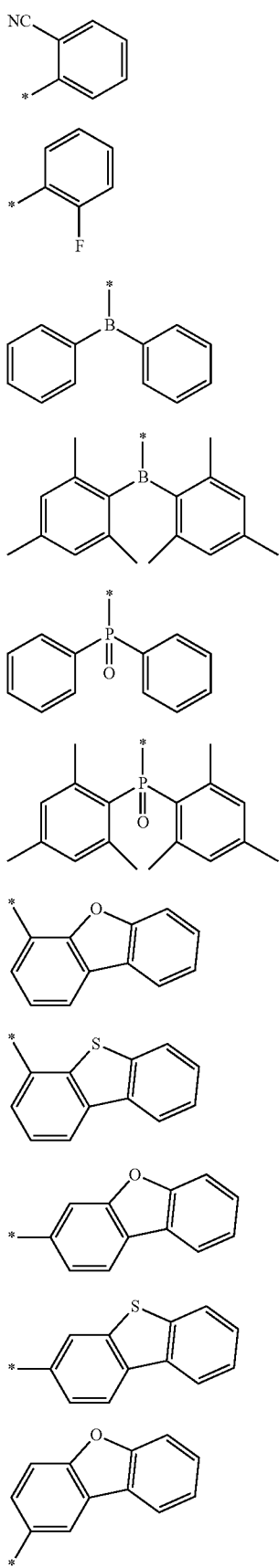

Formula 10-17

Formula 10-18

Formula 10-19

Formula 10-20

Formula 10-21

Formula 10-22

Formula 10-23

Formula 10-24

Formula 10-25

Formula 10-26

Formula 10-27

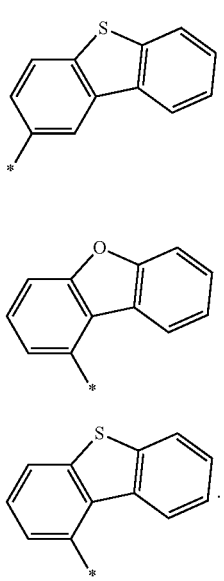

Formula 10-28

Formula 10-29

Formula 10-30

\* in Formulae 9-1 to 9-19 and 10-1 to 10-30 indicates a binding site to a neighboring atom.

b1 in Formula 2 indicates the number of groups $R_{11}$, and may be an integer selected from 0 to 3. When b1 is 2 or greater, two or more groups $R_{11}$ may be identical to or different from each other.

b2 in Formula 2 indicates the number of groups $R_{12}$, and may be an integer selected from 0 to 4. When b2 is 2 or greater, two or more groups $R_{12}$ may be identical to or different from each other.

b3 in Formula 2 indicates the number of groups $R_{13}$, and may be an integer selected from 1 to 3. When b3 is 2 or greater, two or more groups $R_{13}$ may be identical to or different from each other. For example, b3 may be 1 or 2, or 1.

b5 in Formula 2 indicates the number of groups *—[Si$(R_1)(R_2)(R_3)$], and may be an integer selected from 1 to 3. When b5 is 2 or greater, two or more groups *—[Si$(R_1)(R_2)(R_3)$] may be identical to or different from each other. For example, b5 may be 1 or 2, or 1.

At least one $R_3$ in Formula 2 may be connected to at least one $R_{13}$ to form a substituted or unsubstituted saturated or unsaturated $C_2$-$C_{30}$ cyclic ring. The substituted or unsubstituted saturated or unsaturated $C_2$-$C_{30}$ cyclic ring will be described below.

In an embodiment, b3 and b5 in Formula 2 may be 1, and $R_3$ and $R_{13}$ may be connected to each other to form a substituted or unsubstituted saturated or unsaturated $C_2$-$C_{30}$ cyclic ring.

Each of * and *' in Formula 2 indicates a binding site to M in Formula 1.

$R_1$ to $R_3$ in Formula 2 may all be identical; or $R_1$ and $R_3$ are identical to each other and $R_2$ and $R_1$ are different from each other; or $R_1$ to $R_3$ may all be different.

In an embodiment, $L_1$ in Formula 1 may be selected from ligands represented by Formulae 2-1 to 2-6:

Formula 2-1

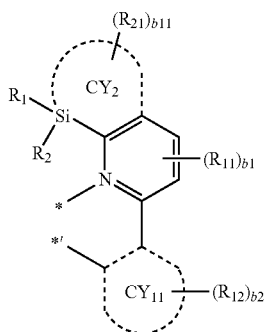

Formula 2-2

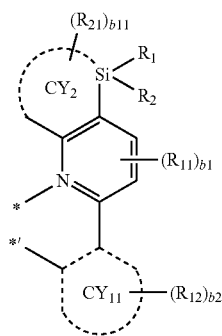

Formula 2-3

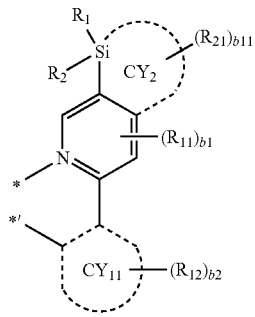

Formula 2-4

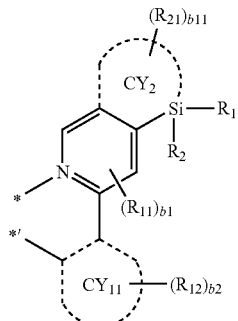

Formula 2-5

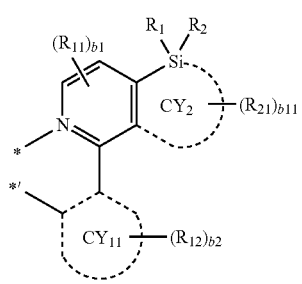

Formula 2-6

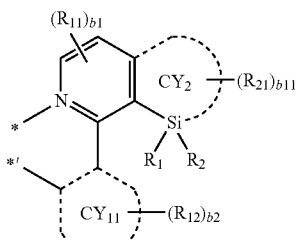

$CY_{11}$, $R_1$, $R_2$, $R_{11}$, $R_{12}$, b1 and b2 in Formulae 2-1 to 2-6 are the same as described above, $CY_2$ is a saturated or unsaturated $C_2$-$C_{30}$ cyclic ring formed by connecting $R_3$ and $R_{13}$.

Descriptions of $R_{21}$ are the same as those of $R_{11}$, b11 is an integer selected from 0 to 10, and each of * and *' indicates a binding site to M in Formula 1.

For example, $CY_2$ in Formulae 2-1 to 2-6 may be selected from silolane, 2,3-dihydro-1H-silole, 2,5-dihydro-1H-silole, 3,4-dihydro-2H-silole, silole, 2,3-dihydro-1H-benzo[b]silole, benzosilole, silinane, tetrahydrosiline, dihydrosiline, tetrahydrobenzosiline, and dihydrobenzosiline.

For example, $L_1$ in Formula 1 may be selected from groups represented by Formulae 2-3, 2-4, and 2-6, but is not limited thereto.

In some embodiments, $L_1$ in Formula 1 may be selected from groups represented by Formulae 2(1) to 2(36):

Formula 2(1)

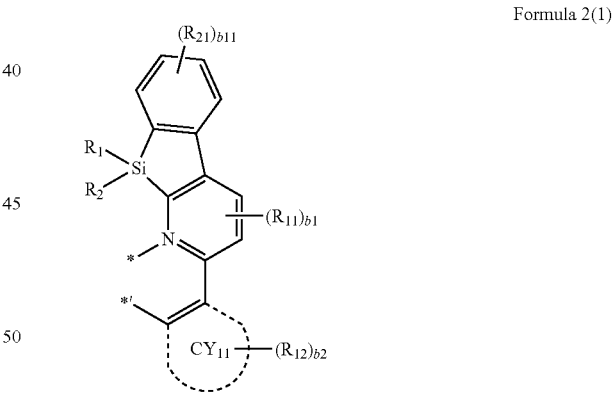

Formula 2(2)

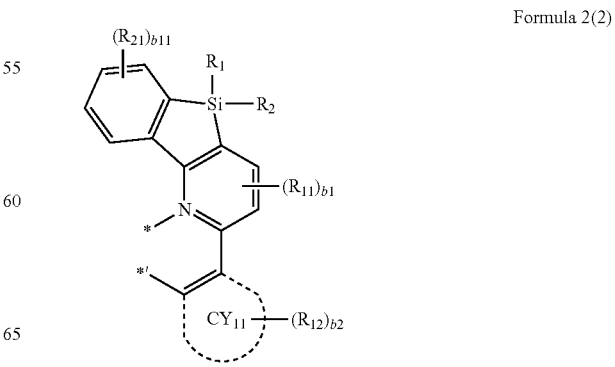

Formula 2(3)
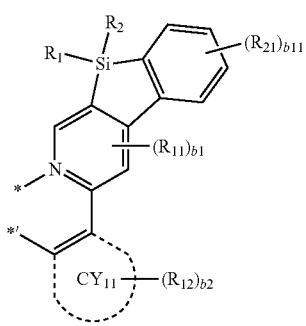
Formula 2(4)
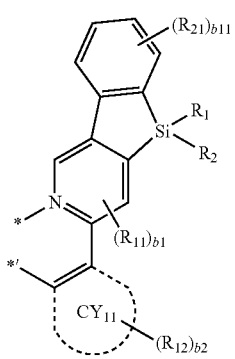
Formula 2(5)
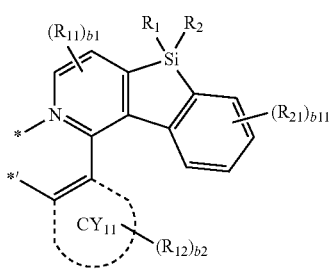
Formula 2(6)
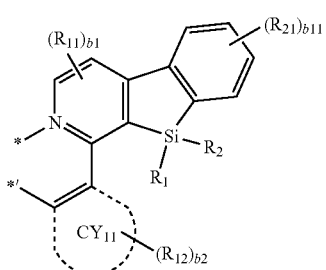
Formula 2(7)
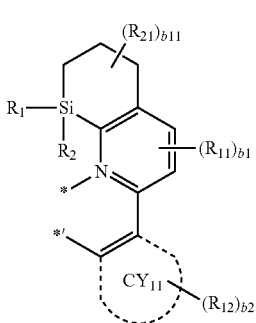
Formula 2(8)
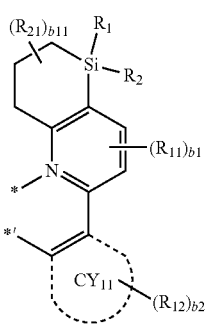
Formula 2(9)
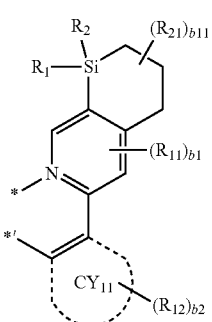
Formula 2(10)
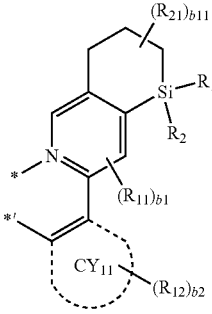
Formula 2(11)
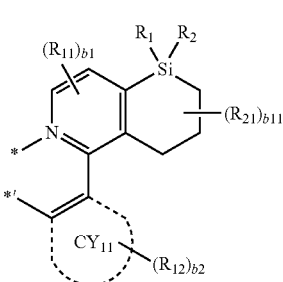
Formula 2(12)
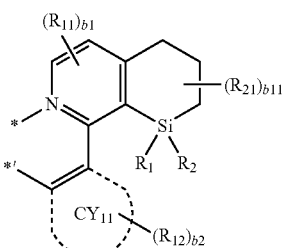

Formula 2(13)
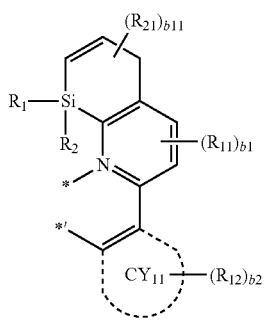
Formula 2(14)
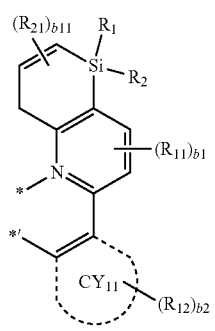
Formula 2(15)
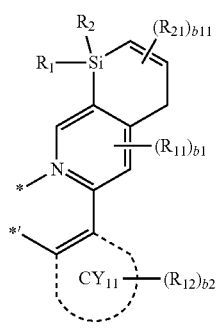
Formula 2(16)
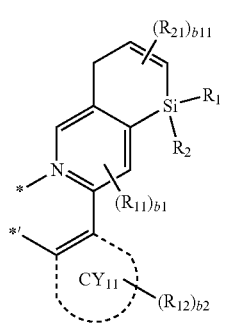
Formula 2(17)
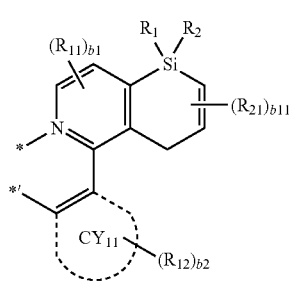
Formula 2(18)
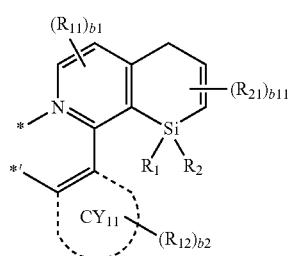
Formula 2(19)
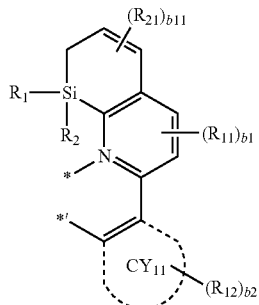
Formula 2(20)
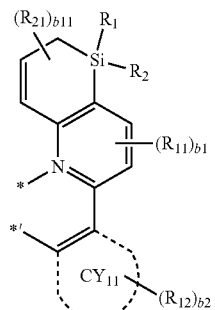
Formula 2(21)
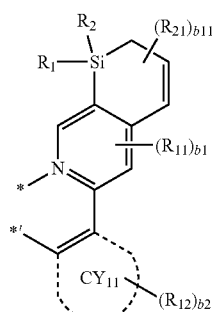
Formula 2(22)
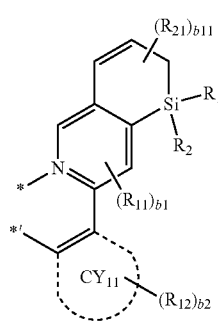

Formula 2(23)
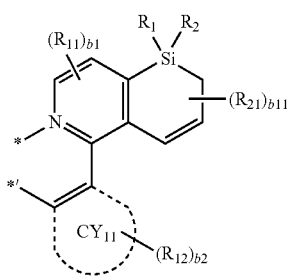
Formula 2(24)
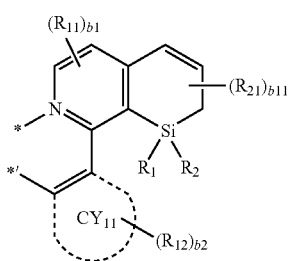
Formula 2(25)
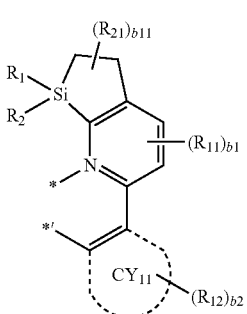
Formula 2(26)
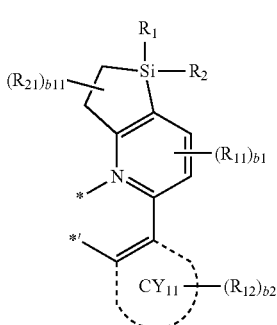
Formula 2(27)
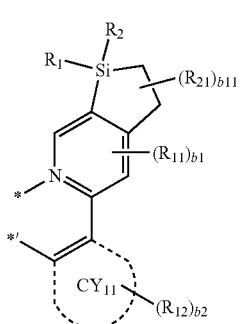
Formula 2(28)
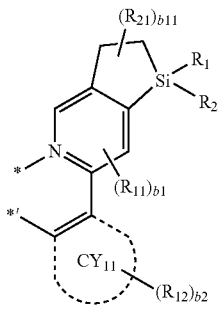
Formula 2(29)
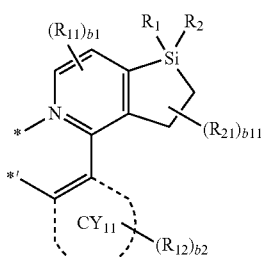
Formula 2(30)
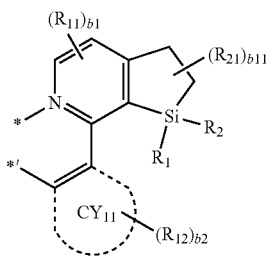
Formula 2(31)
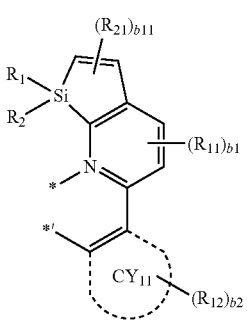
Formula 2(32)
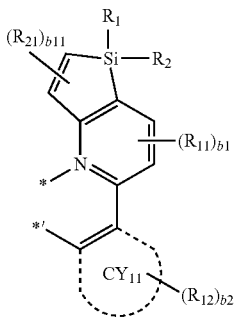

-continued

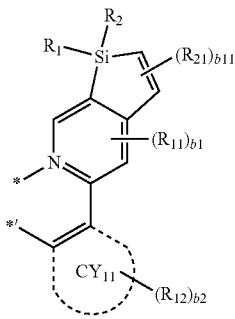

Formula 2(33)

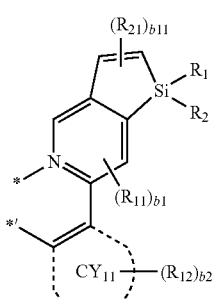

Formula 2(34)

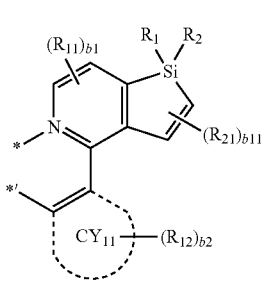

Formula 2(35)

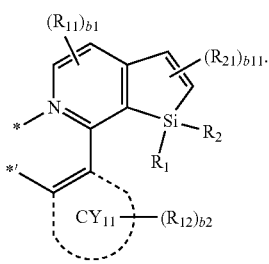

Formula 2(36)

In Formulae 2A(1) to 2(36), descriptions of $R_1$, $R_2$, $R_{11}$, $R_{12}$, b1, and b2 are the same as described above, descriptions of $R_{21}$ are the same as those of $R_{11}$, b11 is an integer selected from 0 to 6, and each of * and *' indicates a binding site to M in Formula 1.

For example, $CY_{11}$ in Formulae 2(1) to 2(36) may be selected from a benzene, a naphthalene, a fluorene, a triphenylene, a carbazole, a dibenzofuran, and a dibenzothiophene.

In an embodiment, $L_1$ in Formula 1 may be selected from groups represented by Formula 2(3), 2(4), 2(6), 2(9), 2(12), 2(27), and 2(28), and in Formulae 2(3), 2(4), 2(6), 2(9), 2(12), 2(27), and 2(28), $CY_{11}$ is a benzene or a naphthalene, $R_{11}$, $R_{12}$, and $R_{21}$ are each independently selected from hydrogen, deuterium, —F, a cyano group, a nitro group, —$SF_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —$B(Q_6)(Q_7)$ and —$P(=O)(Q_8)(Q_9)$, wherein $Q_6$ to $Q_9$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group, and $R_1$ and $R_2$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group, but they are not limited thereto.

In some embodiments, L$_1$ in Formula 1 may be selected from groups represented by Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10:

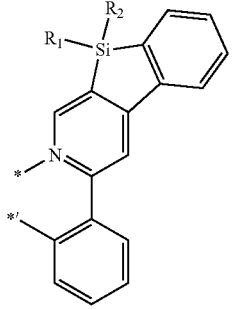

Formula 2A-1

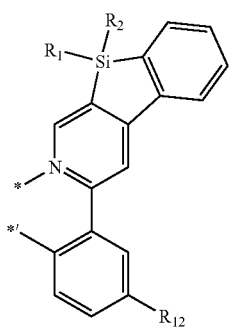

Formula 2A-2

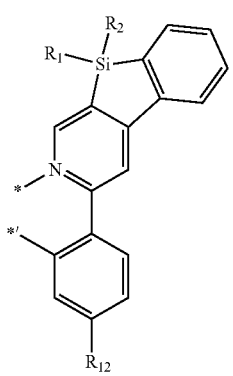

Formula 2A-3

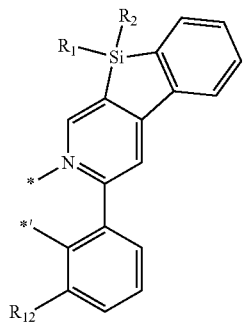

Formula 2A-4

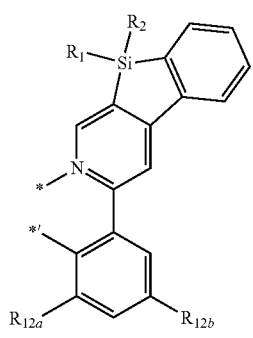

Formula 2A-5

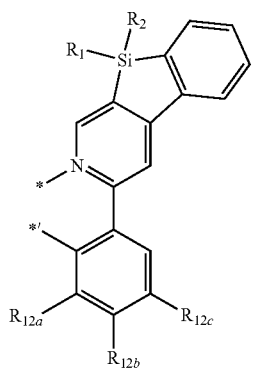

Formula 2A-6

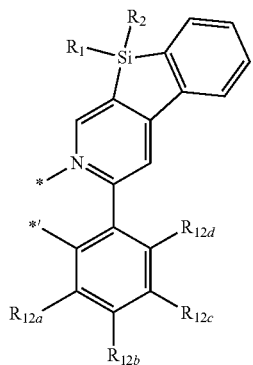

Formula 2A-7

-continued
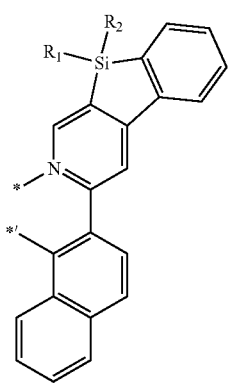
Formula 2A-8
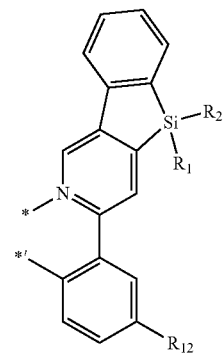
Formula 2B-2
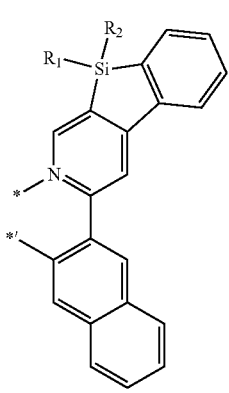
Formula 2A-9
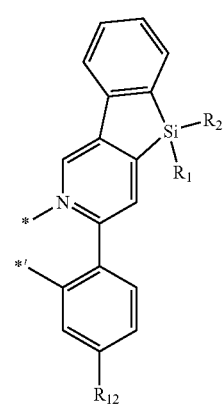
Formula 2B-3
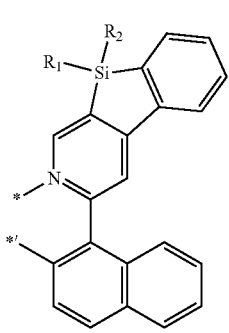
Formula 2A-10
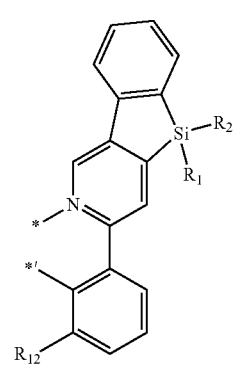
Formula 2B-4
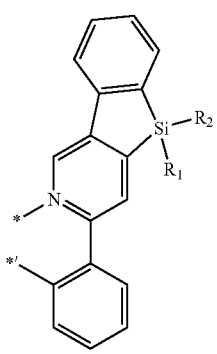
Formula 2B-1
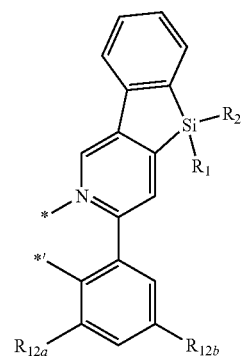
Formula 2B-5

Formula 2B-6
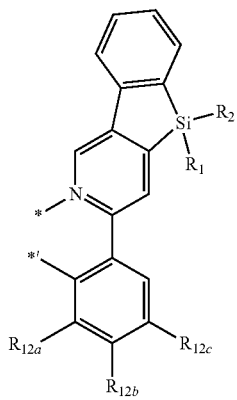
Formula 2B-7
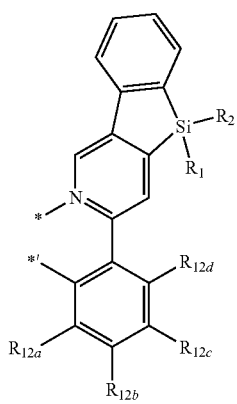
Formula 2B-8
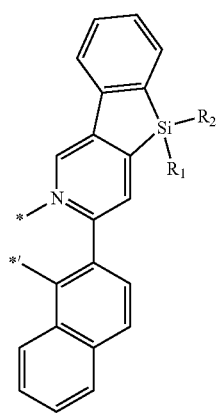
Formula 2B-9
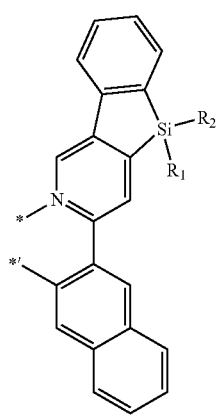
Formula 2B-10
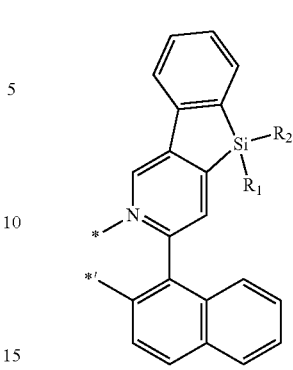
Formula 2C-1
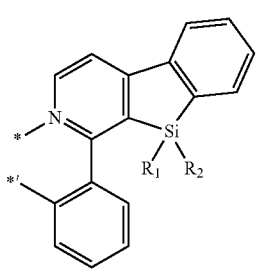
Formula 2C-2
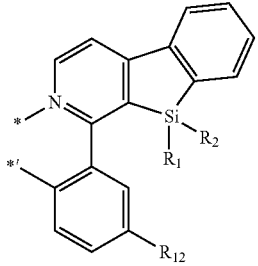
Formula 2C-3
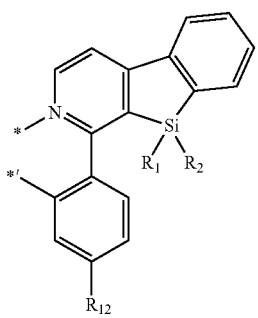
Formula 2C-4
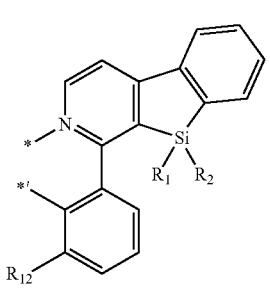

-continued
Formula 2C-5
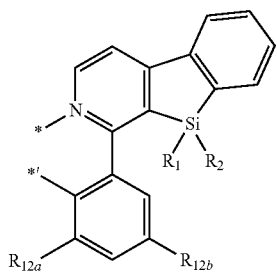
Formula 2C-6
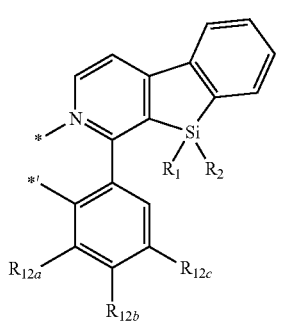
Formula 2C-7
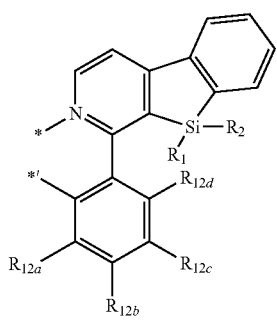
Formula 2C-8
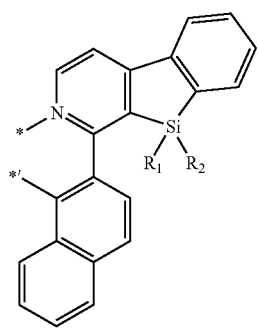
Formula 2C-9
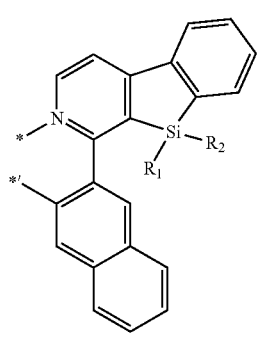
-continued
Formula 2C-10
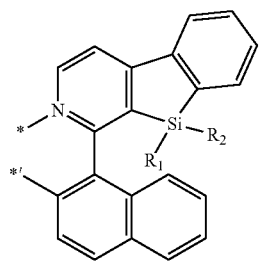
Formula 2D-1
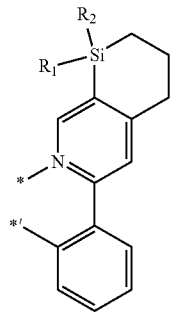
Formula 2D-2
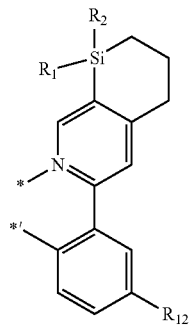
Formula 2D-3
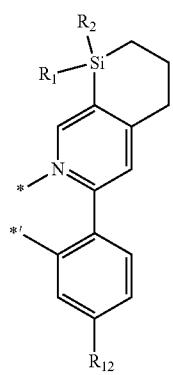
Formula 2D-4
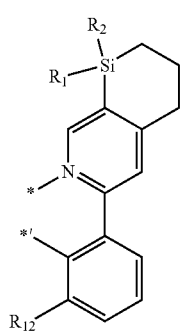

Formula 2D-5
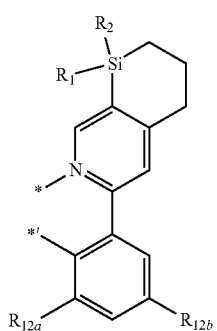
Formula 2D-6
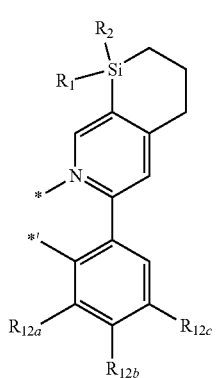
Formula 2D-7
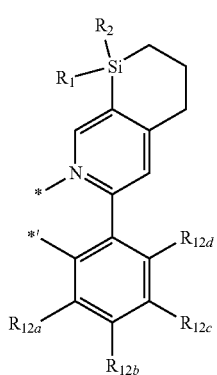
Formula 2D-8
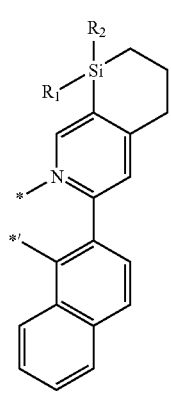
Formula 2D-9
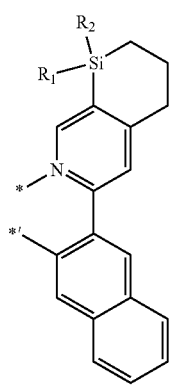
Formula 2D-10
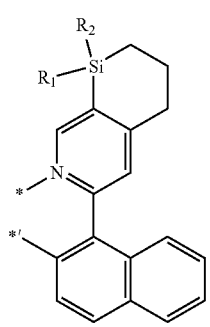
Formula 2E-1
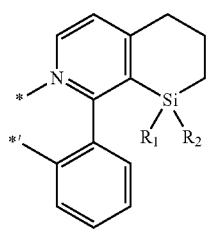
Formula 2E-2
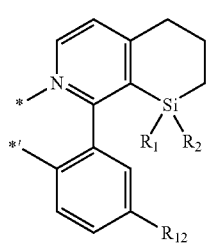
Formula 2E-3
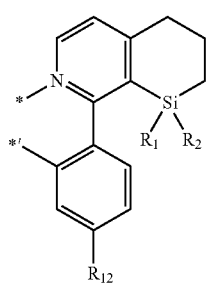

Formula 2E-4
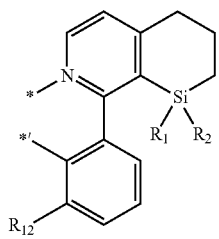
Formula 2E-5
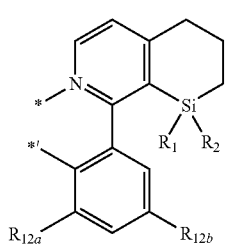
Formula 2E-6
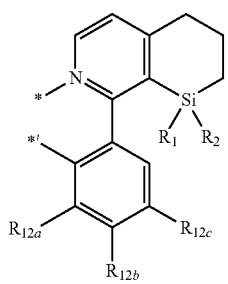
Formula 2E-7
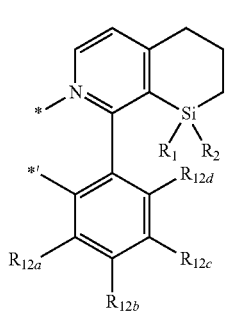
Formula 2E-8
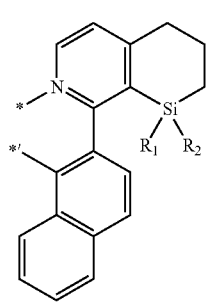
Formula 2E-9
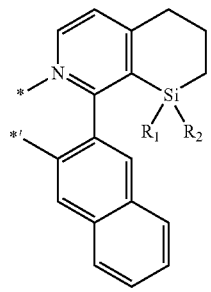
Formula 2E-10
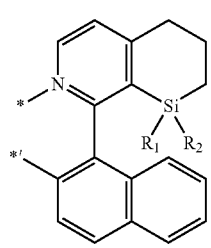
Formula 2F-1
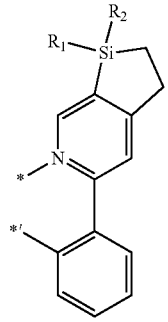
Formula 2F-2
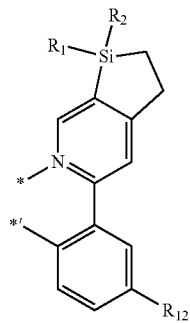
Formula 2F-3
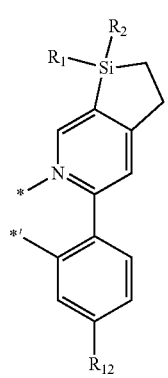

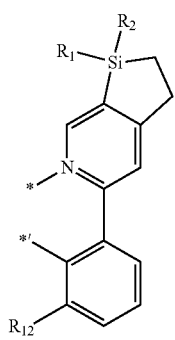
Formula 2F-4
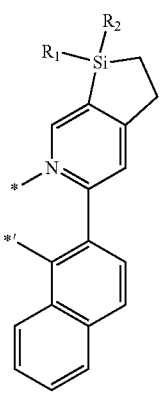
Formula 2F-8
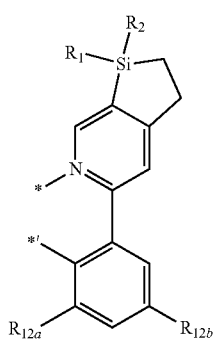
Formula 2F-5
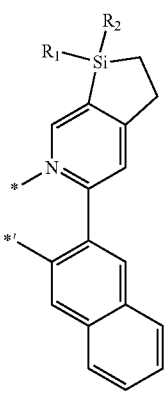
Formula 2F-9
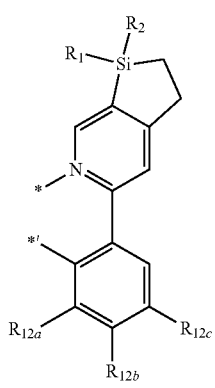
Formula 2F-6
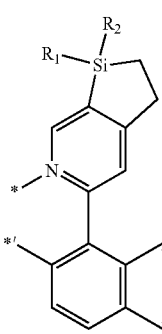
Formula 2F-10
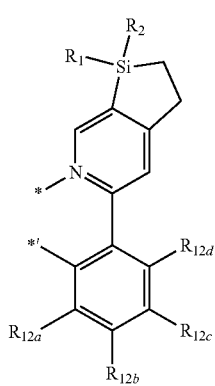
Formula 2F-7
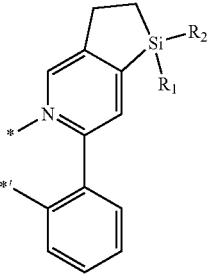
Formula 2G-1

-continued

Formula 2G-2

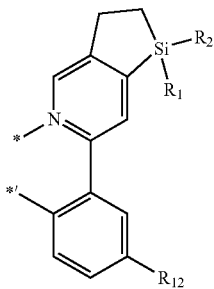

Formula 2G-3

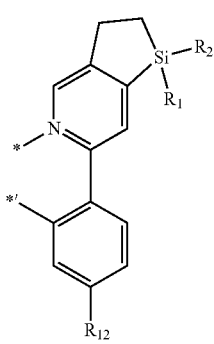

Formula 2G-4

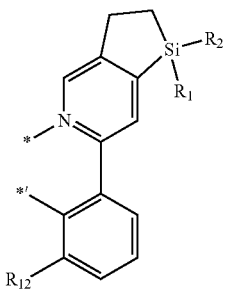

Formula 2G-5

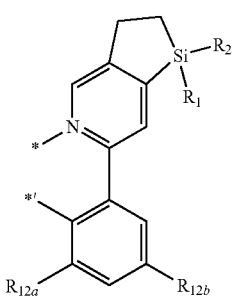

Formula 2G-6

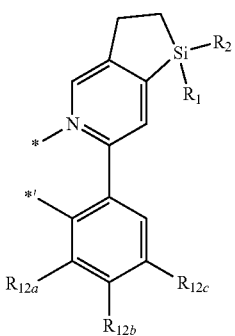

-continued

Formula 2G-7

Formula 2G-8

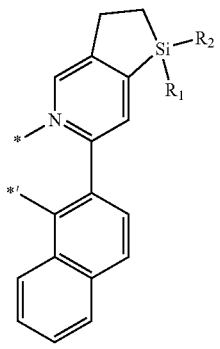

Formula 2G-9

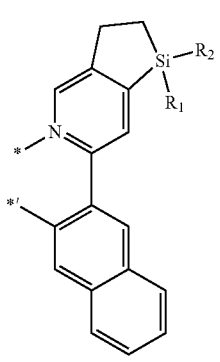

Formula 2G-10

Regarding Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10, descriptions of $R_1$, $R_2$, and $R_{12}$ are the same as described above, each of * and *' indicates a binding site to M in Formula 1, and descriptions of $R_{12a}$ to $R_{12d}$ are understood by referring to the descriptions of $R_{12}$, provided that $R_{12}$, and $R_{12a}$ to $R_{12d}$ are not hydrogen.

For example, in Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10, $R_{12}$ and $R_{12a}$ to $R_{12d}$ are each independently selected from deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, and $R_1$ and $R_2$ are each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and —Si(Q$_1$)(Q$_2$)(Q$_3$); and an n-propyl group, an isopropyl group, an n-butyl group, an isobutyl group, a sec-butyl group, a tert-butyl group, an n-pentyl group, an isopentyl group, a sec-pentyl group, a tert-pentyl group, and a phenyl group, each substituted with at least one selected from deuterium and a C$_1$-C$_{10}$ alkyl group, wherein Q$_1$ to Q$_3$ are each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group, but they are not limited thereto.

L$_2$ in Formula 1 may be selected from groups represented by Formulae 3A to 3G:

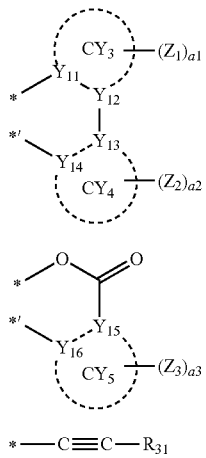

Formula 3A

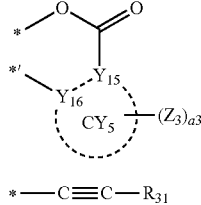

Formula 3B

Formula 3C

Formula 3D

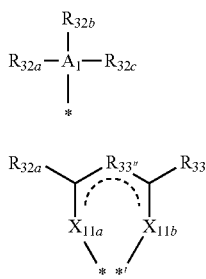

Formula 3E

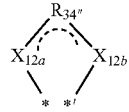

Formula 3F

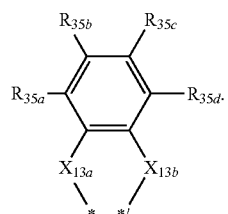

Formula 3G

In Formulae 3A to 3G,

Y$_{11}$ to Y$_{16}$ may be each independently carbon (C) or nitrogen (N), and Y$_{11}$ and Y$_{12}$ may be connected to each other via a single bond or a double bond, Y$_{13}$ and Y$_{14}$ may be connected to each other via a single bond or a double bond, and Y$_{15}$ and Y$_{16}$ may be connected to each other via a single bond or a double bond, CY$_3$ to CY$_5$ may be each independently selected from a C$_5$-C$_{60}$ carbocyclic group and a C$_2$-C$_{60}$ heterocyclic group, a1 to a3 are each independently an integer selected from 1 to 5, A$_1$ is P or As, X$_{11a}$, X$_{11b}$, X$_{12a}$, X$_{12b}$, X$_{13a}$, and X$_{13b}$ may be each independently selected from N, O, N(R$_{34}$), P(R$_{35}$)(R$_{36}$) and As(R$_{37}$)(R$_{38}$), provided that X$_{12a}$, X$_{12b}$, X$_{13a}$, and X$_{13b}$ are neither N nor O, R$_{33''}$ and R$_{34''}$ may be each independently selected from a single bond, a double bond, a substituted or unsubstituted C$_1$-C$_5$ alkylene group, a substituted or unsubstituted C$_2$-C$_5$ alkenylene group, and a substituted or unsubstituted C$_6$-C$_{10}$ arylene group, Z$_1$ to Z$_3$, R$_{31}$, R$_{32a}$, R$_{32b}$, R$_{32c}$, R$_{33a}$, R$_{33b}$, R$_{34}$ to R$_{38}$, R$_{35a}$, R$_{35b}$, R$_{35c}$, and R$_{35d}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_4$)(Q$_5$), —B(Q$_6$)(Q$_7$), and —P(=O)(Q$_8$)(Q$_9$), each of * and *' indicates a binding site to M in Formula 1, and at least one of substituents of the substituted C$_1$-C$_5$ alkylene group, substituted C$_2$-C$_5$ alkenylene group, substituted C$_6$-C$_{10}$ arylene group, substituted C$_1$-C$_{60}$ alkyl group, substituted C$_2$-C$_{60}$ alkenyl group, substituted C$_2$-C$_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), and —P(=O)($Q_{28}$)($Q_{29}$); and —Si($Q_{31}$)($Q_{32}$)($Q_{33}$), —N($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

$CY_3$ to $CY_5$ in Formulae 3A and 3B may be each independently selected from a cyclopentadiene, a benzene, an indene, a 1,2,3,4-tetrahydronaphthalene, a naphthalene, an azulene, a heptalene, an indacene, an acenaphthylene, a fluorene, a spiro-bifluorene, a benzofluorene, a dibenzofluorene, a phenalene, a phenanthrene, an anthracene, a fluoranthene, a triphenylene, a pyrene, a chrysene, naphthacene, a picene, a perylene, a pentacene, a hexacene, a rubicene, a coronene, an ovalene, a pyrrole, an isoindole, an indole, an indazole, a pyrazole, an imidazole, a triazole, an oxazole, an isoxazole, an oxadiazole, a thiazole, an isothiazole, a thiadiazole, a purine, a pyridine, a pyrimidine, a pyrazine, a pyridazine, a triazine, a 5,6,7,8-tetrahydroquinoline, a 5,6,7,8-tetrahydroisoquinoline, a quinoline, an isoquinoline, a benzoquinoline, a phthalazine, a naphthyridine, a quinoxaline, a quinazoline, a cinnoline, a phenanthrididine, an acridine, a phenanthroline, a phenazine, a benzoimidazole, a benzofuran, a benzothiophene, an isobenzothiazole, a benzoxazole, an isobenzoxazole, a benzocarbazole, a dibenzocarbazole, an imidazopyridine, an imidazopyrimidine, a dibenzofuran, a dibenzothiophene, a dibenzothiophene sulfone, a carbazole, a dibenzosilole, a benzofuropyridine, and a benzothienopyridine.

In an embodiment, $L_2$ in Formula 1 may be selected from ligands represented by Formulae 3A, 3B, and 3F, $Y_{11}$ in Formula 3A may be nitrogen, $Y_{12}$ to $Y_{14}$ in Formula 3A may each be carbon, $CY_3$ in Formula 3A may be a pyridine, a 5,6,7,8-tetrahydroquinoline, a 5,6,7,8-tetrahydroisoquinoline, a quinoline, and an isoquinoline, $CY_4$ in Formula 3A may be a benzene, a 1,2,3,4-tetrahydronaphthalene, a naphthalene, a fluorene, a dibenzofuran, a dibenzothiophene, a benzofuropyridine, and a benzothienopyridine, $Y_{15}$ in Formula 3B may be carbon, $Y_{16}$ in Formula 3B may be nitrogen, $CY_5$ in Formula 3B may each be a pyridine or a pyrimidine, $Z_1$ to $Z_3$ in Formulae 3A and 3B may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —$SF_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —CF₂H, —CFH₂, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD₃, —CD₂H, —CDH₂, —CF₃, —CF₂H, —CFH₂, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —Si($Q_1$)($Q_2$)($Q_3$), —N($Q_4$)($Q_5$), —B($Q_6$)($Q_7$), and —P(=O)($Q_8$)($Q_9$), a1 to a3 may be each independently an integer selected from 0 to 4, and from among groups $Z_1$ in the number of a1, groups $Z_2$ in the number of a2, and groups $Z_3$ in the number of a3, two or more neighboring substituents may be optionally combined with each other to form a $C_5$-$C_{30}$ carbocyclic group or a $C_2$-$C_{30}$ heterocyclic group, wherein $Q_1$ to $Q_9$ may be each independently selected from —CH₃, —CD₃, —CD₂H, —CDH₂, —CH₂CH₃, —CH₂CD₃, —CH₂CD₂H, —CH₂CDH₂, —CHDCH₃, —CHDCD₂H, —CHDCDH₂, —CHDCD₃, —CD₂CD₃, —CD₂CD₂H, and —CD₂CDH₂;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium and a $C_1$-$C_{10}$ alkyl group, $X_{12a}$ and $X_{12b}$ in Formula 3F may each be O, and $R_{34''}$ in Formula 3F may be selected from a $C_2$-$C_5$ alkenylene group; and a $C_2$-$C_5$ alkenylene group, substituted with at least one selected from deuterium, a $C_1$-$C_{10}$ alkyl group, a $C_1$-$C_{10}$ alkoxy group, and a phenyl group, but is not limited thereto.

In some embodiments, $L_2$ in Formula 1 may be selected from ligands represented by Formulae 3-1 to 3-111:

Formula 3-1

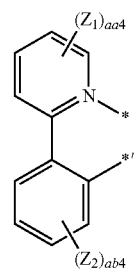

Formula 3-2
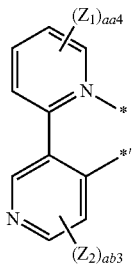
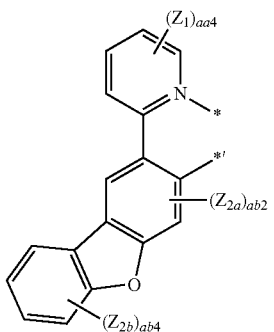
Formula 3-3
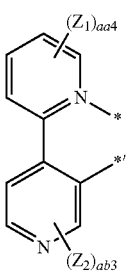
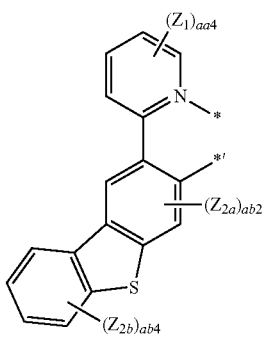
Formula 3-4
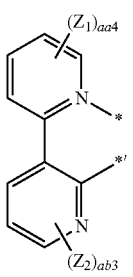
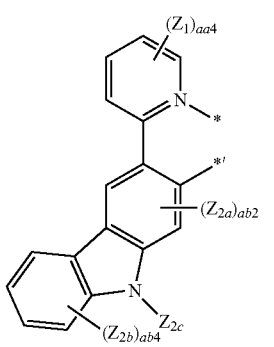
Formula 3-5
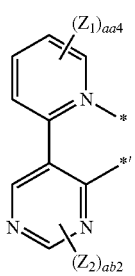
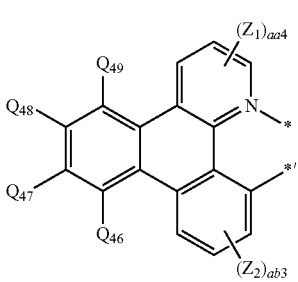
Formula 3-6
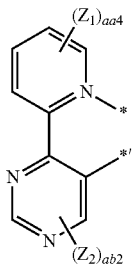
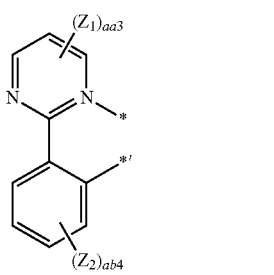
Formula 3-7
Formula 3-8
Formula 3-9
Formula 3-10
Formula 3-11

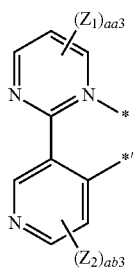
Formula 3-12
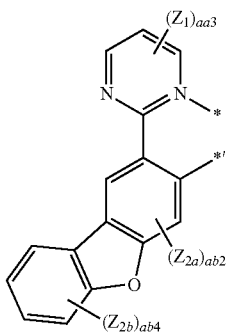
Formula 3-17
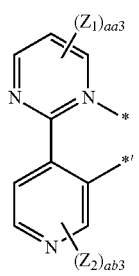
Formula 3-13
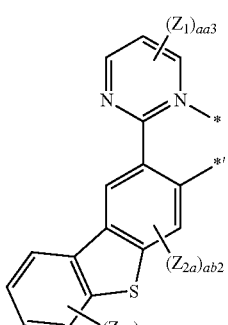
Formula 3-18
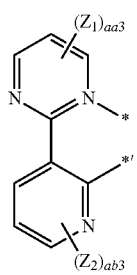
Formula 3-14
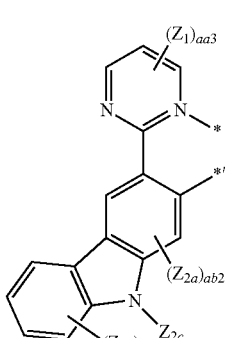
Formula 3-19
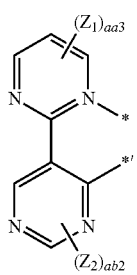
Formula 3-15
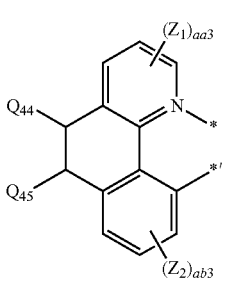
Formula 3-20
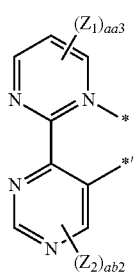
Formula 3-16
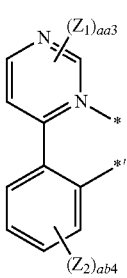
Formula 3-21

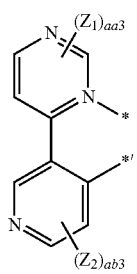
Formula 3-22
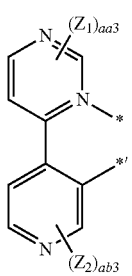
Formula 3-23
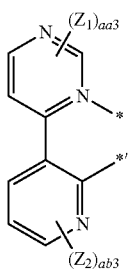
Formula 3-24
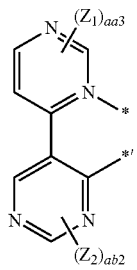
Formula 3-25
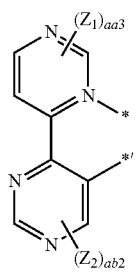
Formula 3-26
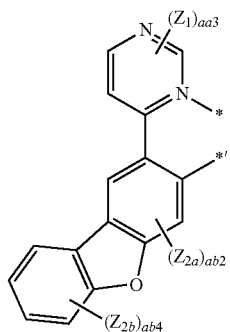
Formula 3-27
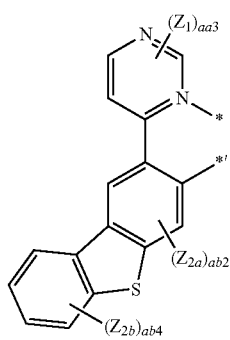
Formula 3-28
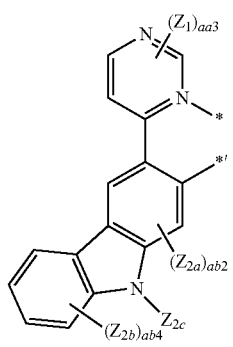
Formula 3-29
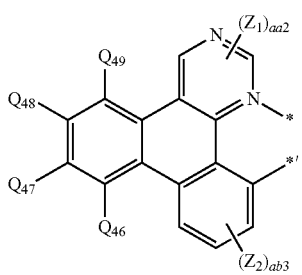
Formula 3-30
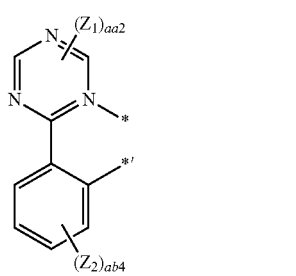
Formula 3-31

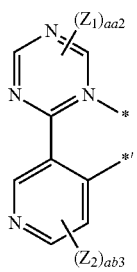
Formula 3-32
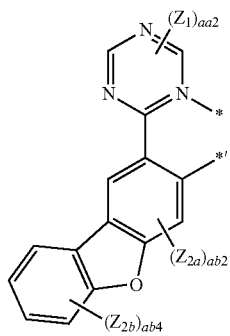
Formula 3-37
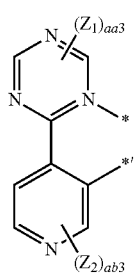
Formula 3-33
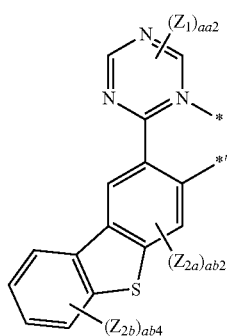
Formula 3-38
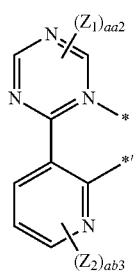
Formula 3-34
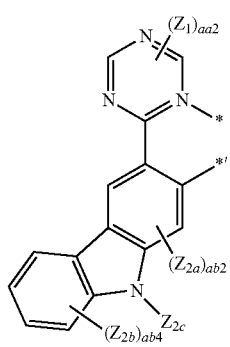
Formula 3-39
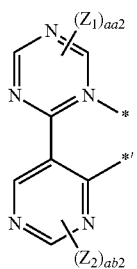
Formula 3-35
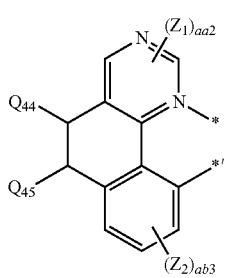
Formula 3-40
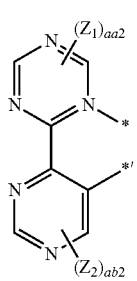
Formula 3-36
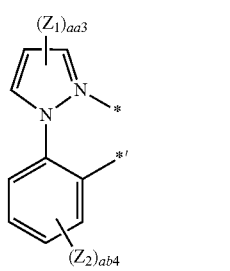
Formula 3-41

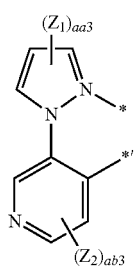
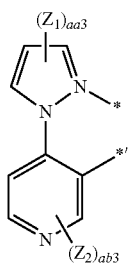
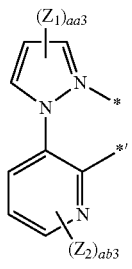
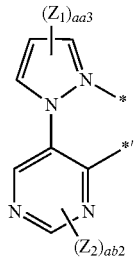
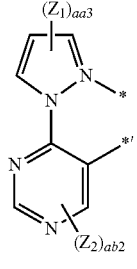
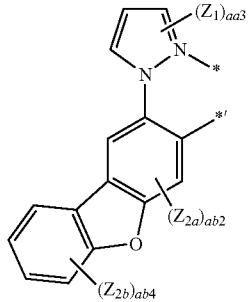
Formula 3-42
Formula 3-43
Formula 3-44
Formula 3-45
Formula 3-46
Formula 3-47
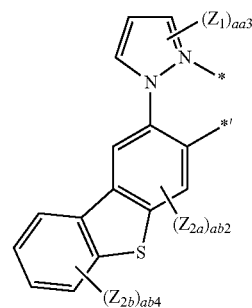
Formula 3-48
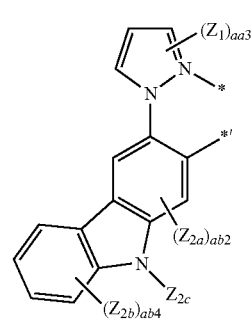
Formula 3-49
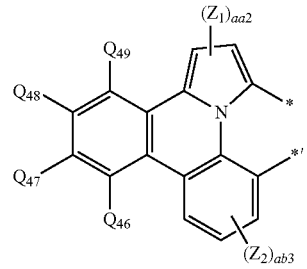
Formula 3-50
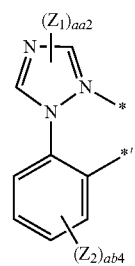
Formula 3-51
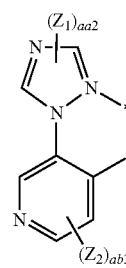
Formula 3-52

Formula 3-53
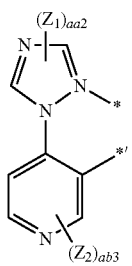
Formula 3-54
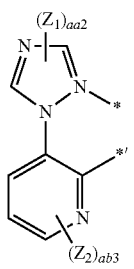
Formula 3-55
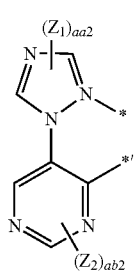
Formula 3-56
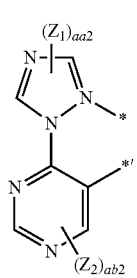
Formula 3-57
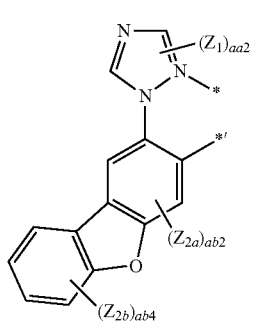
Formula 3-58
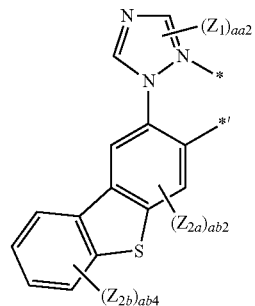
Formula 3-59
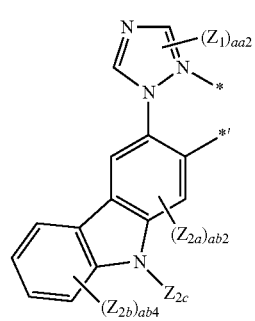
Formula 3-60
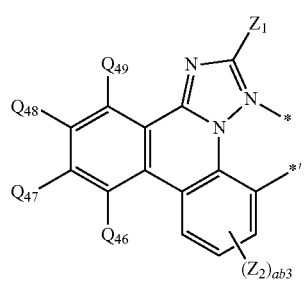
Formula 3-61
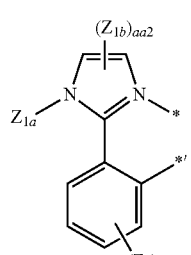
Formula 3-62
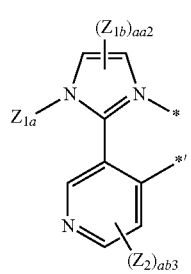

Formula 3-63
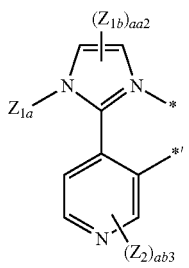
Formula 3-64
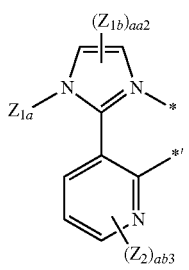
Formula 3-65
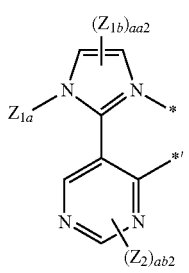
Formula 3-66
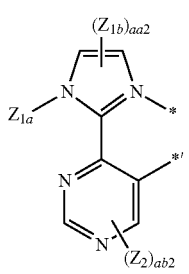
Formula 3-67
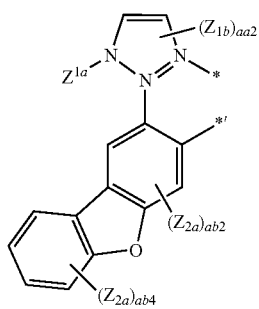
Formula 3-68
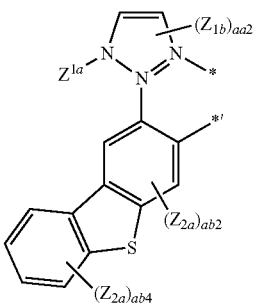
Formula 3-69
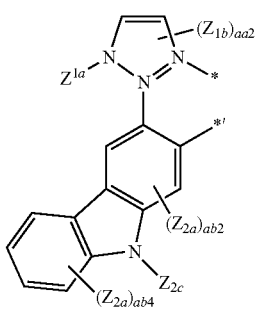
Formula 3-70
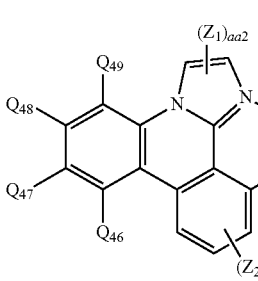
Formula 3-71
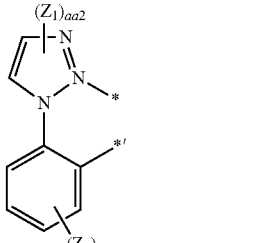
Formula 3-72
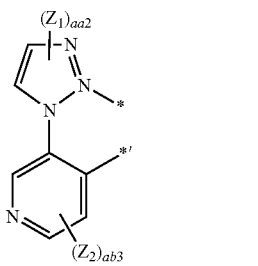

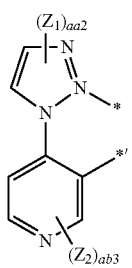
Formula 3-73

Formula 3-74
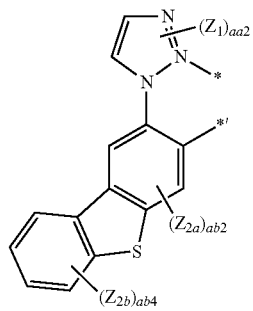
Formula 3-78
Formula 3-75
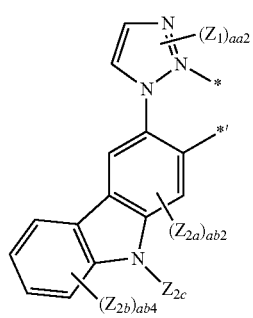
Formula 3-79
Formula 3-76
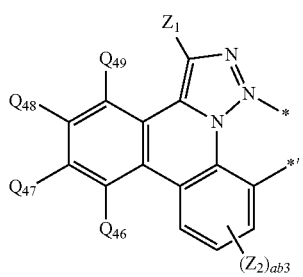
Formula 3-80
Formula 3-77
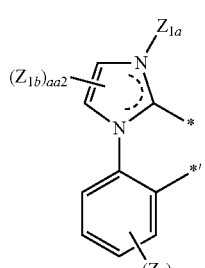
Formula 3-81
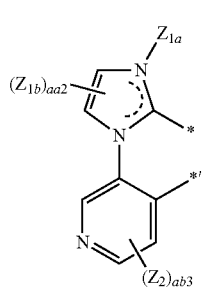
Formula 3-82

-continued

Formula 3-83

Formula 3-84

Formula 3-85

Formula 3-86

Formula 3-87

-continued

Formula 3-88

Formula 3-89

Formula 3-90

Formula 3-91

Formula 3-92

-continued
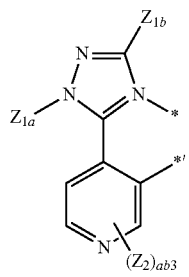
Formula 3-93
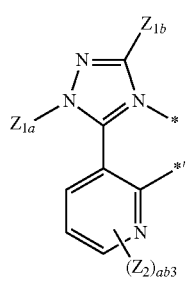
Formula 3-94
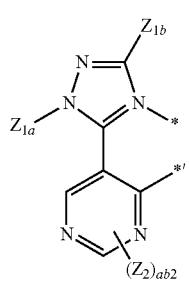
Formula 3-95
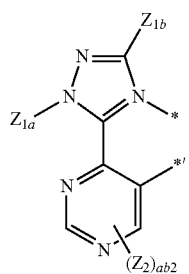
Formula 3-96
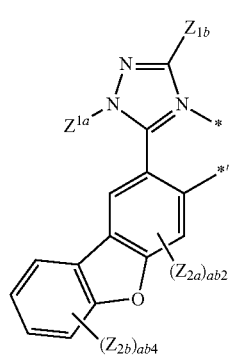
Formula 3-97
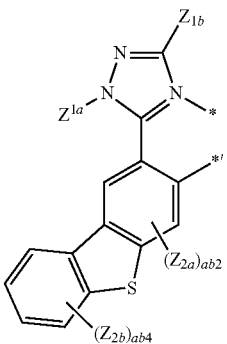
Formula 3-98
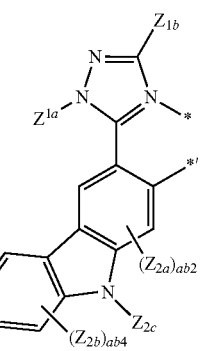
Formula 3-99
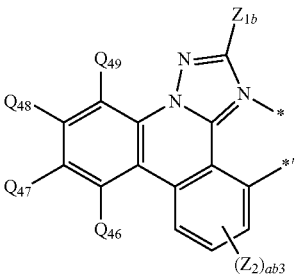
Formula 3-100
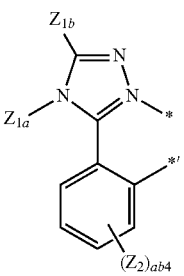
Formula 3-101
Formula 3-102

Formula 3-103
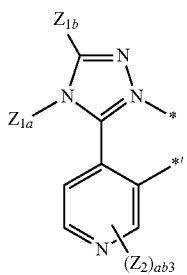

Formula 3-104
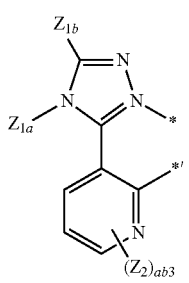

Formula 3-105
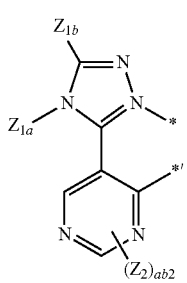

Formula 3-106
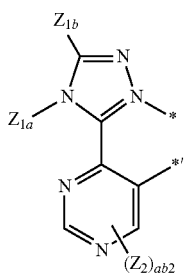

Formula 3-107
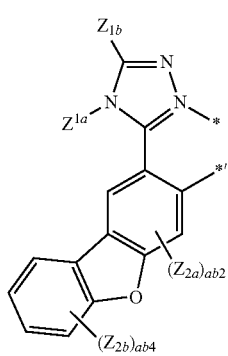

Formula 3-108

Formula 3-109
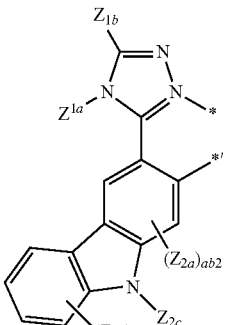

Formula 3-110
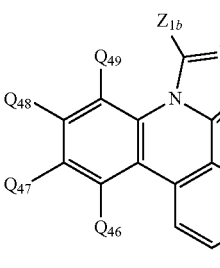

Formula 3-111
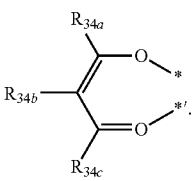

In Formulae 3-1 to 3-111, $Z_1$, $Z_2$, $Z_{1a}$, $Z_{1b}$, $Z_{2a}$, $Z_{2b}$, $Z_{2c}$, $R_{34a}$, $R_{34b}$, and $R_{34c}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —Si(Q$_1$)(Q$_2$)(Q$_3$), —N(Q$_4$)(Q$_5$), —B(Q$_6$)(Q$_7$), and —P(=O)(Q$_8$)(Q$_9$), from among groups $Z_1$, $Z_2$, $Z_{1a}$, $Z_{1b}$, $Z_{2a}$, $Z_{2b}$, $Z_{2c}$, $R_{34a}$, $R_{34b}$, and $R_{34c}$, two or more neighboring substituents are optionally combined with each other to form a $C_5$-$C_{30}$ carbocyclic group or a $C_2$-$C_{30}$ heterocyclic group, $Q_1$ to $Q_9$ may be each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from a deuterium and a $C_1$-$C_{10}$ alkyl group, aa2 and ab2 are each independently 1 or 2, aa3 and ab3 are each independently an integer selected from 1 to 3, aa4 and ab4 are each independently an integer selected from 1 to 4, and each of * and *' indicates a binding site to M in Formula 1.

In some embodiments, L$_2$ in Formula 1 may be selected from ligands represented by Formula 3-1(1) to 3-1(60), 3-1(61) to 3-1(69), 3-1(71) to 3-1(79), 3-1(81) to 3-1(88), 3-1(91) to 3-1(98), 3-111, and 3-112:

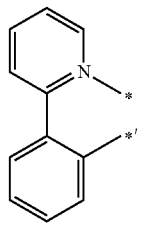

Formula 3-1(1)

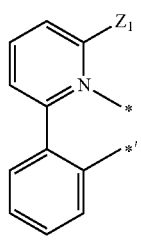

Formula 3-1(2)

-continued
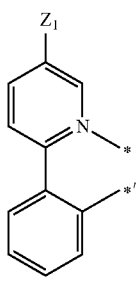
Formula 3-1(3)
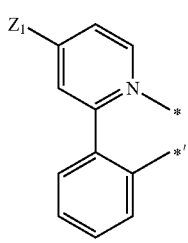
Formula 3-1(4)
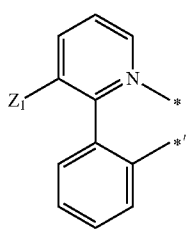
Formula 3-1(5)
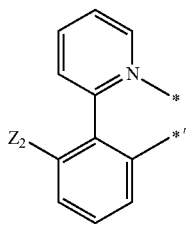
Formula 3-1(6)
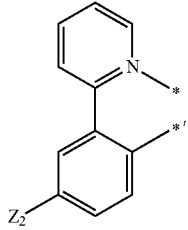
Formula 3-1(7)
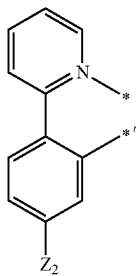
Formula 3-1(8)
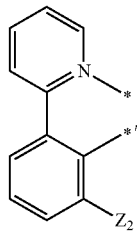
Formula 3-1(9)
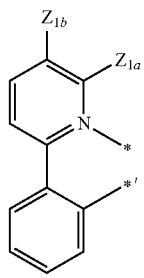
Formula 3-1(10)
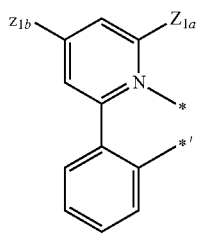
Formula 3-1(11)
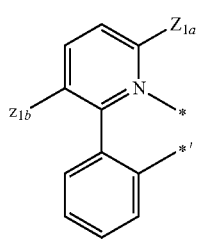
Formula 3-1(12)
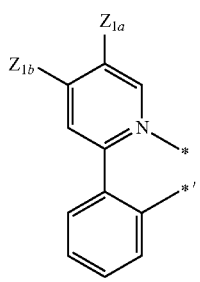
Formula 3-1(13)
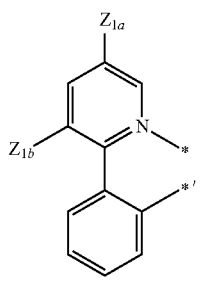
Formula 3-1(14)

-continued
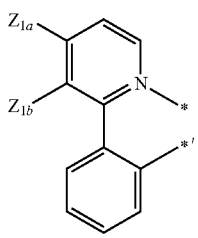
Formula 3-1(15)
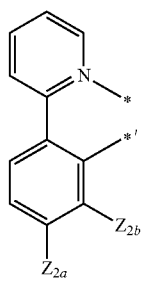
Formula 3-1(16)
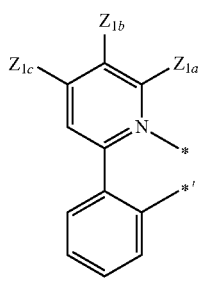
Formula 3-1(17)
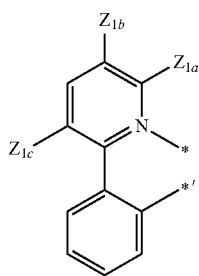
Formula 3-1(18)
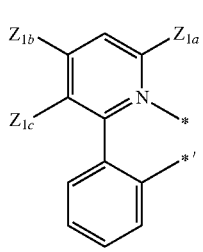
Formula 3-1(19)
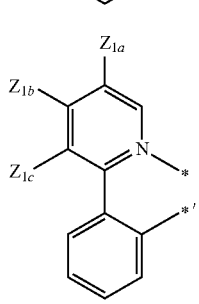
Formula 3-1(20)
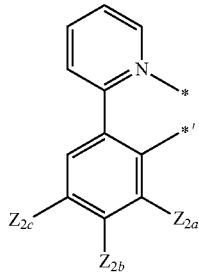
-continued
Formula 3-1(21)
Formula 3-1(22)
Formula 3-1(23)
Formula 3-1(24)
Formula 3-1(25)
Formula 3-1(26)

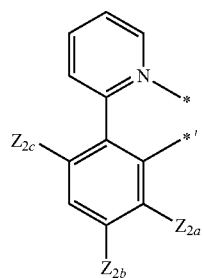 Formula 3-1(27)
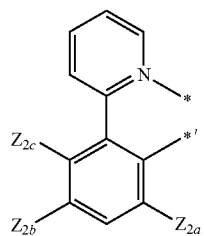 Formula 3-1(28)
 Formula 3-1(29)
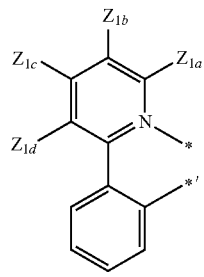 Formula 3-1(30)
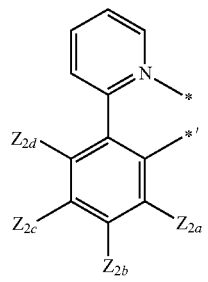 Formula 3-1(31)
 Formula 3-1(32)
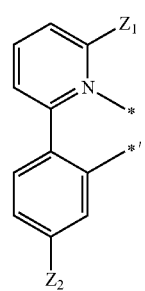 Formula 3-1(33)
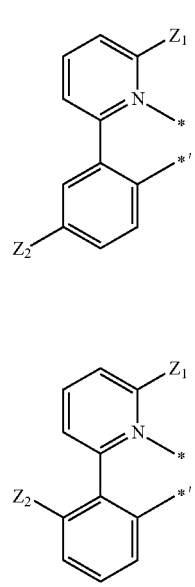 Formula 3-1(34)
Formula 3-1(35)
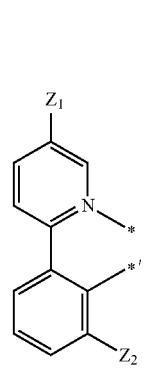 Formula 3-1(36)
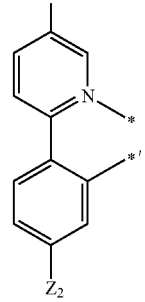 Formula 3-1(37)

-continued
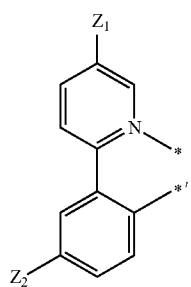
Formula 3-1(38)
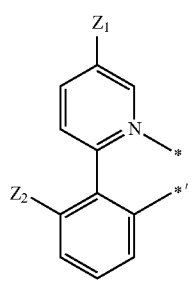
Formula 3-1(39)
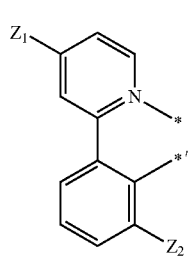
Formula 3-1(40)
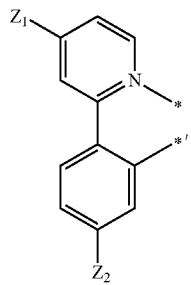
Formula 3-1(41)
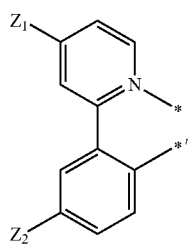
Formula 3-1(42)
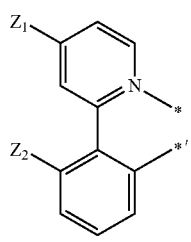
Formula 3-1(43)
-continued
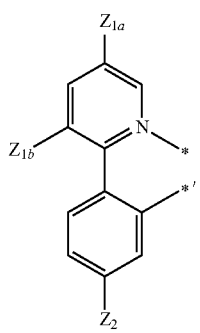
Formula 3-1(44)
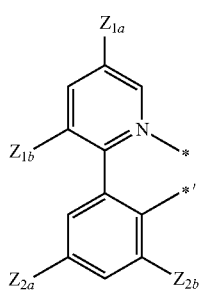
Formula 3-1(45)
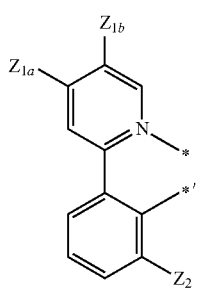
Formula 3-1(46)
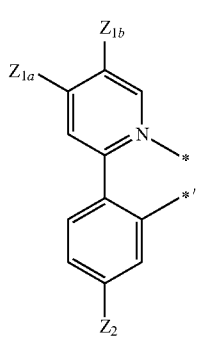
Formula 3-1(47)
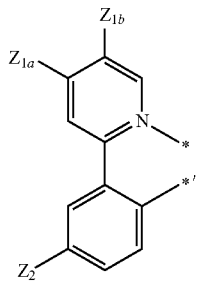
Formula 3-1(48)

Formula 3-1(49)
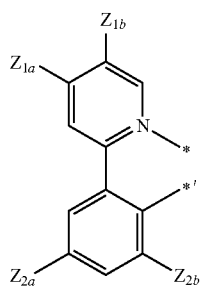
Formula 3-1(50)
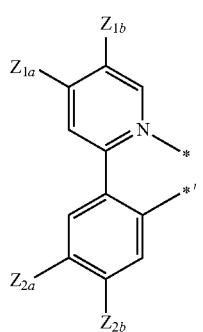
Formula 3-1(51)
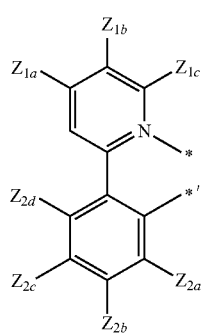
Formula 3-1(52)
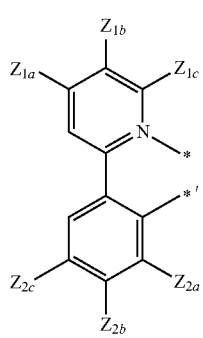
Formula 3-1(53)
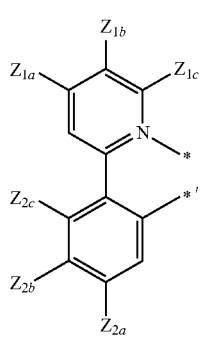
Formula 3-1(54)
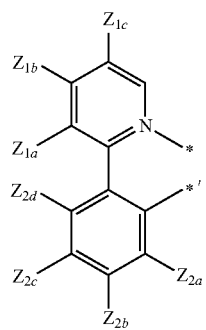
Formula 3-1(55)
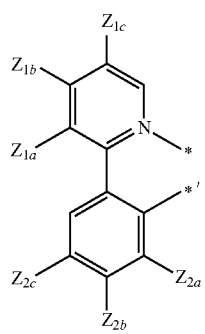
Formula 3-1(56)
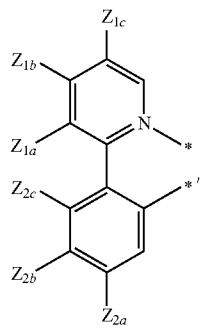
Formula 3-1(57)
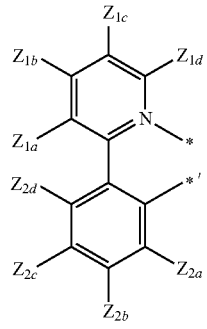
Formula 3-1(58)
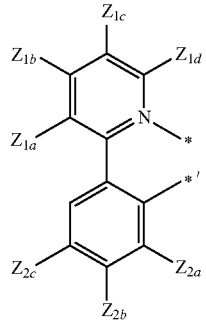

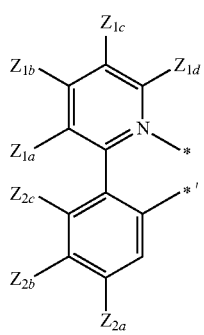
Formula 3-1(59)
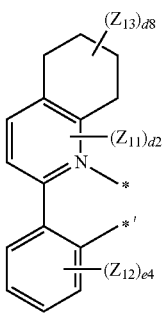
Formula 3-1(64)
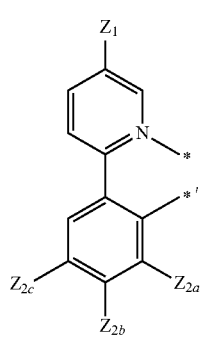
Formula 3-1(60)
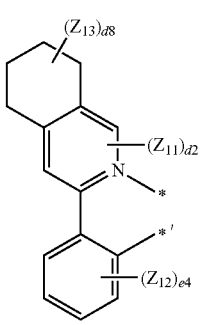
Formula 3-1(65)
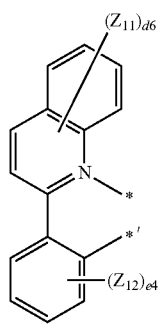
Formula 3-1(61)
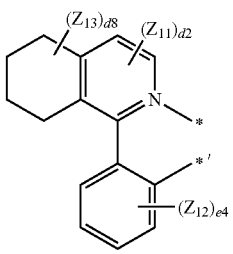
Formula 3-1(66)
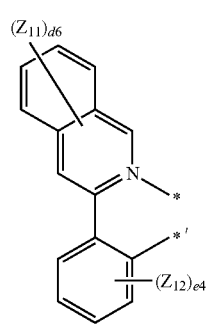
Formula 3-1(62)
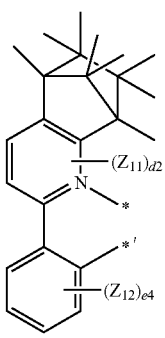
Formula 3-1(67)
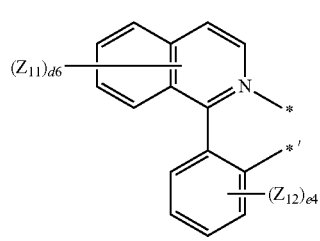
Formula 3-1(63)
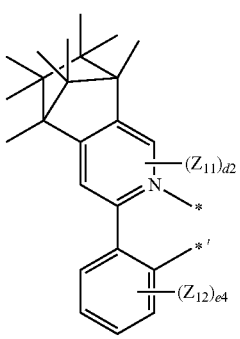
Formula 3-1(68)

-continued
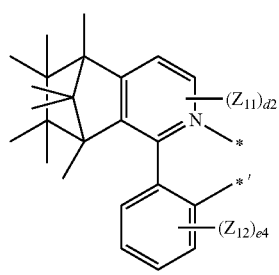
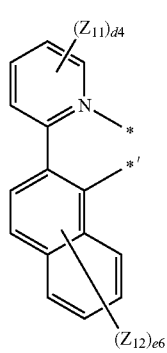
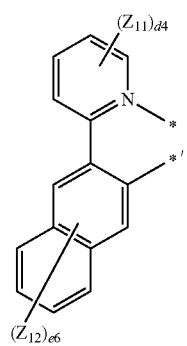
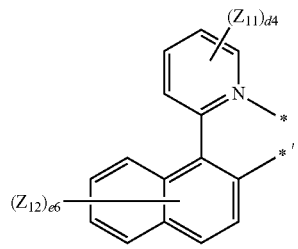
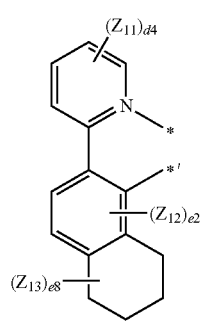
-continued
Formula 3-1(69)
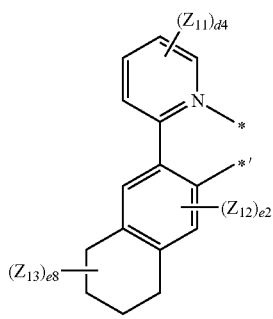
Formula 3-1(75)
Formula 3-1(71)
Formula 3-1(76)
Formula 3-1(72)
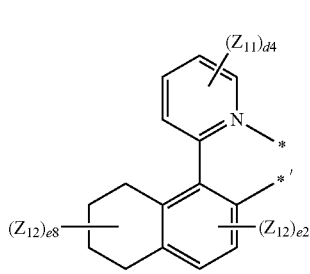
Formula 3-1(77)
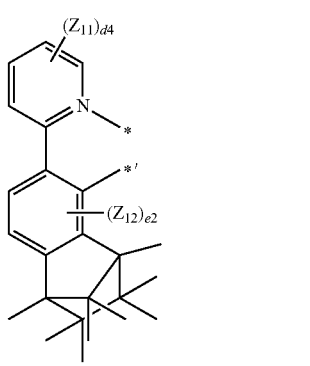
Formula 3-1(73)
Formula 3-1(78)
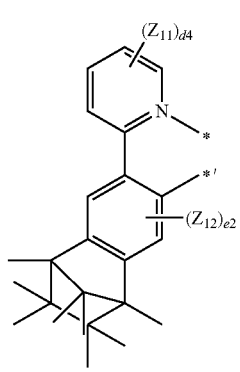
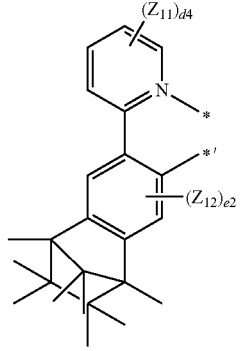
Formula 3-1(74)
Formula 3-1(79)
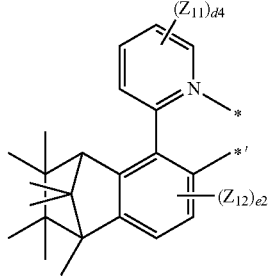

Formula 3-1(81)
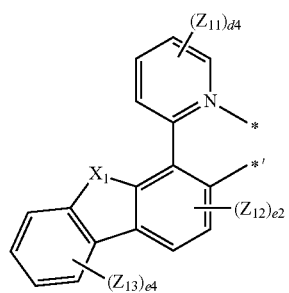
Formula 3-1(82)
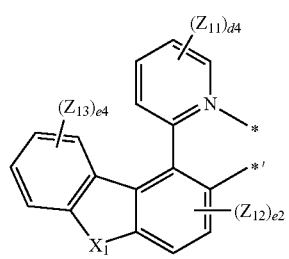
Formula 3-1(83)
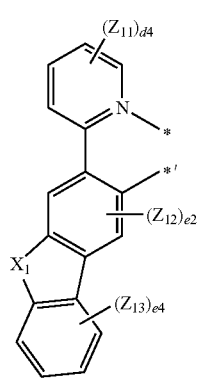
Formula 3-1(84)
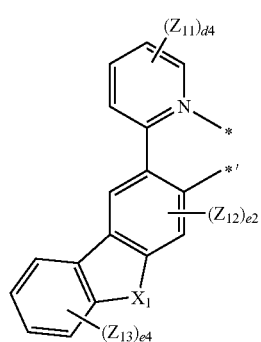
Formula 3-1(85)
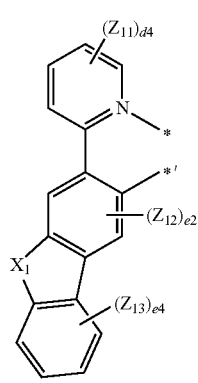
Formula 3-1(86)
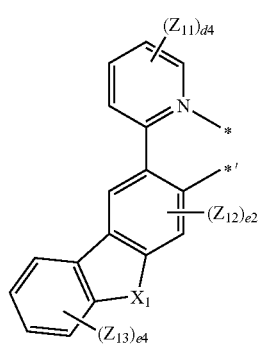
Formula 3-1(87)
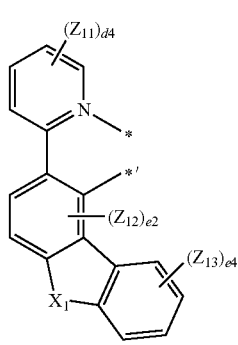
Formula 3-1(88)
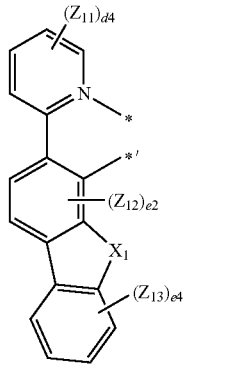
Formula 3-1(91)
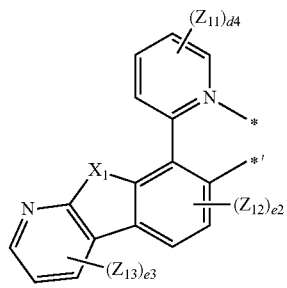
Formula 3-1(92)
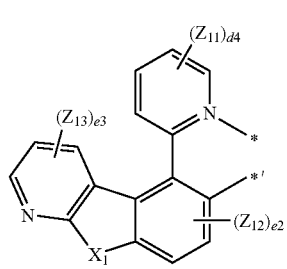

-continued

Formula 3-1(93)

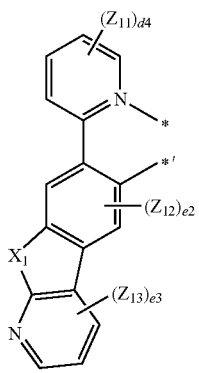

Formula 3-1(94)

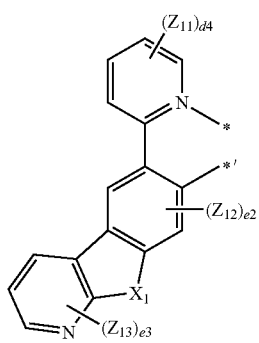

Formula 3-1(95)

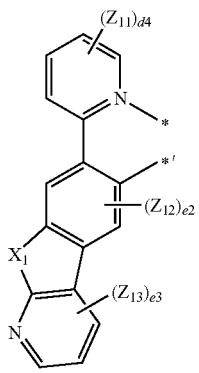

Formula 3-1(96)

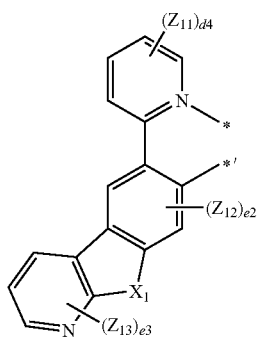

-continued

Formula 3-1(97)

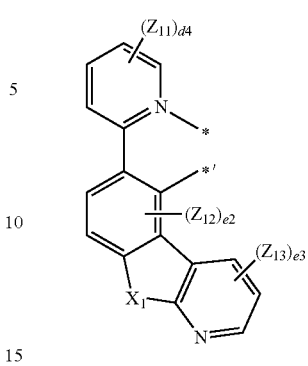

Formula 3-1(98)

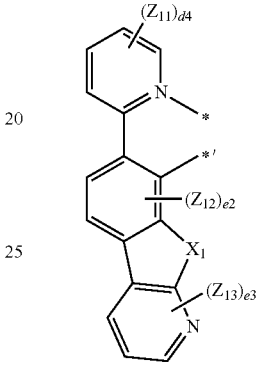

Formula 3-111

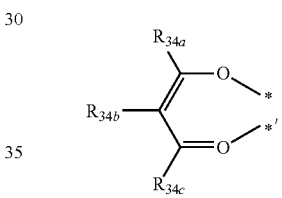

Formula 3-112

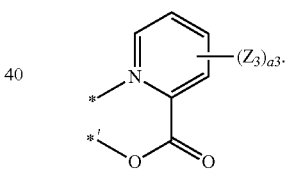

In Formulae 3-1(1) to 3-1(60), 3-1(61) to 3-1(69), 3-1(71) to 3-1(79), 3-1(81) to 3-1(88), 3-1(91) to 3-1(98), 3-111, and 3-112, $Z_1$, $Z_2$, $Z_{1a}$, $Z_{1b}$, $Z_{1c}$, $Z_{1d}$, $Z_{2a}$, $Z_{2b}$, $Z_{2c}$, $Z_{2d}$, $R_{34a}$, $R_{34b}$, and $R_{34c}$ may be each independently deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_1$)(Q$_2$)(Q$_3$), —N(Q$_4$)(Q$_5$), —B(Q$_6$)(Q$_7$), —P(=O)(Q$_8$)(Q$_9$), groups represented by Formulae 9-1 to 9-19, and groups represented by Formulae 10-1 to 10-30, $X_1$ may be O, S, C(Z$_{21}$)(Z$_{22}$), or N(Z$_{23}$), $Z_3$, $Z_{11}$ to $Z_{13}$, and $Z_{21}$ to $Z_{23}$ may be each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_1$)(Q$_2$)(Q$_3$), —N(Q$_4$)(Q$_5$), —B(Q$_6$)(Q$_7$), —P(=O)(Q$_8$)(Q$_9$), groups represented by Formulae 9-1 to 9-19, and groups represented by Formulae 10-1 to 10-30, wherein $Q_1$ to $Q_9$ may be each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from a deuterium and a C$_1$-C$_{10}$ alkyl group, d2 and e2 are each independently 0 or 2, e3 is an integer selected from 0 to 3, d4 and e4 are each independently an integer selected from 0 to 4, d6 and e6 are each independently an integer selected from 0 to 6, d8 and e8 are each independently an integer selected from 0 to 8, and each of * and *' indicates a binding site to M in Formula 1.

In an embodiment, L$_1$ in Formula 1 may be selected from ligands represented by Formulae 2-1 to 2-6 (for example, ligands represented by Formulae 2(1) to 2(36)), and L$_2$ in Formula 1 may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), 3-111, and 3-112.

In some embodiments, L$_1$ in Formula 1 may be selected from ligands represented by Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10, and L$_2$ in Formula 1 may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), 3-111, and 3-112, but they are not limited thereto.

The organometallic compound represented by Formula 1 may be selected from Compounds 1 to 270, but is not limited thereto:

1
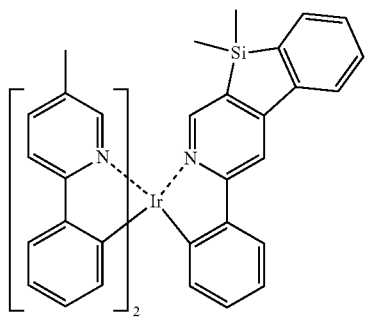

2
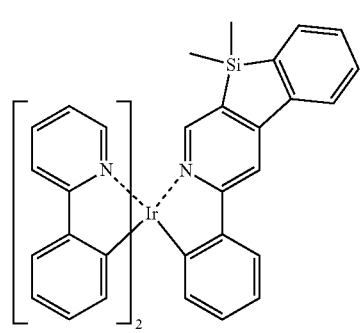

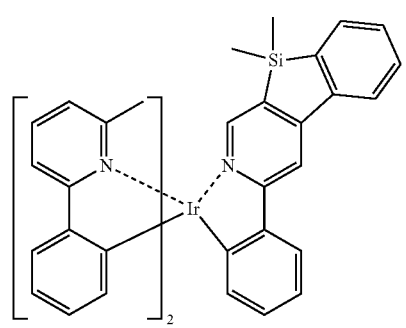

-continued

3
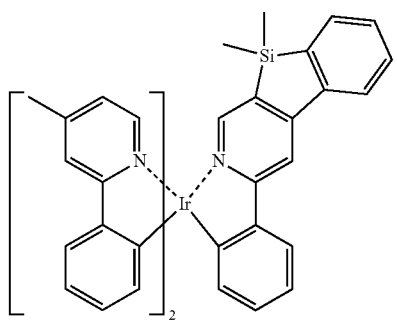

4
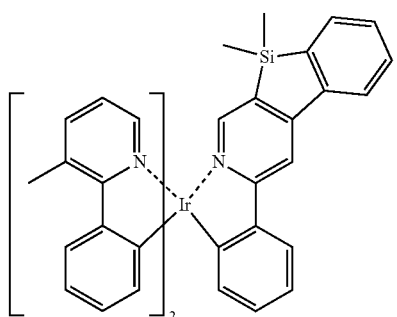

5
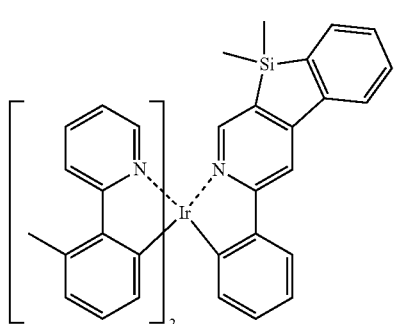

6
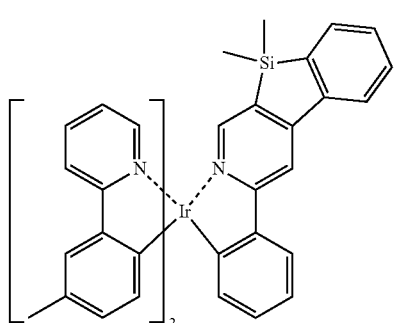

7

8
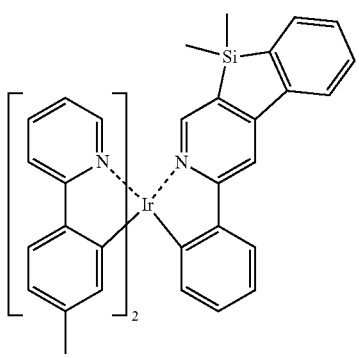
9
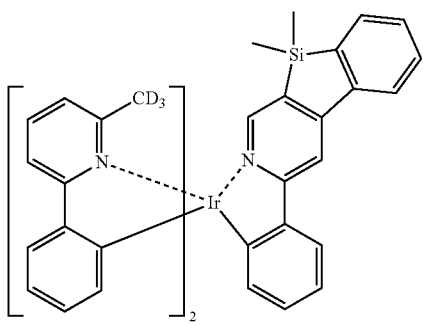
10
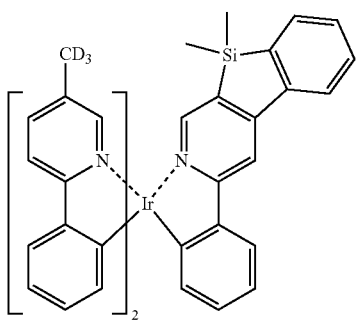
11
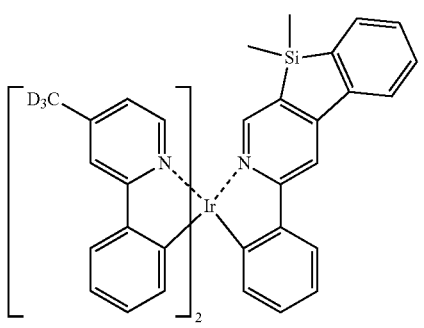
12
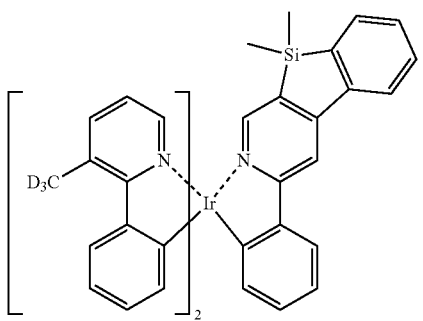
13
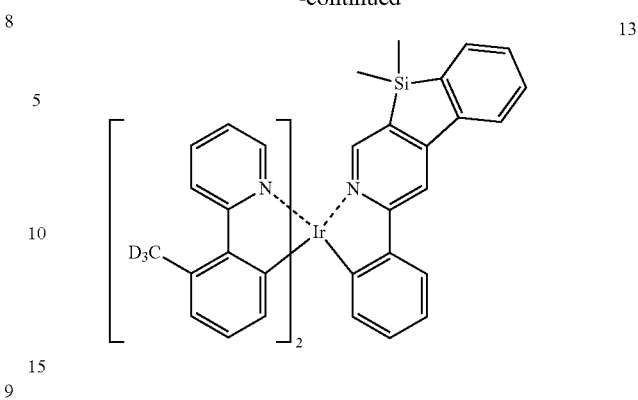
14
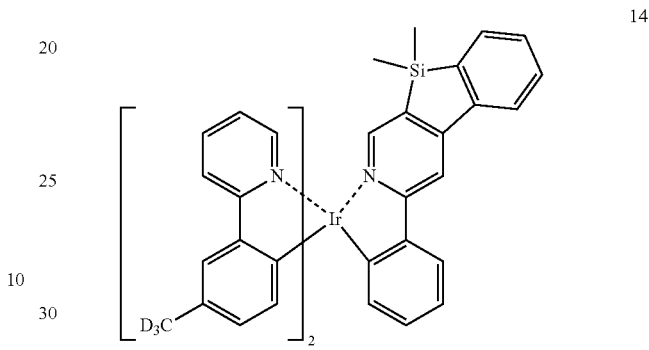
15
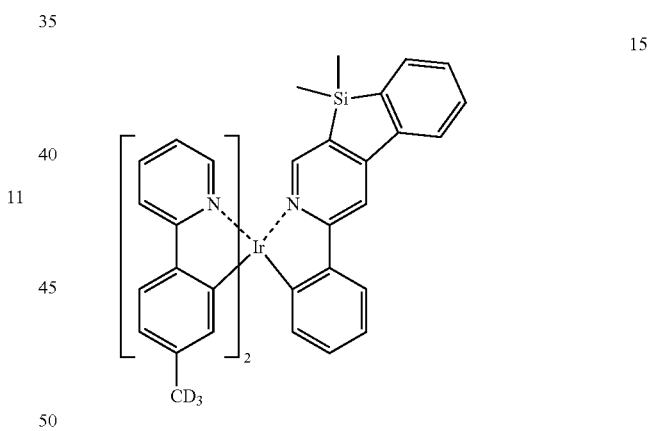
16
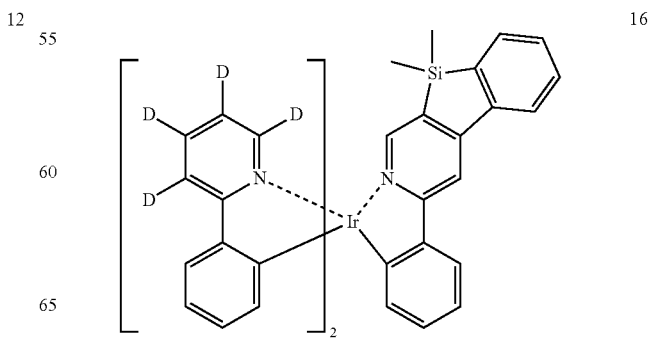

17
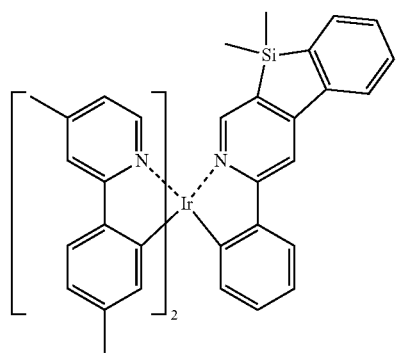
18
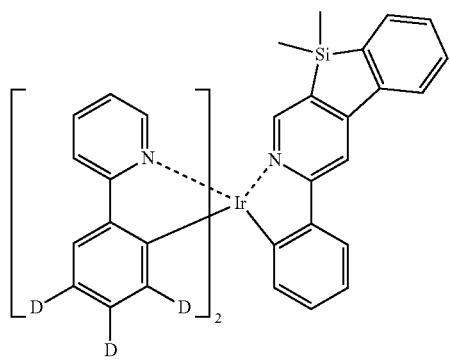
21
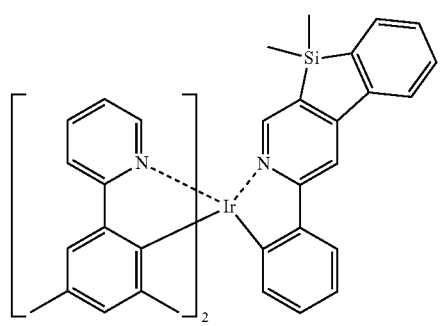
22
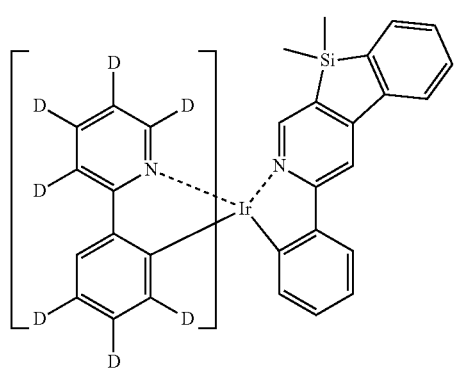
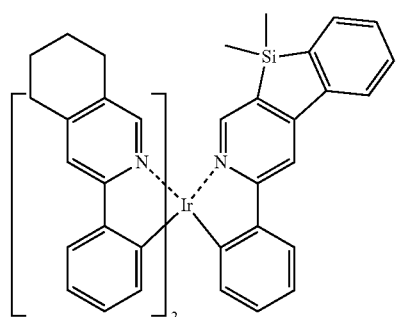
23
19
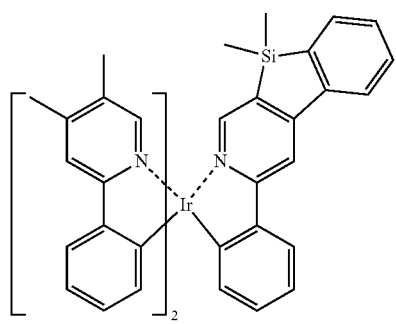
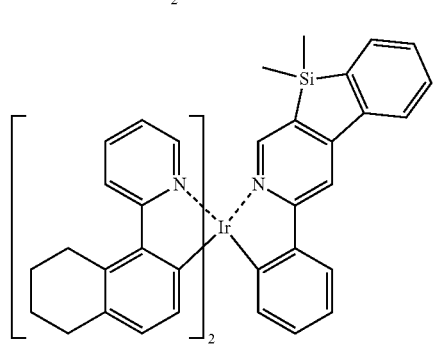
24
20
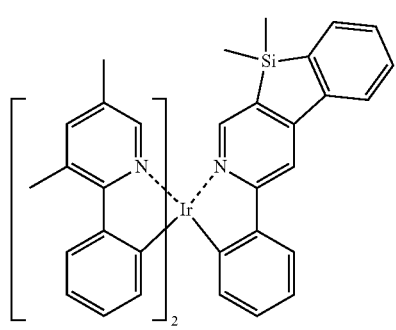
25
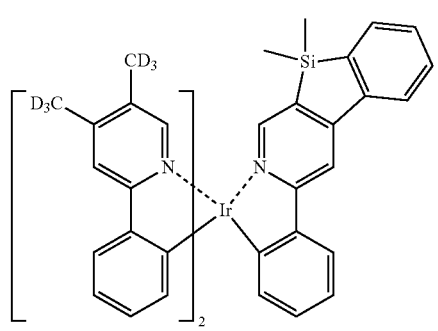

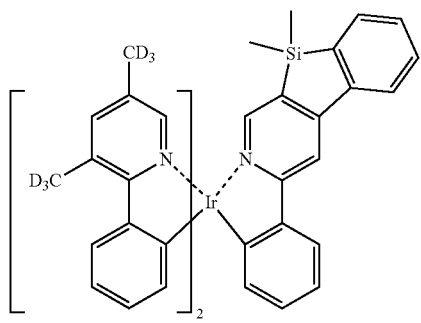
26
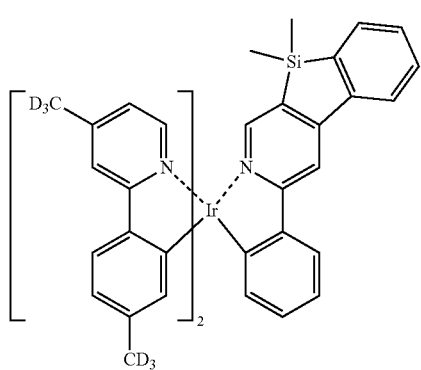
27
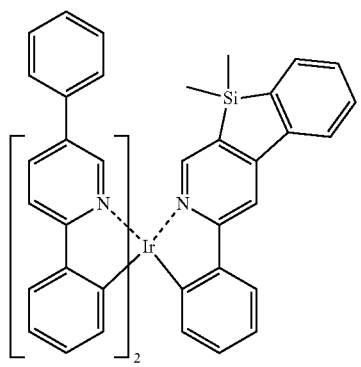
28
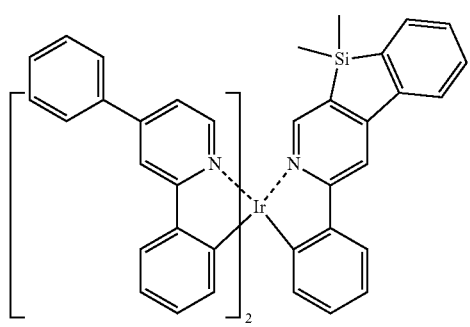
29
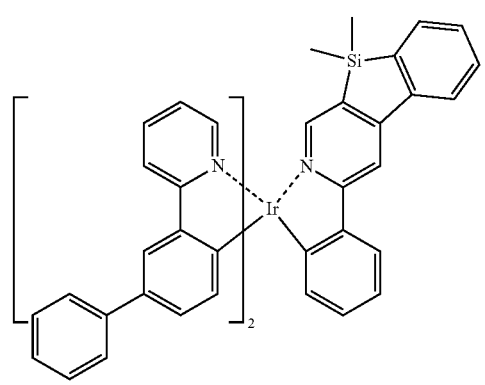
30
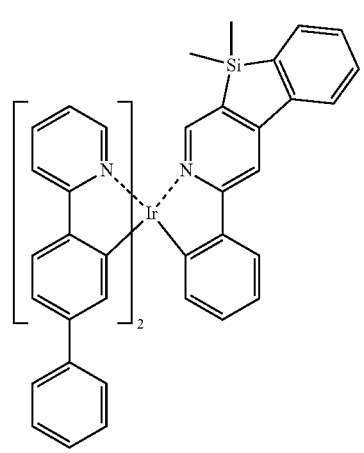
31
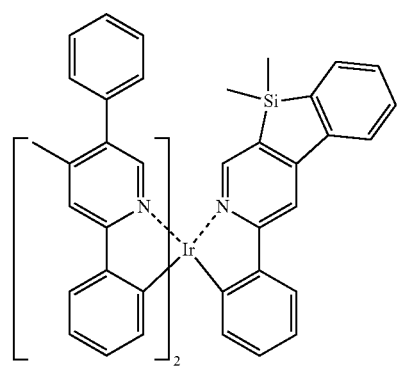
32
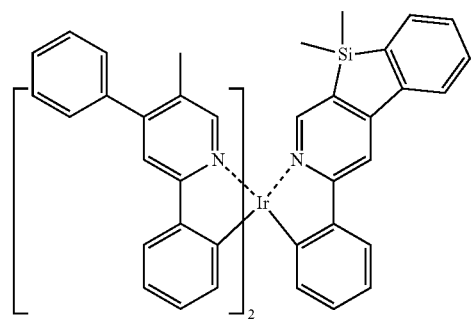
33

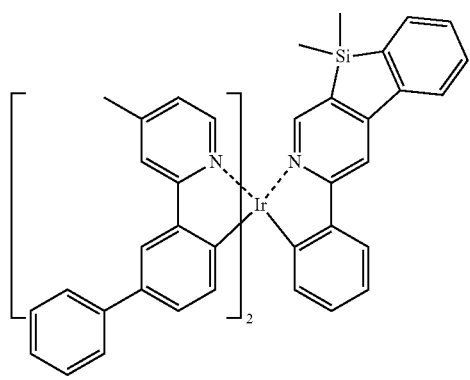
34
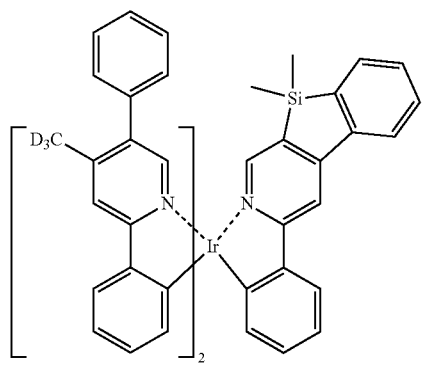
35
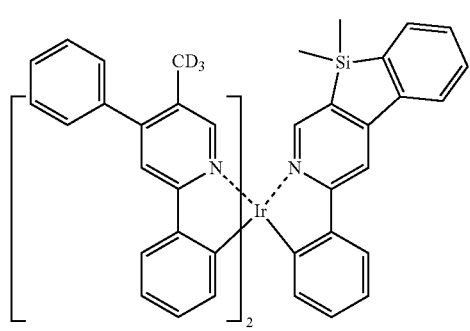
36
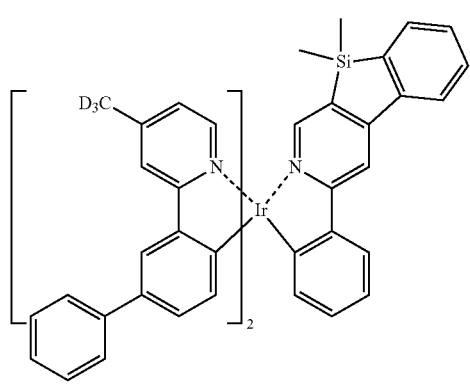
37
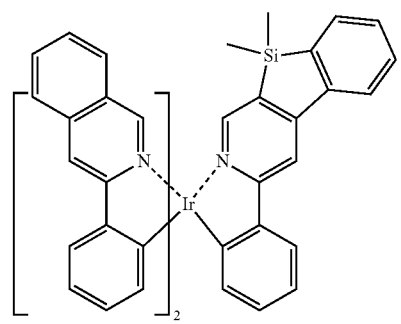
38
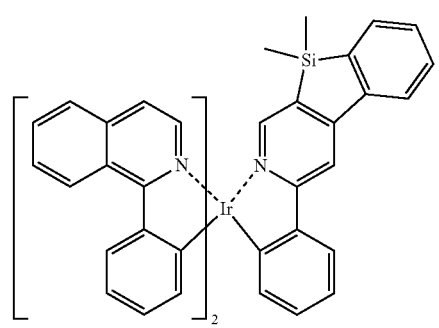
39
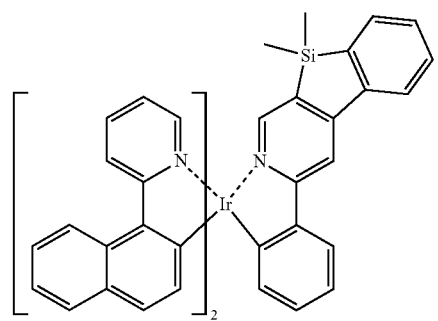
40
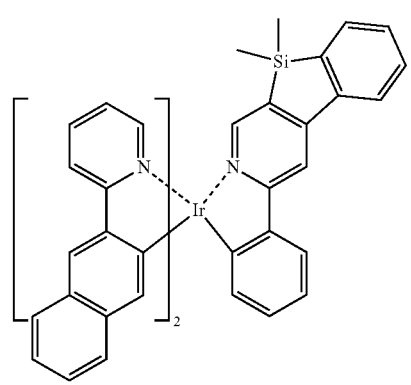
41

42
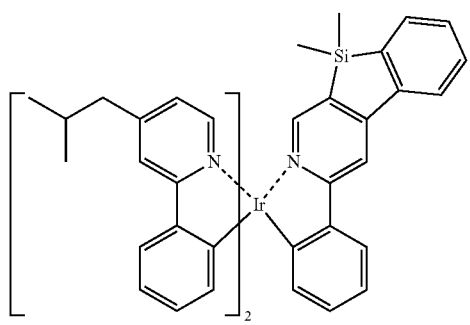
43
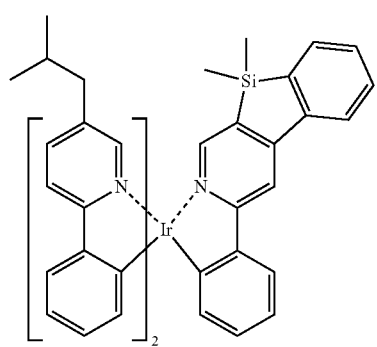
44
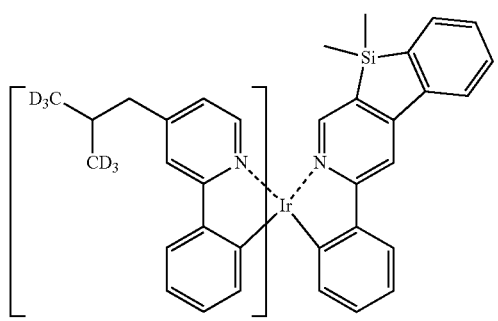
45
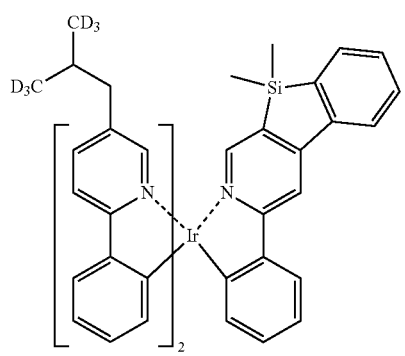
46
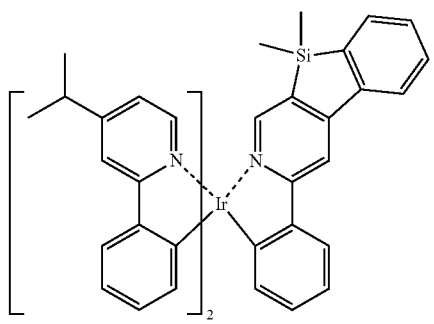
47
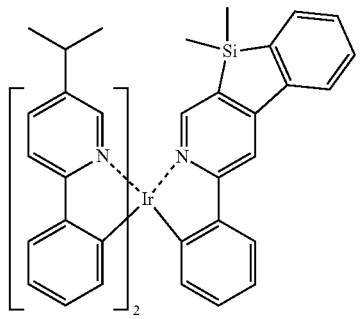
48
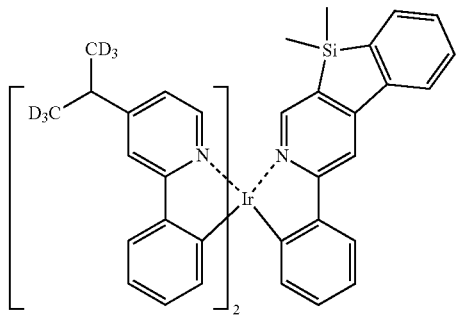
49
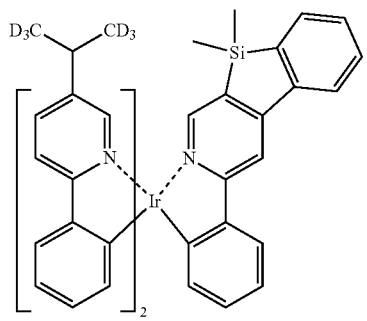
50
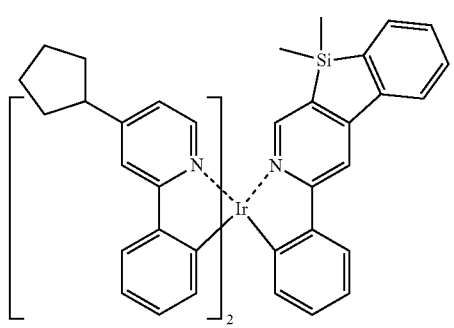

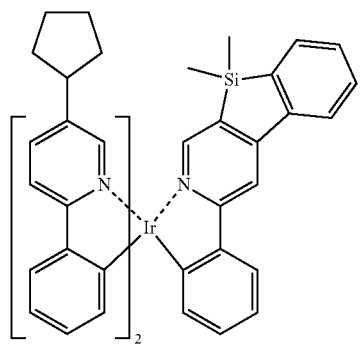
51
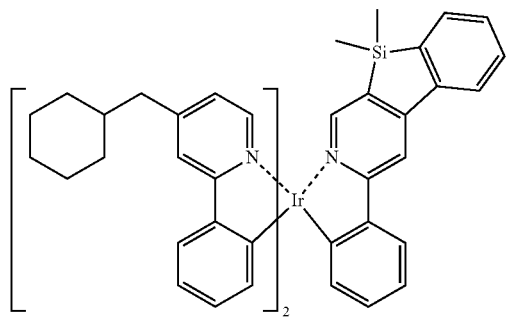
52
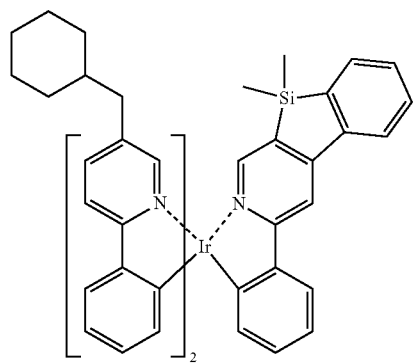
53
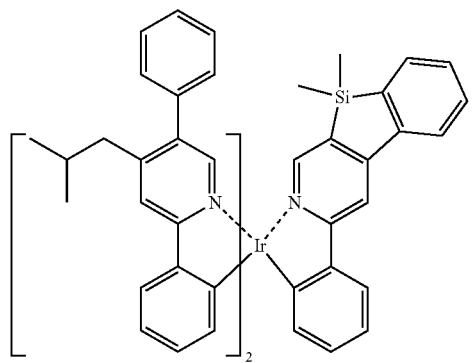
54
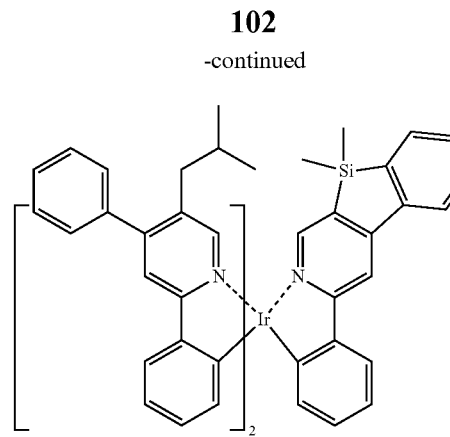
55
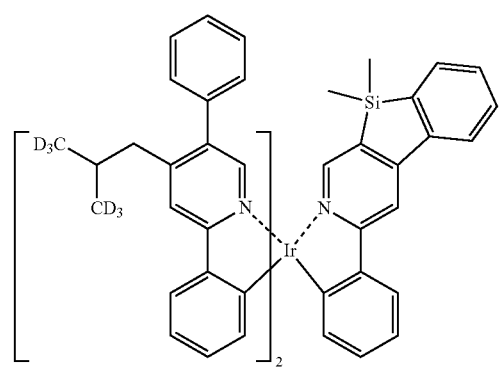
56
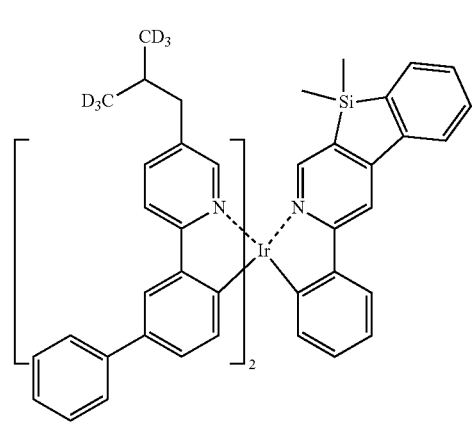
57
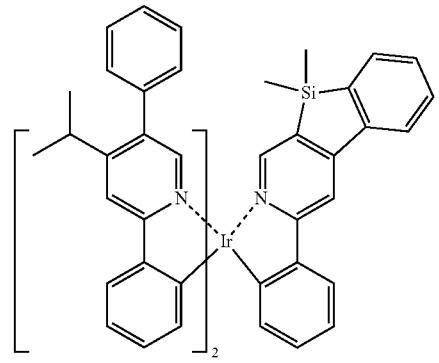
58

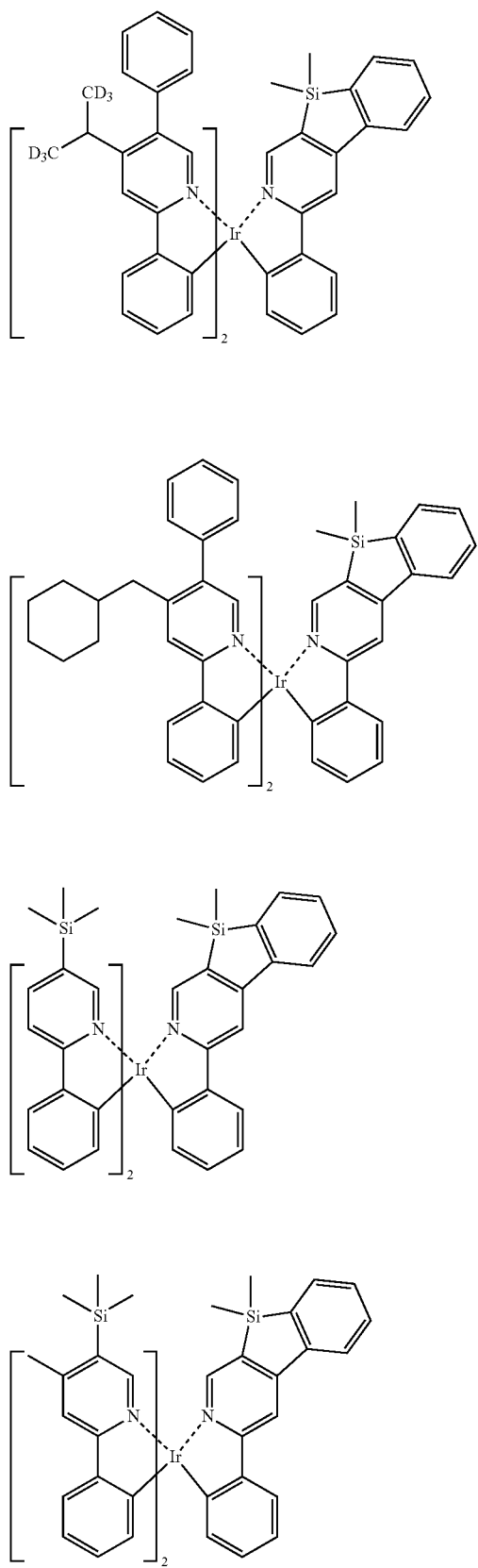
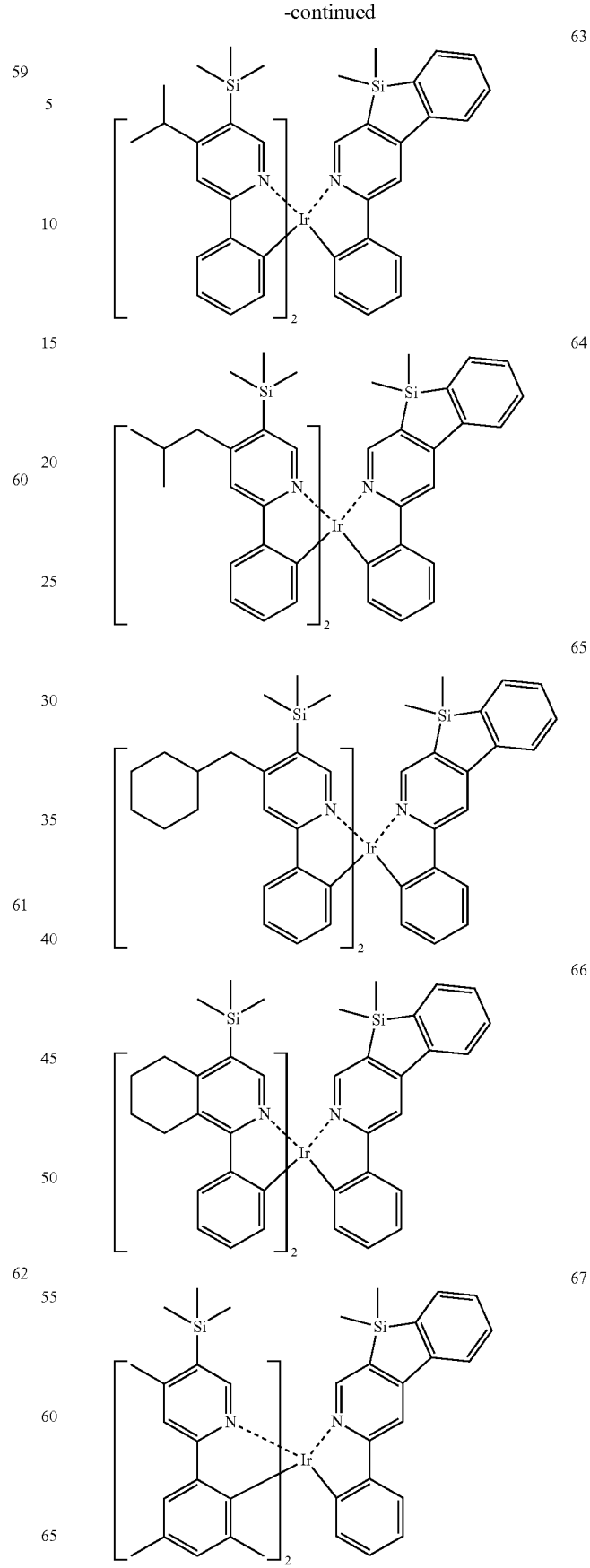

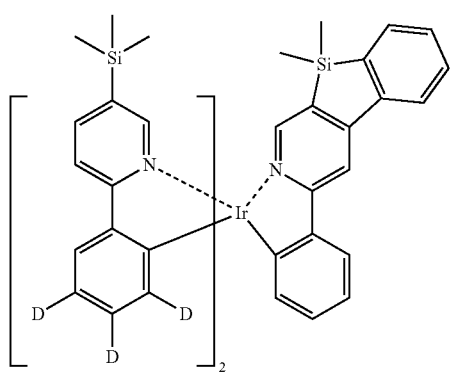
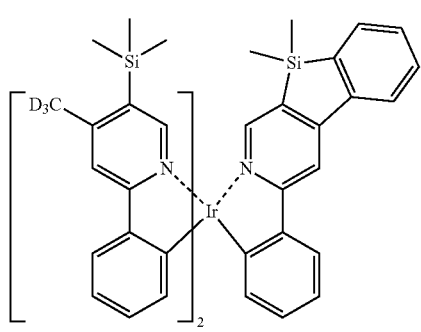
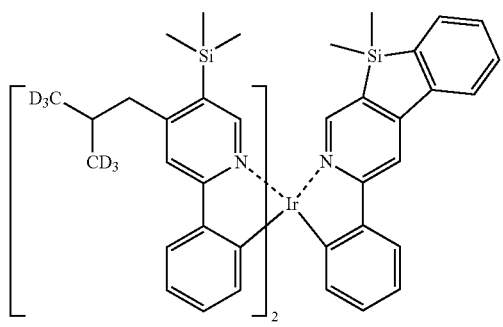
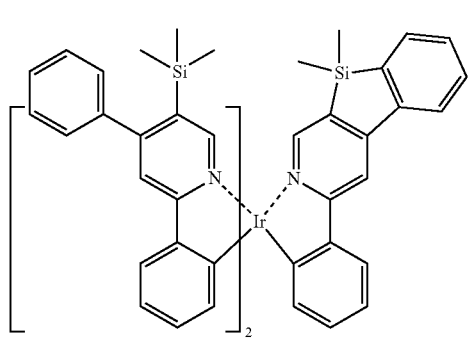
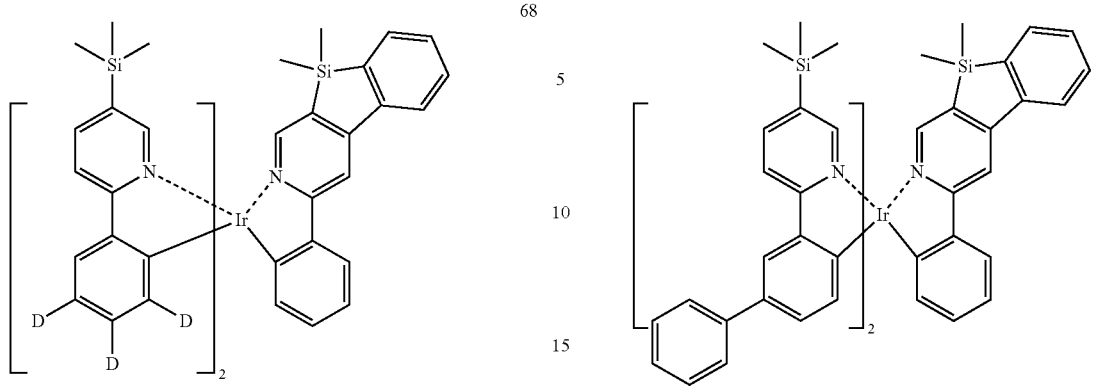
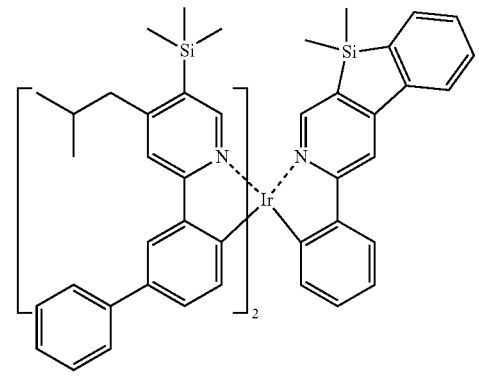
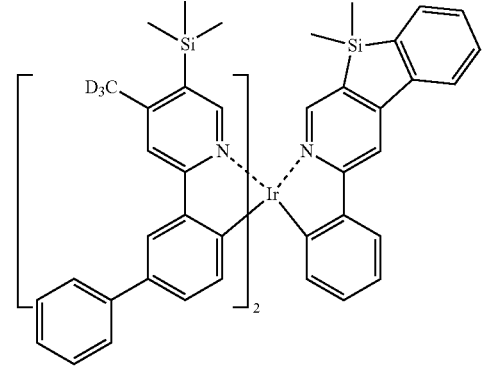

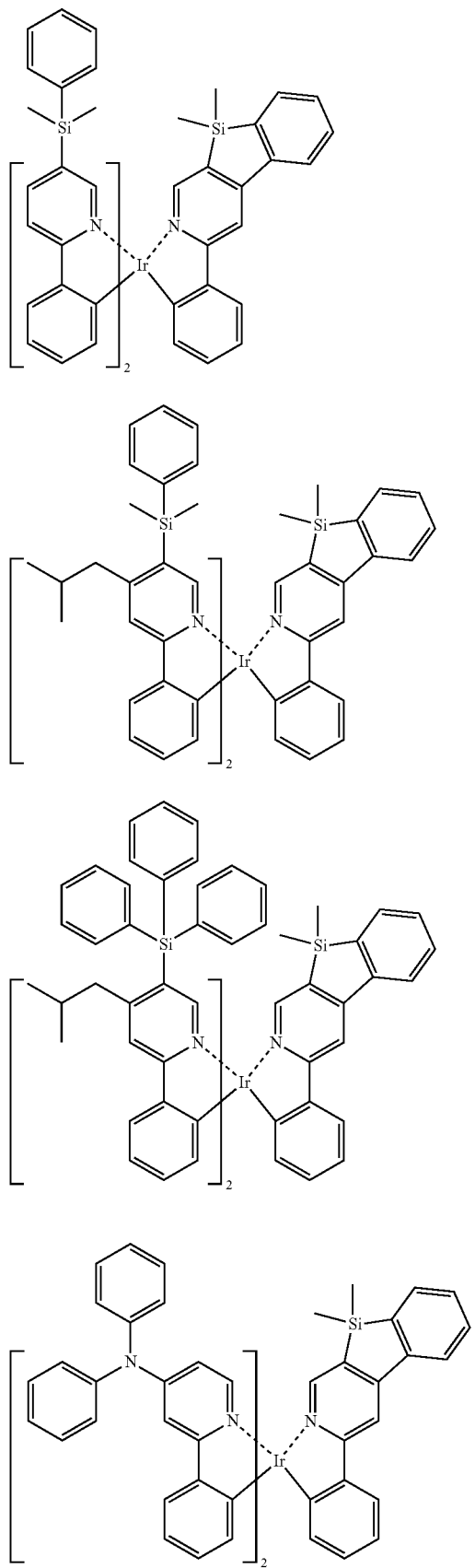

84
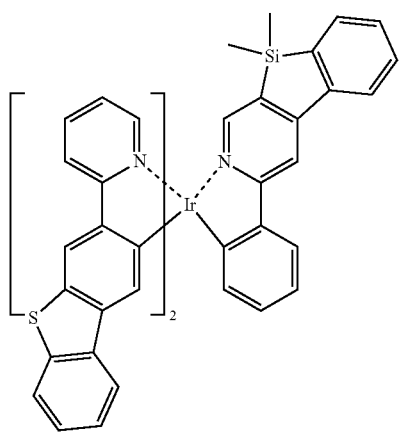
85
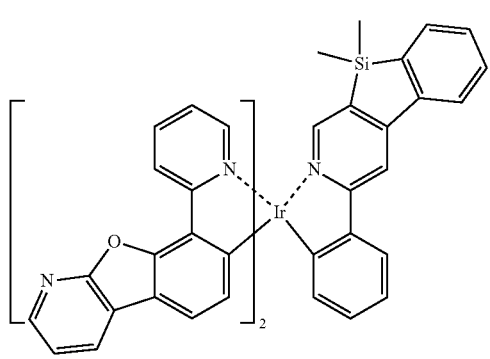
86
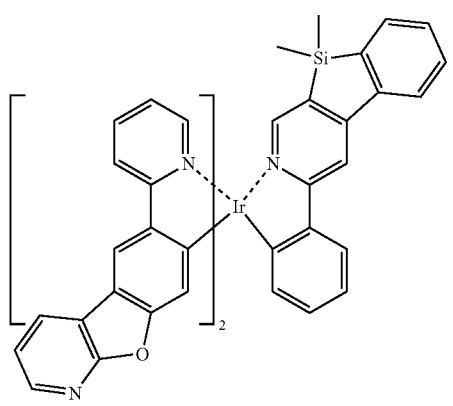
87
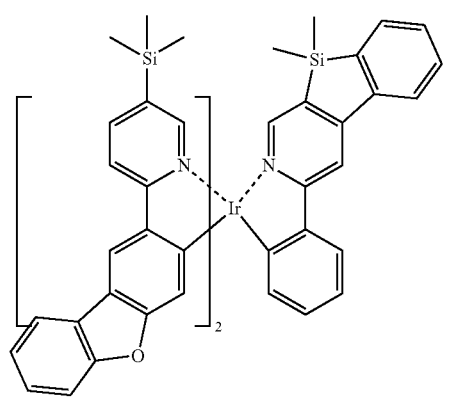
88
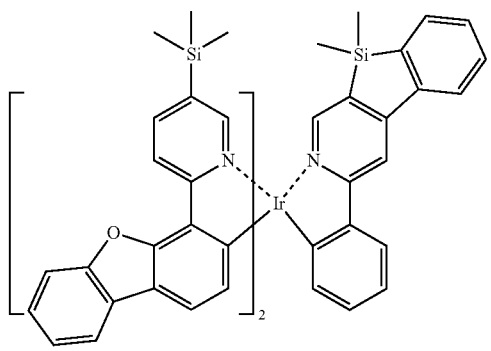
89
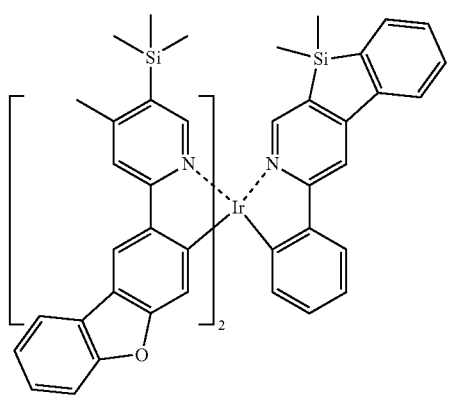
90
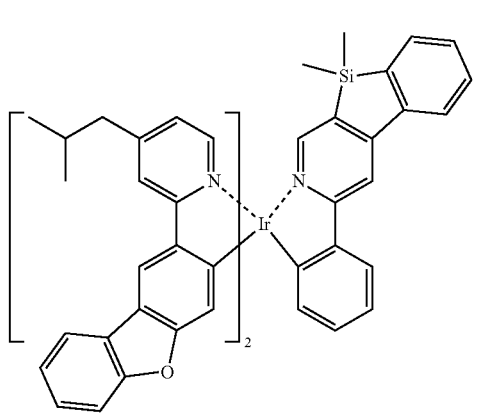
91
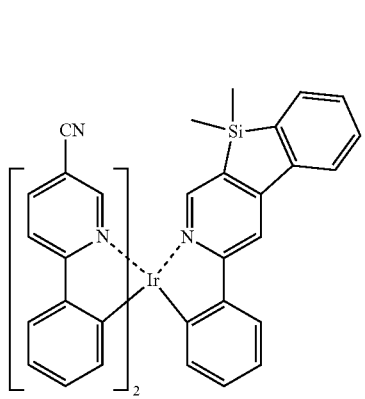

92
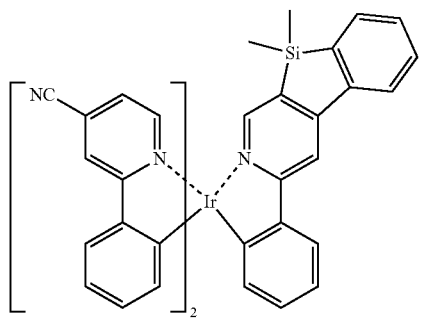
93
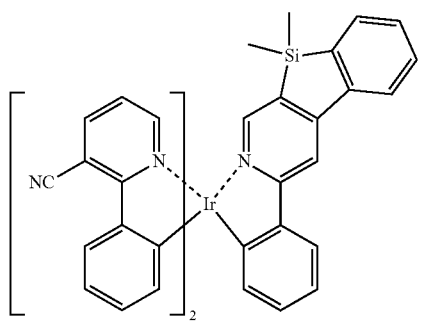
94
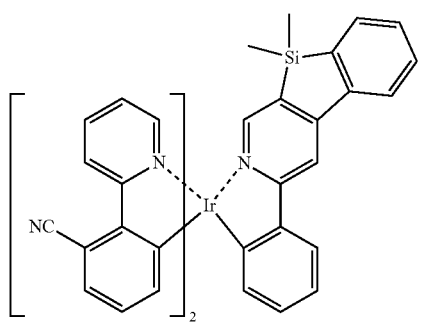
95
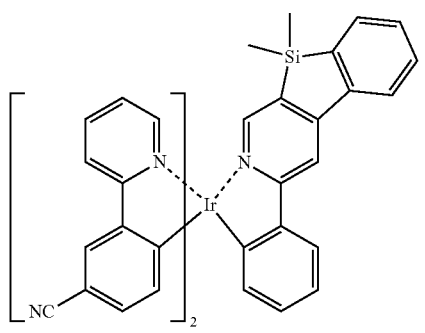
96
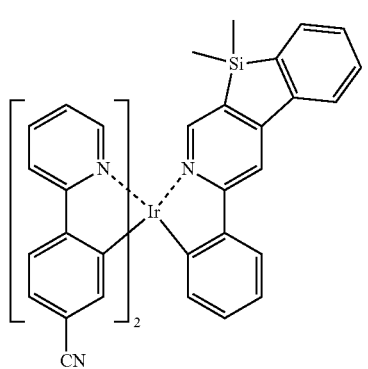
97
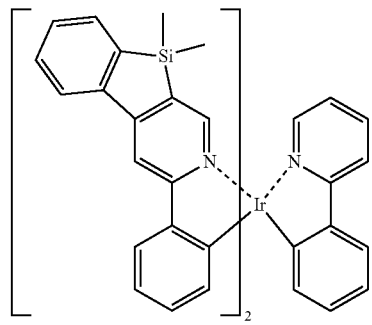
98
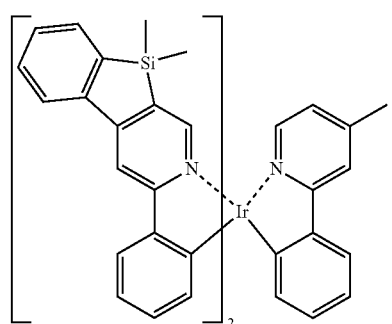
99
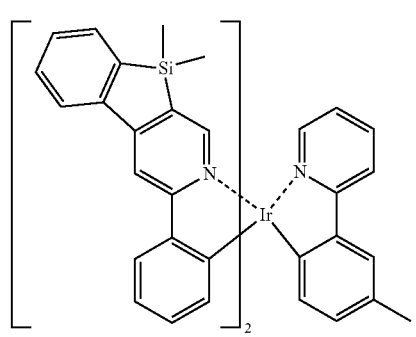
100
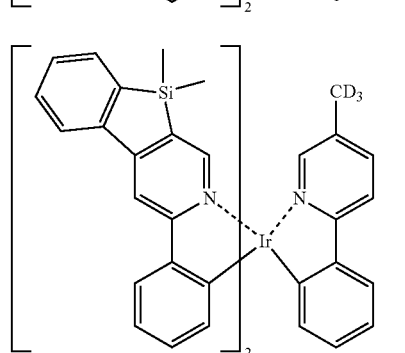
101
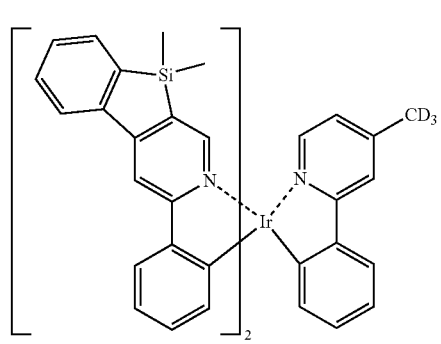

113
-continued
102
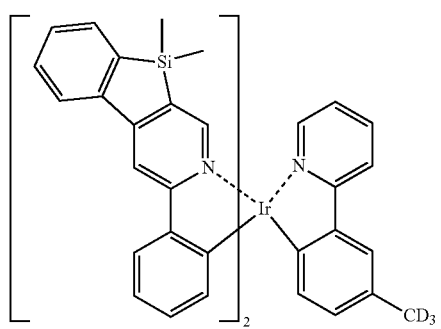
103
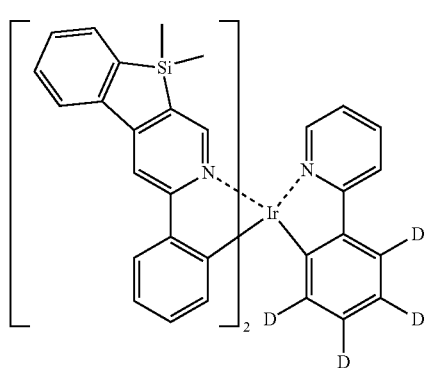
104
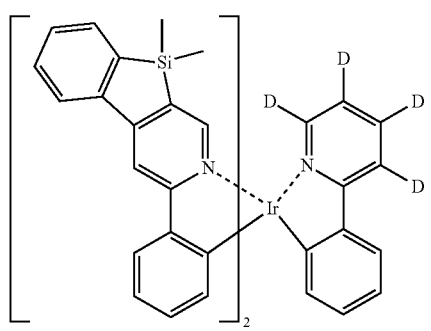
105
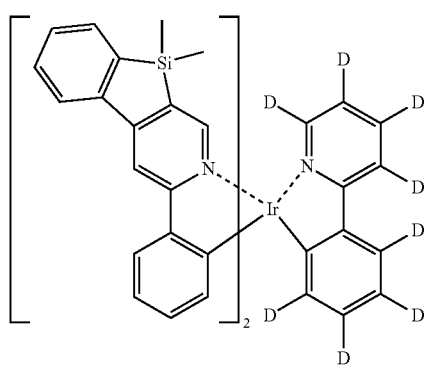
114
-continued
106
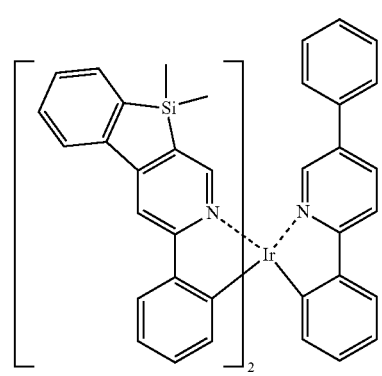
107
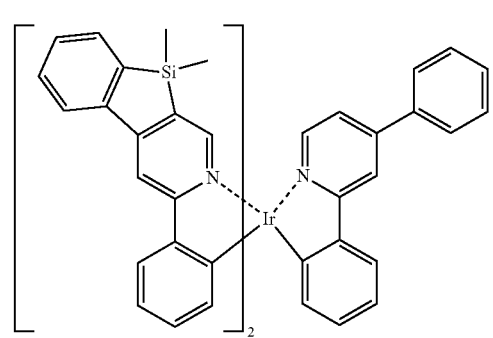
108
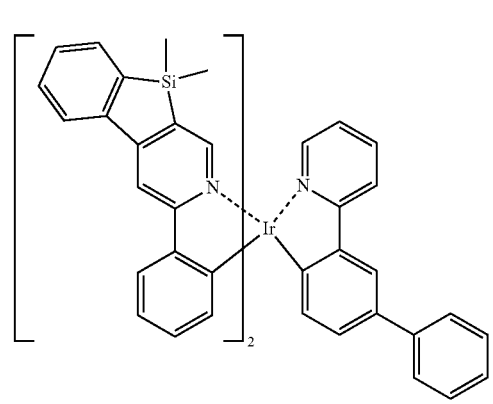
109
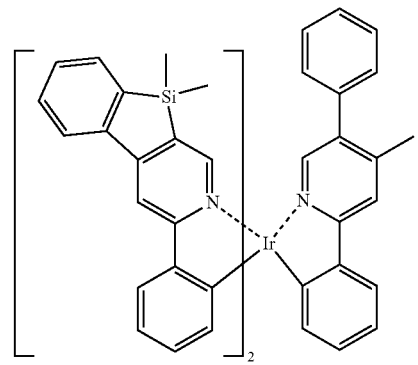

110
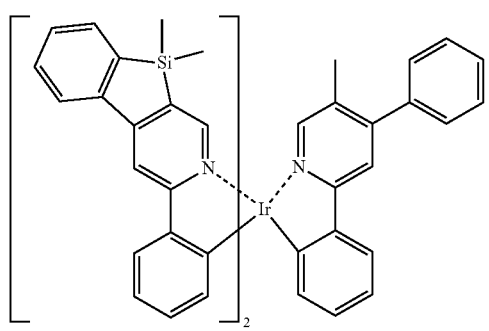
111
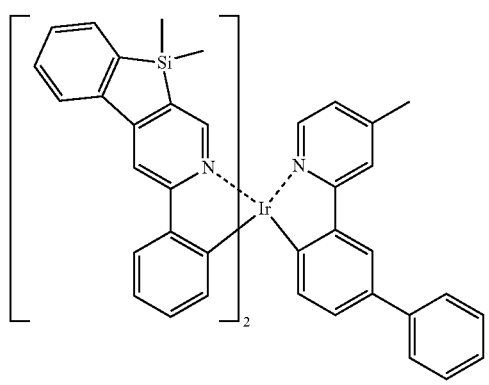
112
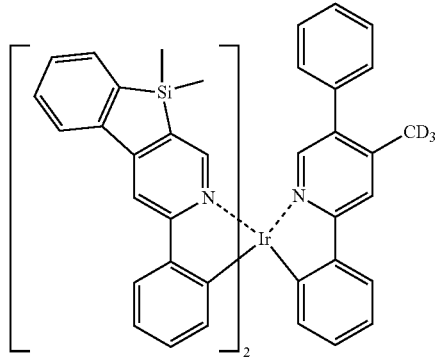
113
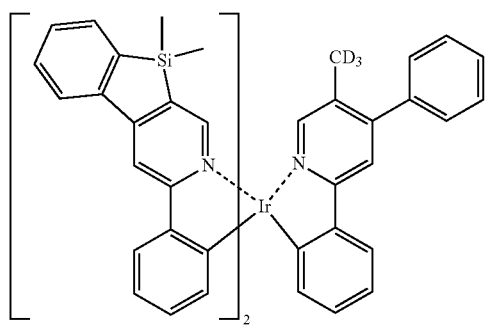
114
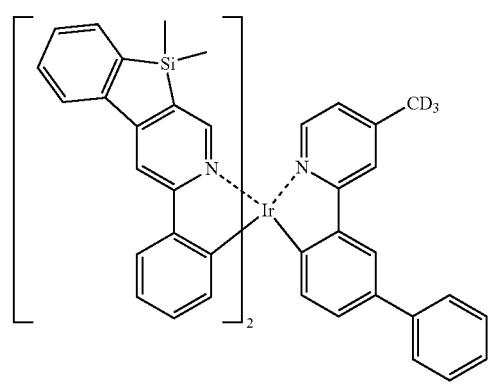
115
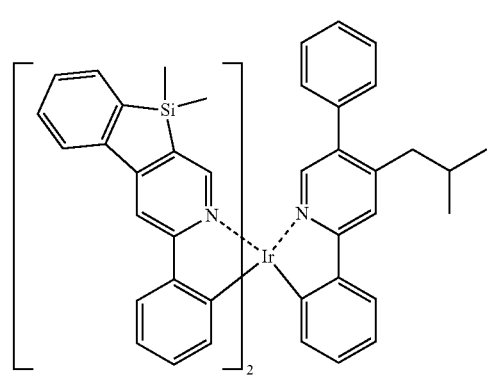
116
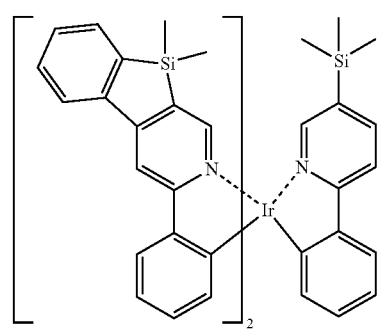
117
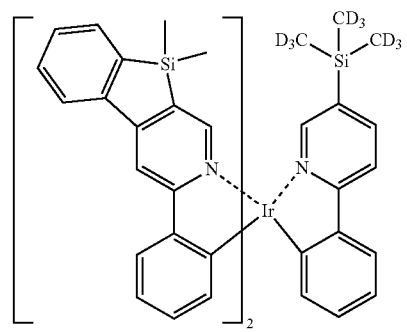

117
-continued
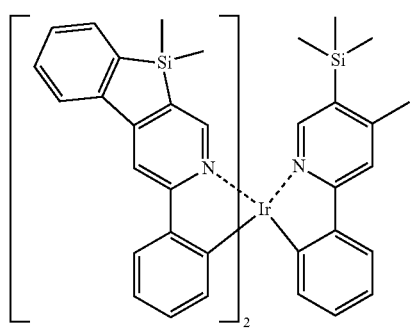
118
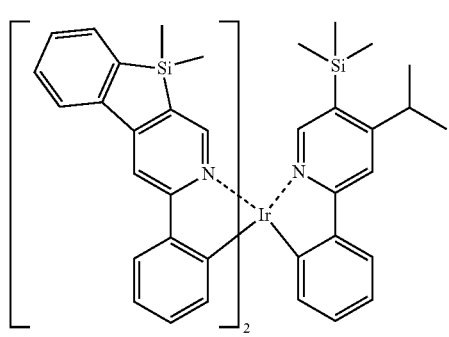
119
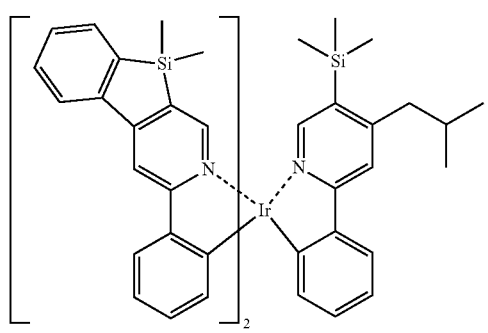
120
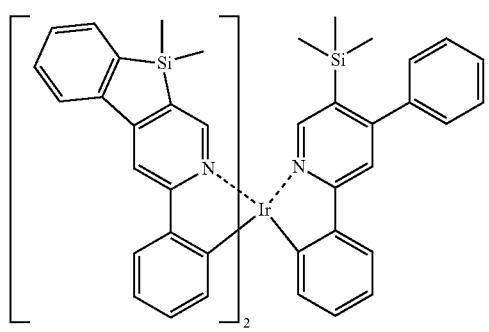
121
118
-continued
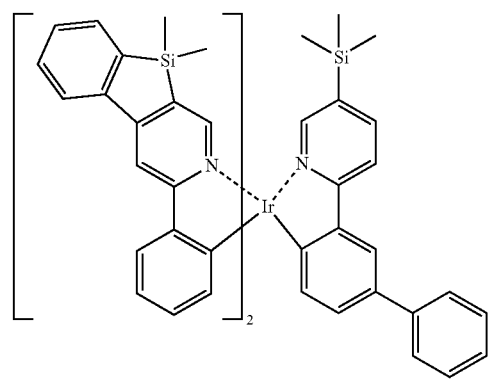
122
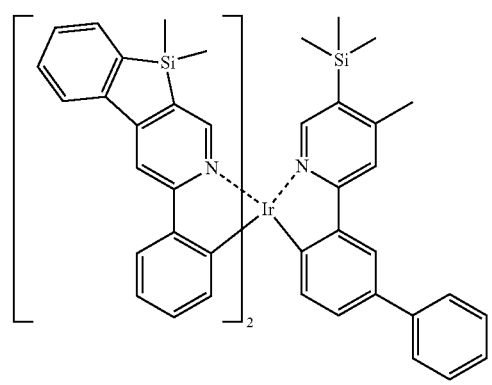
123
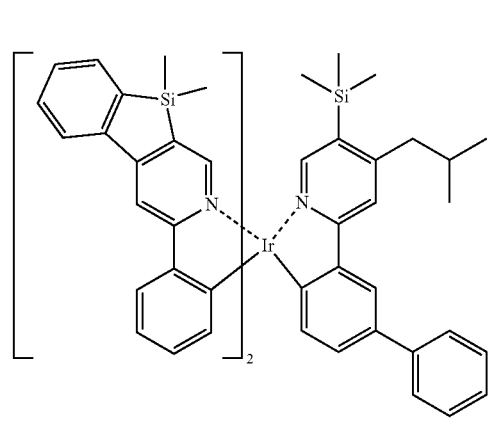
124
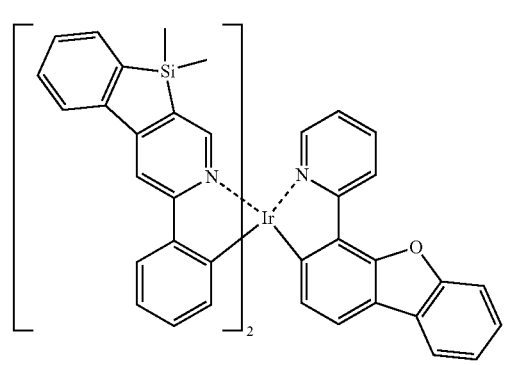
125

126 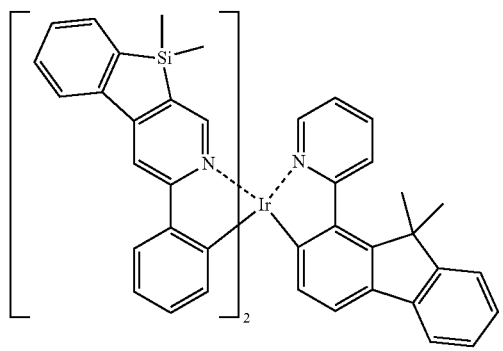
127 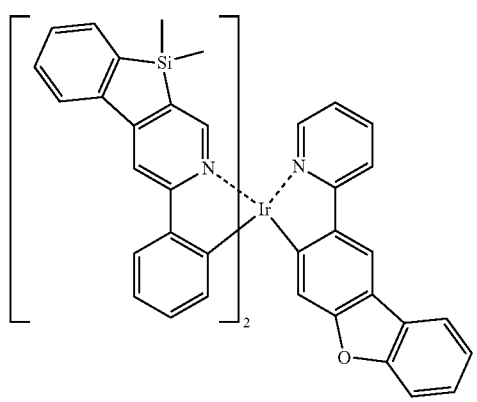
128 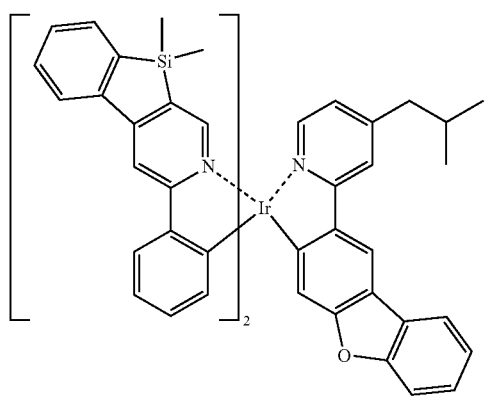
129 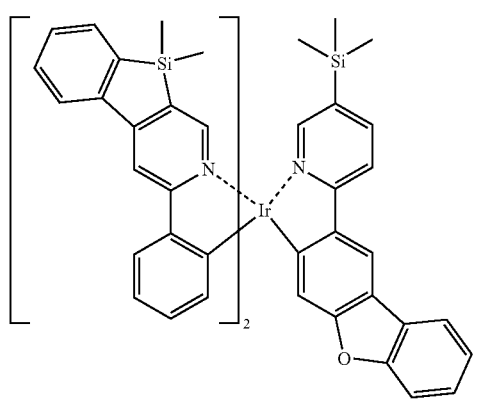
130 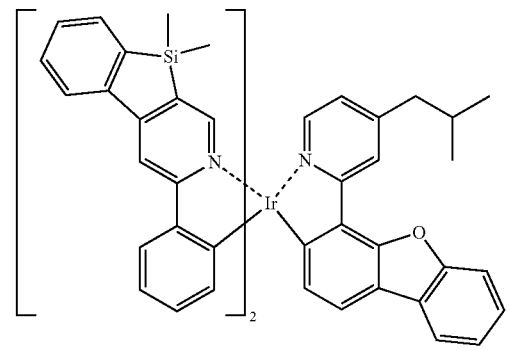
131 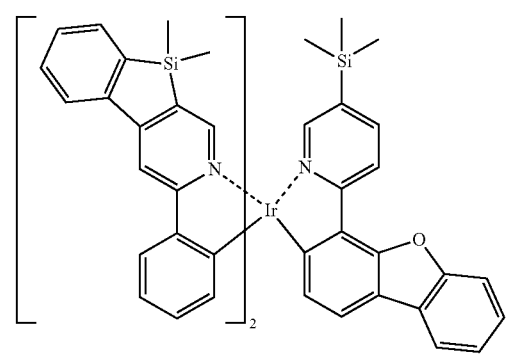
132 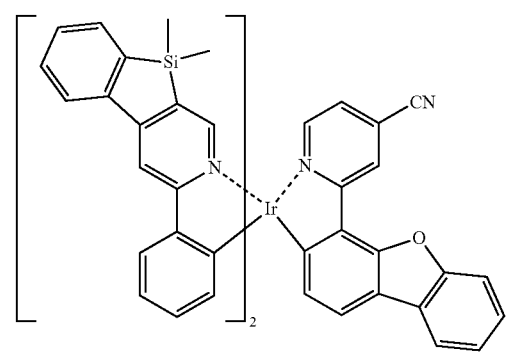
133 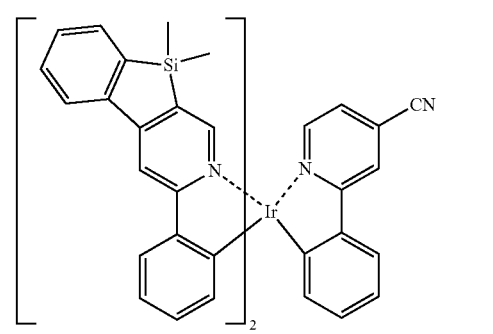

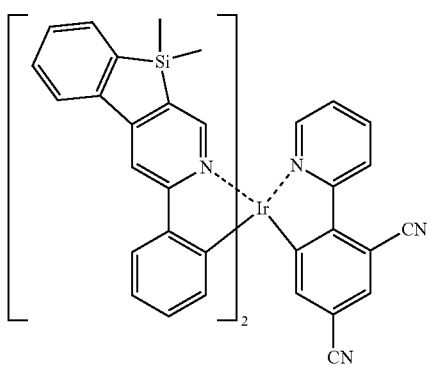
134
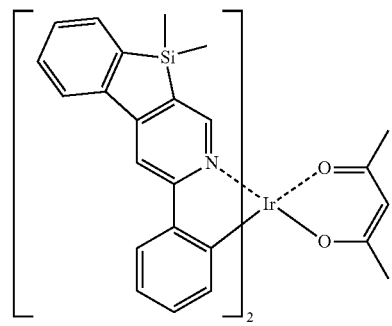
138
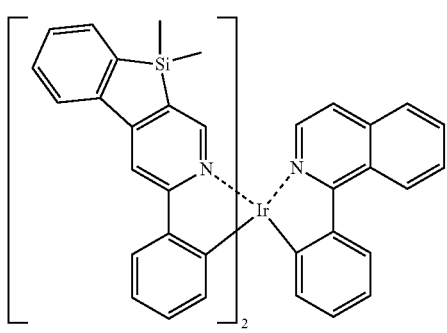
135
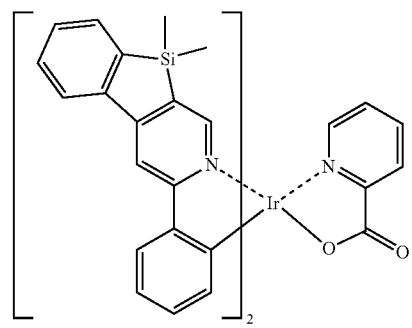
139
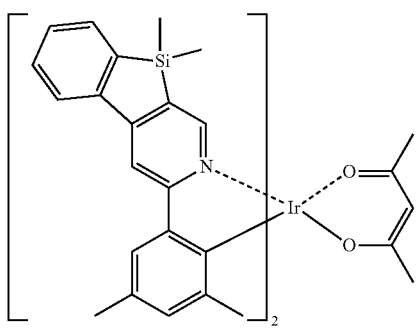
136
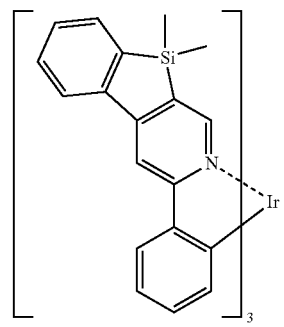
140
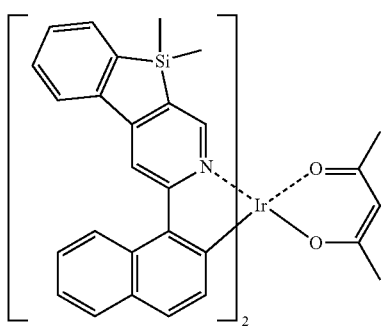
137
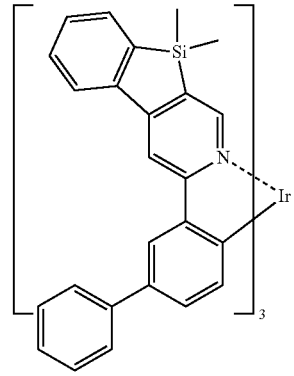
141

123
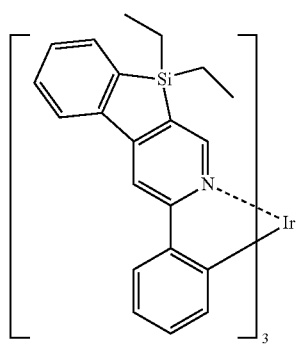
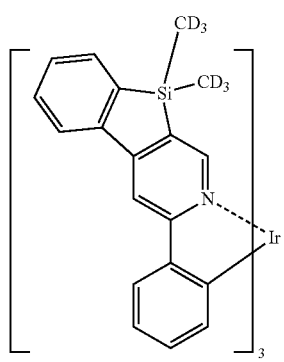
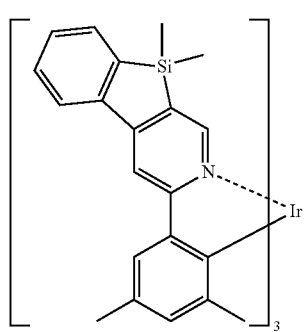
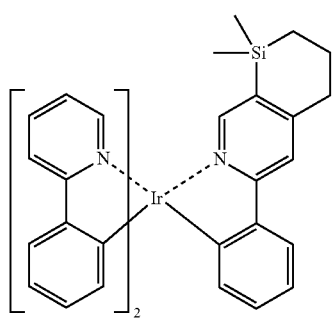
124
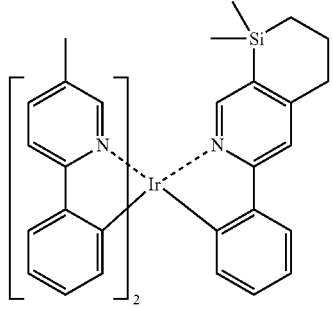
142
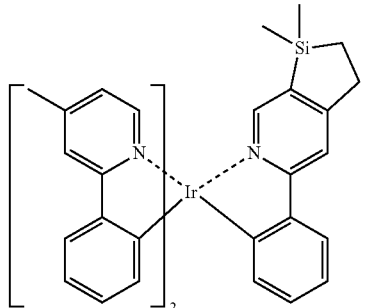
143
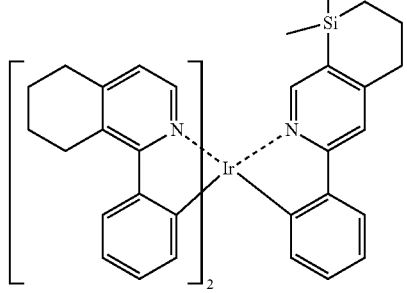
144
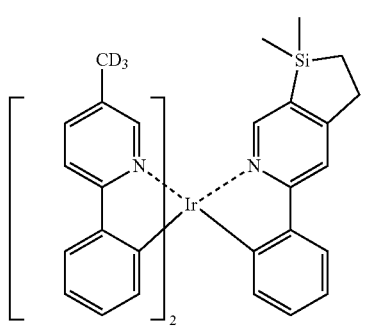
145
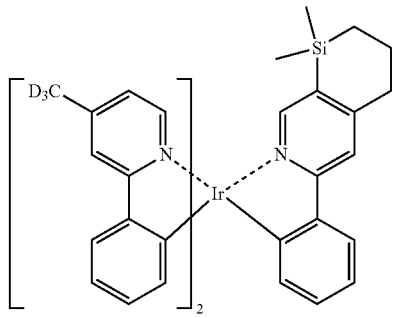
146
147
148
149
150

151
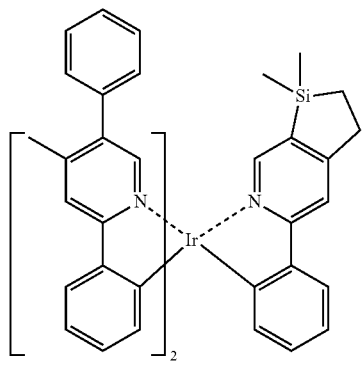
152
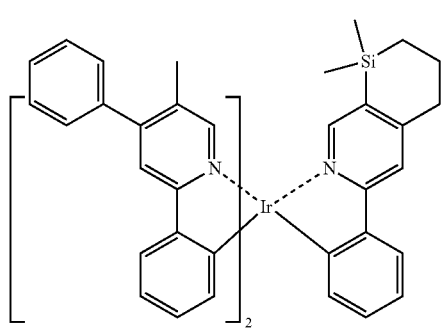
153
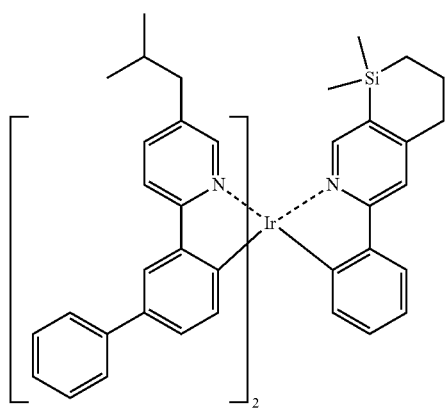
154
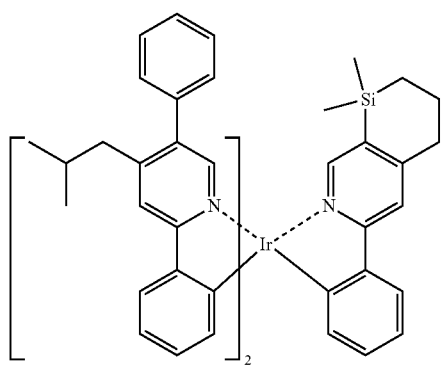
155
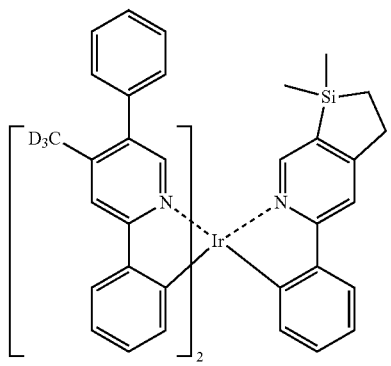
156
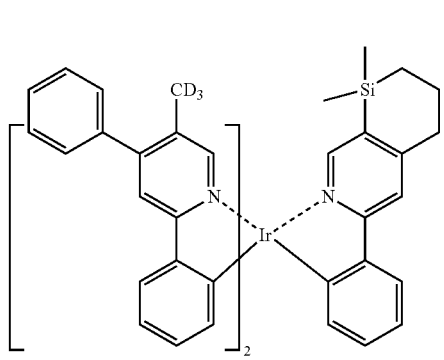
157
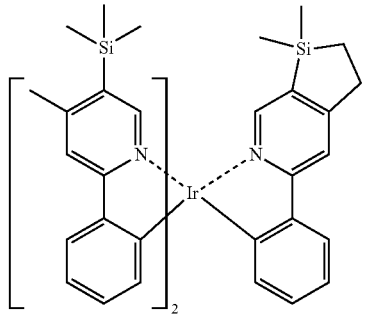
158
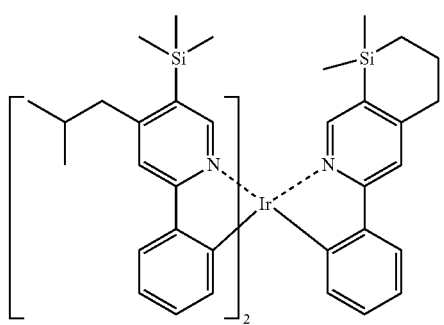

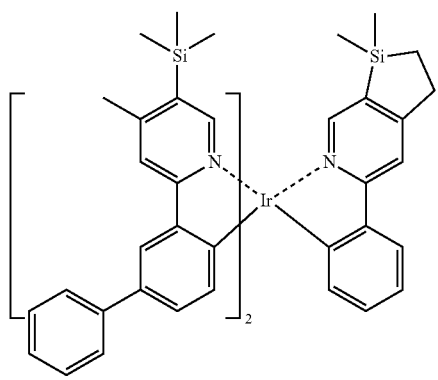
159
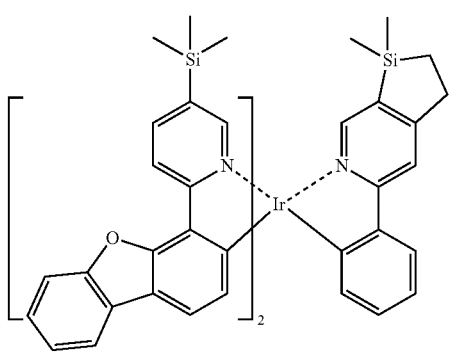
163
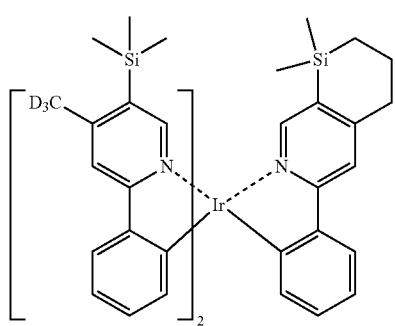
160
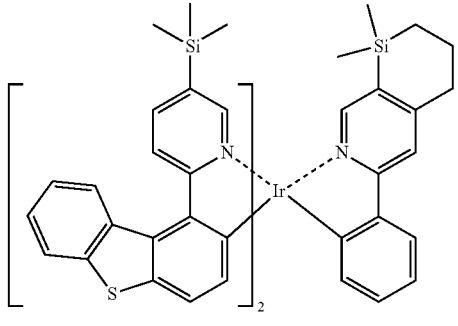
164
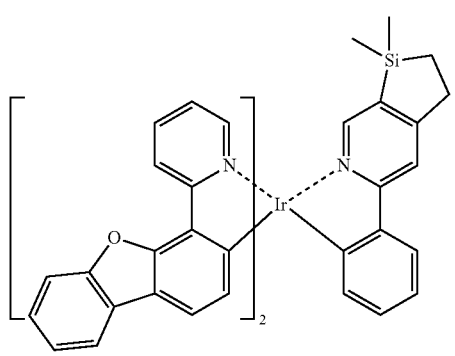
161
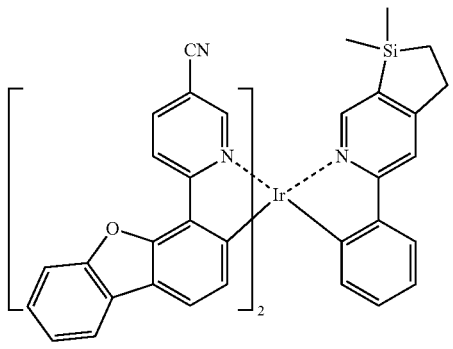
165
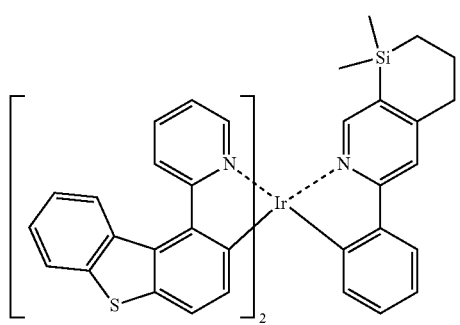
162
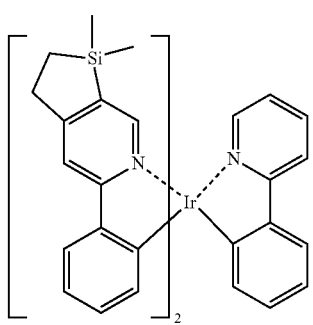
166

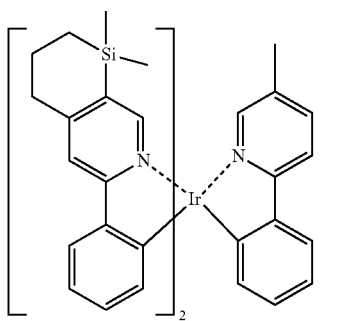
167
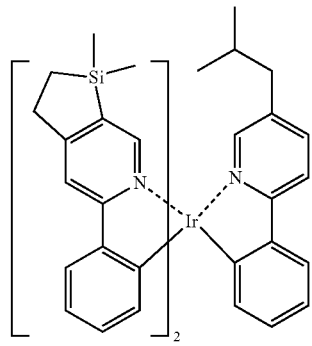
172
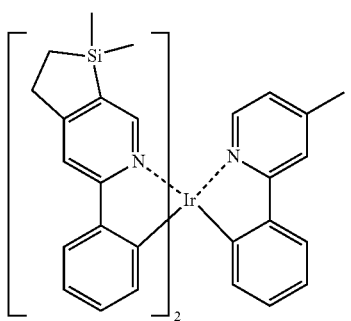
168
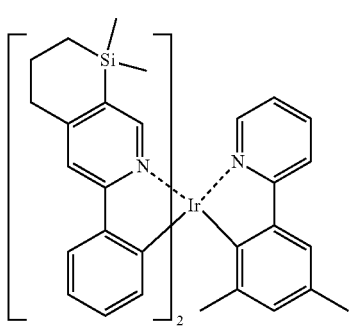
169
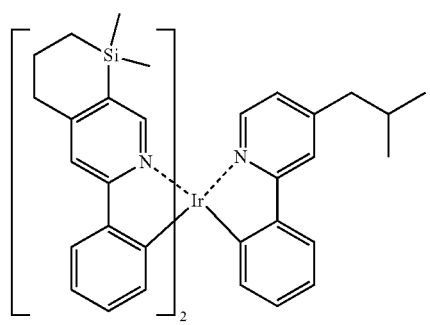
173
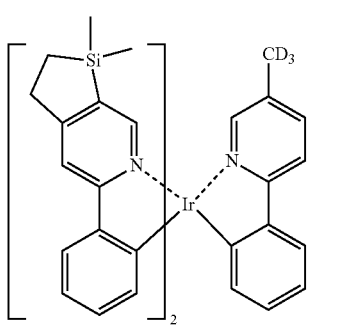
170
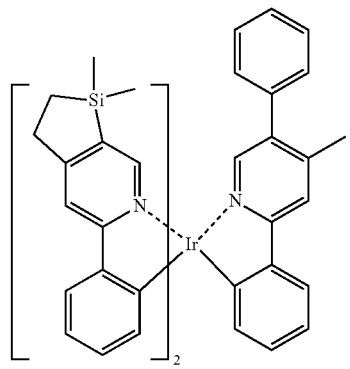
174
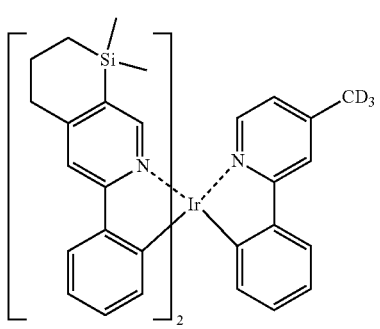
171
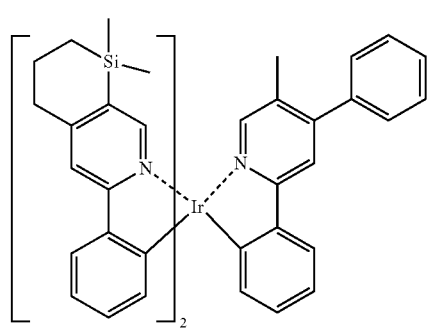
175

176
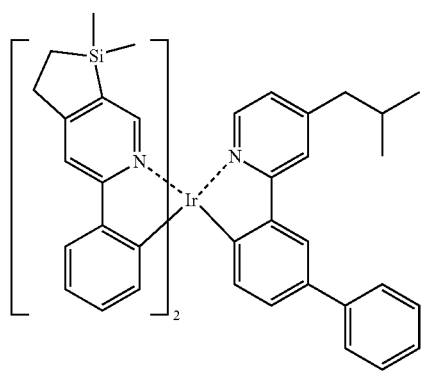
177
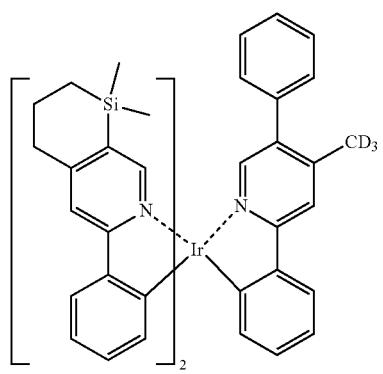
178
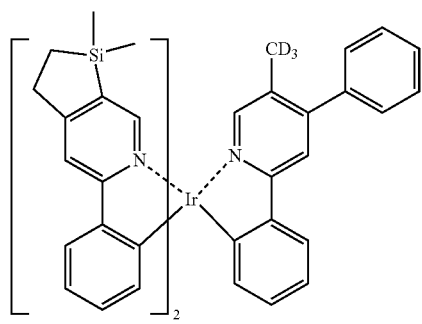
179
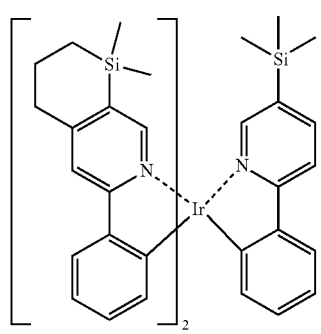
180
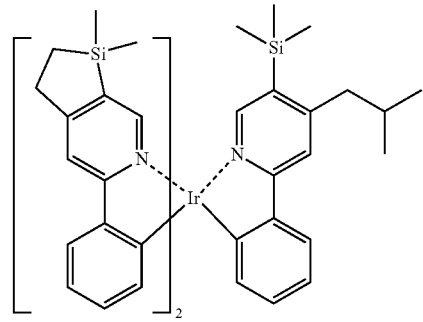
181
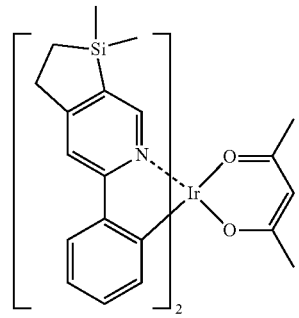
182
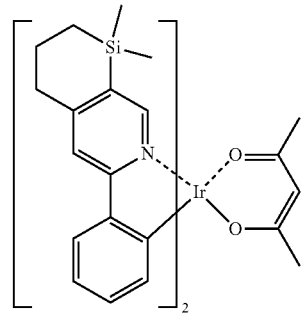
183
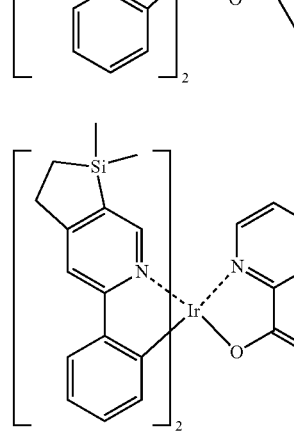
184
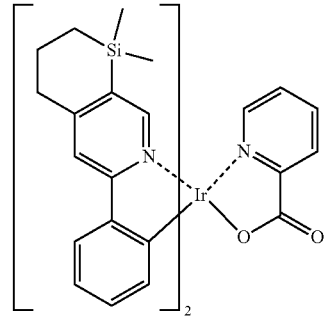

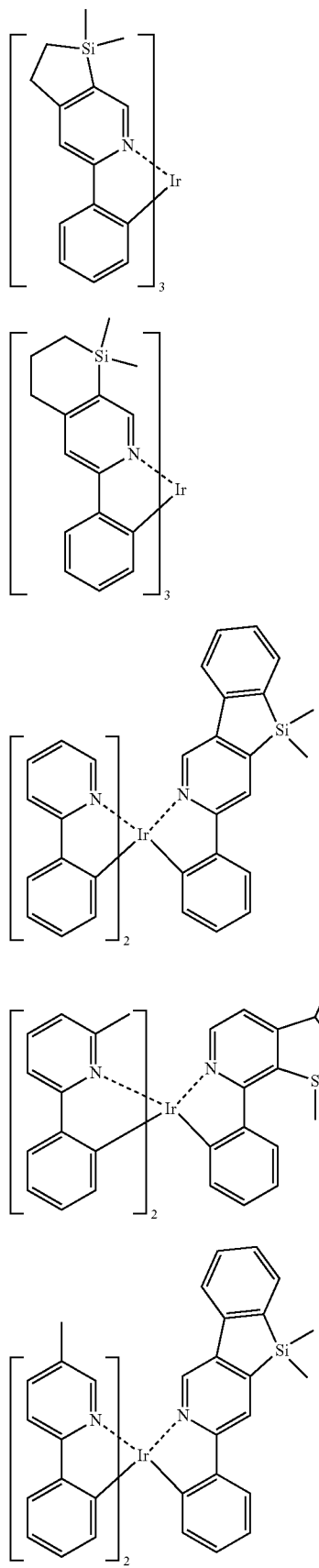
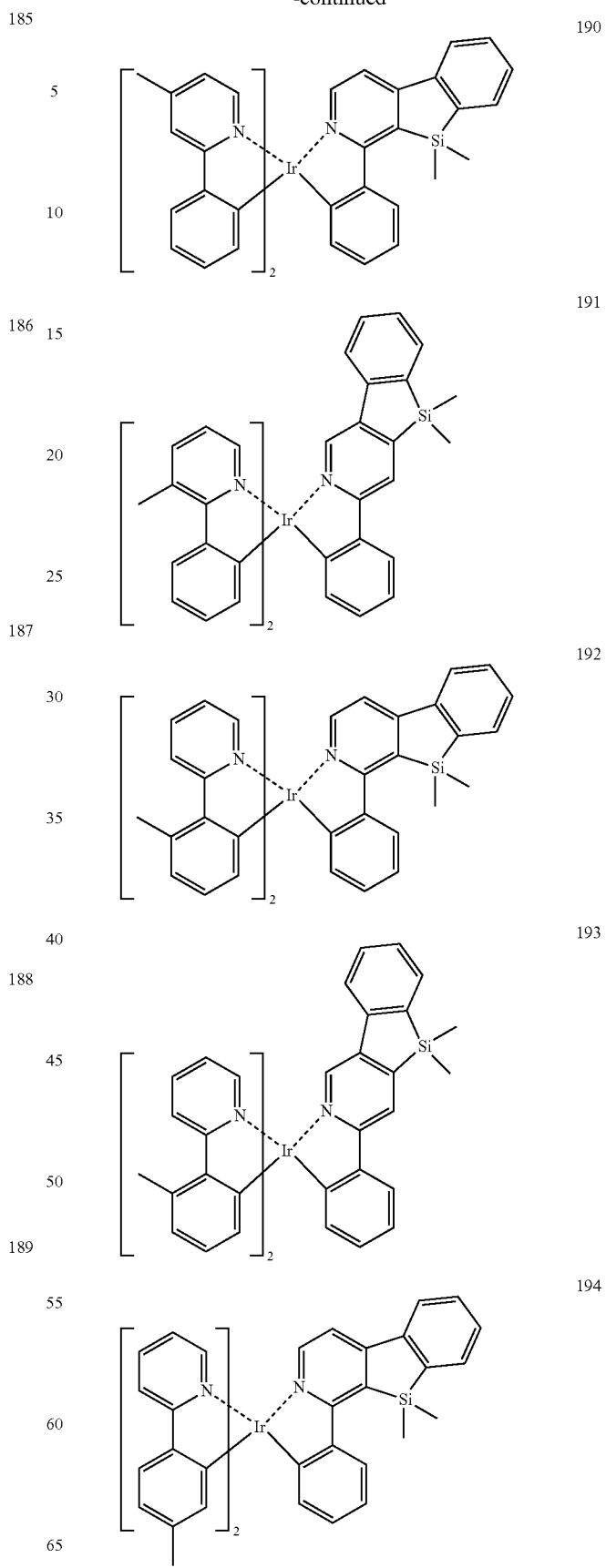

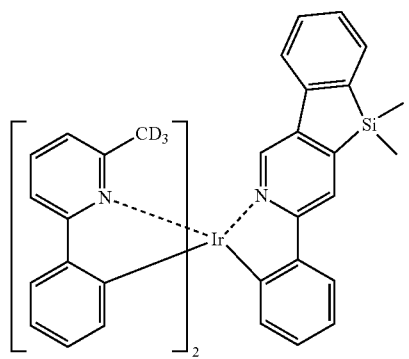
195
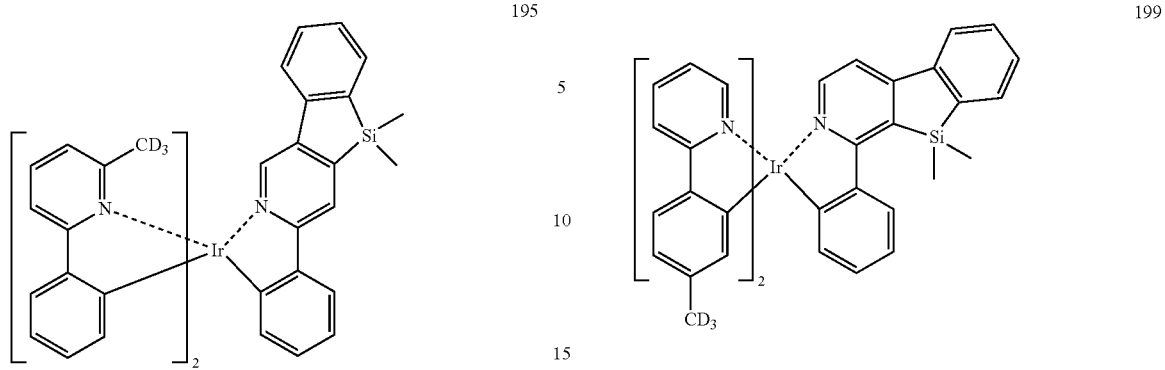
199
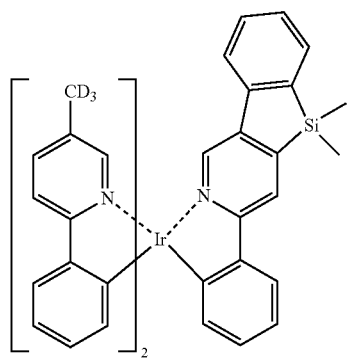
196
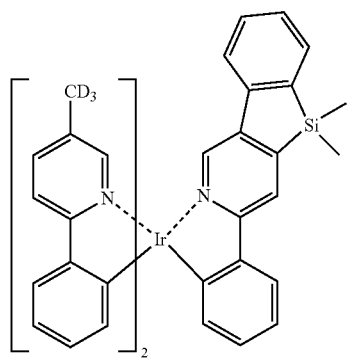
200
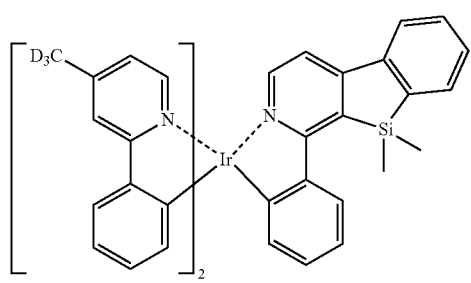
197
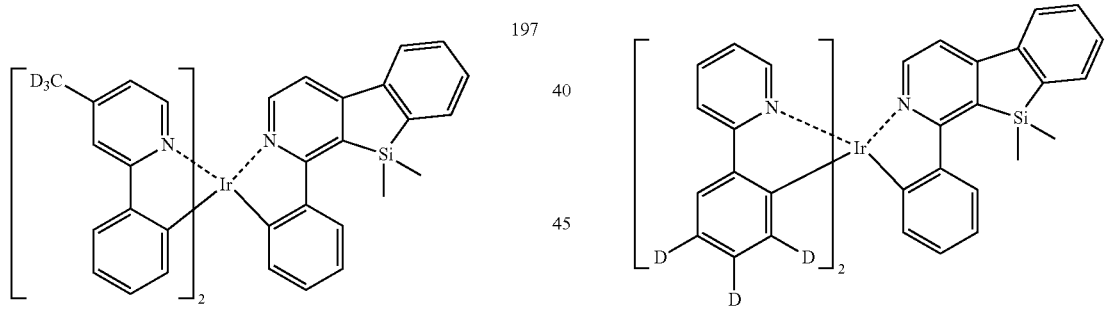
201
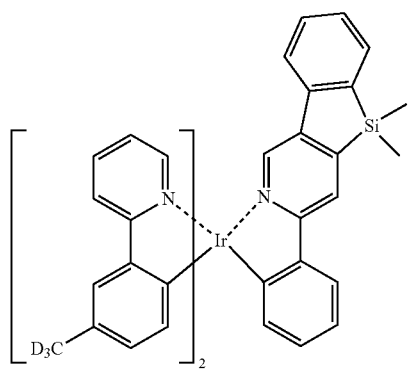
198
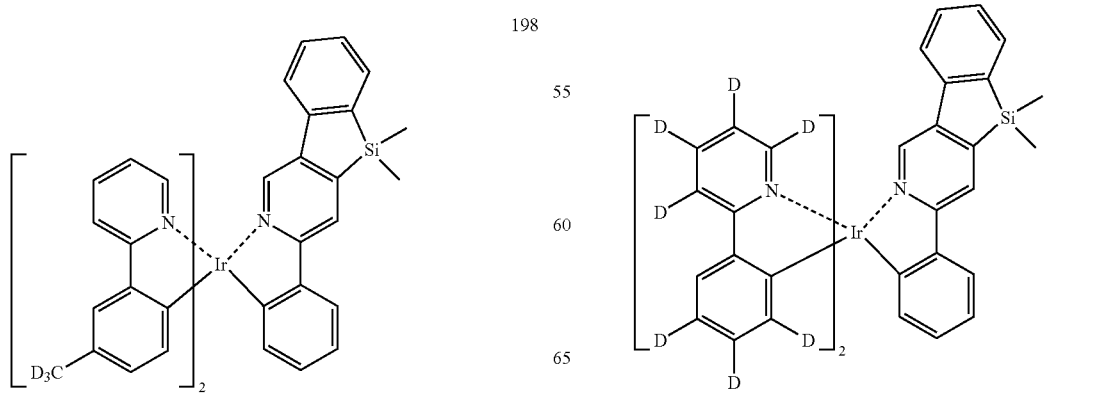
202

203
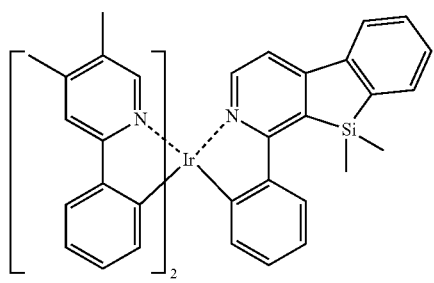
204
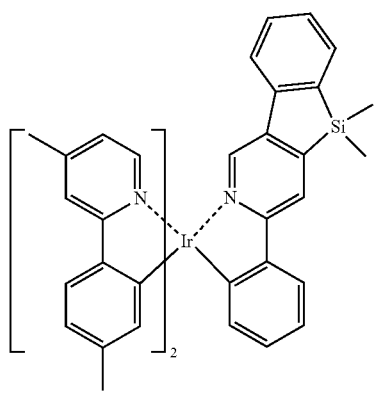
205
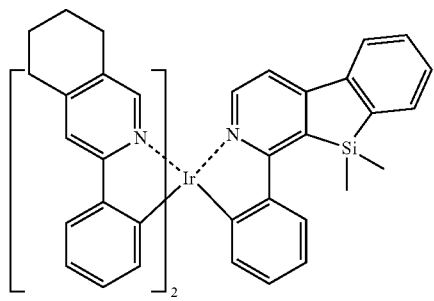
206
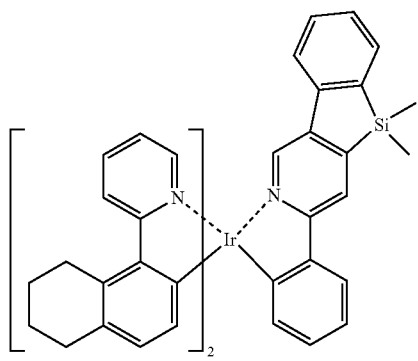
207
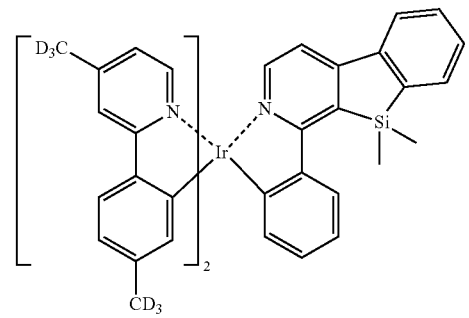
208
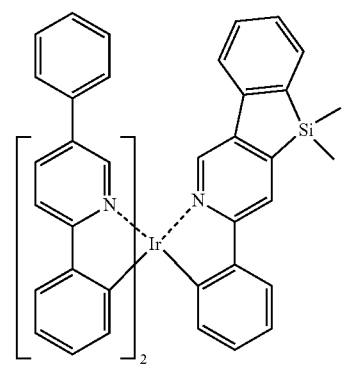
209
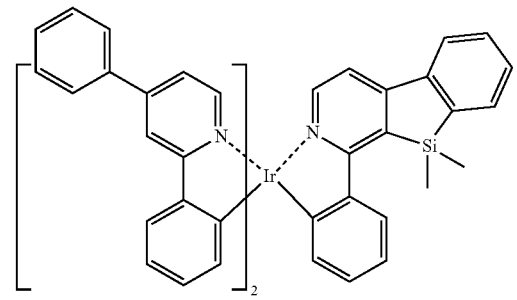
210
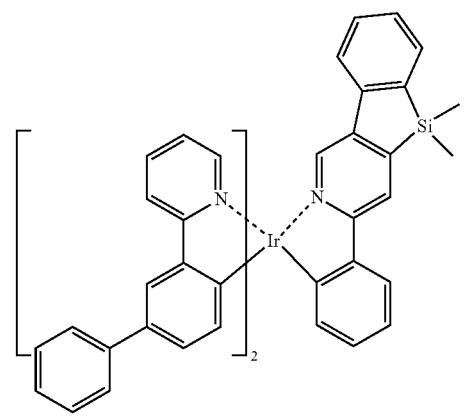

211 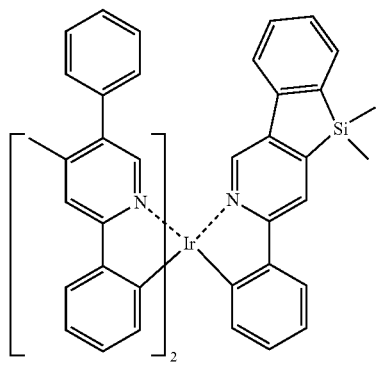
212 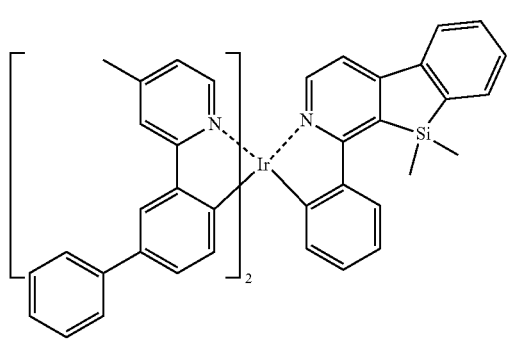
213 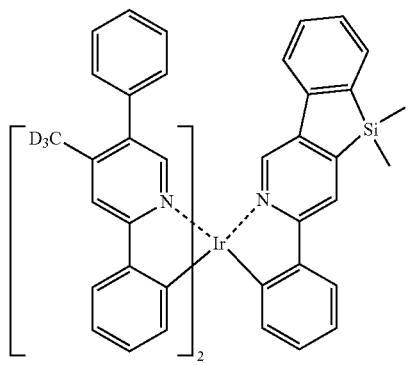
214 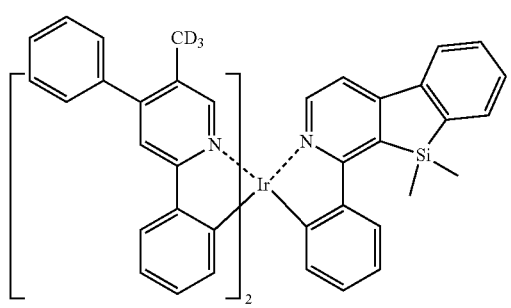
215 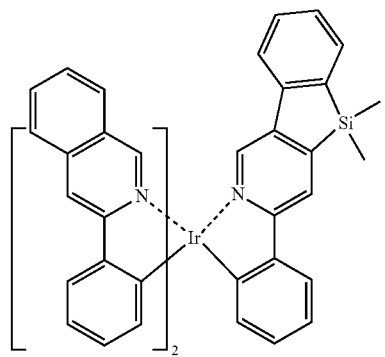
216 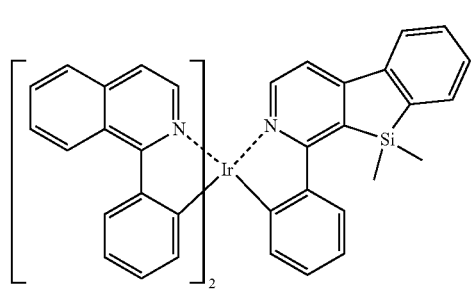
217 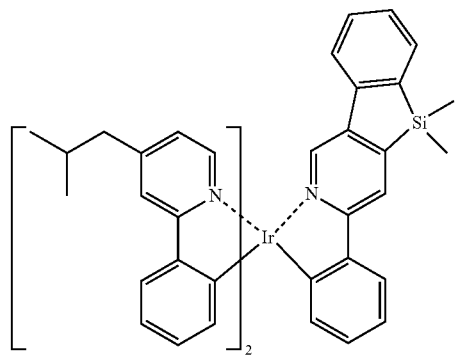
218 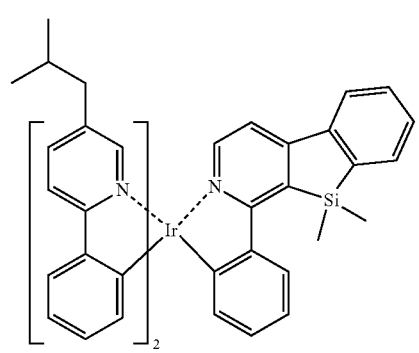

-continued
219
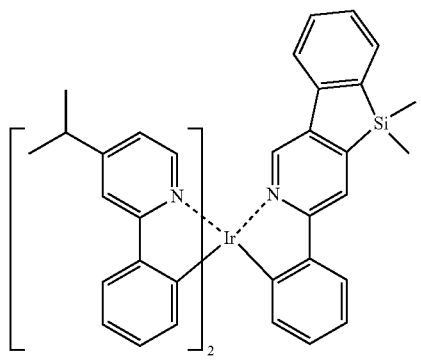
220
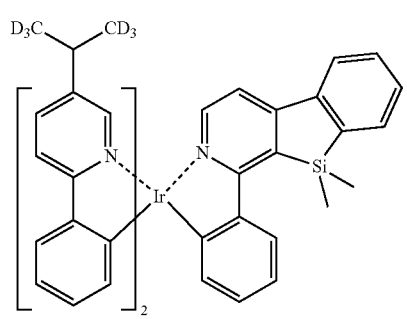
221
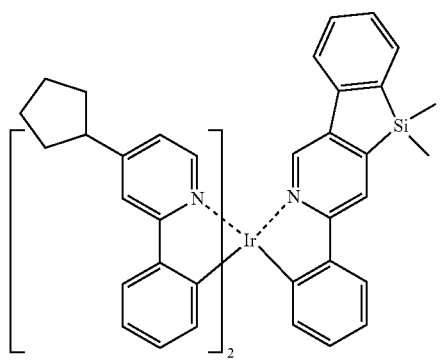
222
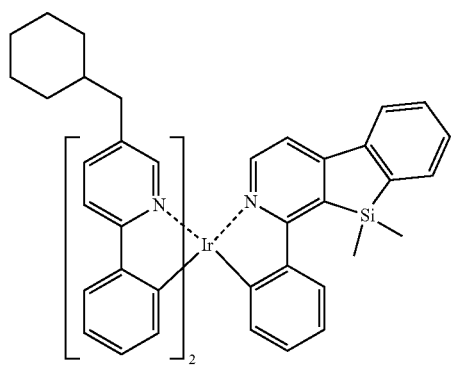
-continued
223
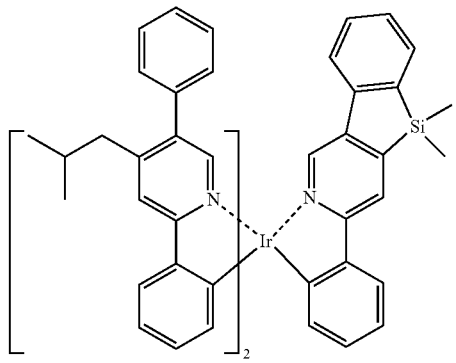
224
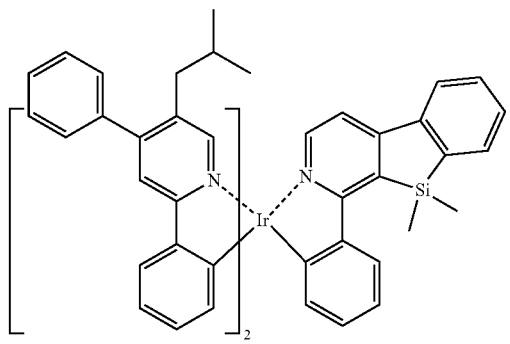
225
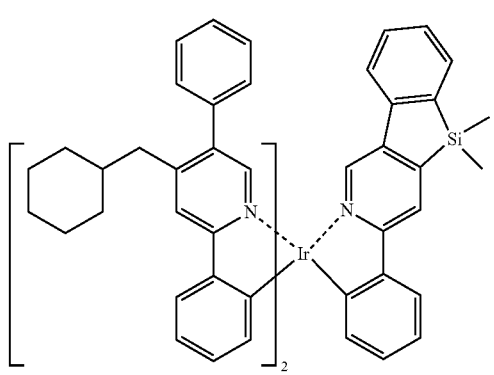
226
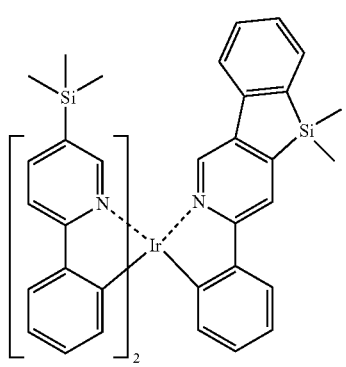

227 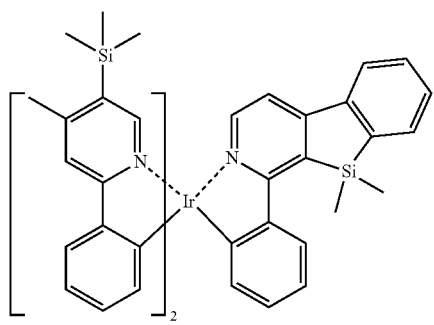
228 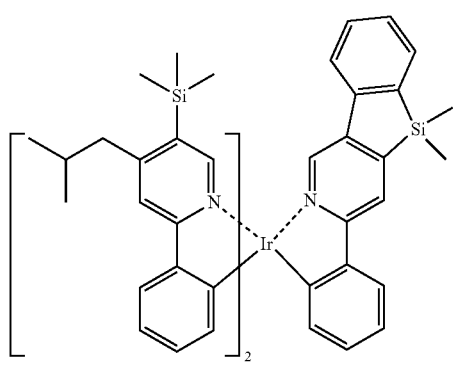
229 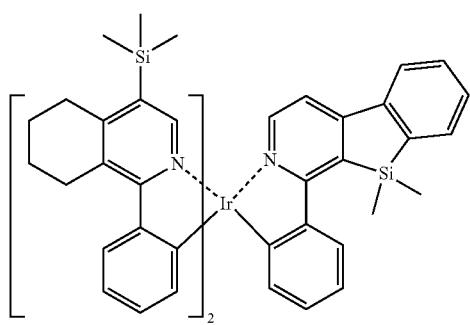
230 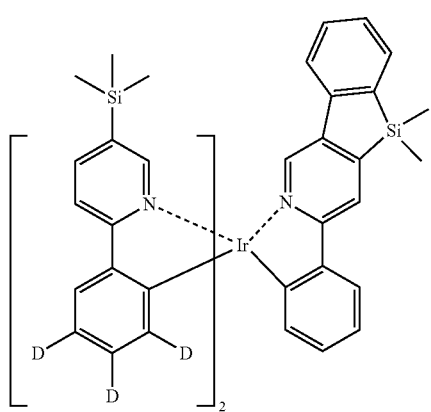
231 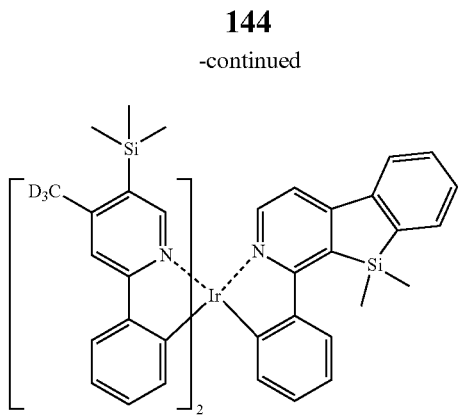
232 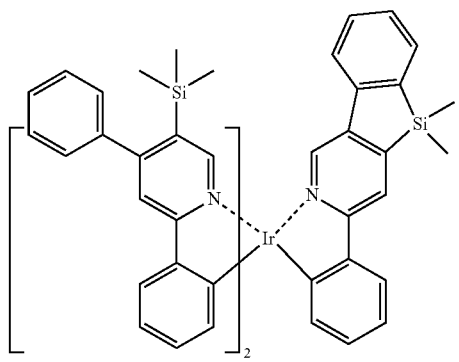
233 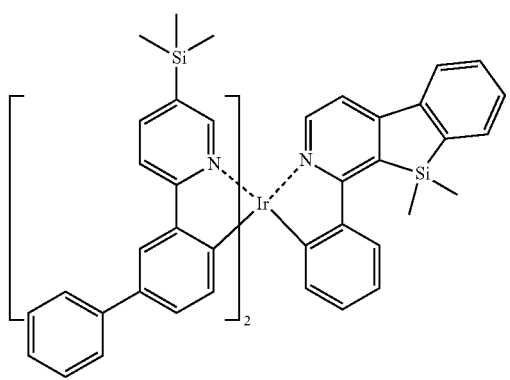
234 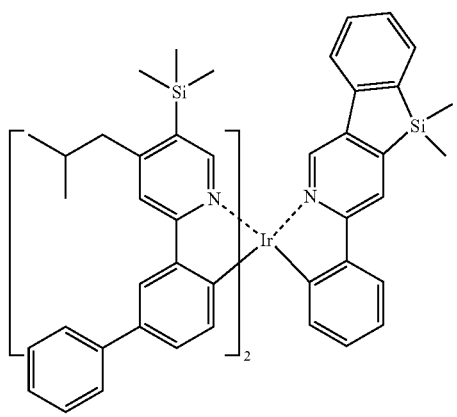

-continued
235 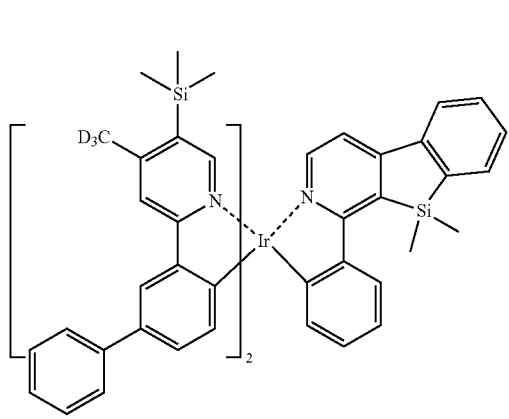
236 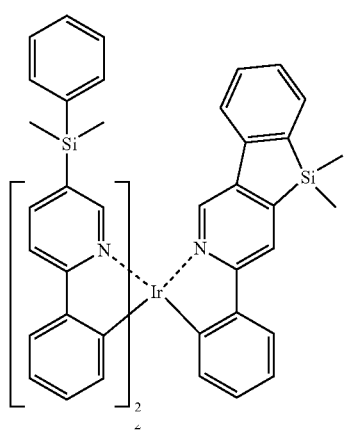
237 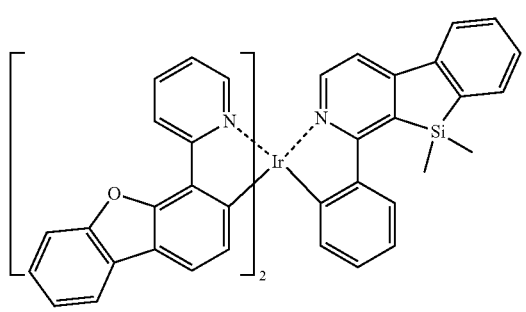
238 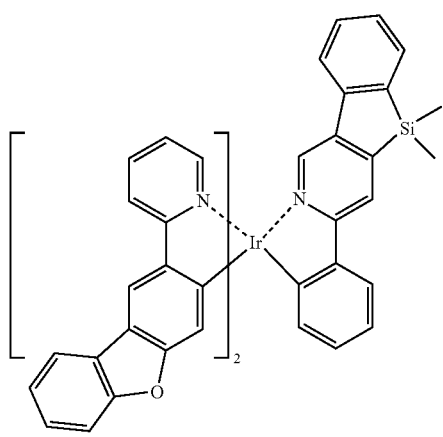
-continued
239 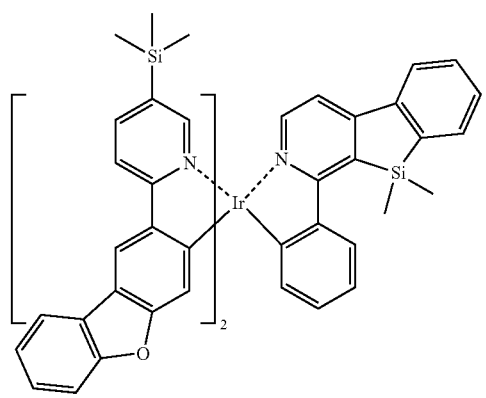
240 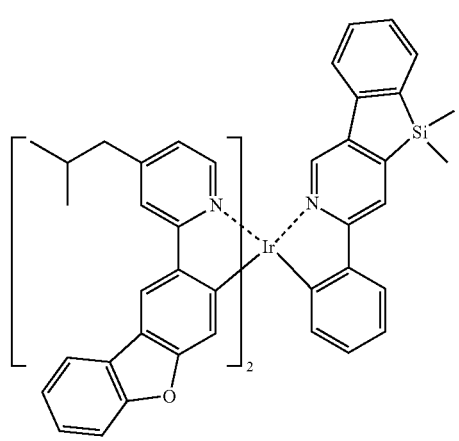
241 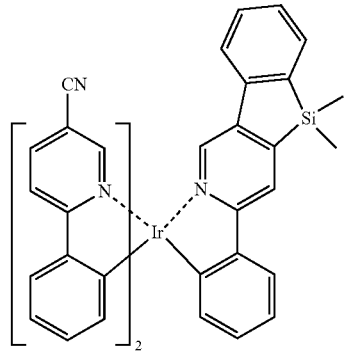
242 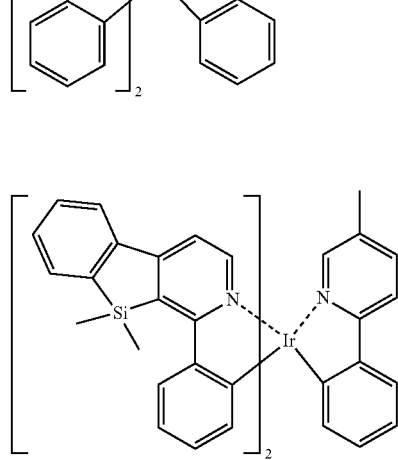

243
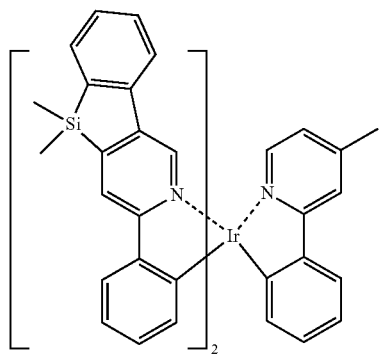
244
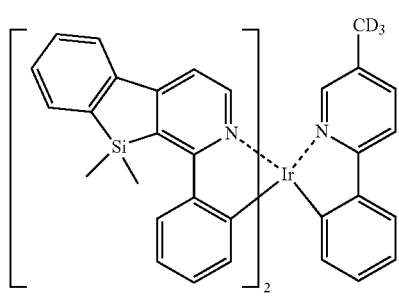
245
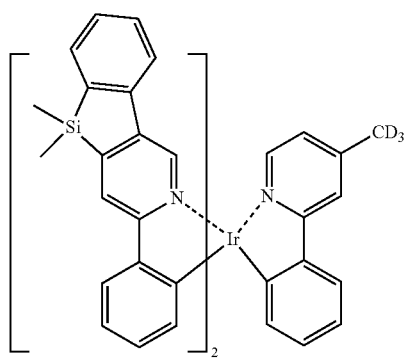
246
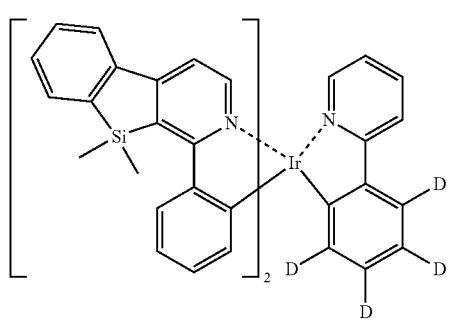
247
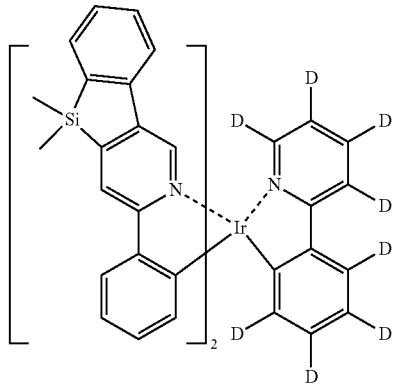
248
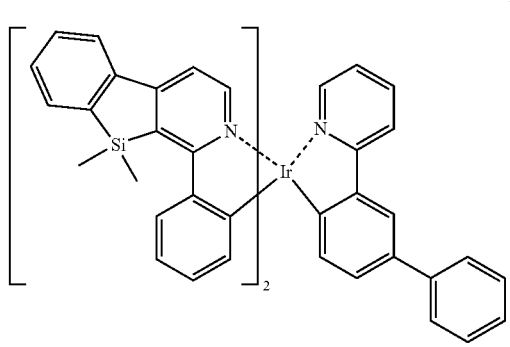
249
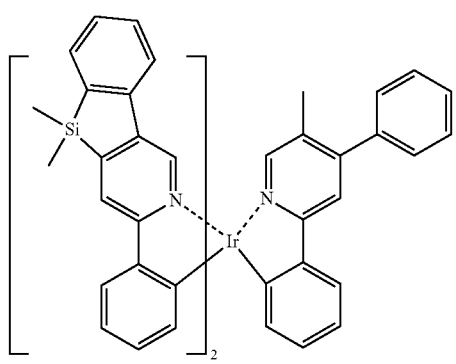
250
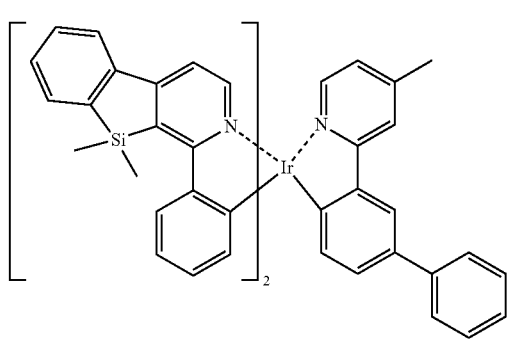

251
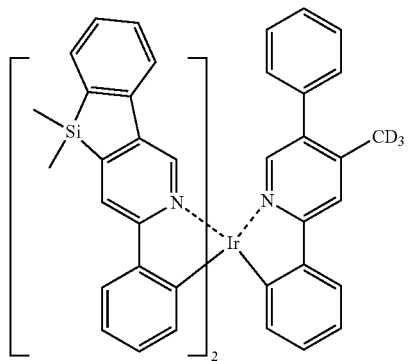
252
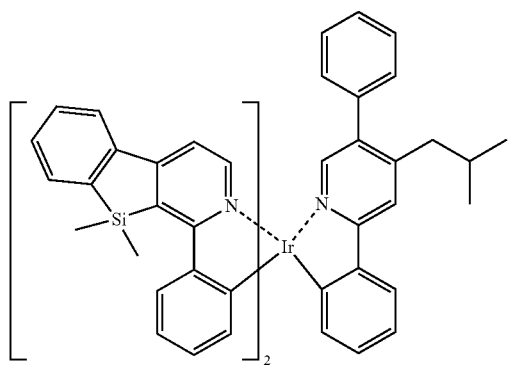
253
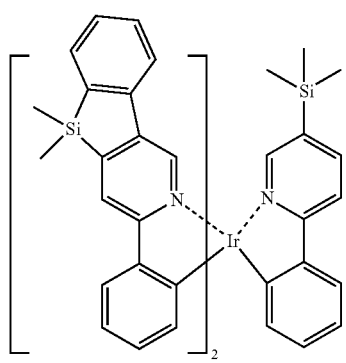
254
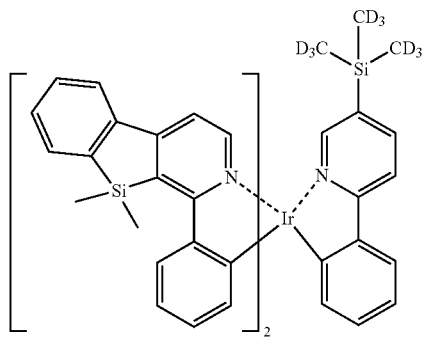
255
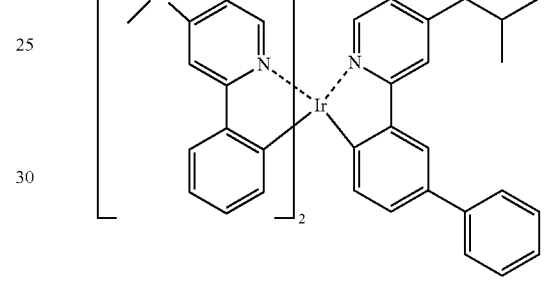
256
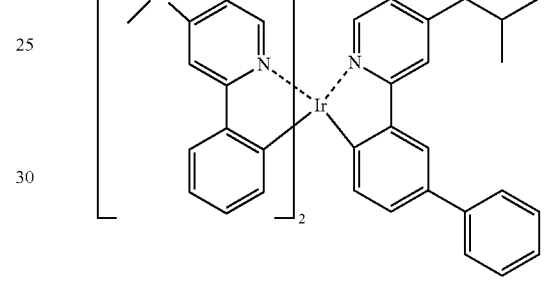
257
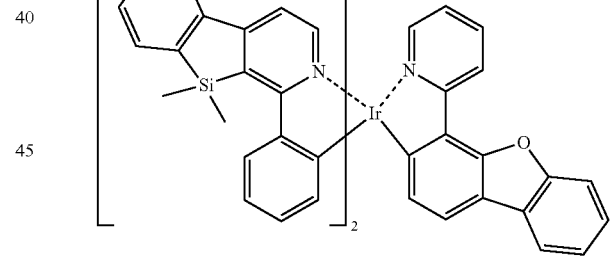
258
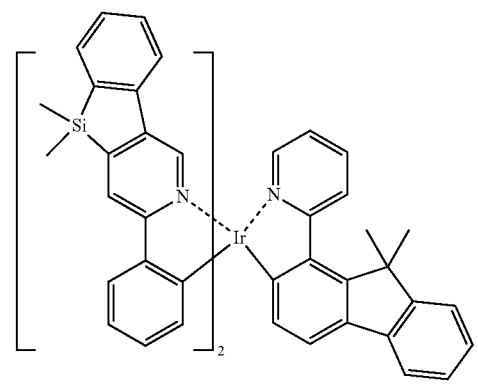

259
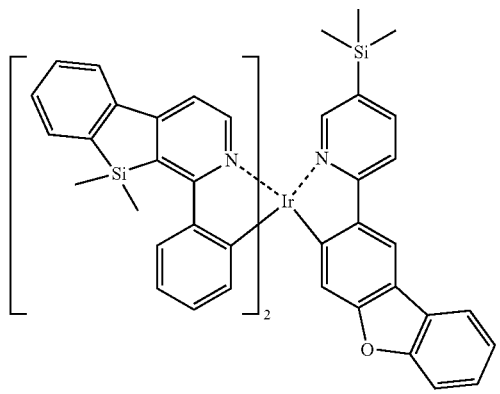
260
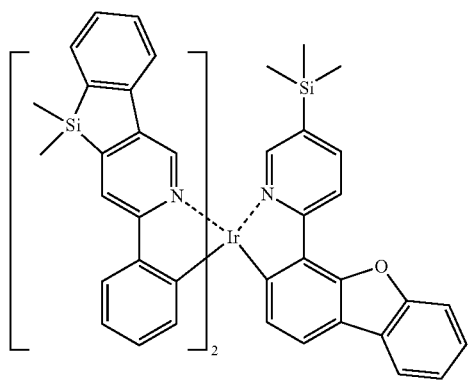
261
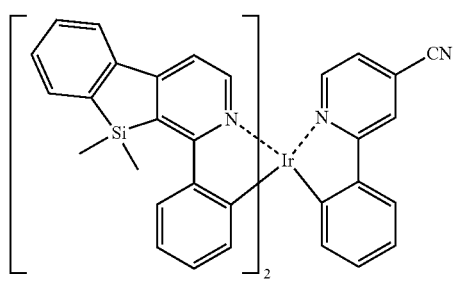
262
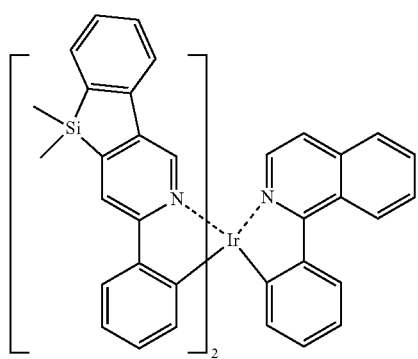
263
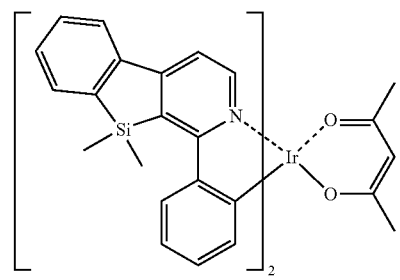
264
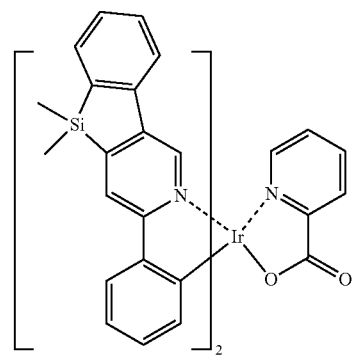
265
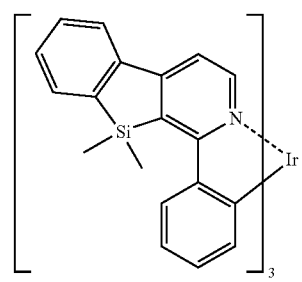
266
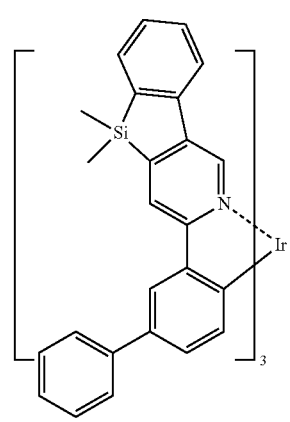
267
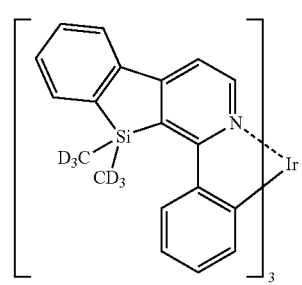

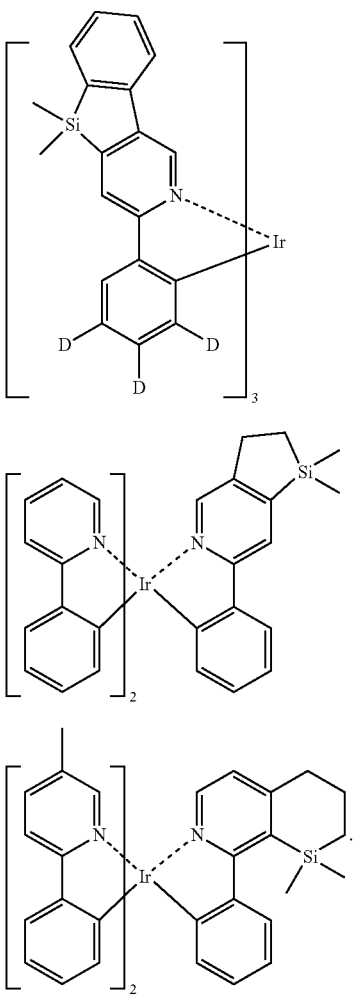

In the organometallic compound represented by Formula 1, $L_1$ is represented by Formula 2 in which b3 and b5 are each independently 1 or greater, and at least one $R_3$ is connected to at least one $R_{13}$ to form a saturated or unsaturated $C_2$-$C_{30}$ cyclic ring. While not wishing to be bound by a theory, it is understood that due to this structure, the organometallic compound represented by Formula 1 may have high stability, and accordingly, an organic light-emitting device including the organometallic compound may have a long lifespan.

For example, highest occupied molecular orbital (HOMO), lowest unoccupied molecular orbital (LUMO), and triplet ($T_1$) energy levels of some of the organometallic compounds illustrated above were evaluated by using a DFT (Density Functional Theory) method of Gaussian program (structurally optimized at a level of B3LYP, 6-31G(d,p)). Evaluation results are shown in Table 1 below.

TABLE 1

| Compound No. | HOMO (eV) | LUMO (eV) | $T_1$ energy level (eV) |
| --- | --- | --- | --- |
| 1 | −4.768 | −1.576 | 2.380 |
| 116 | −4.752 | −1.574 | 2.368 |
| 136 | −4.707 | −1.588 | 2.260 |
| 137 | −4.798 | −1.674 | 2.084 |
| 140 | −4.729 | −1.574 | 2.365 |

TABLE 1-continued

| Compound No. | HOMO (eV) | LUMO (eV) | $T_1$ energy level (eV) |
| --- | --- | --- | --- |
| 144 | −4.638 | −1.527 | 2.302 |
| 145 | −4.804 | −1.177 | 2.620 |

As confirmed in view of Table 1, the organometallic compound represented by Formula 1 may have electric characteristics that are suitable for a material for electric devices, for example, a material for an organic light-emitting device (for example, a dopant).

Synthesis methods of the organometallic compound represented by Formula 1 may be recognizable by one of ordinary skill in the art by referring to Synthesis Examples provided below.

The organometallic compound represented by Formula 1 is suitable for use in an organic layer of an organic light-emitting device, for example, for use as a dopant in an emission layer of an organic layer. Accordingly, another aspect of the present disclosure provides an organic light-emitting device that includes: a first electrode; a second electrode; and an organic layer disposed between the first electrode and the second electrode, wherein the organic layer includes an emission layer and at least one of the organometallic compounds represented by Formula 1.

The organic light-emitting device may have, due to the inclusion of an organic layer including the organometallic compound represented by Formula 1, low driving voltage, high efficiency, high power, high quantum efficiency, long lifespan and excellent color.

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression that "(an organic layer) includes at least one of organometallic compounds" as used herein may include an embodiment in which "(an organic layer) includes identical organometallic compounds represented by Formula 1 and an embodiment in which (an organic layer) includes two or more different organometallic compounds represented by Formula 1.

For example, the organic layer may include, as the organometallic compound, only Compound 1. In this regard, Compound 1 may be included in an emission layer of the organic light-emitting device. In some embodiments, the organic layer may include, as the organometallic compound, Compound 1 and Compound 2. In this regard, Compound 1 and Compound 2 may be both included in the same layer (for example, Compound 1 and Compound 2 may be both included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, the first electrode may be an anode, the second electrode may be a cathode, and the organic layer may include a hole transport region disposed between the first electrode and the emission layer and an electron transport region disposed between the emission layer and the second electrode, wherein the hole transport region may include at least one selected from a hole injection layer, a hole transport layer, and an electron blocking layer, and wherein the electron transport region may include at least one selected from a hole blocking layer, an electron transport layer, and an electron injection layer.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-resistance.

The first electrode 11 may be formed by depositing or sputtering a material for forming the first electrode 11 on the substrate. The first electrode 11 may be an anode. The material for the first electrode 11 may be selected from materials with a high work function to facilitate hole injection. The first electrode 11 may be a reflective electrode or a transmissive electrode. The material for the first electrode 11 may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for the first electrode 11.

The first electrode 11 may have a single-layer structure or a multi-layer structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

An injection layer may be formed on the first electrode 11 by using various methods, such as vacuum deposition, spin coating, casting, or Langmuir-Blodgett (LB).

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to the conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (Pani/PSS), a compound represented by Formula 201 below, and a compound represented by Formula 202 below:

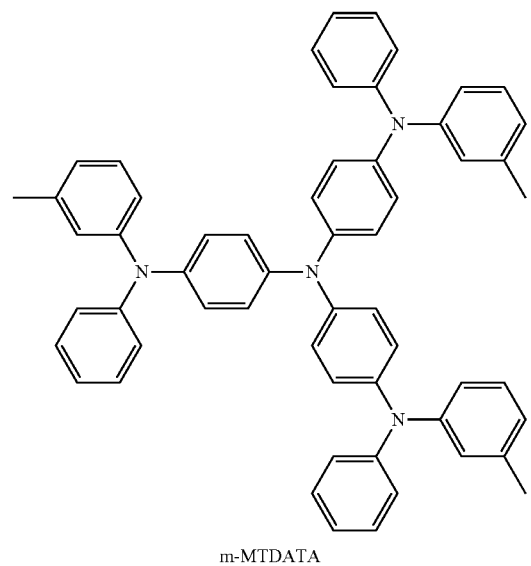

m-MTDATA

-continued
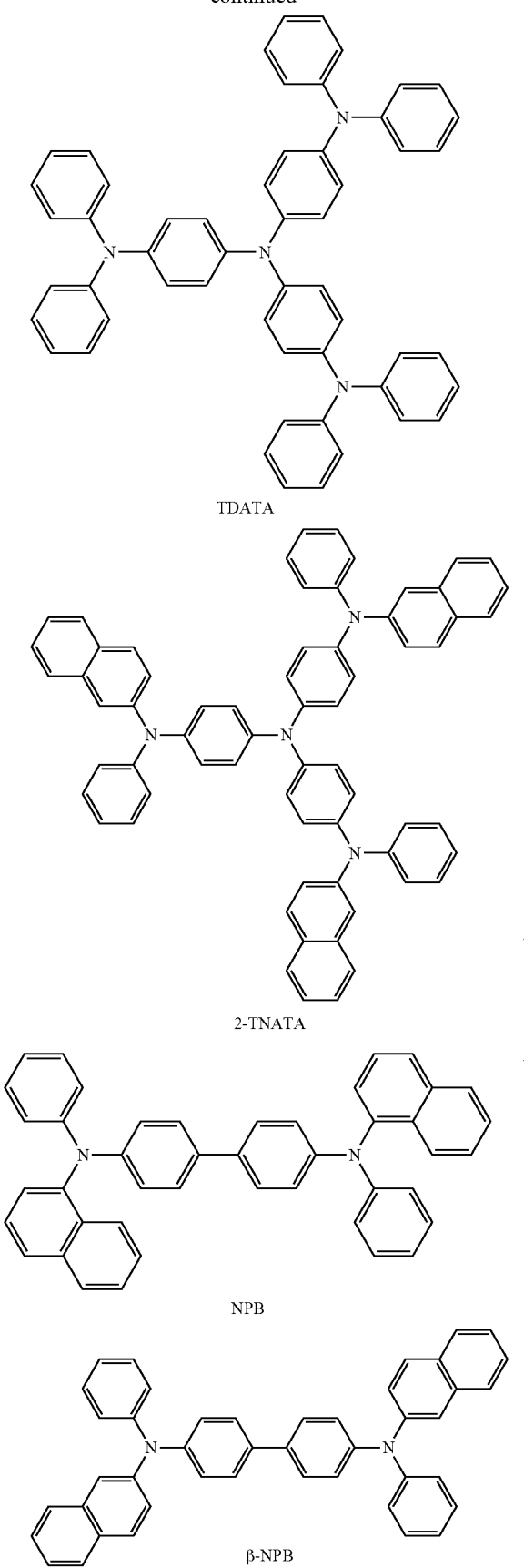
TDATA
2-TNATA
NPB
β-NPB
-continued
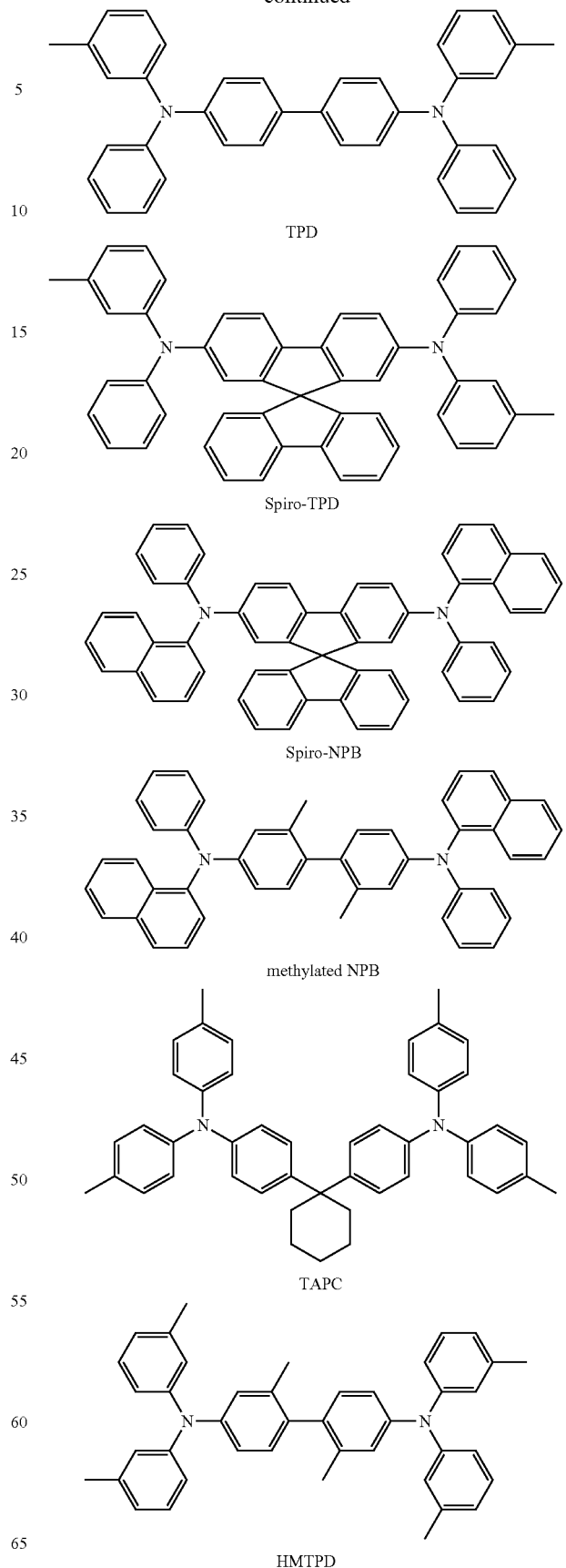
TPD
Spiro-TPD
Spiro-NPB
methylated NPB
TAPC
HMTPD Formula 201

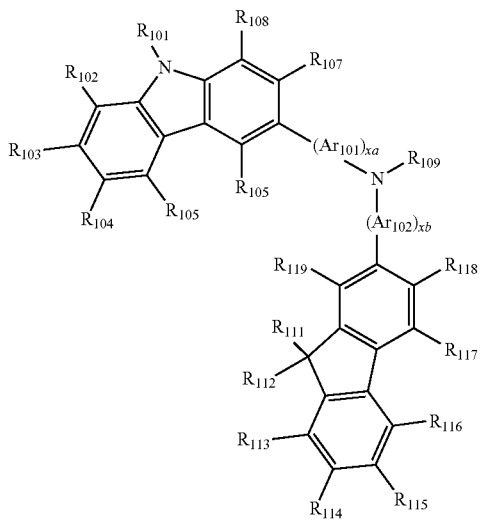

Formula 202

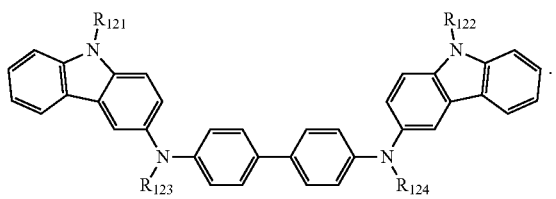

Ar$_{101}$ and Ar$_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may be each independently an integer of 0 to 5, or 0, 1, or 2. For example, xa is 1 and xb is 0, but xa and xb are not limited thereto.

$R_{101}$ to $R_{108}$, $R_{111}$ to $R_{119}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but is not limited thereto:

Formula 201A

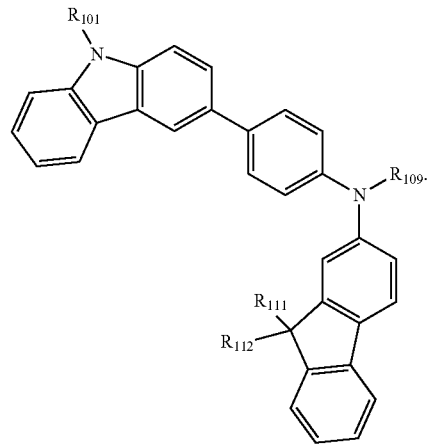

Descriptions of $R_{101}$, $R_{111}$, $R_{112}$, and $R_{109}$ in Formula 201A are the same as described above.
For example, the compound represented by Formula 201 and the compound represented by Formula 202 may include Compounds HT1 to HT20, but they are not limited thereto:
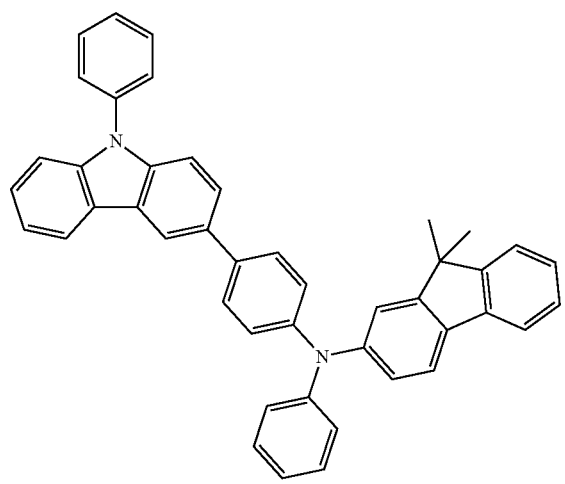
HT1
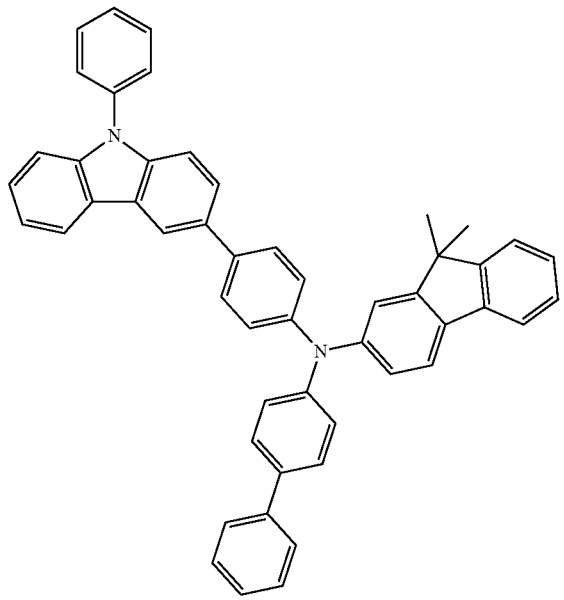
HT3
-continued
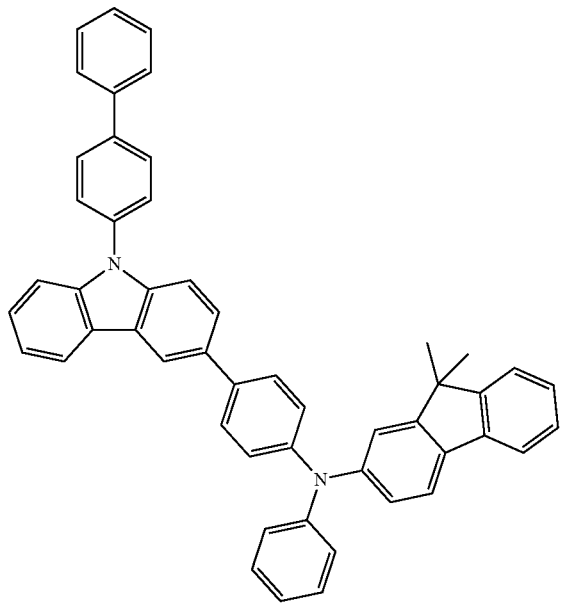
HT2
HT4

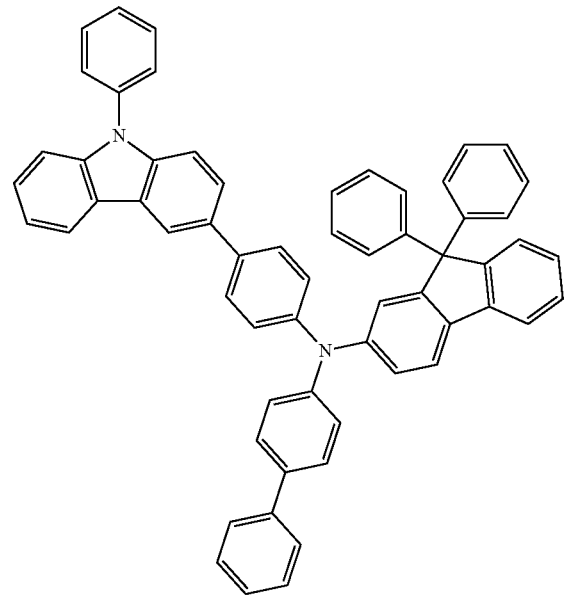
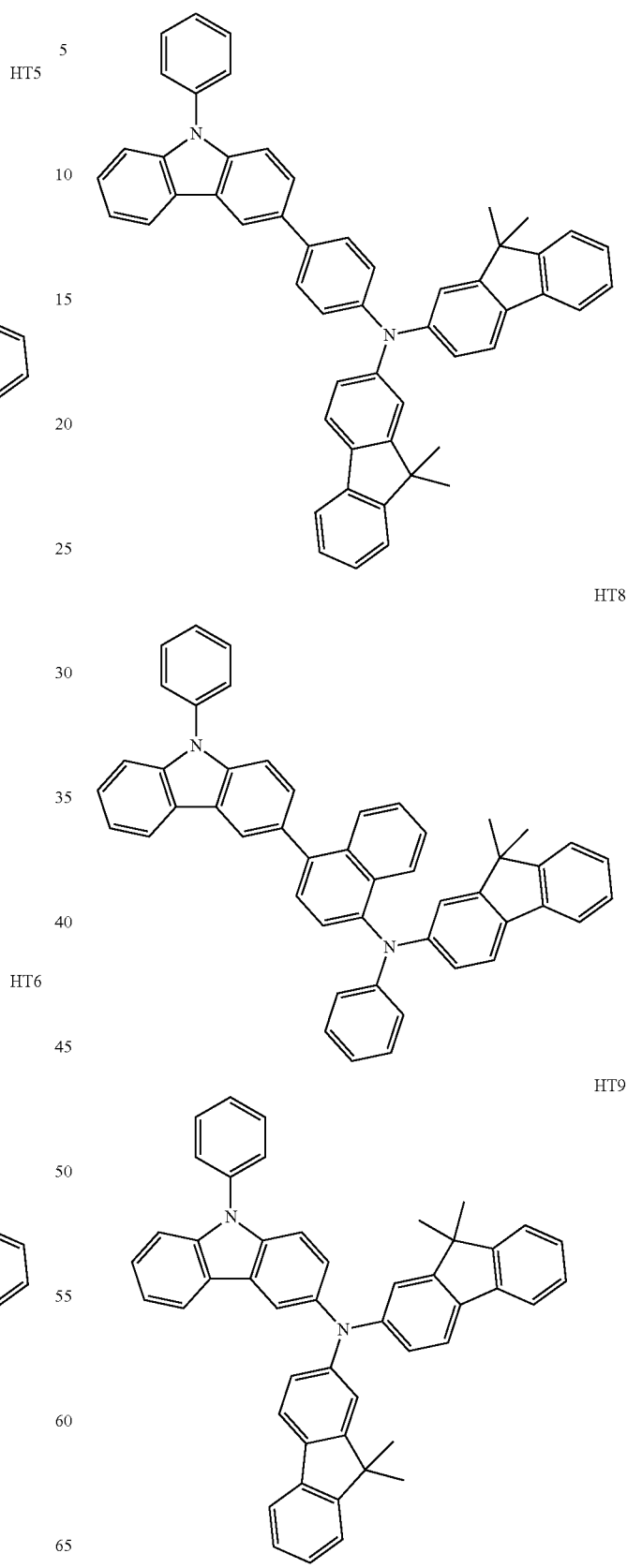

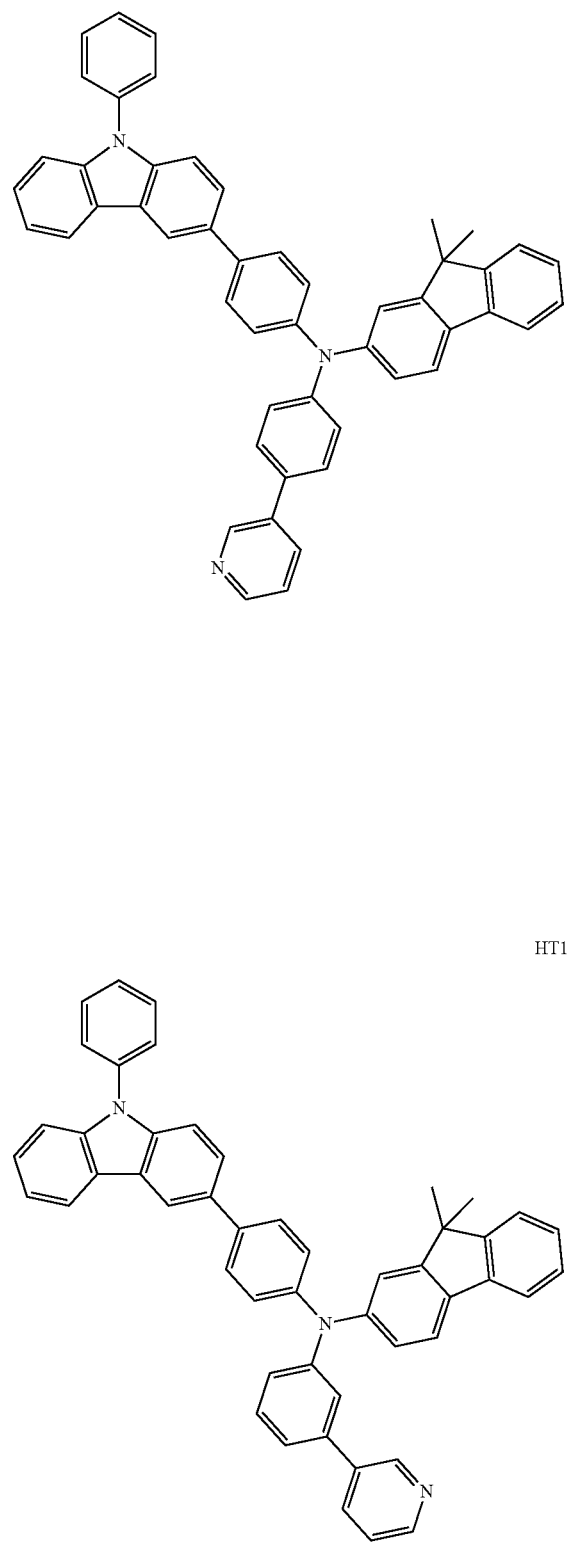
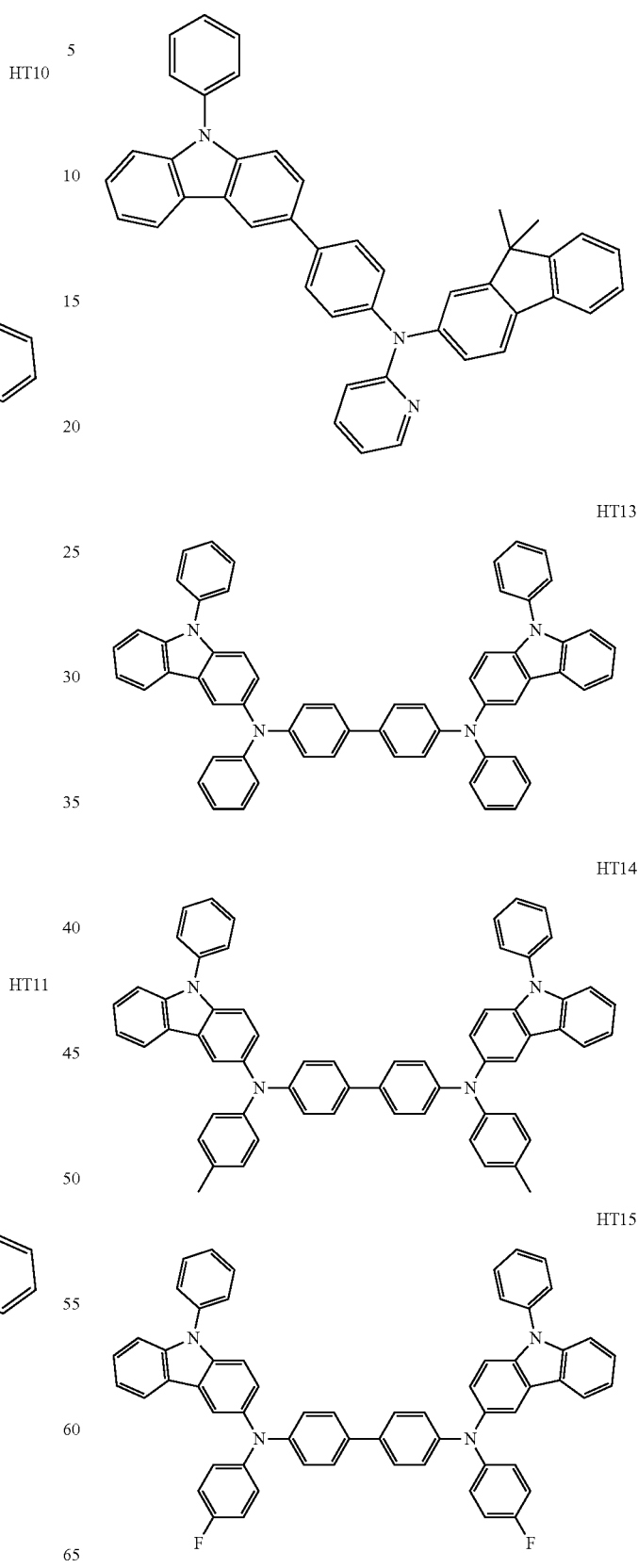

HT16
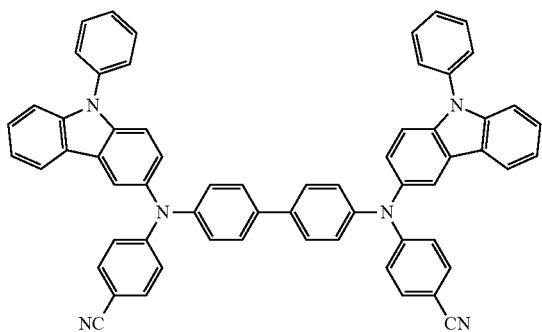

HT20
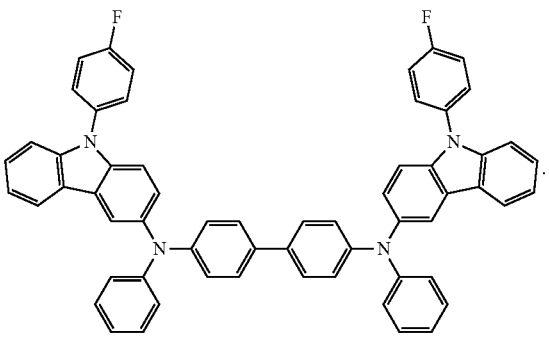

HT17
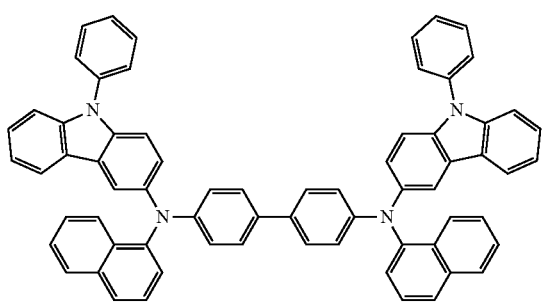

HT18

HT19
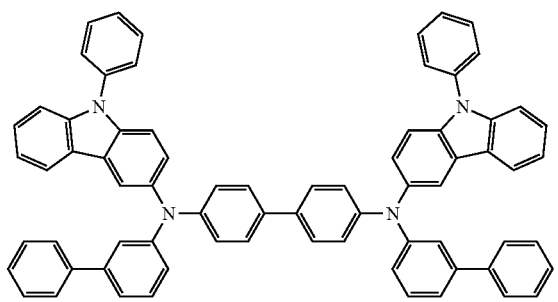

A thickness of the hole transport region may be in a range of about 100 Angstrom (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 below, but are not limited thereto.

Compound HT-D1
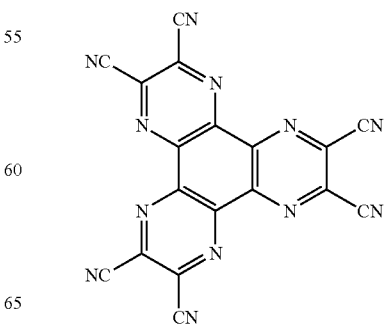

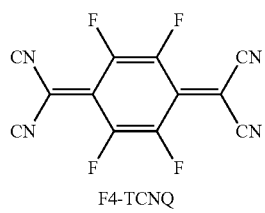

F4-TCNQ

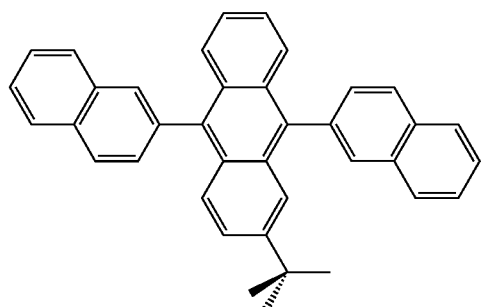

TBADN

The hole transport region may include a buffer layer.

Also, the buffer layer may compensate for an optical resonance distance according to a wavelength of light emitted from the emission layer, and thus, the efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, Mcp, Compound HSO, and Compound H51:

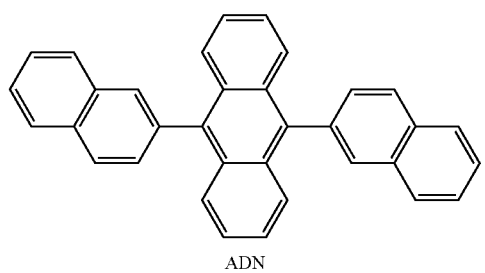

ADN

CBP

CDBP

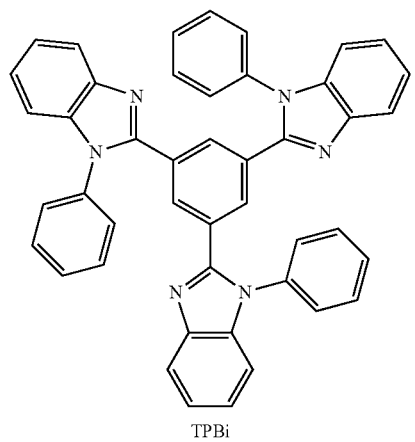

TPBi

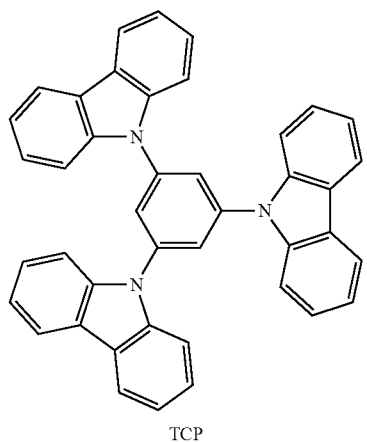

TCP

-continued

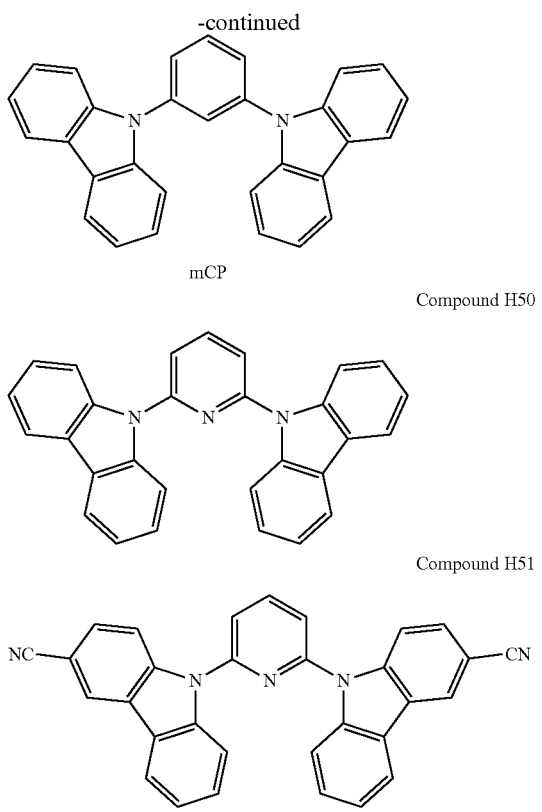

mCP

Compound H50

Compound H51

In some embodiments, the host may further include a compound represented by Formula 301 below.

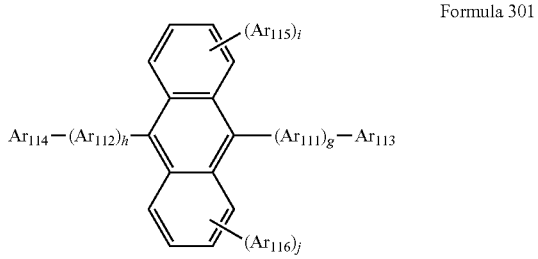

Formula 301

$Ar_{111}$ and $Ar_{112}$ in Formula 301 may be each independently selected from a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may be each independently selected from a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

g, h, l, and j in Formula 301 may be each independently an integer of 0 to 4, for example, an integer of 0, 1, or 2.

$Ar_{113}$ to $Ar_{116}$ in Formula 301 may be each independently selected from a $C_1$-$C_{10}$ alkyl group, substituted with at least one selected from a phenyl group, a naphthyl group, and an anthracenyl group;

a phenyl group, a naphthyl group, an anthracenyl group, a pyrenyl, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

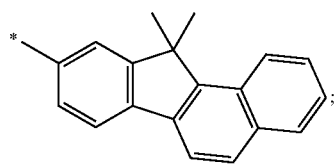 [SMILES: Cc1ccc2c(c1)C(C)(C)c1c-2ccc2ccccc12]

but embodiments are not limited thereto.

In some embodiments, the host may include a compound represented by Formula 302 below:

Formula 302

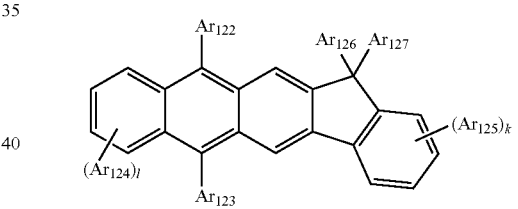

$Ar_{122}$ to $Ar_{125}$ in Formula 302 are the same as described in detail in connection with $Ar_{113}$ in Formula 301.

$Ar_{126}$ and $Ar_{127}$ in Formula 302 may be each independently a $C_1$-$C_{10}$ alkyl group (for example, a methyl group, an ethyl group, or a propyl group).

k and l in Formula 302 may be each independently an integer of 0 to 4. For example, k and l may be 0, 1, or 2.

The compound represented by Formula 301 and the compound represented by Formula 302 may include Compounds H1 to H42 illustrated below, but they are not limited thereto:

H1

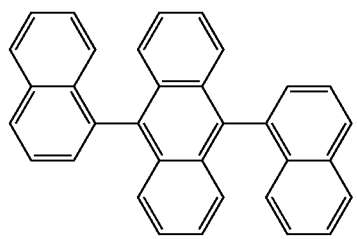

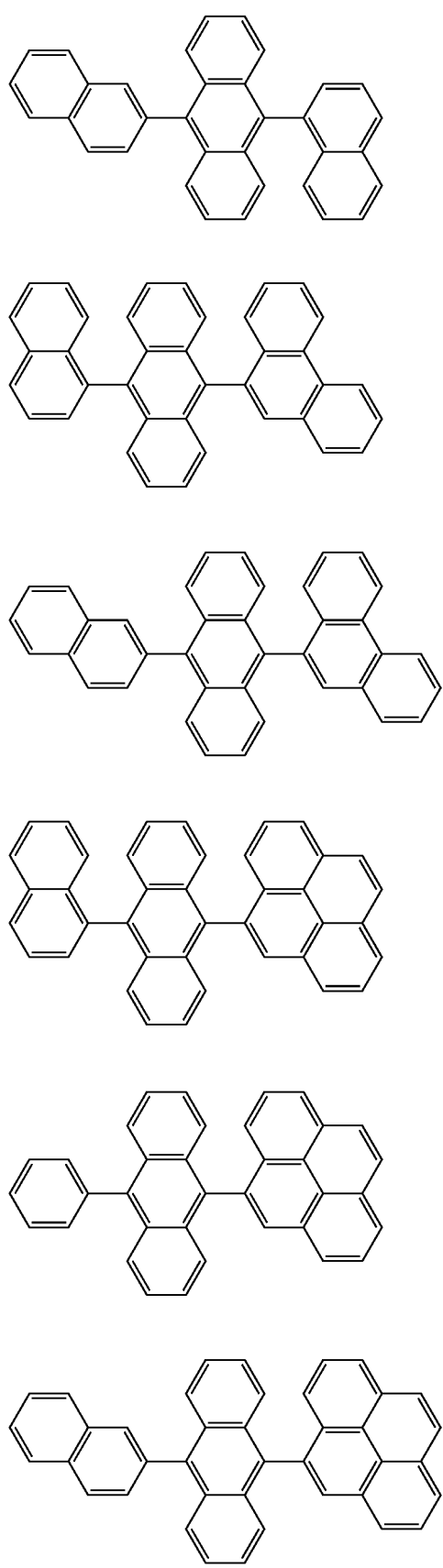

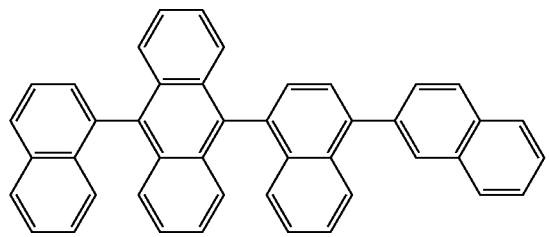

H24
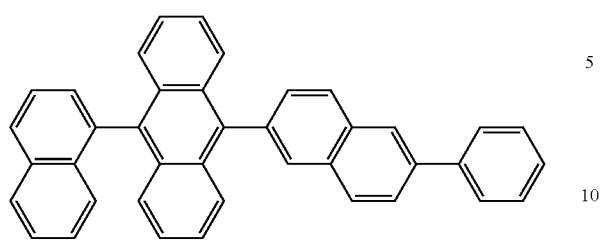
H25
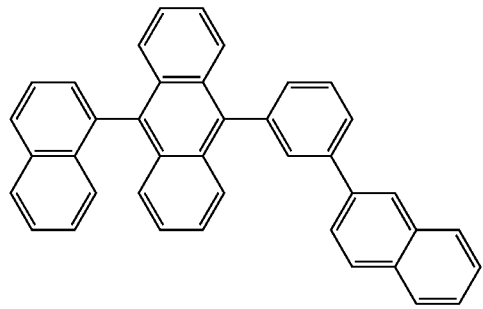
H26
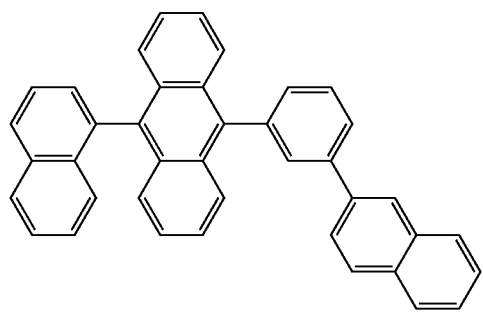
H27
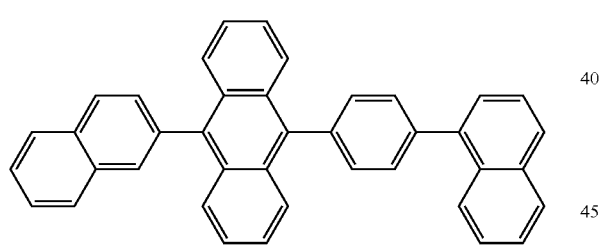
H28
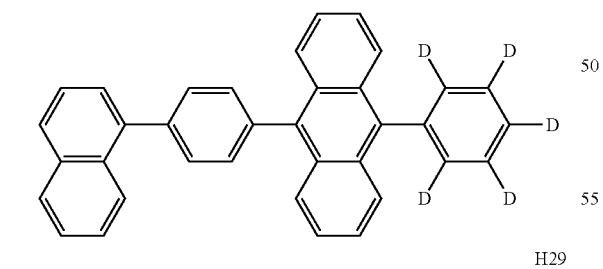
H29
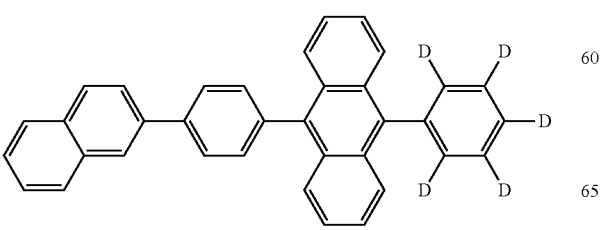
H30
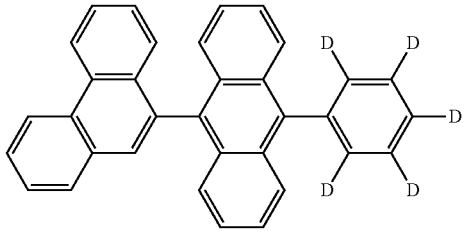
H31
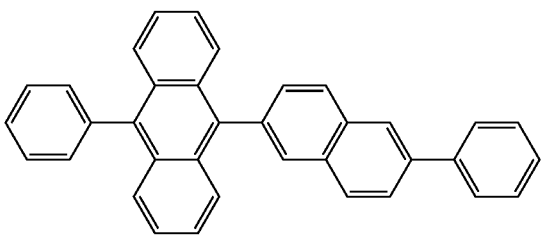
H32
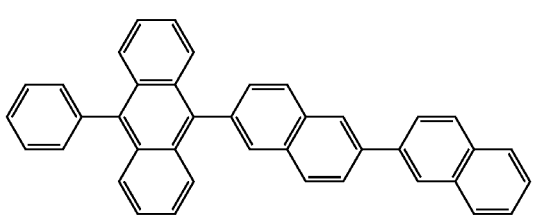
H33
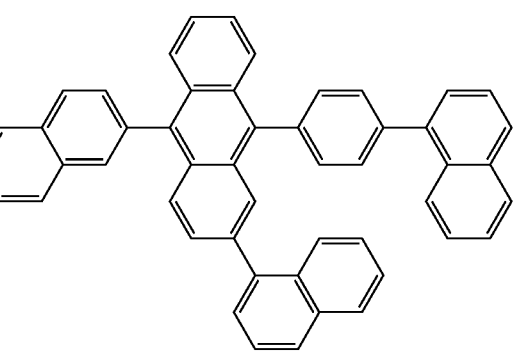
H34
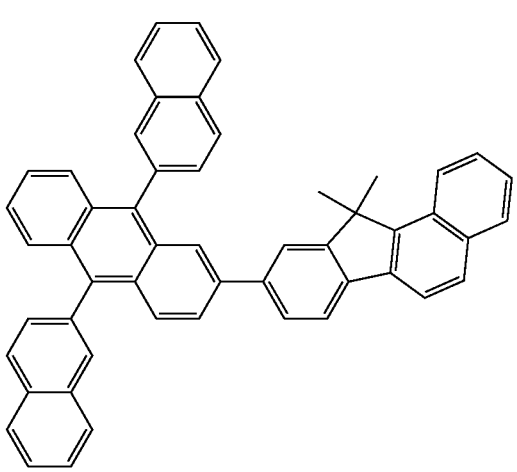

H35
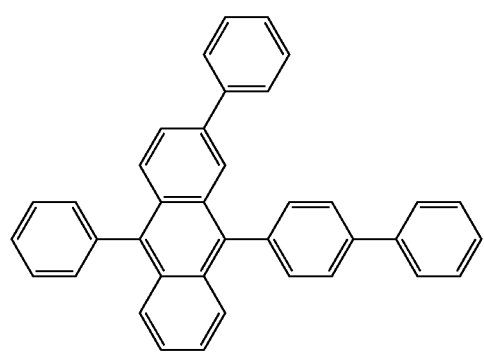
H36
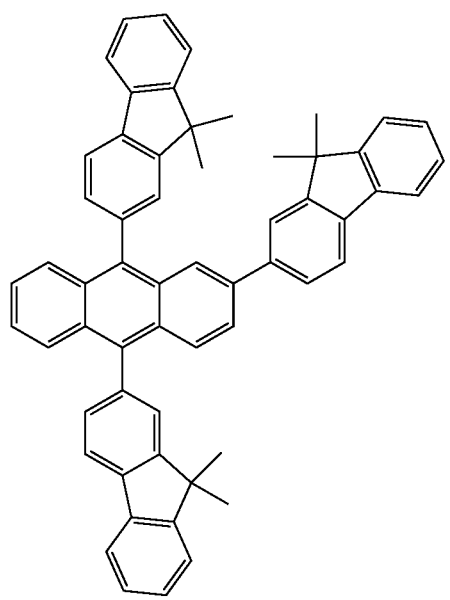
H37
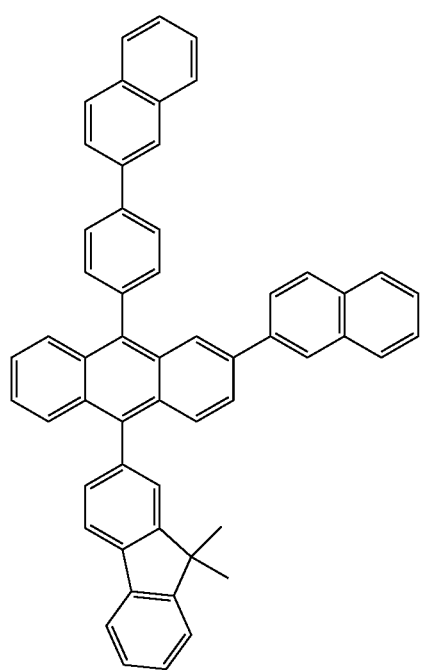
H38
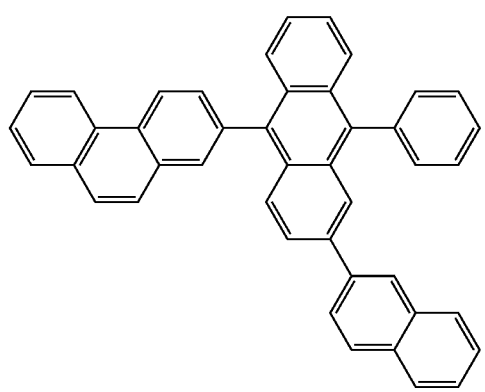
H39
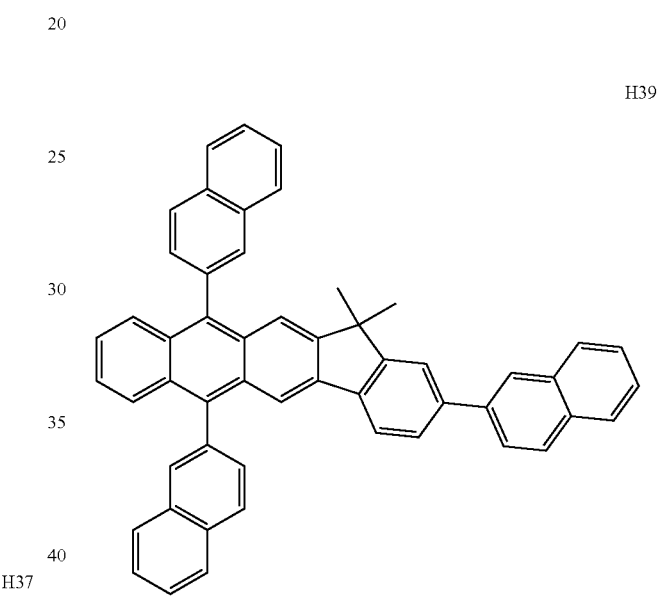
H40
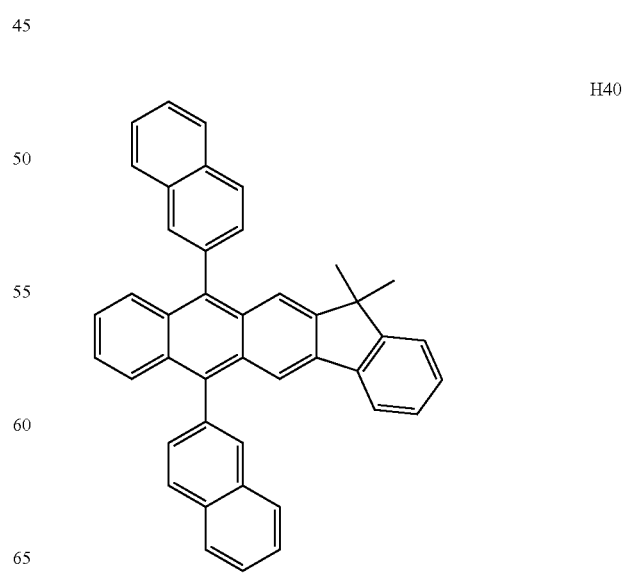

H41

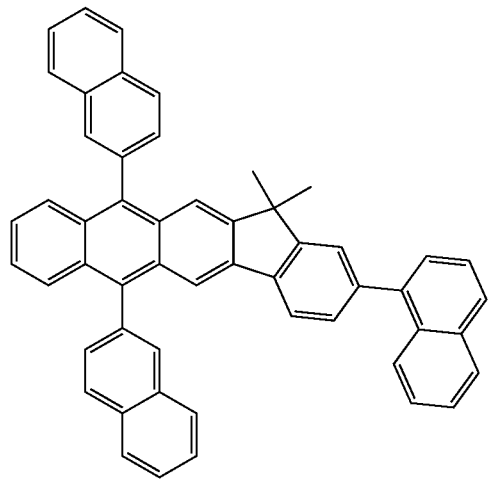

H42

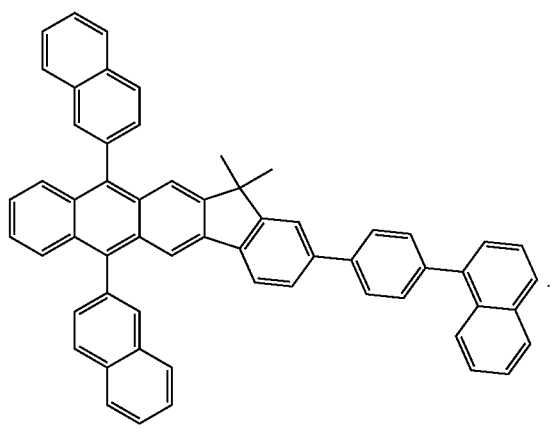

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP, Bphen, and Balq but is not limited thereto.

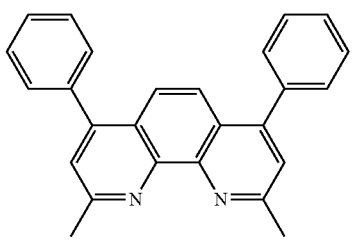

BCP

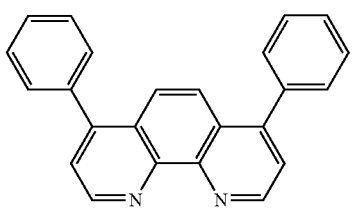

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq$_3$, Balq, TAZ, and NTAZ:

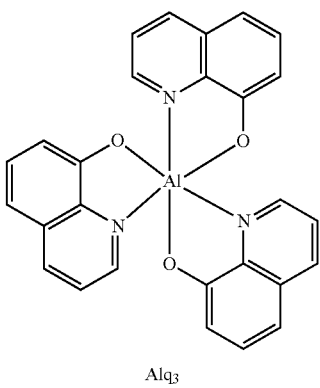

Alq$_3$

-continued

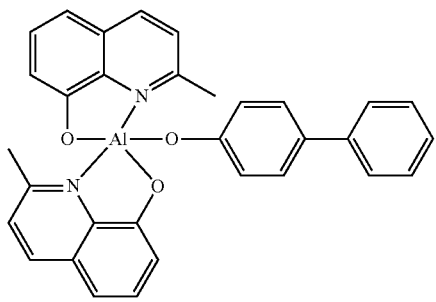

Balq

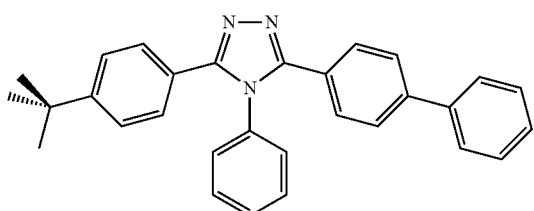

TAZ

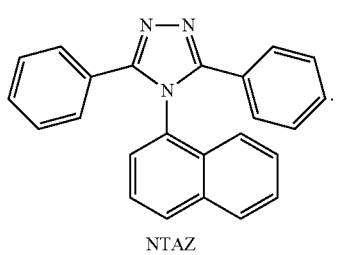

NTAZ

In some embodiments, the electron transport layer may include at least one of ET1 and ET2, but are not limited thereto:

ET1

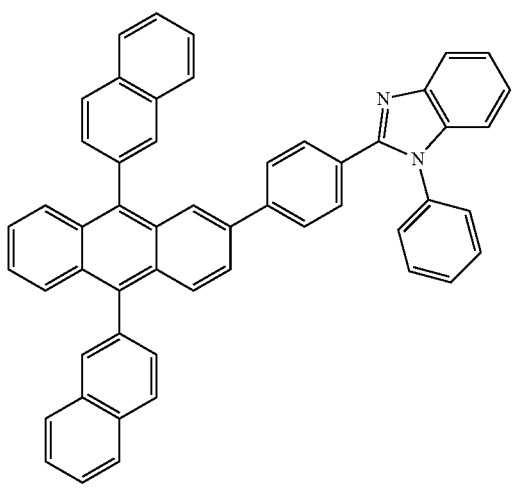

-continued

ET2

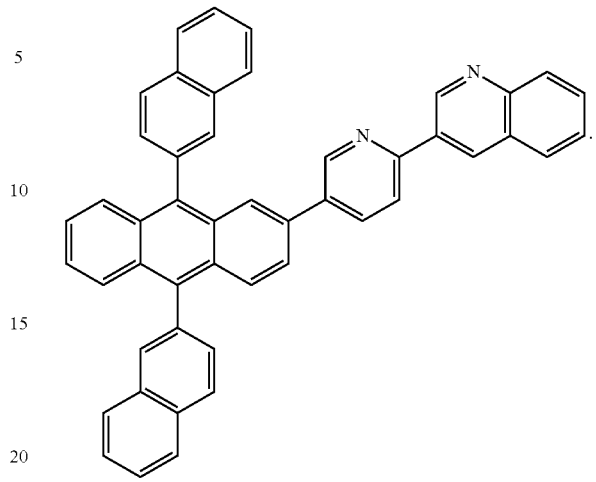

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

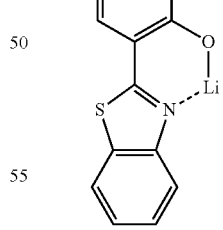

ET-D2

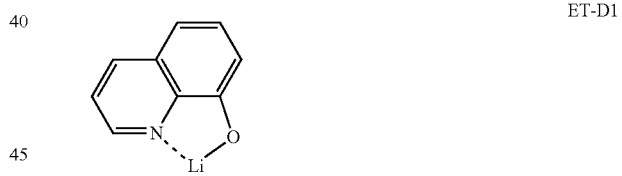

The electron transport layer may include an electron injection layer (EIL) that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as a material for forming the second electrode 19. In some embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by placing at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by placing at least one carbon trip bond in the middle or at the terminal of the $C_2$-$C_{60}$ alkyl group. Detailed examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, P, Si, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, Si, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, Si, and S as a ring-forming atom, and 1 to 60 carbon atoms. A $C_1$-$C_{60}$ heteroarylene group as used herein refers to a divalent group having a carbocyclic aromatic system that has at least one hetero atom selected from N, O, P, Si, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group (for example, having 8 to 60 carbon atoms) that has two or more rings condensed to each other, only carbon atoms as a ring forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, having 2 to 60 carbon atoms) that has two or more rings condensed to each other, has a heteroatom selected from N, O P, and S, other than carbon atoms, as a ring forming atom, and which is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

In the present specification, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$, may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the substituents listed above, the number of carbon atoms in the resulting "substituted" group may be the number of atoms contained in the original (base) group plus the number of carbon atoms (if any) contained in the substituent. For example, the "substituted $C_1$-$C_{30}$ alkyl" may refer to a $C_1$-$C_{30}$ alkyl group substituted with $C_{6-60}$ aryl group, in which the total number of carbon atoms may be $C_7$-$C_{90}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1

Synthesis of Compound 1

Synthesis of Compound M2A

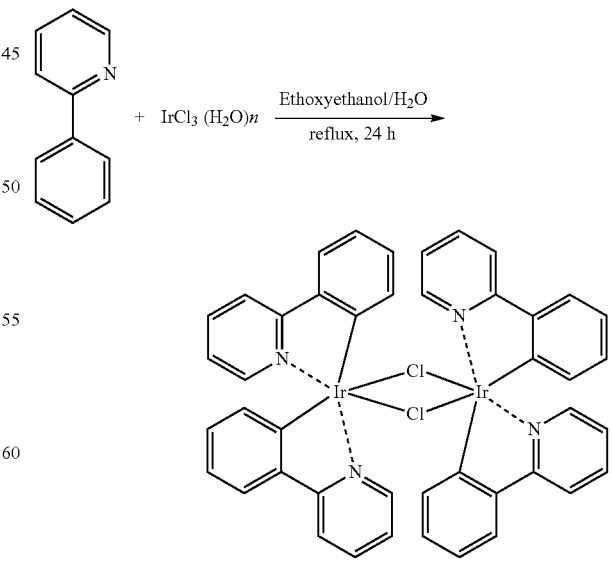

Compound M2A

2-Phenylpyridine (7.82 grams (g), 50.37 millimoles (mmol)) and iridium chloride (7.89 g, 22.39 mmol) were mixed with 210 milliliters (mL) of ethoxyethanol and 70 mL of distilled water, and the mixture was stirred under reflux for 24 hours to carry out a reaction. The reaction mixture was subsequently cooled to room temperature. The resulting solid was separated by filtration, and thoroughly washed with water, methanol, and hexane, sequentially in this stated order. The obtained solid was dried in a vacuum oven to obtain 11.20 g (93%) of Compound M2A.

Synthesis of Compound M1A

Synthesis of Compound 1

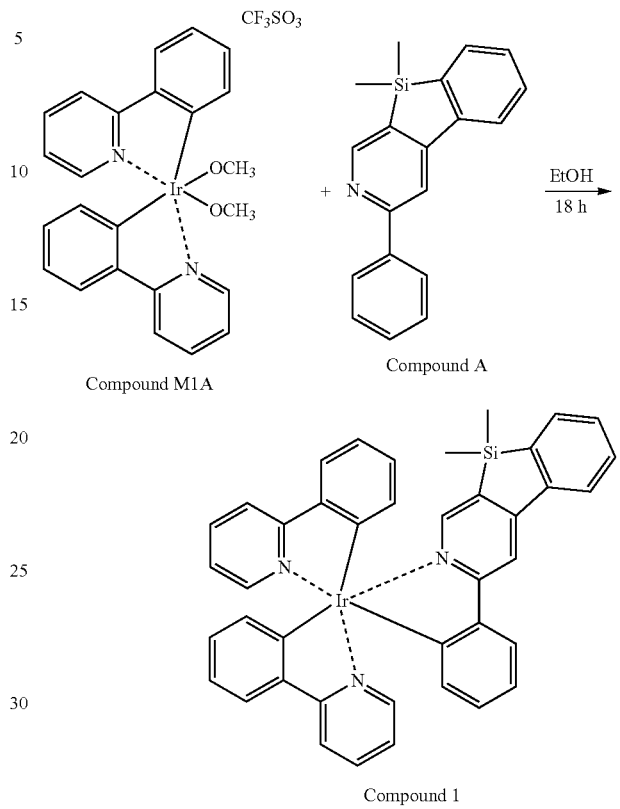

Compound M1A

Compound A

Compound 1

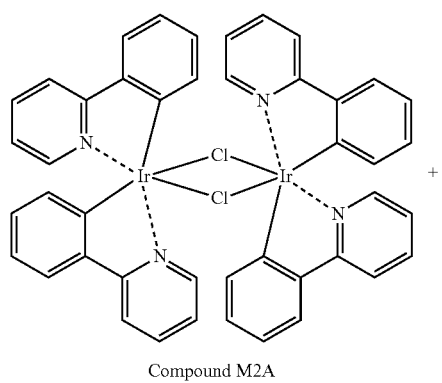

Compound M2A

+

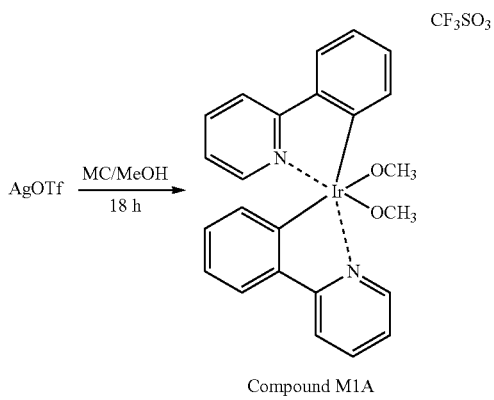

Compound M1A

Compound M2A (4.51 g, 4.20 mmol) was mixed with 45 mL of methylene chloride (MC), and AgOTf (2.16 g, 8.41 mmol) dissolved in 15 mL of methanol was added thereto. Thereafter, while light was blocked by using aluminum foil, the mixture was stirred at room temperature for 18 hours to carry out a reaction. The generated solid was removed by celite filtration, and a filtrate was subjected to a reduced pressure, thereby obtaining a solid (Compound M1A), which was used in the subsequent reaction without any additional purification.

Compound M1A (6 g, 8.41 mmol) and Compound A (3.02 g, 10.51 mmol) were mixed with 90 mL of ethanol, and the mixture was stirred under reflux for 18 hours to carry out a reaction. The reaction mixture was subsequently cooled. The resultant mixture was filtered to obtain a solid, which was thoroughly washed with ethanol and hexane, and subjected to column chromatography using MC and hexane, thereby obtaining 1.76 g (27%) of Compound 1. The obtained compound was confirmed by Mass and HPLC analysis.

HRMS (MALDI) calcd for $C_{41}H_{32}IrN_3Si$: m/z 787.1995. Found: 787.1999.

Synthesis Example 2

Synthesis of Compound 11

Synthesis of Compound M2B

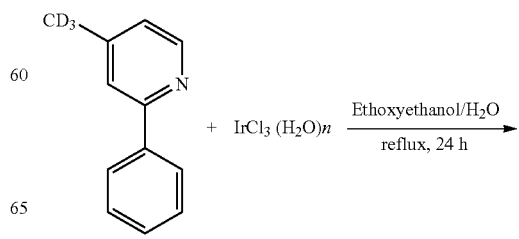

-continued

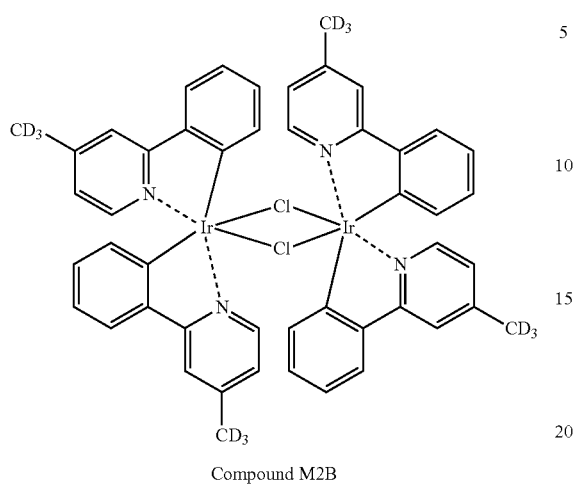

Compound M2B

4-Methyl(D$_3$)-2-phenylpyridine (6.80 g, 39.46 mmol) and iridium chloride (6.19 g, 17.54 mmol) were mixed with 120 mL of ethoxyethanol and 40 mL of distilled water, and the mixture was stirred under reflux for 24 hours to carry out a reaction. The reaction mixture was subsequently cooled down to room temperature. The generated solid was separated by filtration, and thoroughly washed with water, methanol, and hexane, sequentially in this stated order. The obtained solid was dried in a vacuum oven to obtain 8.90 g (89%) of Compound M2B.

Synthesis of Compound M1B

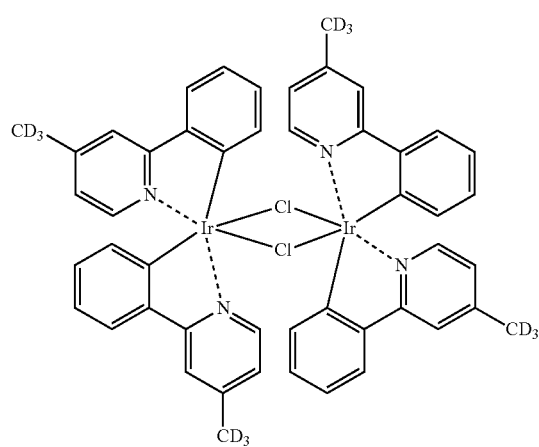

Compound M2B

-continued

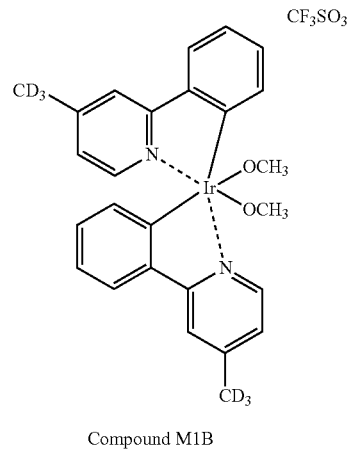

Compound M1B

Compound M2B (5.50 g, 4.83 mmol) was mixed with 45 mL of MC, and AgOTf (2.48 g, 9.65 mmol) dissolved in 15 mL of methanol was added thereto. Thereafter, while light was blocked by using aluminum foil, the resulting mixture was stirred at room temperature for 18 hours to carry out a reaction, thereby generating a solid. The solid was removed by celite filtration, and a filtrate was subjected to reduced pressure, thereby obtaining a solid (Compound M1B), which was used in the subsequent reaction without any additional purification.

Synthesis of Compound 11

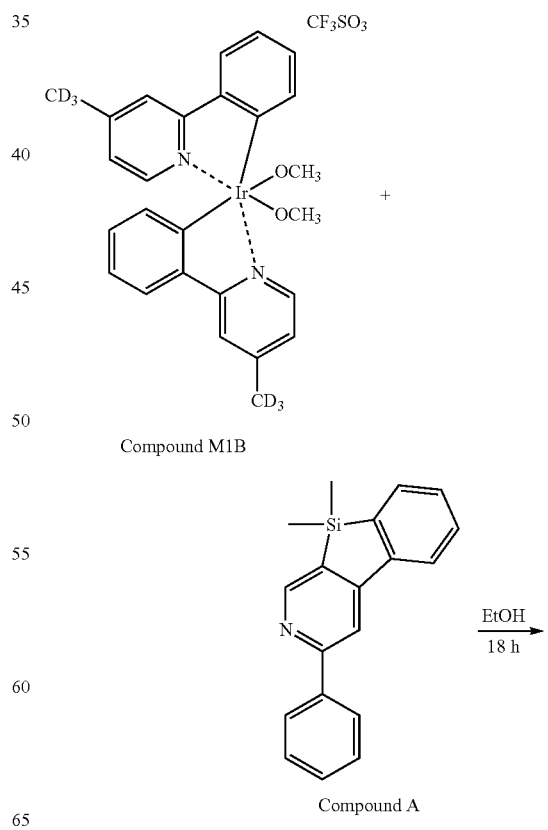

Compound M1B

Compound A

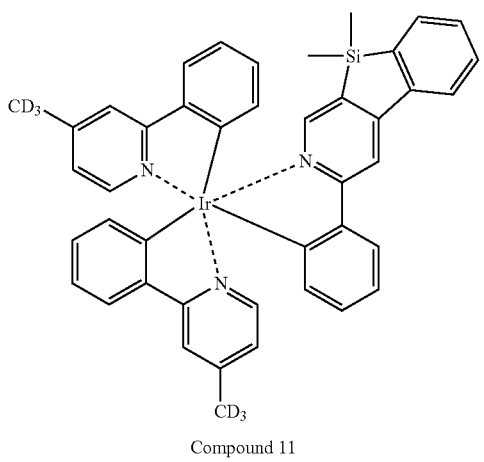

Compound 11

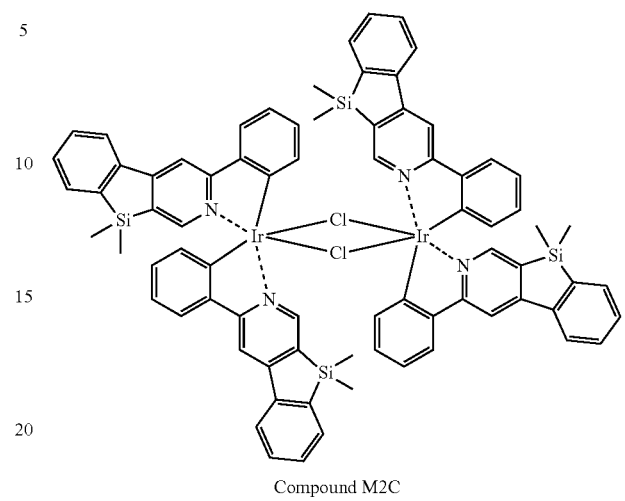

Compound M2C

Compound M1B (7.2 g, 9.66 mmol) and Compound A (3.33 g, 11.59 mmol) were mixed with 80 mL of ethanol, and the mixture was stirred under reflux for 18 hours to carry out a reaction. The reaction mixture was subsequently cooled. The resultant mixture was filtered to obtain a solid, which was thoroughly washed with ethanol and hexane, and subjected to column chromatography using MC and hexane, thereby obtaining 1.1 g (14%) of Compound 11. The obtained compound was confirmed by Mass and HPLC analysis.

HRMS (MALDI) calcd for $C_{43}H_{30}D_6IrN_3Si$: m/z 821.2684. Found: 821.2685.

Synthesis Example 3

Synthesis of Compound 97

Synthesis of Compound M2C

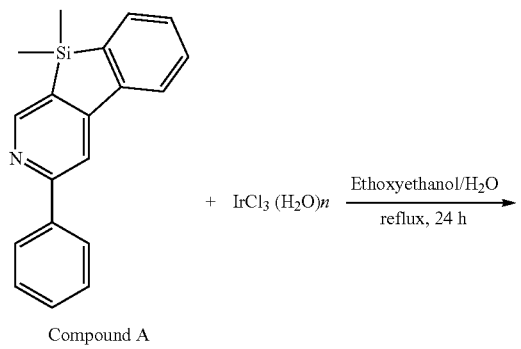

Compound A

Compound A (9.70 g, 33.73 mmol) and iridium chloride (5.29 g, 14.99 mmol) were mixed with 120 mL of ethoxyethanol and 40 mL of distilled water, and the mixture was stirred under reflux for 24 hours to carry out a reaction, and subsequently cooled down to room temperature, thereby generating a solid. The solid was separated by filtration, and thoroughly washed with water, methanol, and hexane, sequentially in this stated order. The obtained solid was dried in a vacuum oven to obtain 9.2 g (77%) of Compound M2C.

Synthesis of Compound M1C

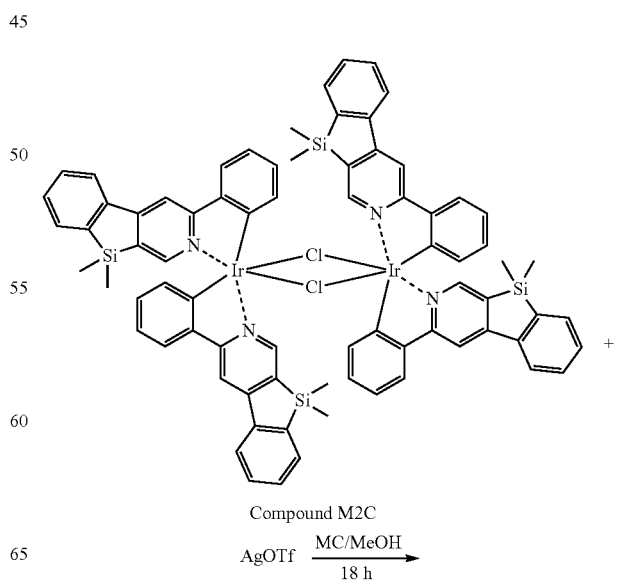

Compound M2C $\xrightarrow[18\ h]{\text{MC/MeOH}}$ AgOTf

-continued

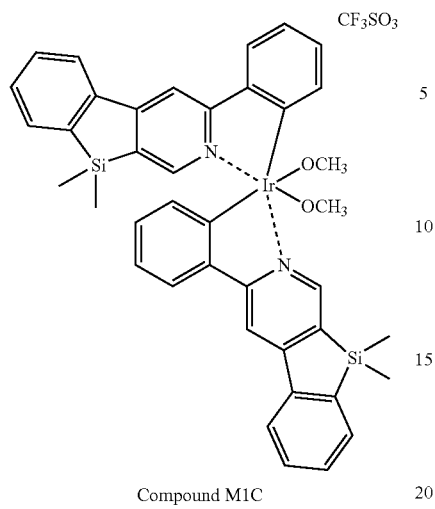

Compound M1C

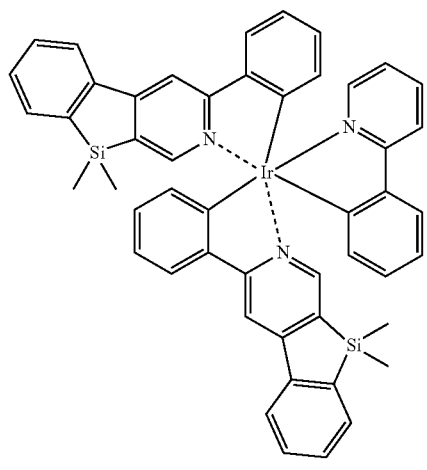

Compound 97

Compound M2C (4.91 g, 3.07 mmol) was mixed with 45 mL of MC, and AgOTf (1.58 g, 6.13 mmol) dissolved in 15 mL of methanol was added thereto. Thereafter, while light was blocked by using aluminum foil, the resulting mixture was stirred at room temperature for 18 hours to carry out a reaction, thereby generating a solid. The solid was removed by celite filtration, and a filtrate was subjected to reduced pressure, thereby obtaining a solid (Compound M1C), which was used for the subsequent reaction without any additional purification.

Synthesis of Compound 97

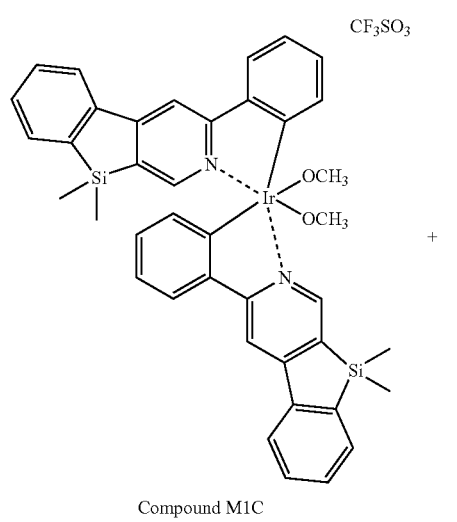

Compound M1C

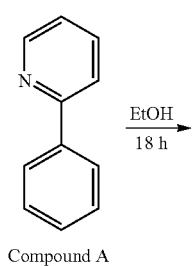

Compound A

Compound M1C (6 g, 6.14 mmol) and Compound A (1.14 g, 7.36 mmol) were mixed with 80 mL of ethanol, and the mixture was stirred under reflux for 18 hours to carry out a reaction. The reaction mixture was subsequently cooled. The resultant mixture was filtered to obtain a solid, which was thoroughly washed with ethanol and hexane, and subjected to column chromatography using MC and hexane, thereby obtaining 0.86 g (15%) of Compound 97. The obtained compound was confirmed by Mass and HPLC analysis.

HRMS (MALDI) calcd for $C_{49}H_{40}IrN_3Si_2$: m/z 919.2390. Found: 919.2385.

Synthesis Example 4

Synthesis of Compound 116

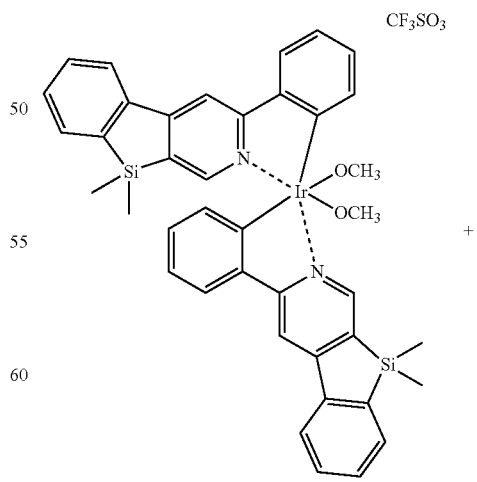

Compound M1C

Synthesis Example 5

Synthesis of Compound 120

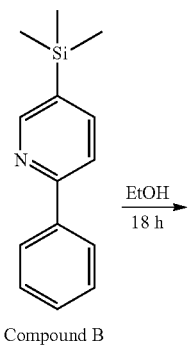

Compound B

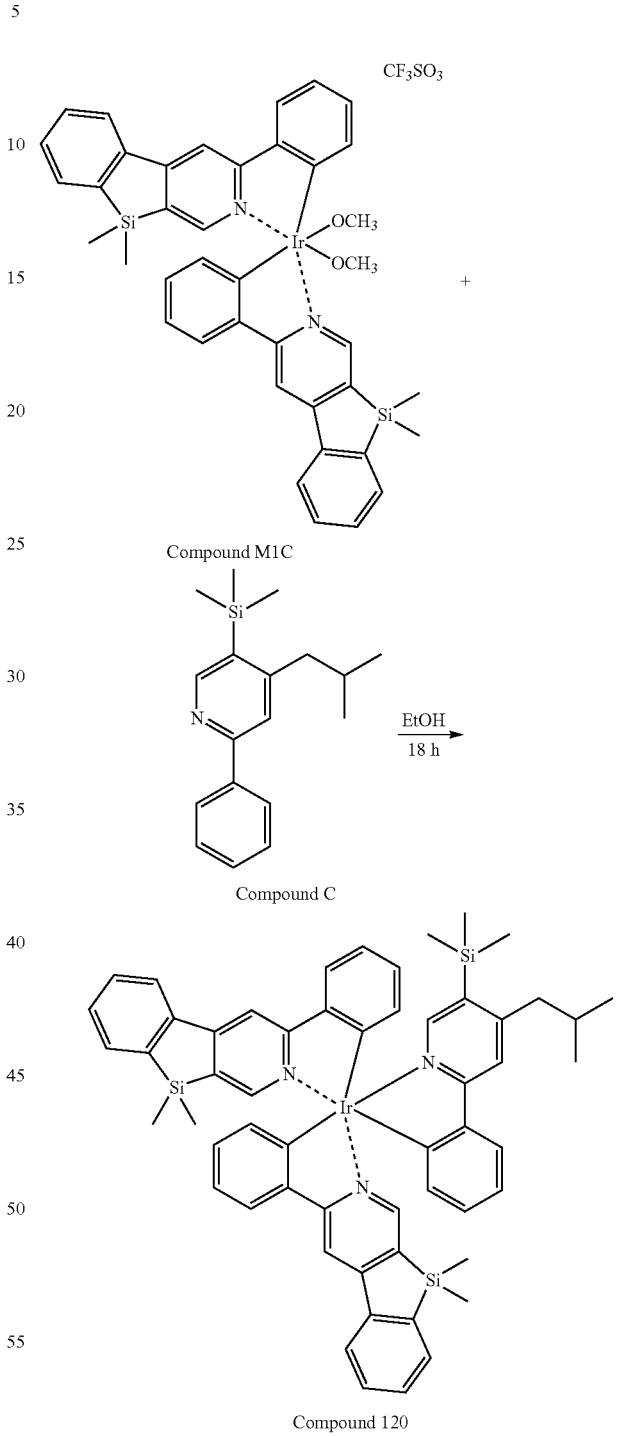

Compound M1C

Compound C

Compound 120

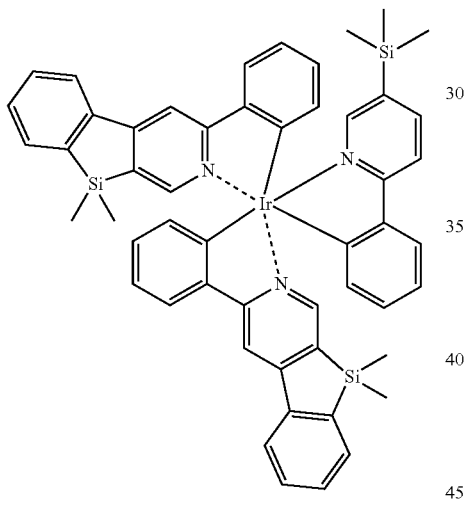

Compound 116

Compound M1C (6 g, 6.14 mmol) and Compound B (1.67 g, 7.36 mmol) were mixed with 70 mL of ethanol, and the mixture was stirred under reflux for 18 hours to carry out a reaction. The reaction mixture was subsequently cooled. The resultant mixture was filtered to obtain a solid, which was thoroughly washed with ethanol and hexane, and subjected to column chromatography using MC and hexane, thereby obtaining 1.39 g (23%) of Compound 116. The obtained compound was confirmed by Mass and HPLC analysis.

HRMS (MALDI) calcd $C_{52}H_{48}IrN_3Si_3$: m/z 991.2785. Found: 991.2781.

Compound M1C (6 g, 6.14 mmol) and Compound C (2.09 g, 7.36 mmol) were mixed with 70 mL of ethanol. The mixture was stirred under reflux for 18 hours to carry out a reaction. The reaction was subsequently cooled. The resultant mixture was filtered to obtain a solid, which was thoroughly washed with ethanol and hexane, and subjected to column chromatography using MC and hexane, thereby obtaining 0.92 g (14%) of Compound 120. The obtained compound was confirmed by Mass and HPLC analysis.

HRMS (MALDI) calcd for $C_{56}H_{56}IrN_3Si_3$: m/z 1047.3411. Found: 1047.3414.

Synthesis Example 6

Synthesis of Compound 138

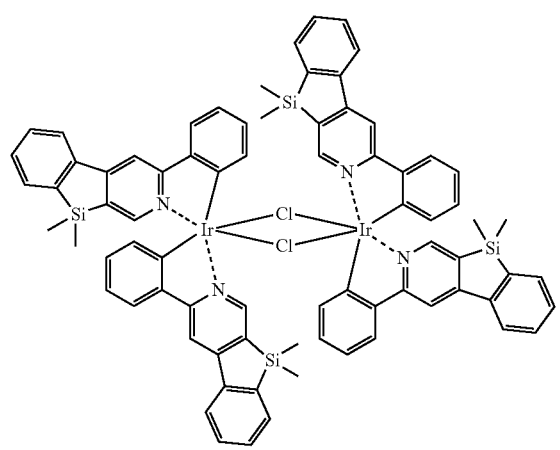

Compound M2C

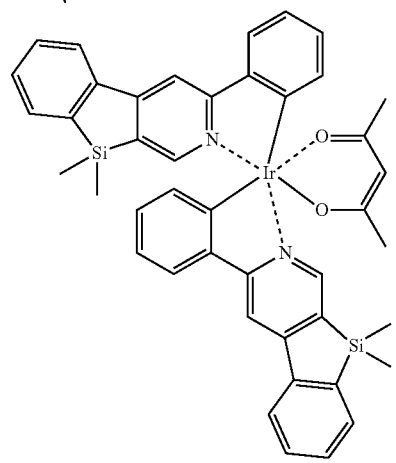

Compound 138

Compound M2C (4.63 g, 2.89 mmol), acetylacetone (2.90 g, 28.93 mmol), and $K_2CO_3$ (4.00 g, 28.93) were mixed with 50 mL of ethoxyethanol, and the mixture was stirred for 18 hours at a temperature of 100° C. to carry out a reaction. The reaction mixture was subsequently cooled. The resultant mixture was filtered to obtain a solid, which was thoroughly washed with ethanol and hexane, and subjected to column chromatography using MC, thereby obtaining 0.90 g (11%) of Compound 138. The obtained compound was confirmed by Mass and HPLC analysis.

HRMS (MALDI) calcd for $C_{43}H_{39}IrN_2O_2Si_2$: m/z 864.2179. Found: 864.2177.

Synthesis Example 7

Synthesis of Compound 140

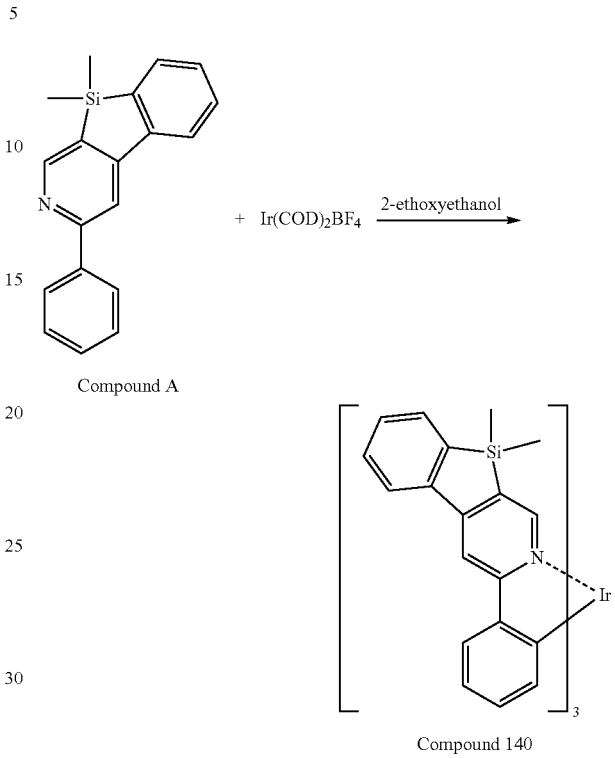

Compound A (4.51 g, 15.69 mmol) and $Ir(COD)_2BF_4$ (2.36 g, 4.76 mmol) were mixed with 50 mL of 2-ethoxyethanol, and the mixture was stirred at a temperature of 120° C. for 18 hours to carry out a reaction. The temperature was decreased and the resulting mixture was filtered to obtain a solid. The solid was subjected to column chromatography using MC and hexane to obtain 0.4 g (8%) of Compound 140. The obtained compound was confirmed by Mass and HPLC analysis.

HRMS (MALDI) calcd for $C_{57}H_{48}IrN_3Si_3$: m/z 1051.2785. Found: 1051.2779.

Example 1

An indium tin oxide (ITO) glass substrate was cut to a size of 50 millimeters (mm)×50 mm×0.5 mm and sonicated in acetone, isopropyl alcohol, and pure water, in each solvent for 15 minutes, and washed by exposure to UV ozone for 30 minutes.

Subsequently, on the ITO electrode (anode) on the glass substrate, m-MTDATA was deposited at a deposition rate of 1 Angstrom per second (Å/sec) to form a hole injection layer having a thickness of 600 Å, and α-NPD was deposited on the hole injection layer at a deposition rate of 1 Å/sec to form a hole transport layer having a thickness of 250 Å.

Compound 1 (dopant) and CBP (host) were co-deposited on the hole transport layer at a deposition rate of 0.1 Å/sec and a deposition rate of 1 Å/sec, respectively, to form an emission layer having a thickness of 400 Å.

BAlq was deposited on the emission layer at a deposition rate of 1 Å/sec to form a hole blocking layer having a thickness of 50 Å, and $Alq_3$ was deposited on the hole blocking layer to form an electron transport layer having a thickness of 300 Å. Then, LiF was deposited on the electron transport layer to form an electron injection layer having a thickness of 10 Å, and Al was vacuum deposited on the electron injection layer to form a second electrode (cathode) having a thickness of 1,200 Å, thereby completing the manufacture of an organic light-emitting device having a structure of ITO/m-MTDATA (600 Å)/α-NPD (250 Å)/CBP+10% (Compound 1) (400 Å)/Balq(50 Å)/Alq$_3$(300 Å)/LiF(10 Å)/Al(1,200 Å).

Examples 2 to 7 and Comparative Example 1

Organic light-emitting devices were manufactured in the same manner as in Example 1, except that in forming an emission layer, for use as a dopant, corresponding compounds shown in Table 2 were used instead of Compound 1.

Evaluation Example 1

Evaluation on Characteristics of Organic Light-Emitting Devices

The driving voltage, current efficiency, power efficiency, color coordinate, and external quantum efficiency of each of the organic light-emitting devices manufactured according to Examples 1 to 7 and Comparative Example 1 were evaluated at a requirement luminance of 6,000 candelas per square meter (cd/m$^2$). The results were shown in Table 2. A current-voltage meter (Keithley 2400) and a luminance meter (Minolta Cs-1000A) were used as evaluation devices.

TABLE 2

| | Dopant | Driving voltage (V) | Efficiency (cd/A) | Power (lm/W) | CIEx | CIEy | Quantum efficiency (%) |
|---|---|---|---|---|---|---|---|
| Example 1 | 1 | 6.2 | 55.0 | 27.9 | 0.59 | 0.36 | 18 |
| Example 2 | 11 | 6.3 | 56.5 | 28.2 | 0.60 | 0.36 | 19 |
| Example 3 | 97 | 6.3 | 57.0 | 28.4 | 0.61 | 0.36 | 19 |
| Example 4 | 116 | 6.2 | 57.0 | 28.9 | 0.61 | 0.35 | 19 |
| Example 5 | 120 | 6.2 | 55.0 | 27.9 | 0.59 | 0.36 | 18 |
| Example 6 | 138 | 6.2 | 54.0 | 27.3 | 0.58 | 0.36 | 19 |
| Example 7 | 140 | 6.2 | 57.0 | 28.9 | 0.61 | 0.36 | 18 |
| Comparative Example 1 | Ir(ppy)$_3$ | 6.5 | 40.2 | 19.4 | 0.330 | 0.604 | 18 |

From Table 2, it was confirmed that the organic light-emitting devices manufactured according to Examples 1 to 7 have a lower driving voltage, a higher current efficiency, a higher power efficiency, and better color coordinate characteristics than the organic light-emitting device manufactured according to Comparative Example 1.

Organometallic compounds according to embodiments have excellent electric characteristics and thermal stability. Accordingly, an organic light-emitting device including such organometallic compounds may have excellent driving voltage, current efficiency, power efficiency, and color purity characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. An organometallic compound represented by Formula 1:

$$M(L_1)_{n1}(L_2)_{n2}$$ Formula 1

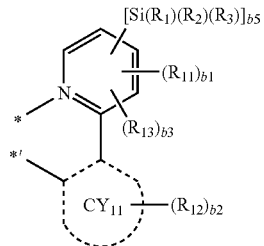

Formula 2 wherein

M in Formula 1 is selected from Ir, Pt, Os, Ti, Zr, Hf, Eu, Tb, Tm, and Rh,

L$_1$ in Formula 1 is selected from ligands represented by Formula 2, n1 is 1, 2, or 3, provided that when n1 is 2 or greater, two or more groups L$_1$ are identical to or different from each other, L$_2$ in Formula 1 is selected from a monovalent organic ligand, a divalent organic ligand, a trivalent organic ligand, and a tetravalent organic ligand, n2 is 0, 1, 2, 3, or 4, provided that when n2 is 2 or greater, two or more groups L$_2$ are identical to or different from each other, L$_1$ and L$_2$ in Formula 1 are different from each other, CY$_{11}$ in Formula 2 is selected from a C$_5$-C$_{30}$ carbocyclic ring and a C$_2$-C$_{30}$ heterocyclic ring, R$_1$ to R$_3$ and R$_{11}$ to R$_{13}$ in Formula 2 are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), and —P(=O)($Q_8$)($Q_9$), b1 in Formula 2 is an integer selected from 0 to 3, b2 in Formula 2 is an integer selected from 0 to 4, b3 and b5 in Formula 2 are each independently an integer selected from 1 to 3, at least one $R_3$ in Formula 2 is connected to at least one $R_{13}$ to form a substituted or unsubstituted saturated or unsaturated $C_2$-$C_{30}$ cyclic ring, each of * and *' in Formula 2 indicates a binding site to M in Formula 1, wherein at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), and —P(=O)($Q_{18}$)($Q_{19}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), and —P(=O)($Q_{28}$)($Q_{29}$); and —Si($Q_{31}$)($Q_{32}$)($Q_{33}$), —N($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

2. The organometallic compound of claim 1, wherein M in Formula 1 is Ir, and the sum of n1 and n2 is 3; or M is Pt, and the sum of n1 and n2 is 2.

3. The organometallic compound of claim 1, wherein $CY_{11}$ in Formula 2 is selected from a benzene, an indene, a naphthalene, an azulene, a heptalene, an indacene, an acenaphthylene, a fluorene, a spiro-bifluorene, a benzofluorene, a dibenzofluorene, a phenalene, a phenanthrene, an anthracene, a fluoranthene, a triphenylene, a pyrene, a chrysene, naphthacene, a picene, a perylene, a pentacene, a hexacene, a rubicene, a coronene, an ovalene, an isoindole, an indole, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzoimidazole, a benzofuran, a benzothiophene, a dibenzofuran, a dibenzothiophene, an isobenzothiazole, a benzoxazole, an isobenzoxazole, a carbazole, a benzocarbazole, a dibenzocarbazole, an imidazopyridine, and an imidazopyrimidine.

4. The organometallic compound of claim 1, wherein $R_{11}$ to $R_{13}$ in Formula 2 are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_6$)(Q$_7$) and —P(=O)(Q$_8$)(Q$_9$), wherein Q$_6$ to Q$_9$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group.

5. The organometallic compound of claim 1, wherein R$_{11}$ to R$_{13}$ in Formula 2 are each independently selected from hydrogen, deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —$B(Q_6)(Q_7)$ and —$P(=O)(Q_8)(Q_9)$, wherein $Q_6$ to $Q_9$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

6. The organometallic compound of claim 1, wherein
$R_1$ to $R_3$ in Formula 2 are each independently selected from
a $C_1$-$C_{10}$ alkyl group, a phenyl group, and —$Si(Q_1)(Q_2)(Q_3)$; and
a $C_1$-$C_{10}$ alkyl group and a phenyl group, each substituted with at least one selected from deuterium and a $C_1$-$C_{10}$ alkyl group,
wherein $Q_1$ to $Q_3$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

7. The organometallic compound of claim 1, wherein
$R_{11}$ to $R_{13}$ in Formula 2 are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, and groups represented by Formulae 10-1 to 10-30, $R_1$ to $R_3$ in Formula 2 are each independently selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and —$Si(Q_1)(Q_2)(Q_3)$; and an n-propyl group, an isopropyl group, an n-butyl group, an isobutyl group, a sec-butyl group, a tert-butyl group, an n-pentyl group, an isopentyl group, a sec-pentyl group, a tert-pentyl group, and a phenyl group, each substituted with at least one selected from a deuterium and a $C_1$-$C_{10}$ alkyl group, wherein $Q_1$ to $Q_3$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group:

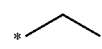

Formula 9-1

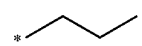

Formula 9-2

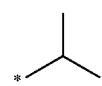

Formula 9-3

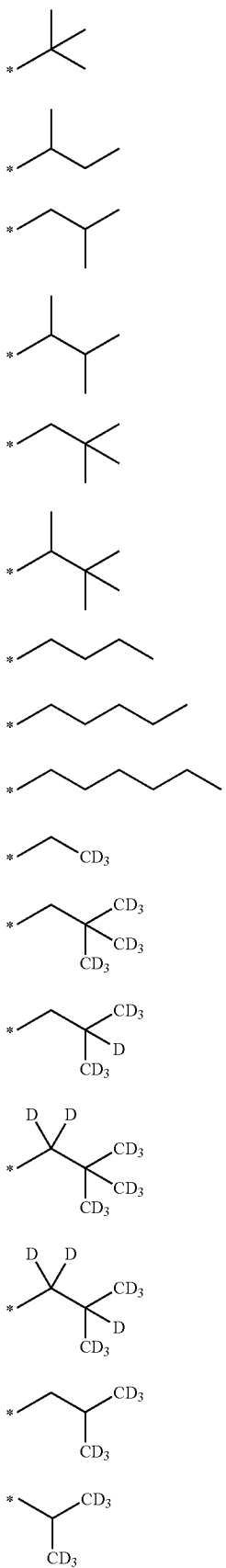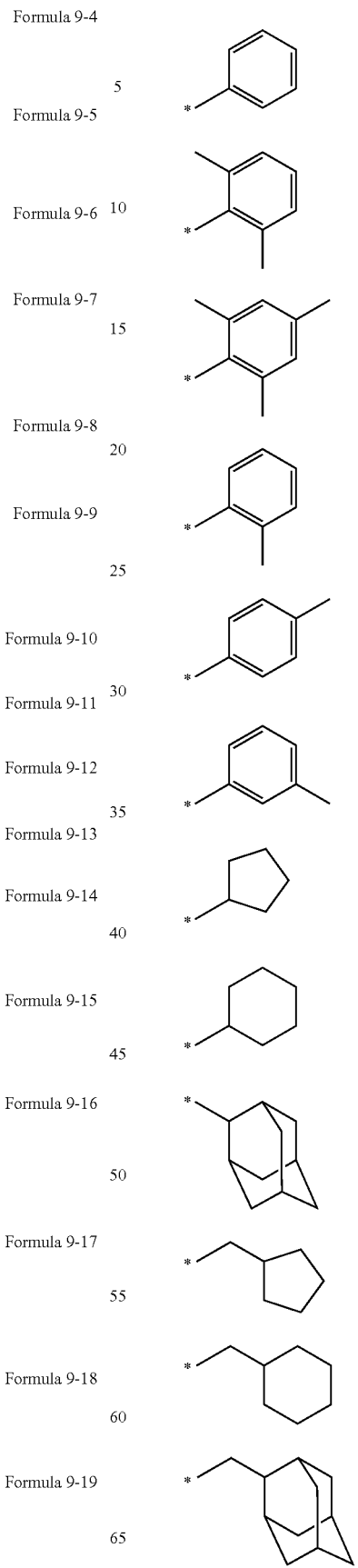
Formula 9-4
Formula 9-5
Formula 9-6
Formula 9-7
Formula 9-8
Formula 9-9
Formula 9-10
Formula 9-11
Formula 9-12
Formula 9-13
Formula 9-14
Formula 9-15
Formula 9-16
Formula 9-17
Formula 9-18
Formula 9-19
Formula 10-1
Formula 10-2
Formula 10-3
Formula 10-4
Formula 10-5
Formula 10-6
Formula 10-7
Formula 10-8
Formula 10-9
Formula 10-10
Formula 10-11
Formula 10-12

-continued

Formula 10-13
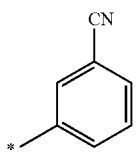

Formula 10-14
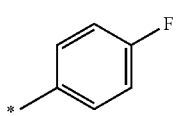

Formula 10-15
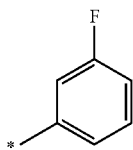

Formula 10-16
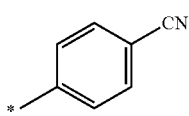

Formula 10-17
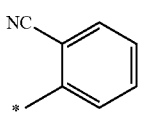

Formula 10-18
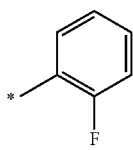

Formula 10-19
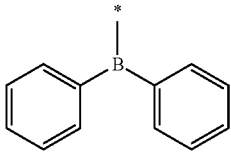

Formula 10-20
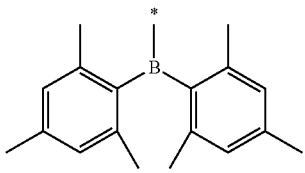

Formula 10-21
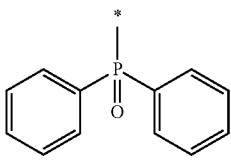

Formula 10-22
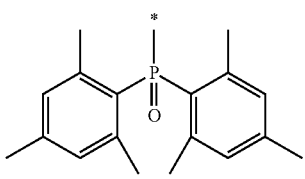

-continued

Formula 10-23
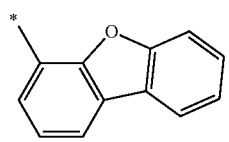

Formula 10-24
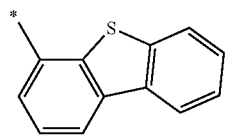

Formula 10-25
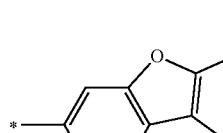

Formula 10-26
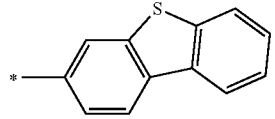

Formula 10-27
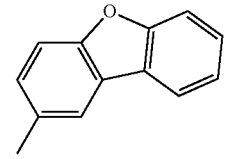

Formula 10-28
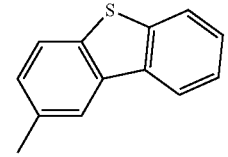

Formula 10-29
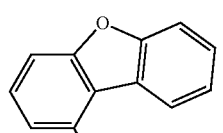

Formula 10-30
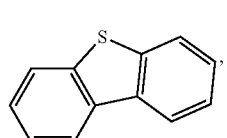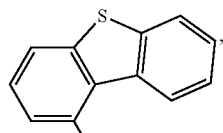

wherein * in Formulae 9-1 to 9-17 and 10-1 to 10-30 indicates a binding site to a neighboring atom.

8. The organometallic compound of claim 1, wherein $L_1$ in Formula 1 is selected from ligands represented by Formulae 2-1 to 2-6:

Formula 2-1

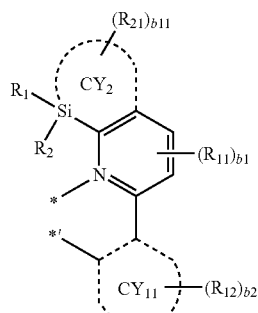

Formula 2-2

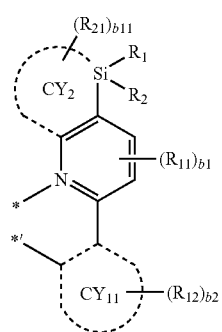

Formula 2-3

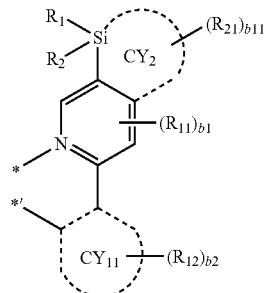

Formula 2-4

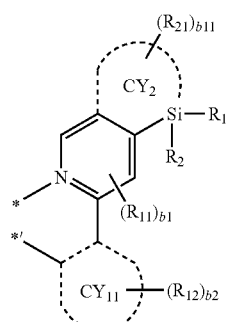

Formula 2-5

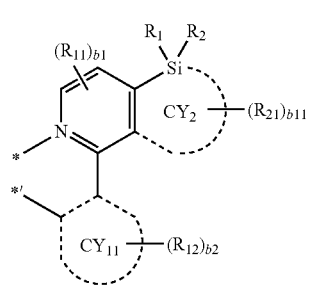

Formula 2-6

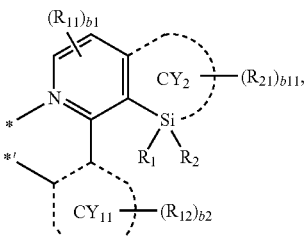

wherein $CY_{11}$, $R_1$, $R_2$, $R_{11}$, $R_{12}$, b1, and b2 in Formulae 2-1 to 2-6 are the same as in claim 1, $CY_2$ is a saturated or unsaturated $C_2$-$C_{30}$ cyclic ring formed by connecting $R_3$ and $R_{13}$, $R_{21}$ is the same as $R_{11}$, b11 is an integer selected from 0 to 10, and each of * and *' indicates a binding site to M in Formula 1.

9. The organometallic compound of claim 8, wherein $CY_2$ is selected from silolane, 2,3-dihydro-1H-silole, 2,5-dihydro-1H-silole, 3,4-dihydro-2H-silole, silole, 2,3-dihydro-1H-benzo[b]silole, benzosilole, silinane, tetrahydrosiline, dihydrosiline, tetrahydrobenzosiline, and dihydrobenzosiline.

10. The organometallic compound of claim 1, wherein $L_1$ in Formula 1 is selected from ligands represented by Formulae 2(1) to 2(36):

Formula 2(1)

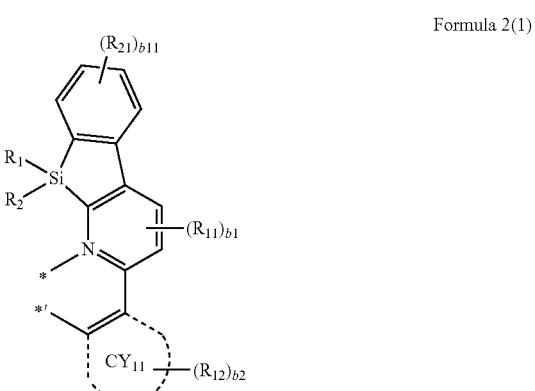

Formula 2(2)

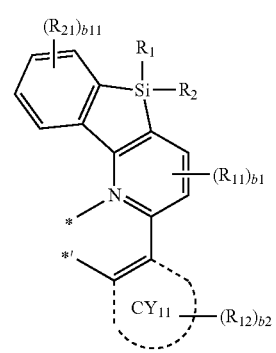

Formula 2(3)
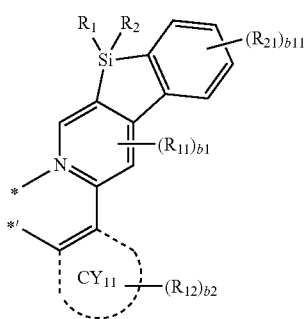
Formula 2(4)
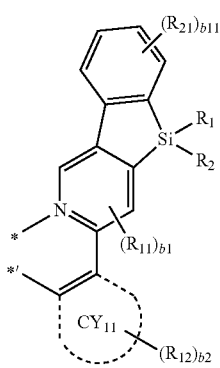
Formula 2(5)
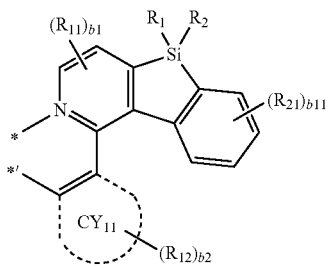
Formula 2(6)
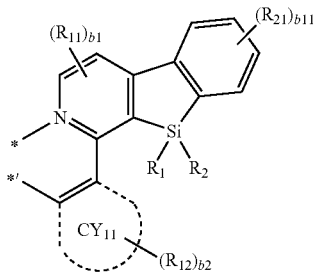
Formula 2(7)
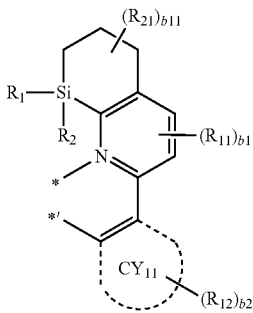
Formula 2(8)
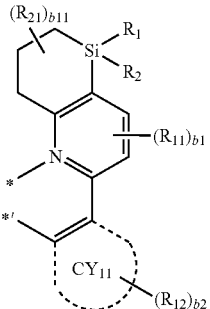
Formula 2(9)
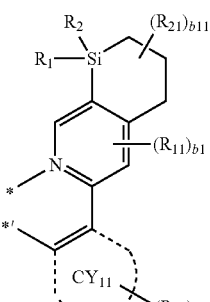
Formula 2(10)
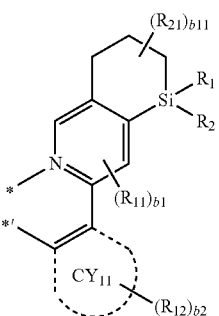
Formula 2(11)
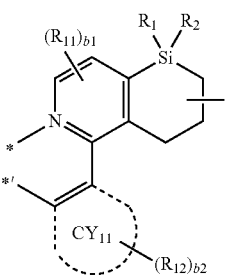
Formula 2(12)
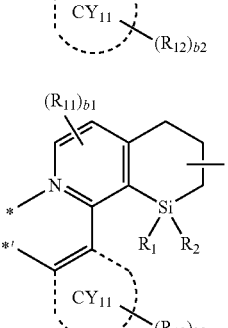

Formula 2(13)
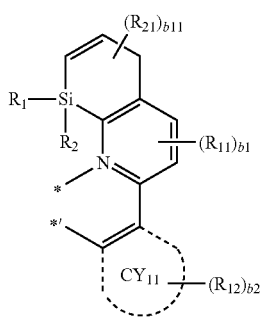
Formula 2(14)
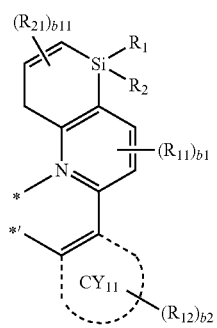
Formula 2(15)
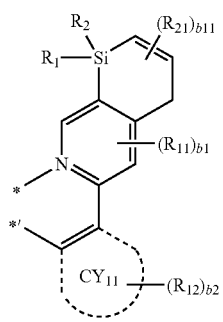
Formula 2(16)
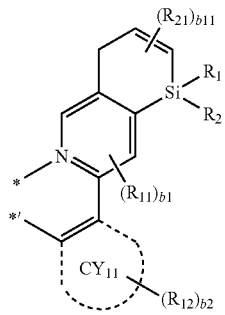
Formula 2(17)
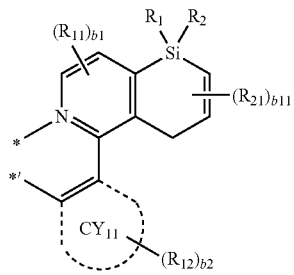
Formula 2(18)
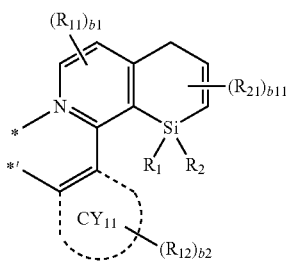
Formula 2(19)
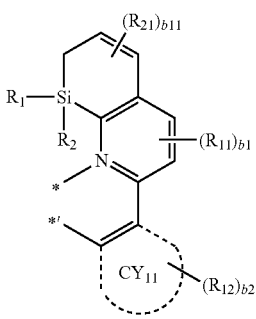
Formula 2(20)
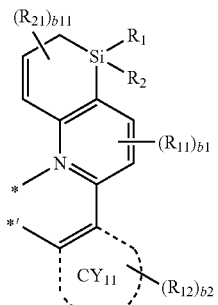
Formula 2(21)
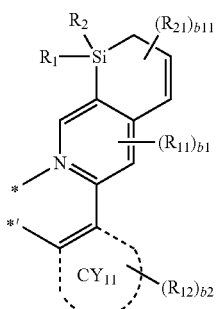
Formula 2(22)
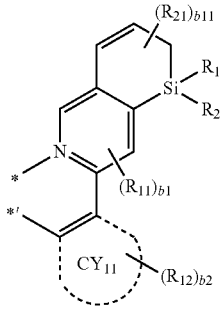

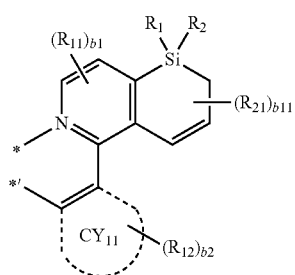
Formula 2(23)
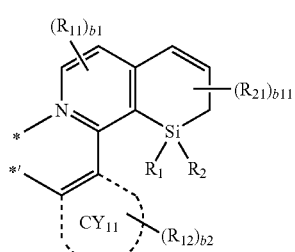
Formula 2(24)
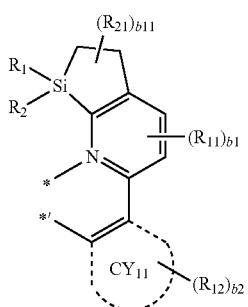
Formula 2(25)
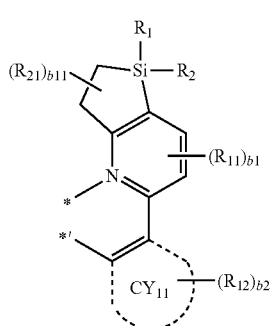
Formula 2(26)
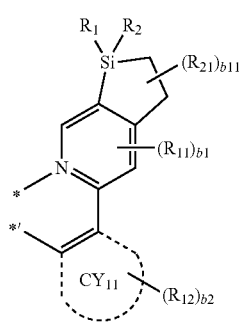
Formula 2(27)
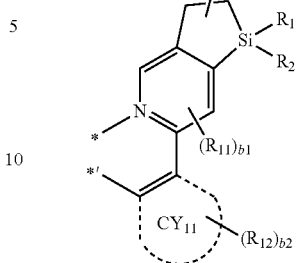
Formula 2(28)
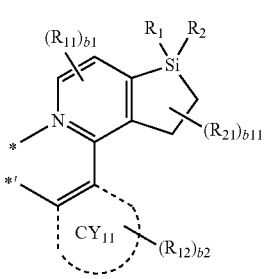
Formula 2(29)
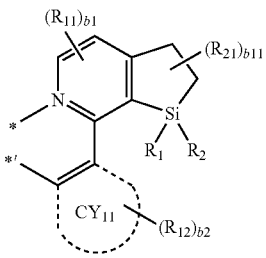
Formula 2(30)
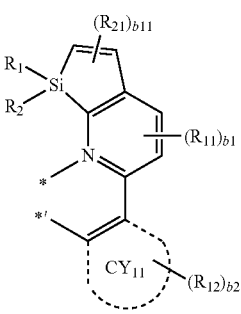
Formula 2(31)
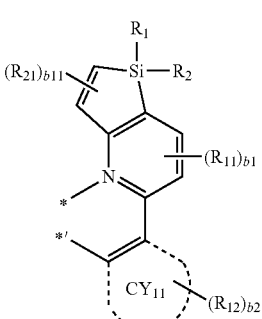
Formula 2(32)

-continued

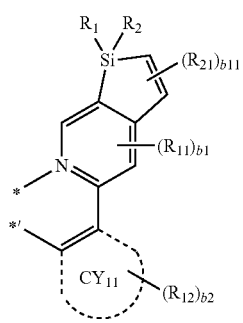

Formual 2(33)

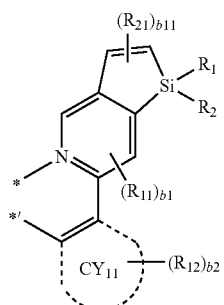

Formula 2(34)

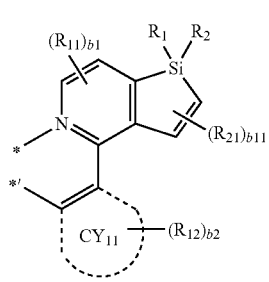

Formula 2(35)

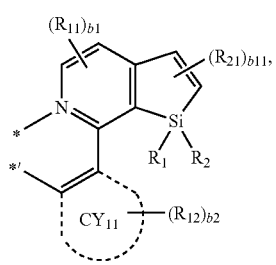

Formula 2(36)

wherein, in Formulae 2A(1) to 2(36),
$R_1$, $R_2$, $R_{11}$, $R_{12}$, b1, and b2 are the same as in claim 1,
$R_{21}$ is the same as $R_{11}$,
b11 is an integer selected from 0 to 6, and
each of * and *' indicates a binding site to M in Formula 1.

11. The organometallic compound of claim 10, wherein $L_1$ in Formula 1 is selected from groups represented by Formulae 2(3), 2(4), 2(6), 2(9), 2(12), 2(27), and 2(28), and
in Formulae 2(3), 2(4), 2(6), 2(9), 2(12), 2(27), and 2(28), $CY_{11}$ is a benzene or a naphthalene,
$R_{11}$, $R_{12}$, and $R_{21}$ are each independently selected from hydrogen, deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and
—B(Q$_6$)(Q$_7$) and —P(=O)(Q$_8$)(Q$_9$),
wherein Q$_6$ to Q$_9$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and
an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group and a phenyl group, and
$R_1$ and $R_2$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group.

12. The organometallic compound of claim 1, wherein $L_1$ in Formula 1 is selected from groups represented by Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10:

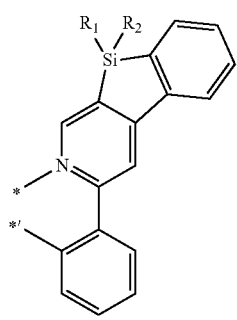

Formula 2A-1

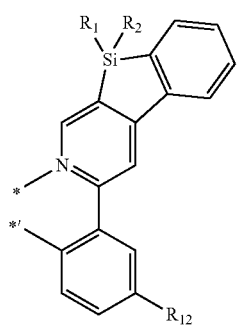

Formula 2A-2

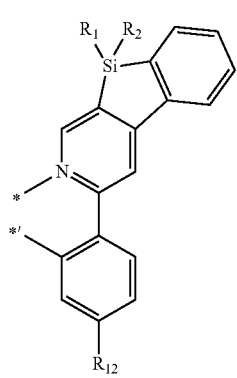

Formula 2A-3

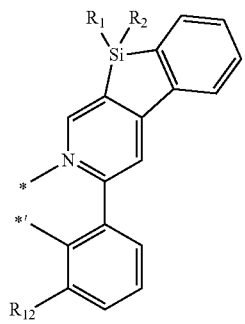

Formula 2A-4

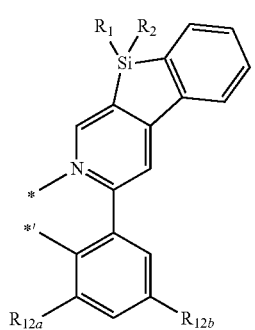

Formula 2A-5

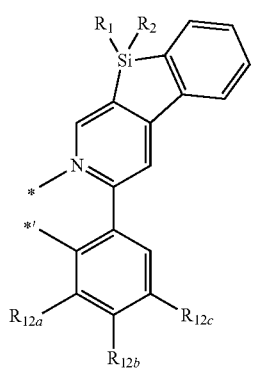

Formula 2A-6

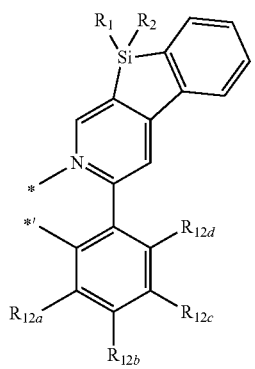

Formula 2A-7

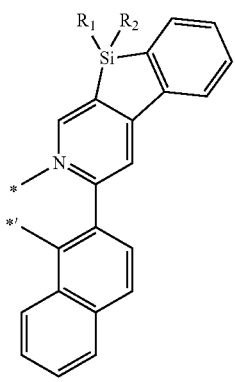
Formula 2A-8
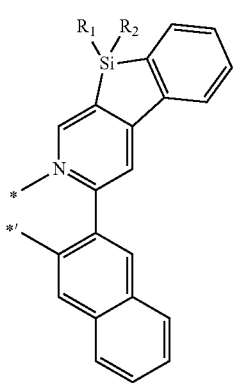
Formula 2A-9
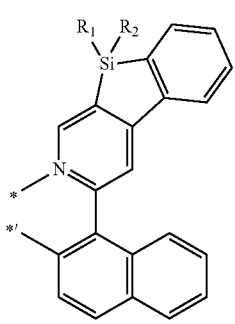
Formula 2A-10
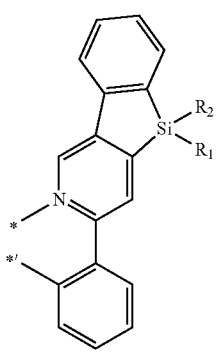
Formula 2B-1
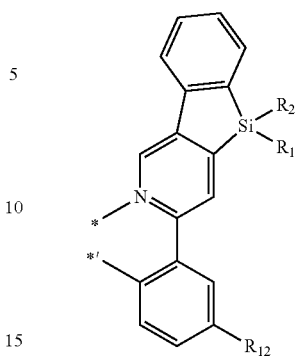
Formula 2B-2
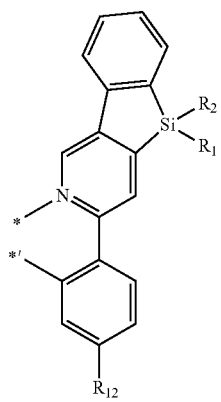
Formula 2B-3
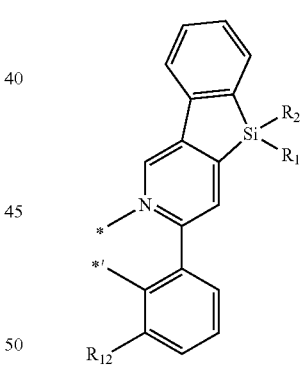
Formula 2B-4
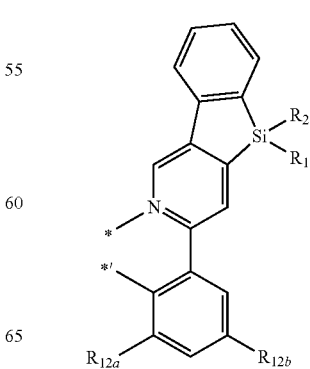
Formula 2B-5

227
-continued
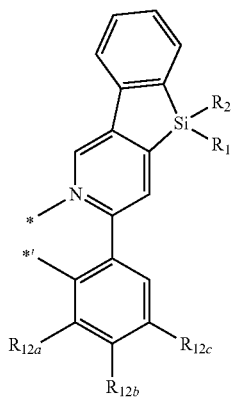
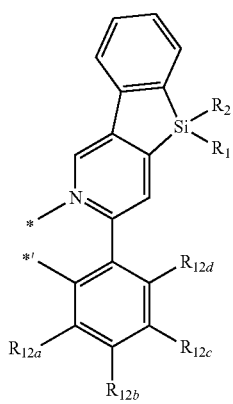
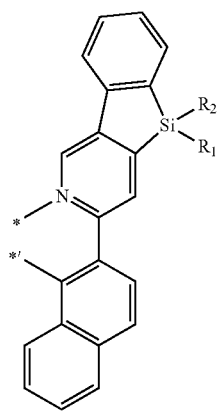
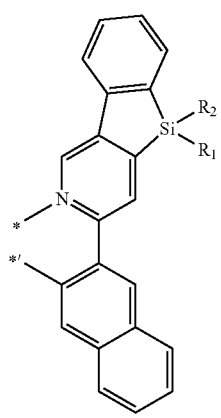
228
-continued
Formula 2B-6
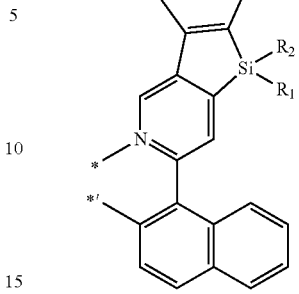
Formula 2B-7
Formula 2B-8
Formula 2B-9
Formula 2B-10
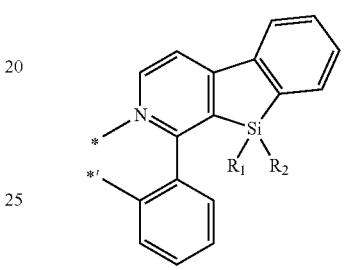
Formula 2C-1
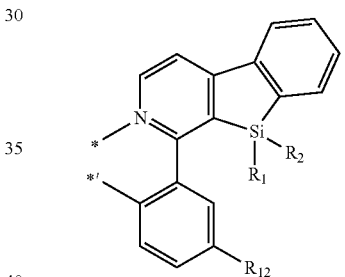
Formula 2C-2
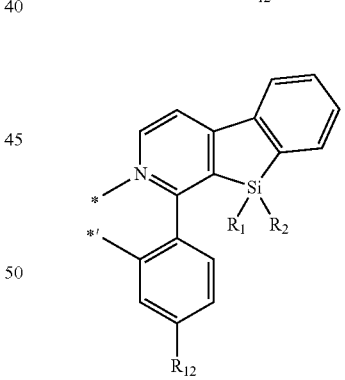
Formula 2C-3
Formula 2C-4
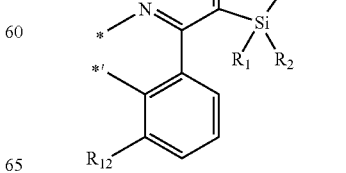

Formula 2C-5
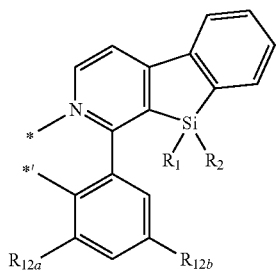
Formula 2C-6
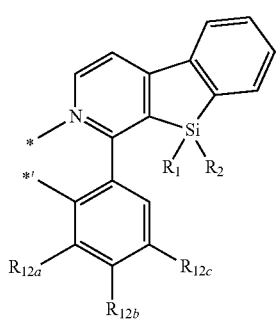
Formula 2C-7
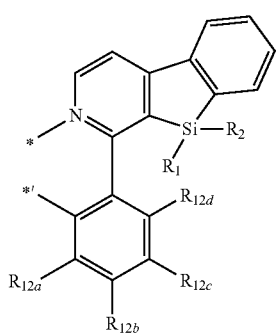
Formula 2C-8
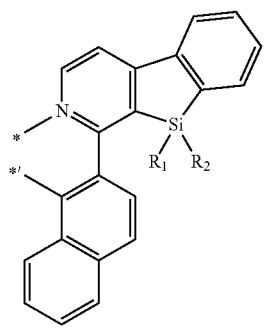
Formula 2C-9
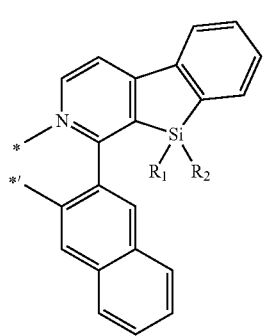
Formula 2C-10
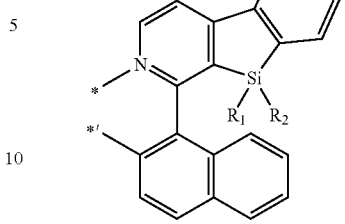
Formula 2D-1
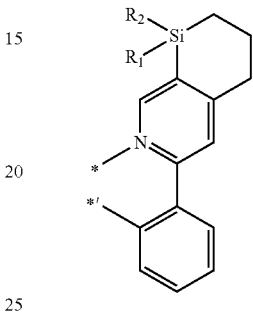
Formula 2D-2
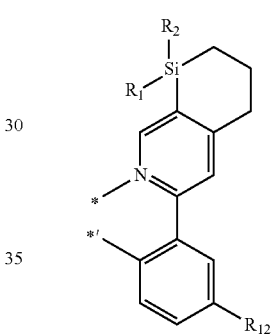
Formula 2D-3
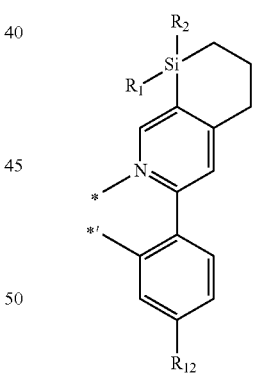
Formula 2D-4
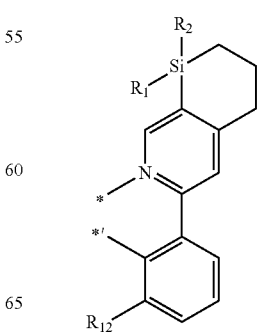

-continued
Formula 2D-5
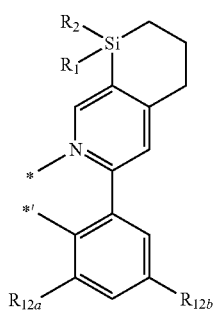
Formula 2D-6
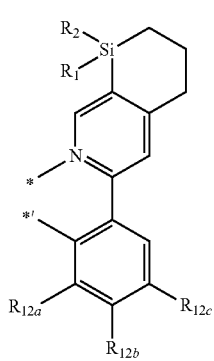
Formula 2D-7
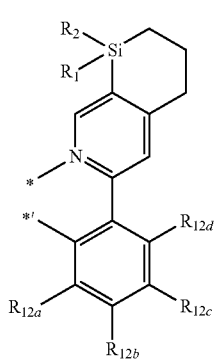
Formula 2D-8
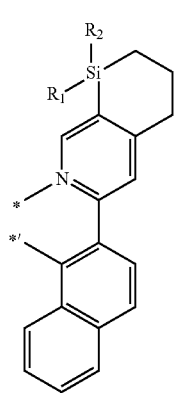
-continued
Formula 2D-9
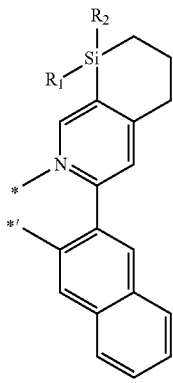
Formula 2D-10
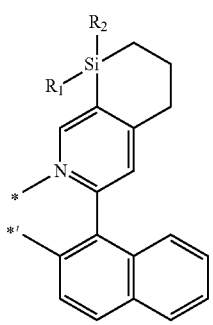
Formula 2E-1
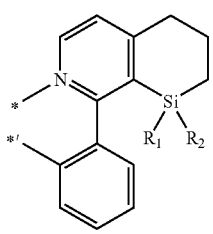
Formula 2E-2
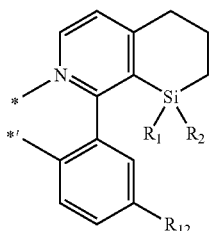
Formula 2E-3
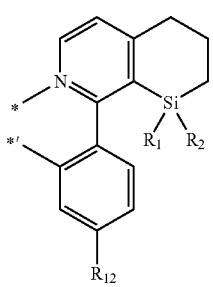

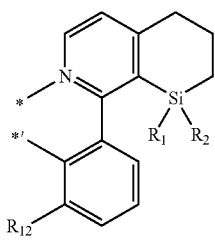
Formula 2E-4
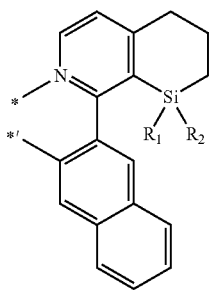
Formula 2E-9
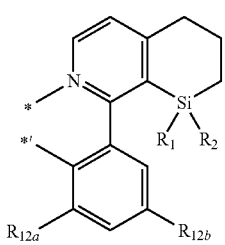
Formula 2E-5
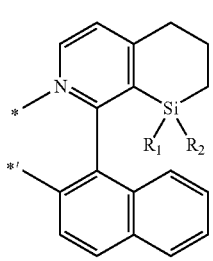
Formula 2E-10
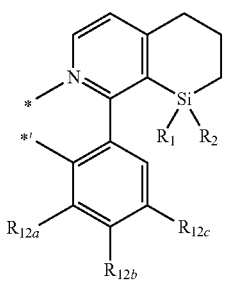
Formula 2E-6
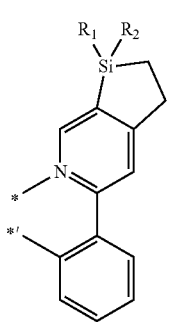
Formula 2F-1
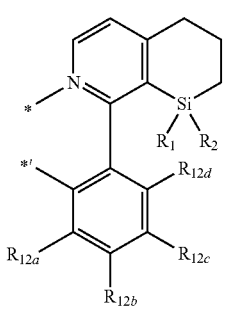
Formula 2E-7
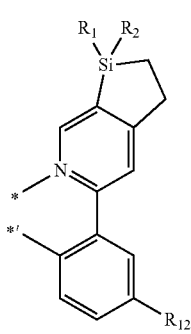
Formula 2F-2
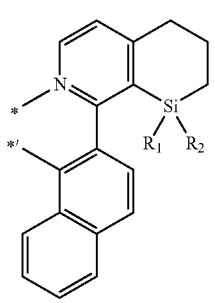
Formula 2E-8
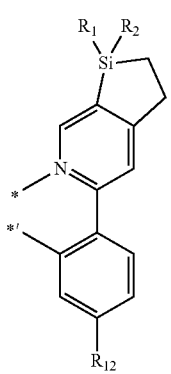
Formula 2F-3

-continued
Formula 2F-4
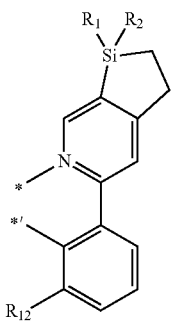
Formula 2F-5
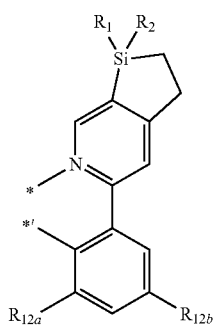
Formula 2F-6
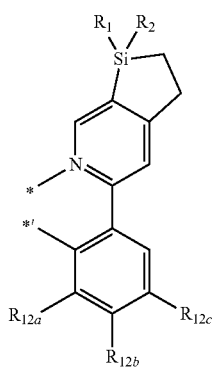
Formula 2F-7
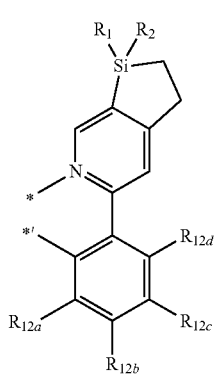
-continued
Formula 2F-8
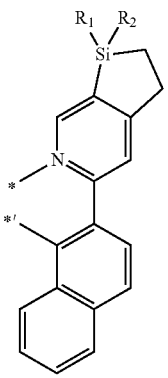
Formula 2F-9
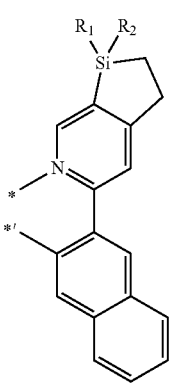
Formula 2F-10
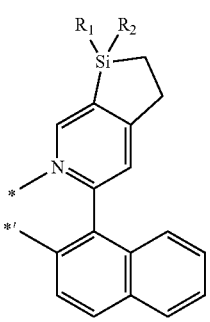
Formula 2G-1
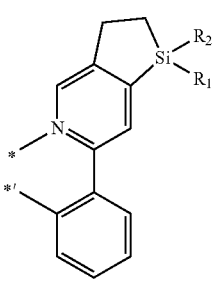
Formula 2G-2

-continued

Formula 2G-3
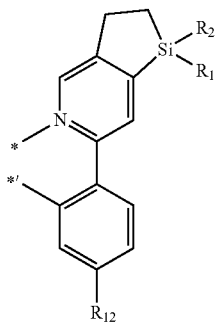

Formula 2G-4
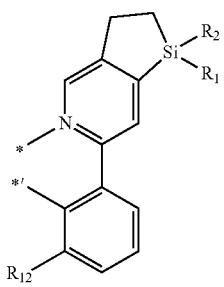

Formula 2G-5
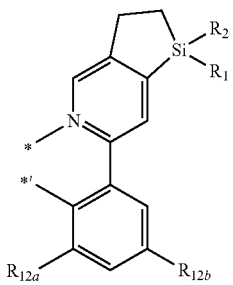

Formula 2G-6
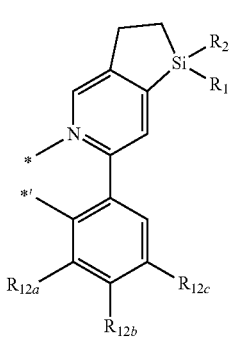

Formula 2G-7
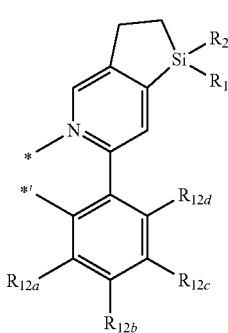

Formula 2G-8
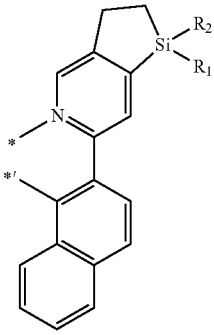

Formula 2G-9
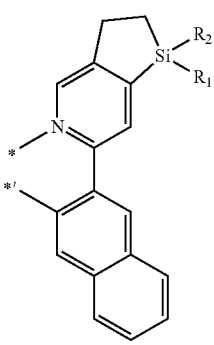

Formula 2G-10
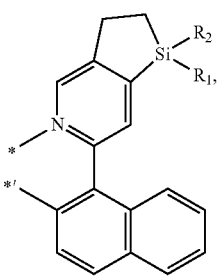

wherein, in Formulae 2A-1 to 2A-10, 2B-1 to 2B-10, 2C-1 to 2C-10, 2D-1 to 2D-10, 2E-1 to 2E-10, 2F-1 to 2F-10, and 2G-1 to 2G-10, $R_{12}$ and $R_{12a}$ to $R_{12d}$ are each independently selected from deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, $R_1$ and $R_2$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and —Si(Q$_1$)(Q$_2$)(Q$_3$); and an n-propyl group, an isopropyl group, an n-butyl group, an isobutyl group, a sec-butyl group, a tert-butyl group, an n-pentyl group, an isopentyl group, a sec-pentyl group, a tert-pentyl group, and a phenyl group, each substituted with at least one selected from deuterium and a C$_1$-C$_{10}$ alkyl group, wherein Q$_1$ to Q$_3$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group, and each of * and *' indicates a binding site to M in Formula 1:

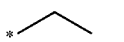
Formula 9-1

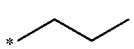
Formula 9-2

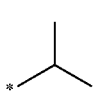
Formula 9-3

Formula 9-4

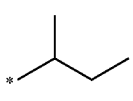
Formula 9-5

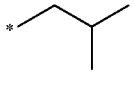
Formula 9-6

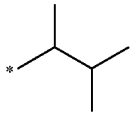
Formula 9-7

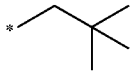
Formula 9-8

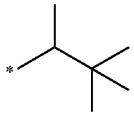
Formula 9-9

Formula 9-10

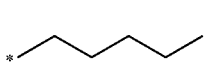
Formula 9-11

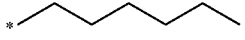
Formula 9-12

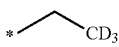
Formula 9-13

-continued

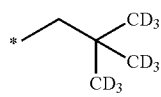
Formula 9-14

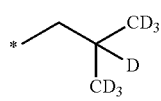
Formula 9-15

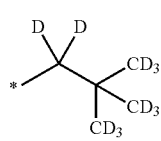
Formula 9-16

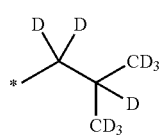
Formula 9-17

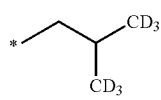
Formula 9-18

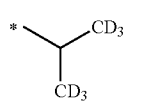
Formula 9-19

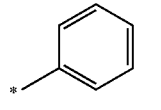
Formula 10-1

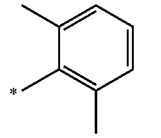
Formula 10-2

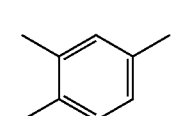
Formula 10-3

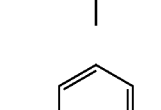
Formula 10-4

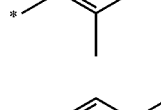
Formula 10-5

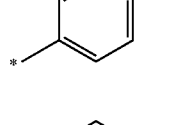
Formula 10-6

-continued
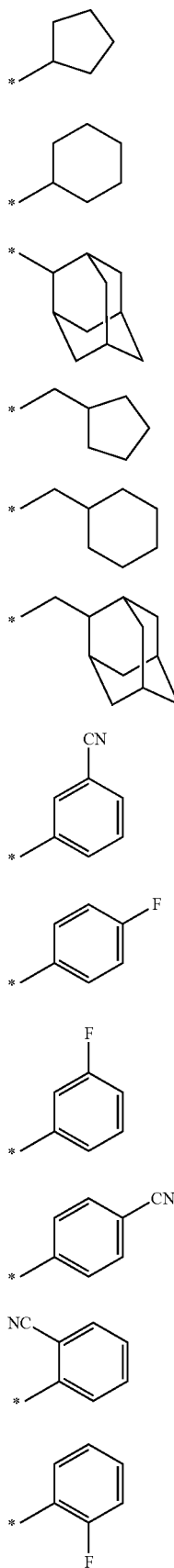
Formula 10-7
Formula 10-8
Formula 10-9
Formula 10-10
Formula 10-11
Formula 10-12
Formula 10-13
Formula 10-14
Formula 10-15
Formula 10-16
Formula 10-17
Formula 10-18
Formula 10-19
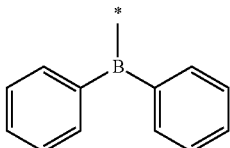
Formula 10-20
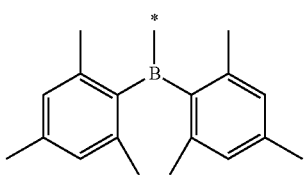
Formula 10-21
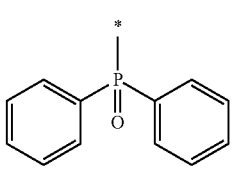
Formula 10-22
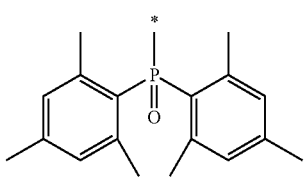
Formula 10-23
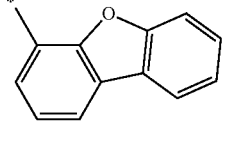
Formula 10-24
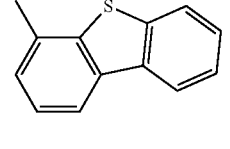
Formula 10-25
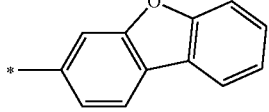
Formula 10-26
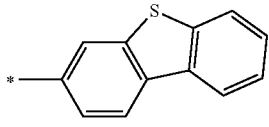
Formula 10-27
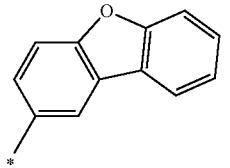

243
-continued

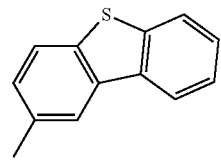
Formula 10-28

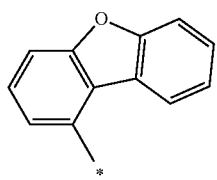
Formula 10-29

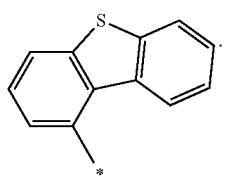
Formula 10-30

13. The organometallic compound of claim 1, wherein $L_2$ in Formula 1 is selected from ligands represented by Formulae 3A to 3G:

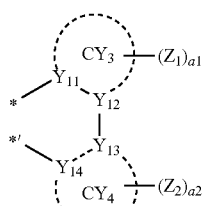
Formula 3A

Formula 3B $$* — C \equiv C — R_{31}$$
Formula 3C

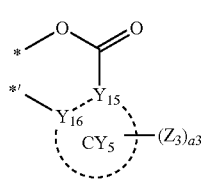
Formula 3D

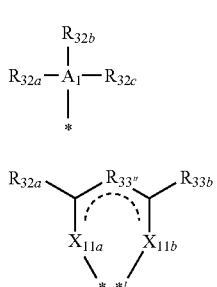
Formula 3E

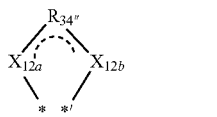
Formula 3F

244
-continued

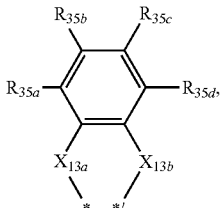
Formula 3G wherein, in Formulae 3A to 3G, $Y_{11}$ to $Y_{16}$ are each independently C or N, $Y_{11}$ and $Y_{12}$ are connected to each other via a single bond or a double bond, $Y_{13}$ and $Y_{14}$ are connected to each other via a single bond or a double bond, $Y_{15}$ and $Y_{16}$ are connected to each other via a single bond or a double bond, $CY_3$ to $CY_5$ are each independently selected from a $C_5$-$C_{60}$ carbocyclic group and a $C_2$-$C_{60}$ heterocyclic group, a1 to a3 are each independently an integer selected from 1 to 5, $A_1$ is P or As, $X_{11a}$, $X_{11b}$, $X_{12a}$, $X_{12b}$, $X_{13a}$, and $X_{13b}$ are each independently selected from N, O, N($R_{34}$), P($R_{35}$)($R_{36}$), and As($R_{37}$)($R_{38}$), provided that $X_{12a}$, $X_{12b}$, $X_{13a}$, and $X_{13b}$ are neither N nor O, $R_{33''}$ and $R_{34''}$ are each independently selected from a single bond, a double bond, a substituted or unsubstituted $C_1$-$C_5$ alkylene group, a substituted or unsubstituted $C_2$-$C_5$ alkenylene group, and a substituted or unsubstituted $C_6$-$C_{10}$ arylene group, $Z_1$ to $Z_3$, $R_{31}$, $R_{32a}$, $R_{32b}$, $R_{32c}$, $R_{33a}$, $R_{33b}$, $R_{34}$ to $R_{38}$, $R_{35a}$, $R_{35b}$, $R_{35c}$, and $R_{35d}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), —B($Q_6$)($Q_7$), and —P(=O)($Q_8$)($Q_9$), each of * and *' indicates a binding site to M in Formula 1, wherein at least one of substituents of the substituted $C_1$-$C_5$ alkylene group, substituted $C_2$-$C_5$ alkenylene group, substituted $C_6$-$C_{10}$ arylene group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), and —P(=O)($Q_{28}$)($Q_{29}$); and —Si($Q_{31}$)($Q_{32}$)($Q_{33}$), —N($Q_{34}$)($Q_{35}$), —B($Q_{36}$)($Q_{37}$), and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

14. The organometallic compound of claim 13, wherein $L_2$ is selected from ligands represented by Formulae 3A, 3B, and 3F, $Y_{11}$ in Formula 3A is N, $Y_{12}$ to $Y_{14}$ in Formula 3A are C, $CY_3$ in Formula 3A is selected from a pyridine, a 5,6,7,8-tetrahydroquinoline, a 5,6,7,8-tetrahydroisoquinoline, a quinoline, and an isoquinoline, $CY_4$ in Formula 3A is selected from a benzene, a 1,2,3,4-tetrahydronaphthalene, a naphthalene, a fluorene, a dibenzofuran, a dibenzothiophene, a benzofuropyridine, and a benzothienopyridine, $Y_{15}$ in Formula 3B is C, $Y_{16}$ in Formula 3B is N, $CY_5$ in Formula 3B is a pyridine or a pyrimidine, $Z_1$ to $Z_3$ in Formulae 3A and 3B are each independently selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$Si(Q_1)(Q_2)(Q_3)$, —$N(Q_4)(Q_5)$, —$B(Q_6)(Q_7)$ and —$P(=O)(Q_8)(Q_9)$, a1 to a3 are each independently an integer selected from 0 to 4, from among groups $Z_1$ in the number of a1, groups $Z_2$ in the number of a2, and groups $Z_3$ in the number of a3, two or more neighboring substituents are optionally combined with each other to form a $C_5$-$C_{30}$ carbocyclic group or $C_2$-$C_{30}$ heterocyclic group, wherein $Q_1$ to $Q_9$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium and a $C_1$-$C_{10}$ alkyl group, each of $X_{12a}$ and $X_{12b}$ in Formula 3F are O, $R_{34''}$ in Formula 3F is selected from a $C_2$-$C_5$ alkenylene group; and a $C_2$-$C_5$ alkenylene group, substituted with at least one selected from deuterium, a $C_1$-$C_{10}$ alkyl group, a $C_1$-$C_{10}$ alkoxy group, and a phenyl group.

15. The organometallic compound of claim 1, wherein $L_2$ in Formula 1 is selected from ligands represented by Formulae 3-1(1) to 3-1(60), 3-1(61) to 3-1(69), 3-1(71) to 3-1(79), 3-1(81) to 3-1(88), 3-1(91) to 3-1(98), 3-111, and 3-112:

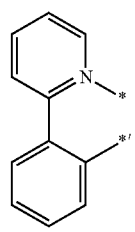

Formula 3-1(1)

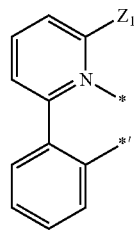

Formula 3-1(2)

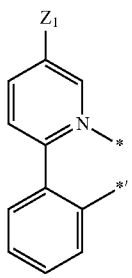
Formula 3-1(3)
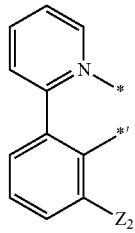
Formula 3-1(9)
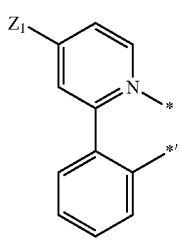
Formula 3-1(4)
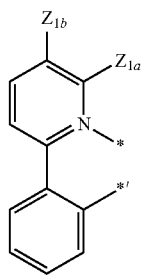
Formula 3-1(10)
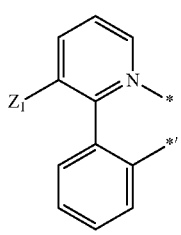
Formula 3-1(5)
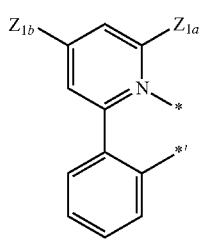
Formula 3-1(11)
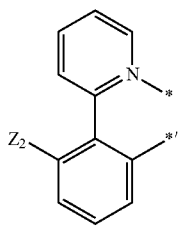
Formula 3-1(6)
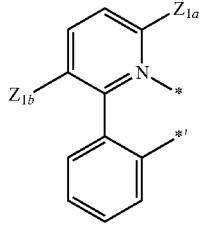
Formula 3-1(12)
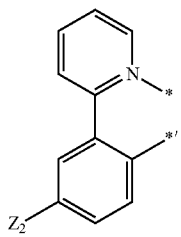
Formula 3-1(7)
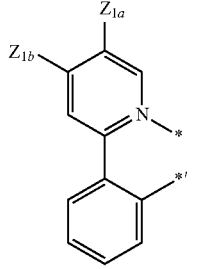
Formula 3-1(13)
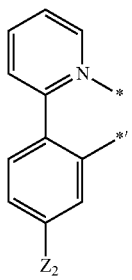
Formula 3-1(8)
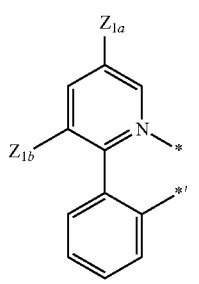
Formula 3-1(14)

Formula 3-1(15)
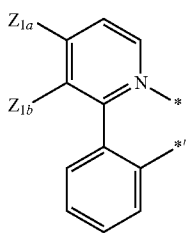
Formula 3-1(16)
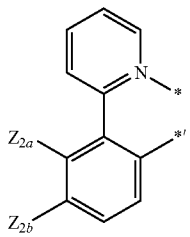
Formula 1-3(17)
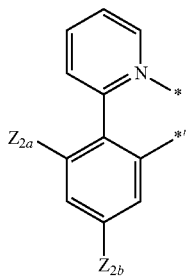
Formula 1-3(18)
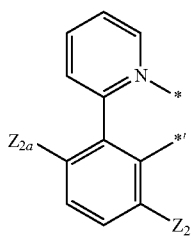
Formula 3-1(19)
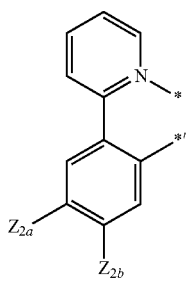
Formula 3-1(20)
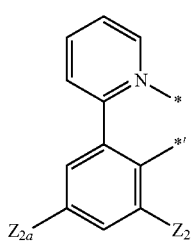
Formula 3-1(21)
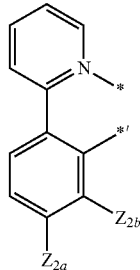
Formula 3-1(22)
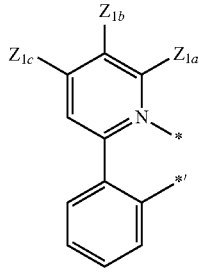
Formula 3-1(23)
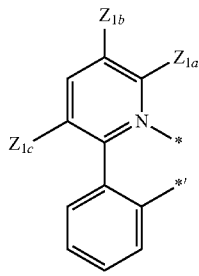
Formula 3-1(24)
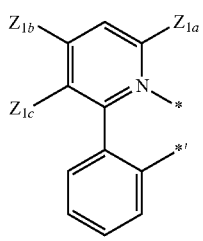
Formula 3-1(25)
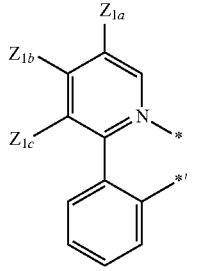
Formula 3-1(26)
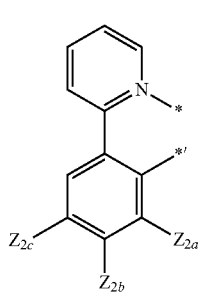

-continued
Formula 3-1(27)
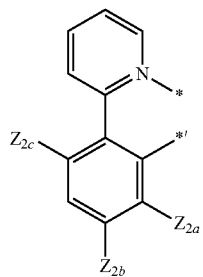
Formula 3-1(28)
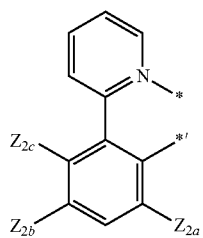
Formula 3-1(29)
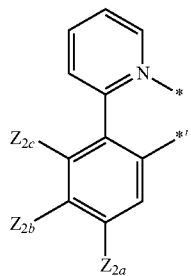
Formula 3-1(30)
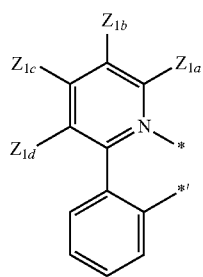
Formula 3-1(31)
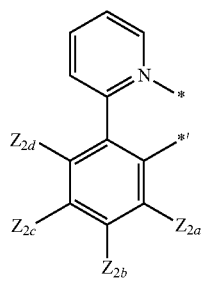
Formula 3-1(32)
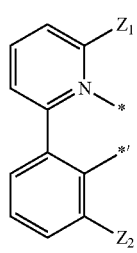
-continued
Formula 3-1(33)
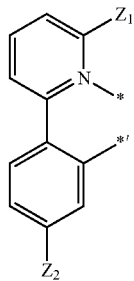
Formula 3-1(34)
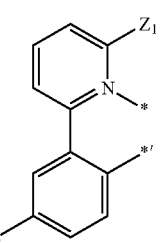
Formula 3-1(35)
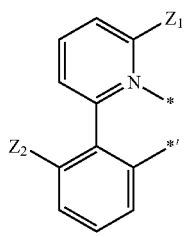
Formula 3-1(36)
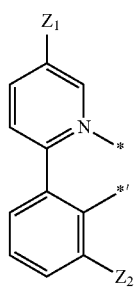
Formula 3-1(37)
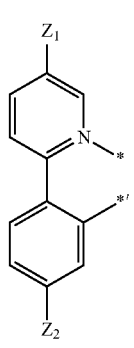

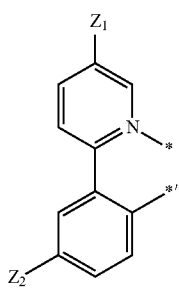
Formula 3-1(38)
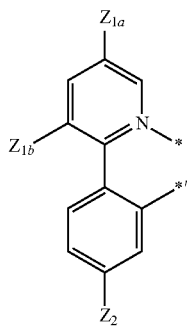
Formula 3-1(44)
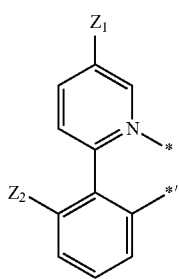
Formula 3-1(39)
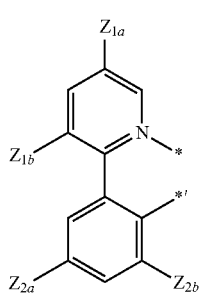
Formula 3-1(45)
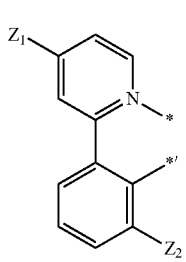
Formula 3-1(40)
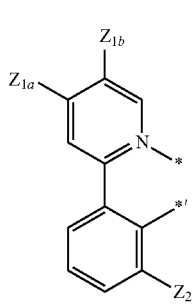
Formula 3-1(46)
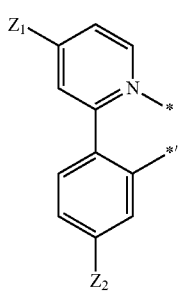
Formula 3-1(41)
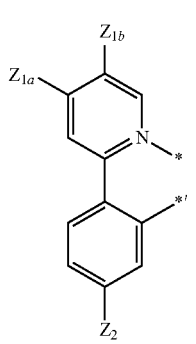
Formula 3-1(47)
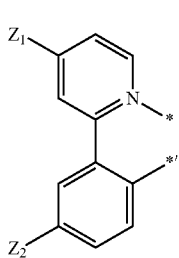
Formula 3-1(42)
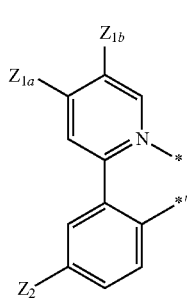
Formula 3-1(48)
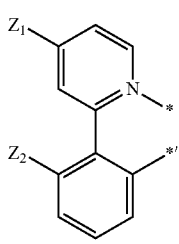
Formula 3-1(43)
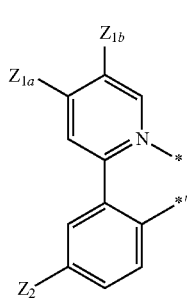

Formula 3-1(49)
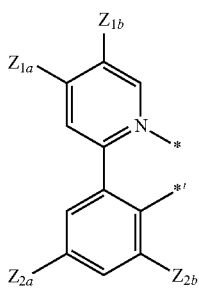
Formula 3-1(50)
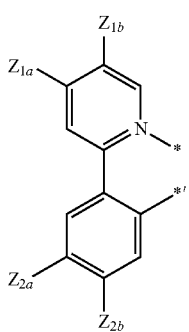
Formula 3-1(51)
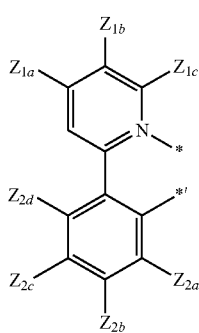
Formula 3-1(52)
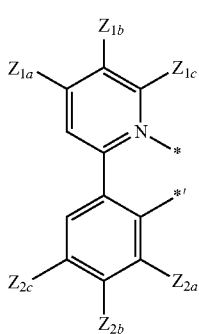
Formula 3-1(53)
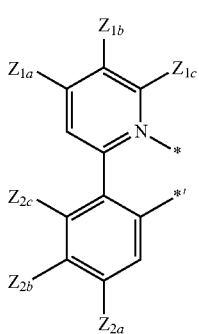
Formula 3-1(54)
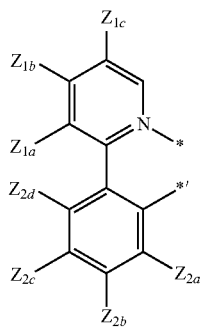
Formula 3-1(55)
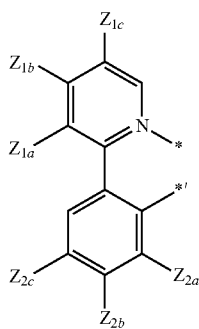
Formula 3-1(56)
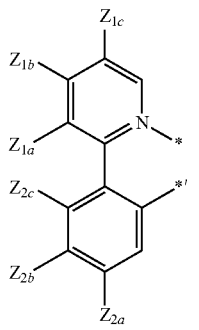
Formula 3-1(57)
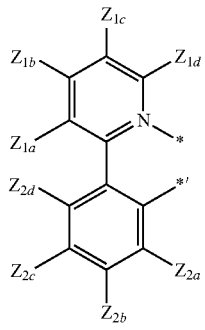
Formula 3-1(58)
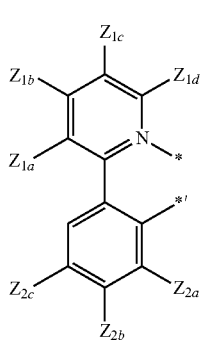

-continued
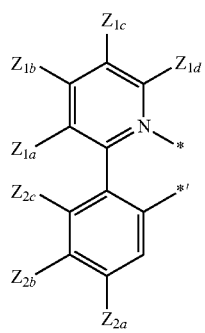
Formula 3-1(59)
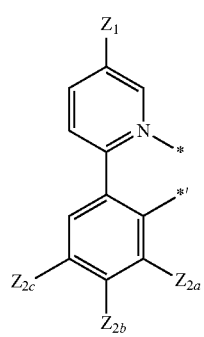
Formula 3-1(60)
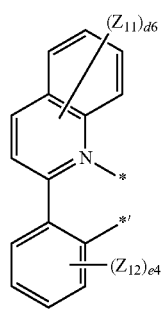
Formula 3-1(61)
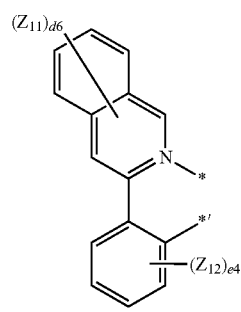
Formula 3-1(62)
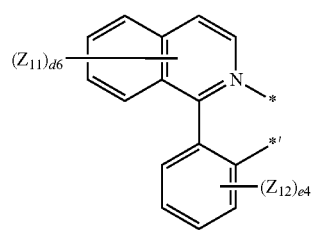
Formula 3-1(63)
-continued
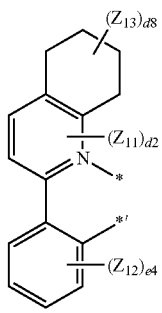
Formula 3-1(64)
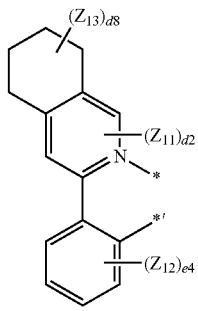
Formula 3-1(65)
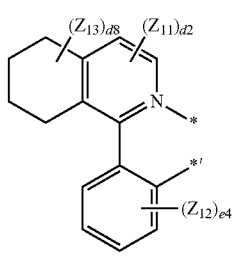
Formula 3-1(66)
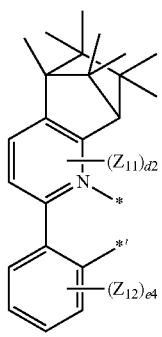
Formula 3-1(67)
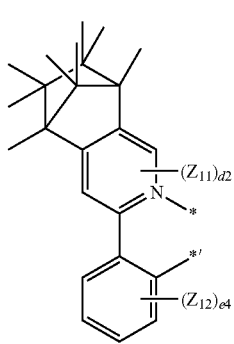
Formula 3-1(68)

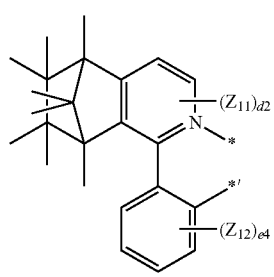
Formula 3-1(69)
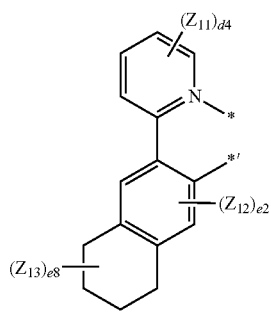
Formula 3-1(75)
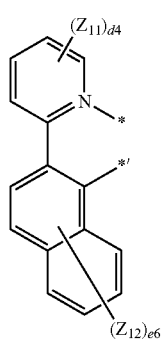
Formula 3-1(71)
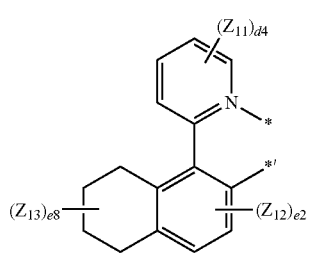
Formula 3-1(76)
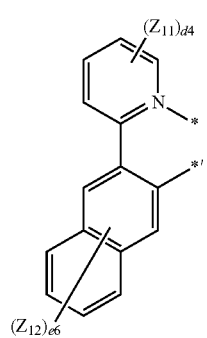
Formula 3-1(72)
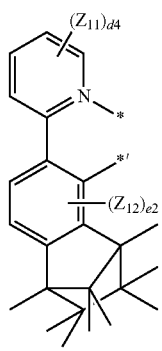
Formula 3-1(77)
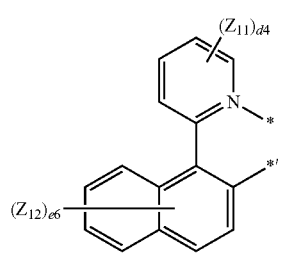
Formula 3-1(73)
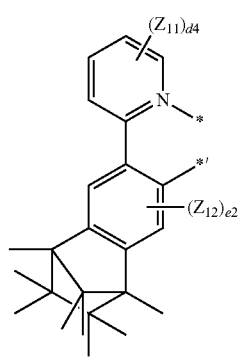
Formula 3-1(78)
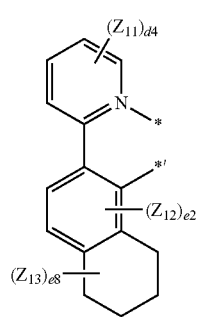
Formula 3-1(74)
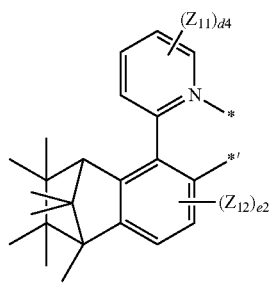
Formula 3-1(79)

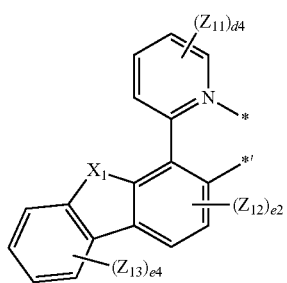
Formula 3-1(81)
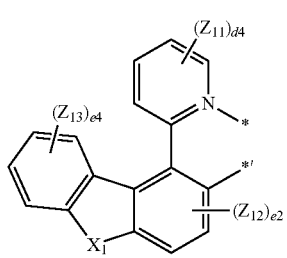
Formula 3-1(82)
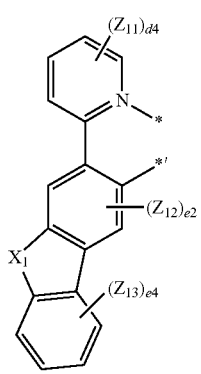
Formula 3-1(83)
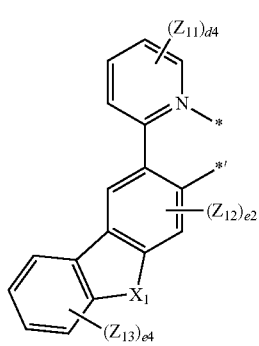
Formula 3-1(84)
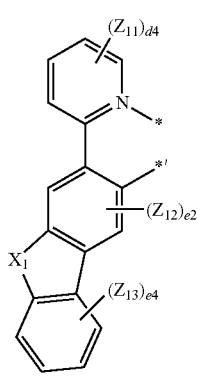
Formula 3-1(85)
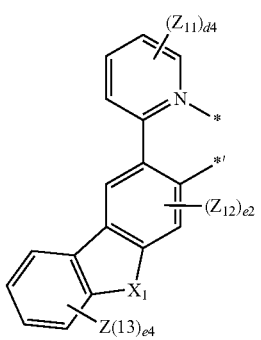
Formula 3-1(86)
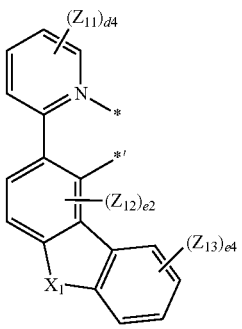
Formula 3-1(87)
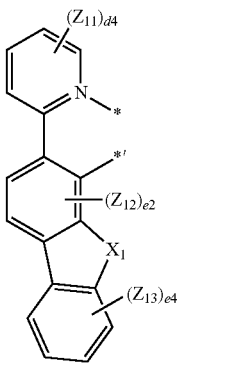
Formula 3-1(88)
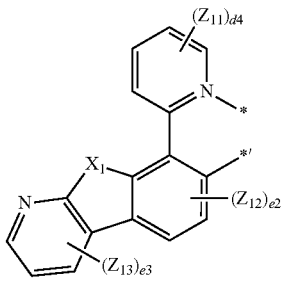
Formula 3-1(91)
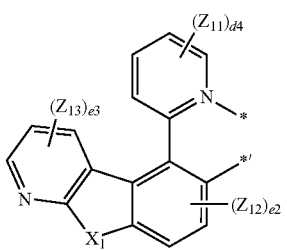
Formula 3-1(92)

Formula 3-1(93)

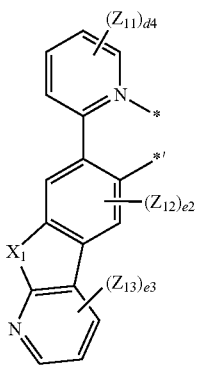

Formula 3-1(94)

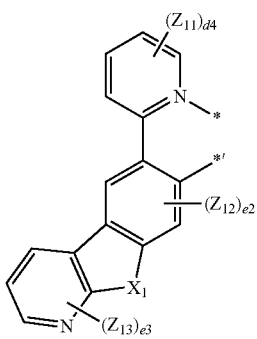

Formula 3-1(95)

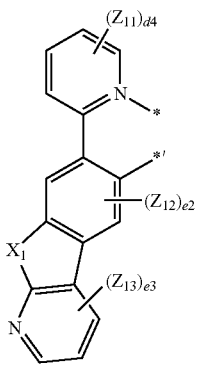

Formula 3-1(96)

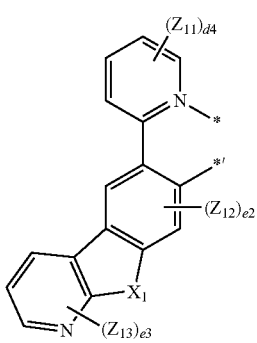

Formula 3-1(97)

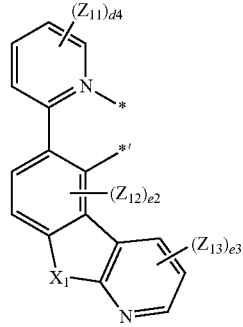

Formula 3-1(98)

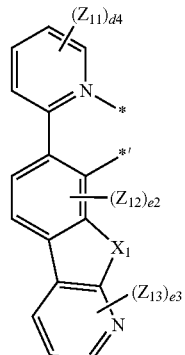

Formula 3-111

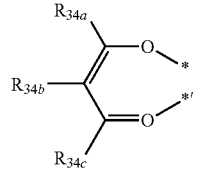

Formula 3-112

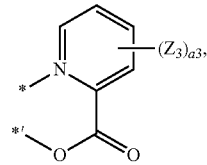

wherein, in Formulae 3-1(1) to 3-1(60), 3-1(61) to 3-1(69), 3-1(71) to 3-1(79), 3-1(81) to 3-1(88), 3-1(91) to 3-1(98), 3-111, and 3-112, $Z_1$, $Z_2$, $Z_{1a}$, $Z_{1b}$, $Z_{1c}$, $Z_{1d}$, $Z_{2a}$, $Z_{2b}$, $Z_{2c}$, $Z_{2d}$, $R_{34a}$, $R_{34b}$, and $R_{34c}$ are each independently selected from deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_1$)(Q$_2$)(Q$_3$), —N(Q$_4$)(Q$_5$), —B(Q$_6$)(Q$_7$), —P(=O)(Q$_8$)(Q$_9$), groups represented by Formulae 9-1 to 9-19, and groups represented by Formulae 10-1 to 10-30, $X_1$ is O, S, a C($Z_{21}$)($Z_{22}$), or N($Z_{23}$), $Z_3$, $Z_{11}$ to $Z_{13}$, and $Z_{21}$ to $Z_{23}$ are each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, —Si(Q$_1$)(Q$_2$)(Q$_3$), —N(Q$_4$)(Q$_5$), —B(Q$_6$)(Q$_7$), —P(=O)(Q$_8$)(Q$_9$), groups represented by Formulae 9-1 to 9-19, and groups represented by Formulae 10-1 to 10-30, wherein $Q_1$ to $Q_9$ are each independently selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from a deuterium and a C$_1$-C$_{10}$ alkyl group, d2 and e2 are each independently 0 or 2, e3 is an integer selected from 0 to 3, d4 and e4 are each independently an integer selected from 0 to 4, d6 and e6 are each independently an integer selected from 0 to 6, d8 and e8 are each independently an integer selected from 0 to 8, and each of * and *' indicates a binding site to M in Formula 1:

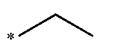

Formula 9-1

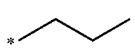

Formula 9-2

Formula 9-3

Formula 9-4

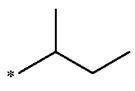

Formula 9-5

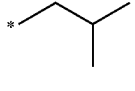

Formula 9-6

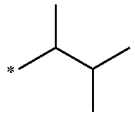

Formula 9-7

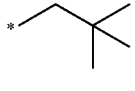

Formula 9-8

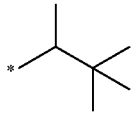

Formula 9-9

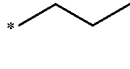

Formula 9-10

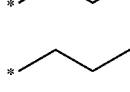

Formula 9-11

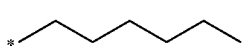

Formula 9-12

-continued

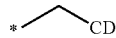

Formula 9-13

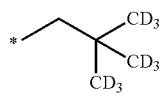

Formula 9-14

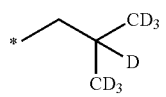

Formula 9-15

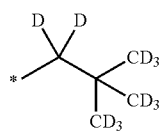

Formula 9-16

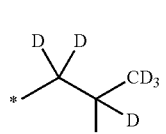

Formula 9-17

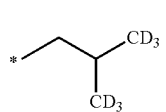

Formula 9-18

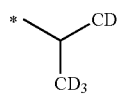

Formula 9-19

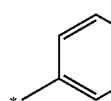

Formula 10-1

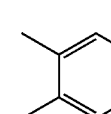

Formula 10-2

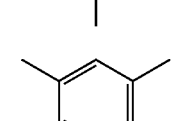

Formula 10-3

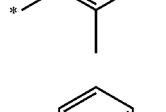

Formula 10-4

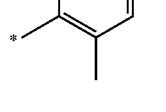

Formula 10-5

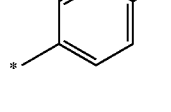

Formula 10-6

-continued
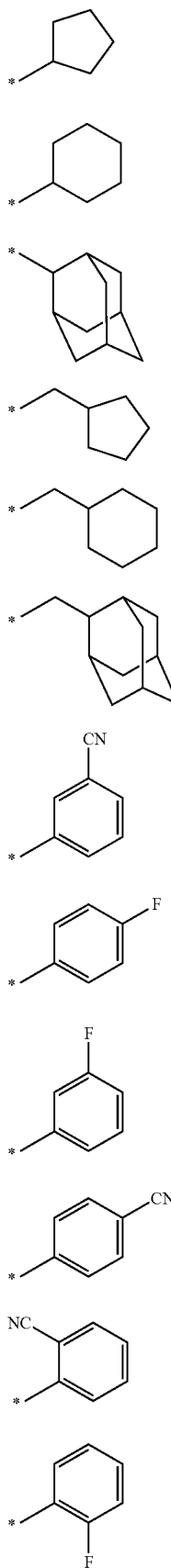
Formula 10-7
Formula 10-8
Formula 10-9
Formula 10-10
Formula 10-11
Formula 10-12
Formula 10-13
Formula 10-14
Formula 10-15
Formula 10-16
Formula 10-17
Formula 10-18
Formula 10-19
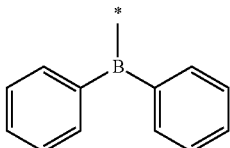
Formula 10-20
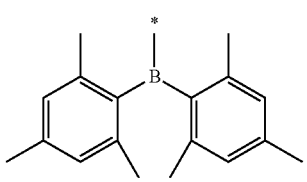
Formula 10-21
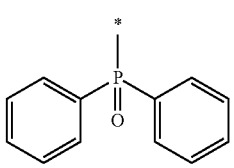
Formula 10-22
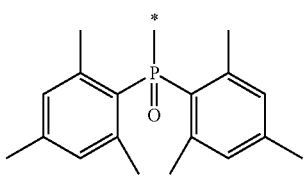
Formula 10-23
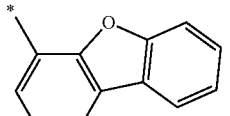
Formula 10-24
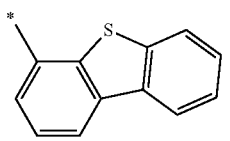
Formula 10-25
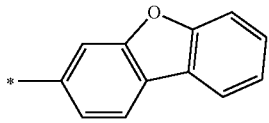
Formula 10-26
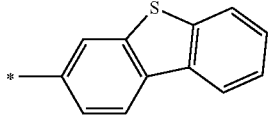
Formula 10-27
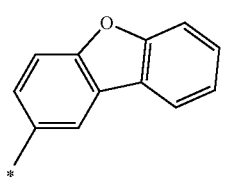

Formula 10-28
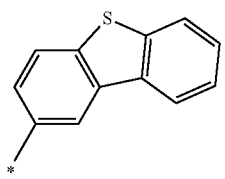
Formula 10-29
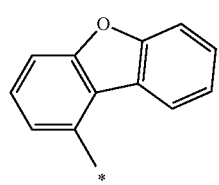
Formula 10-30
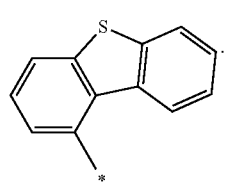
16. The organometallic compound of claim 1, wherein the organometallic compound is selected from Compounds 1 to 270:
1
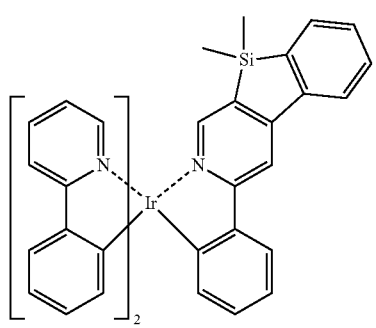
2
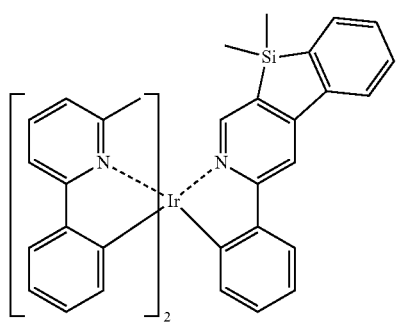
3
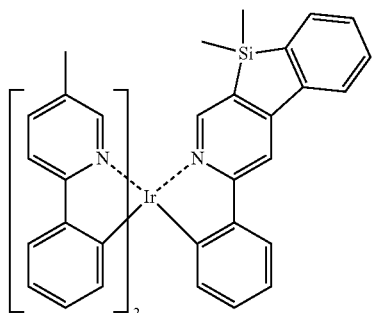
4
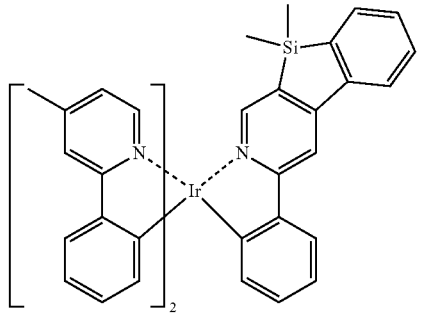
5
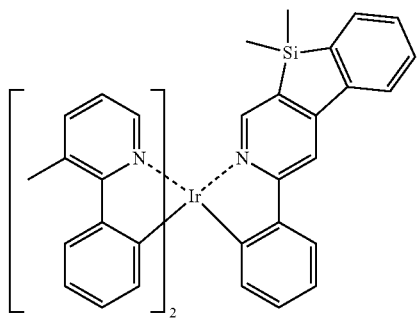
6
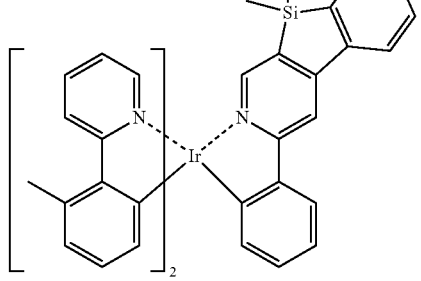
7
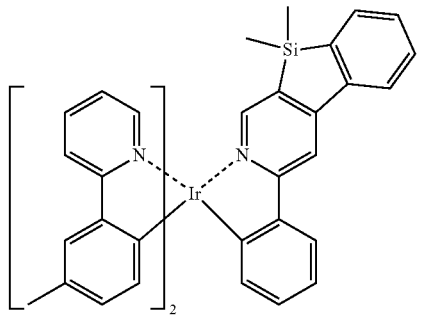

-continued
8
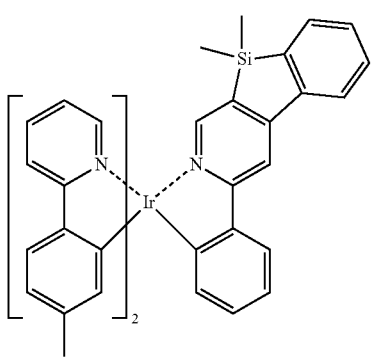
9
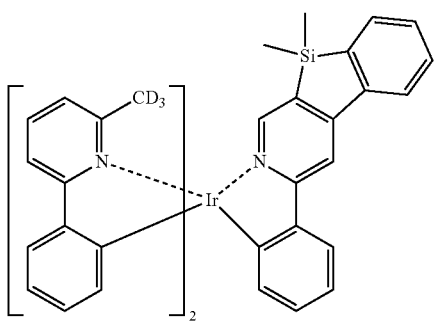
10
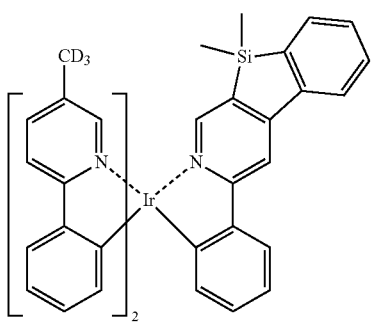
11
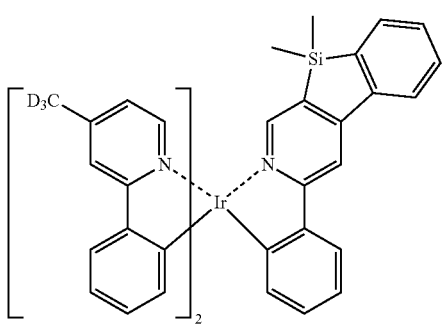
12
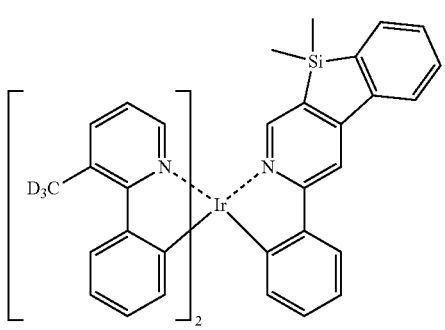
-continued
13
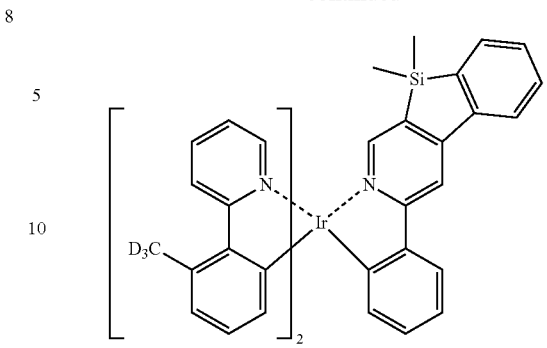
14
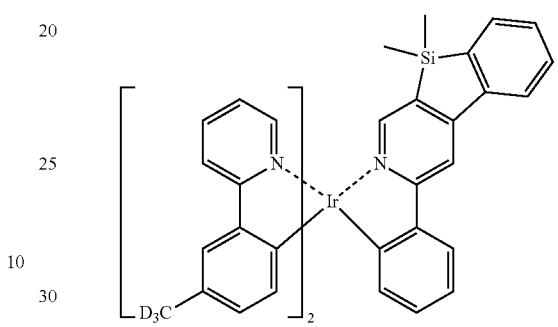
15
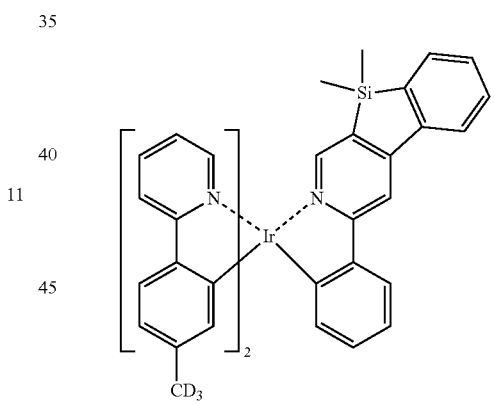
16
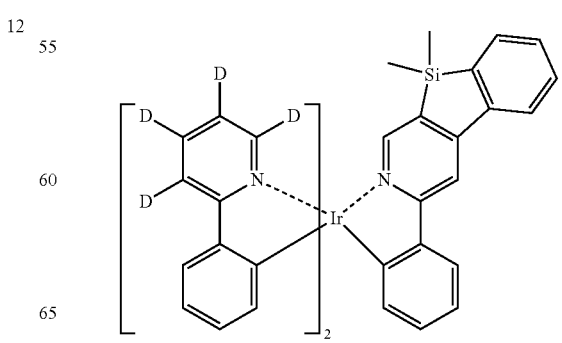

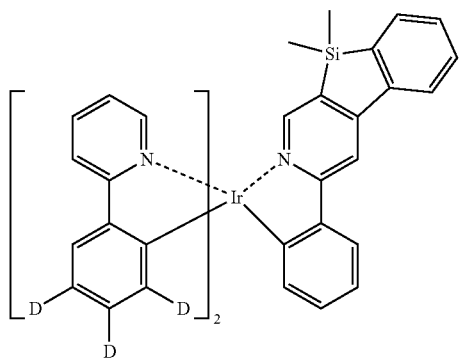
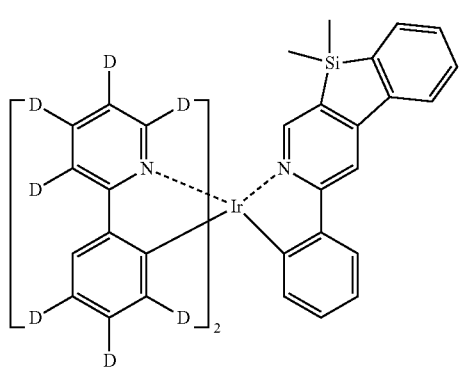
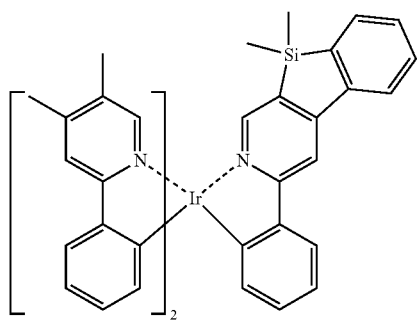
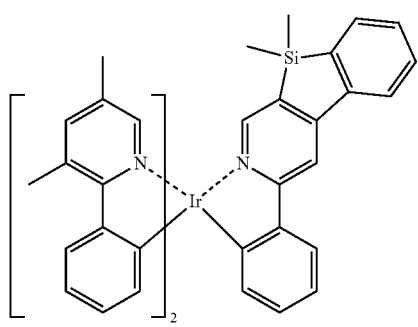
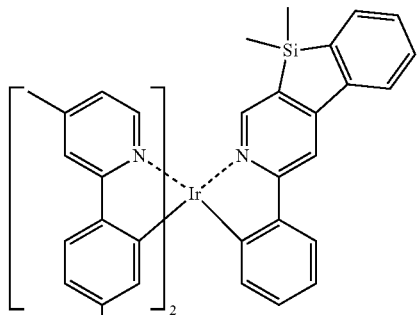
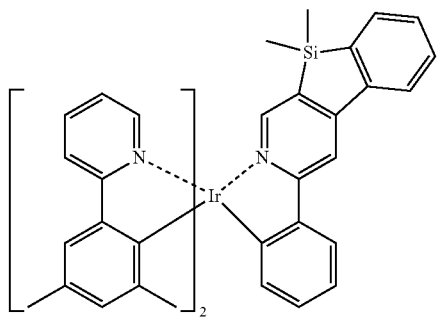
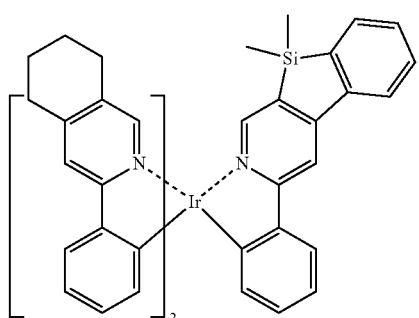
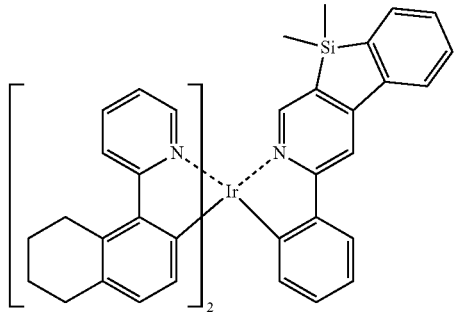
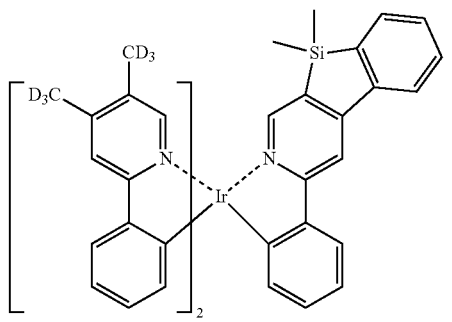

26
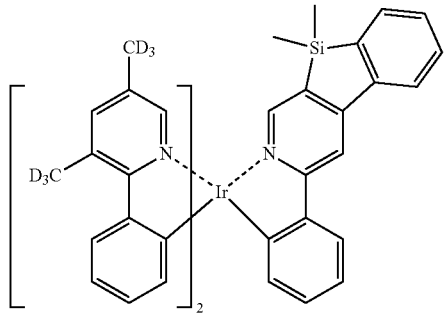
27
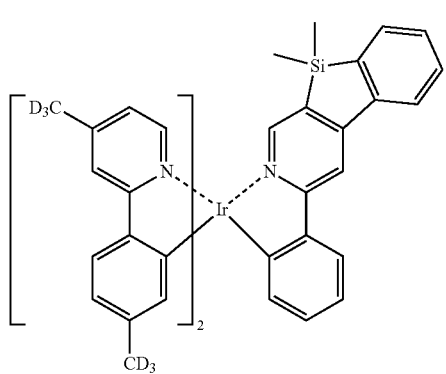
28
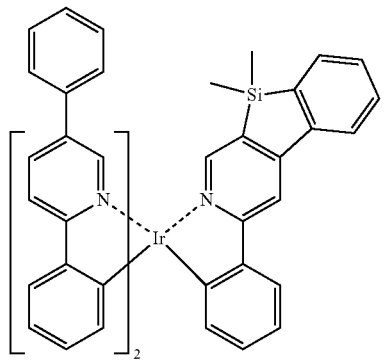
29
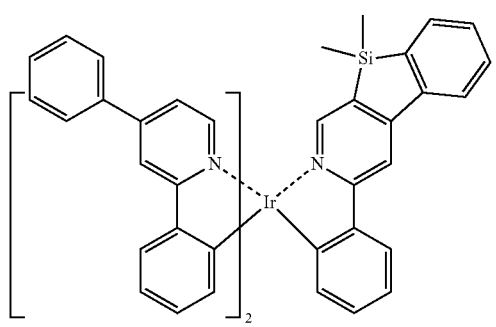
30
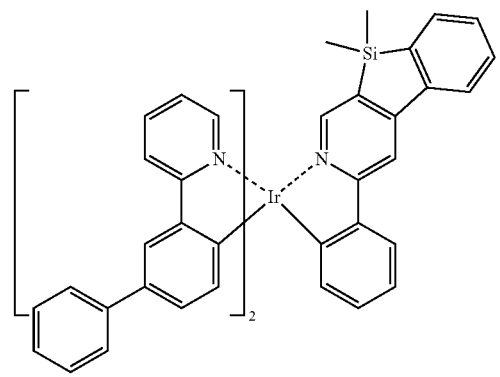
31
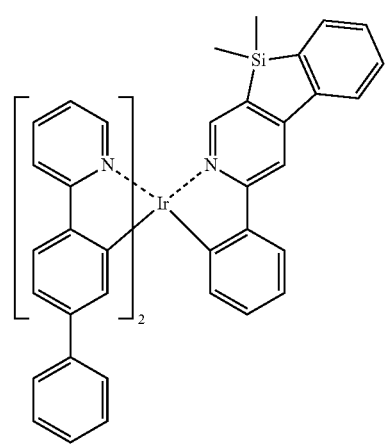
32
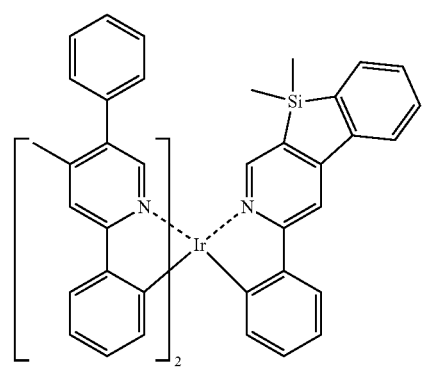
33
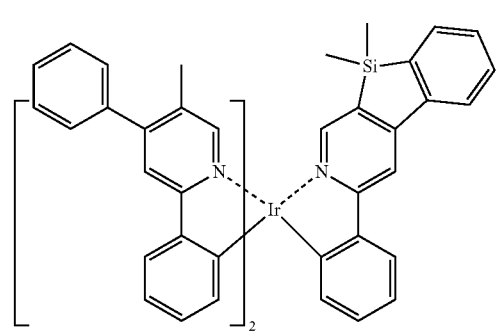

34
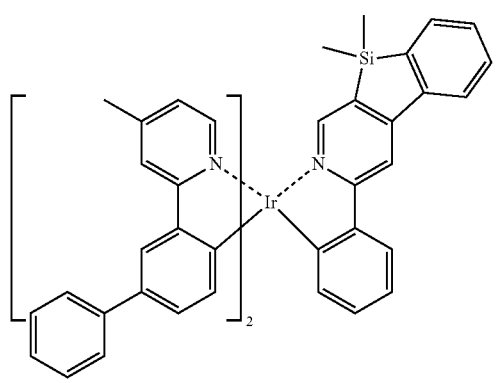
35
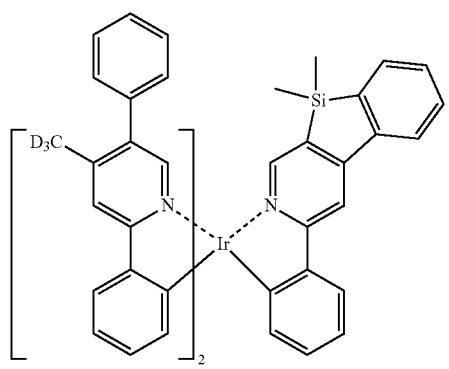
36
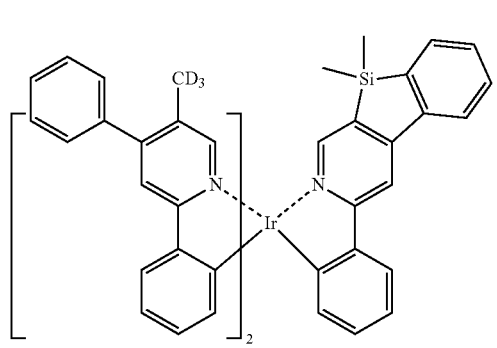
37
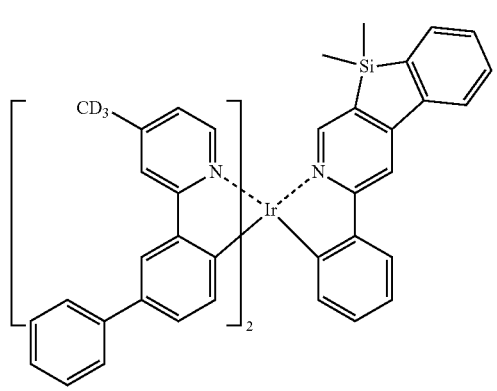
38
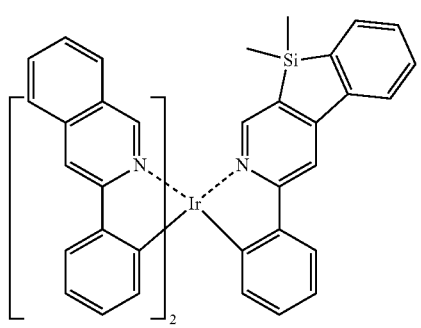
39
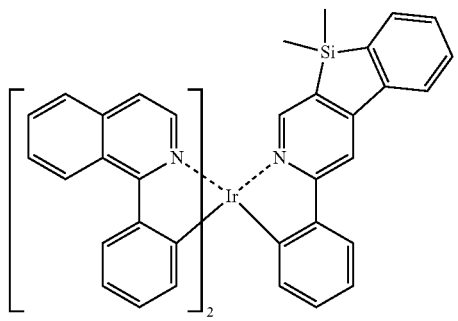
40
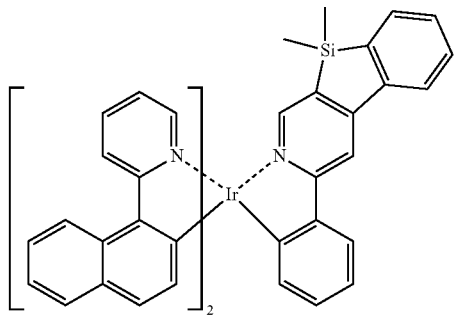
41
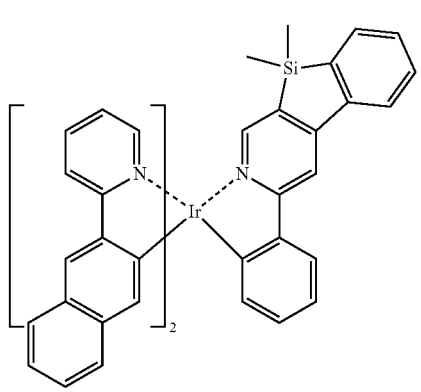

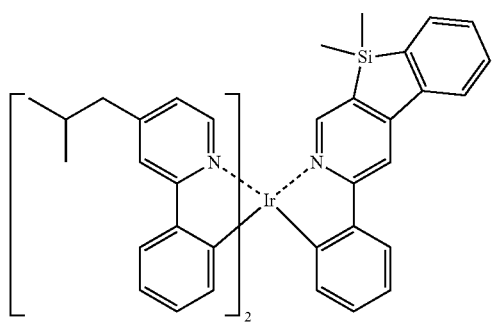
42
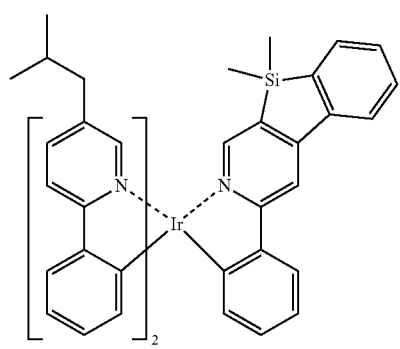
43
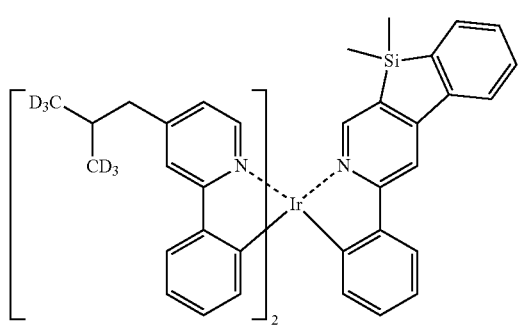
44
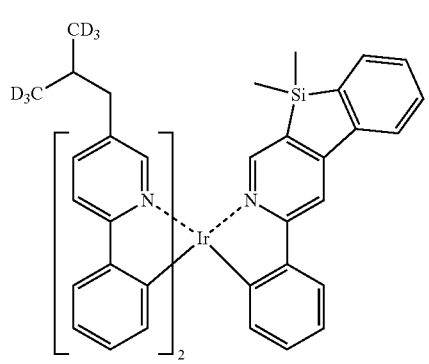
45
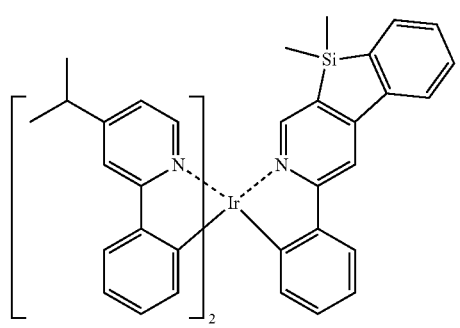
46
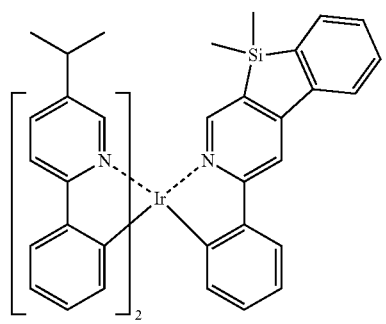
47
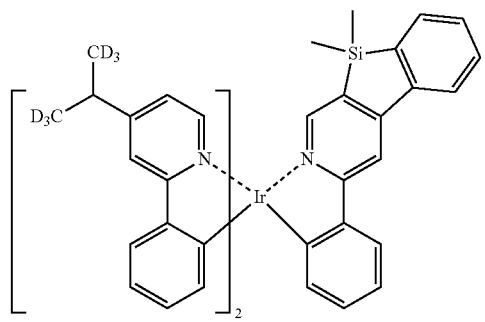
48
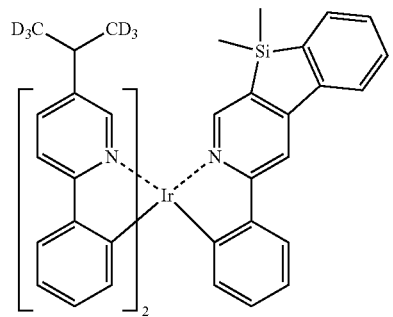
49
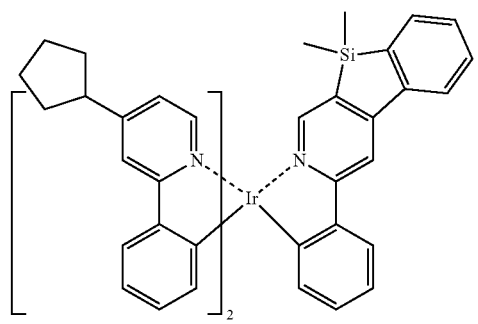
50

51
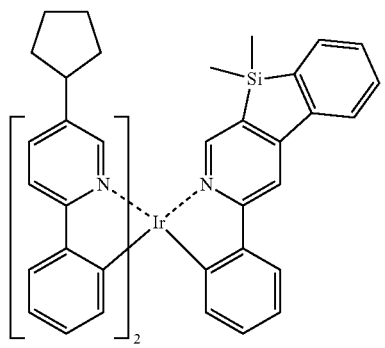
55
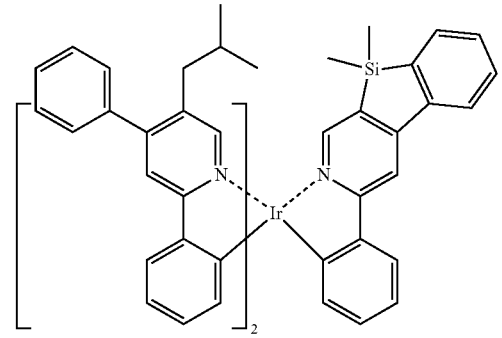
52
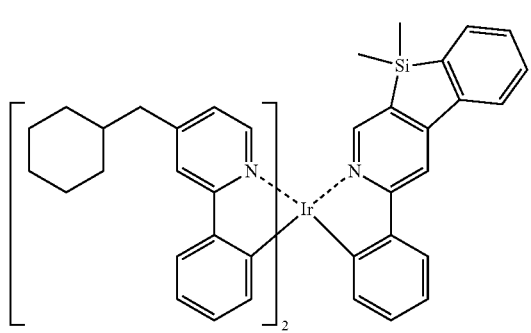
56
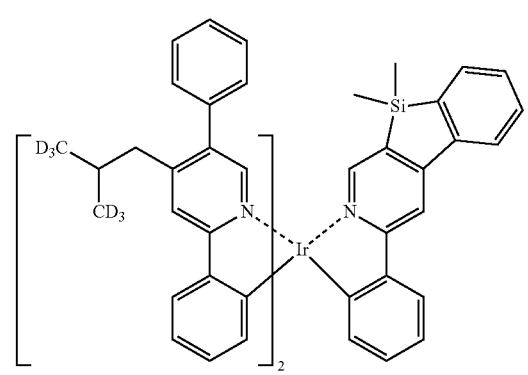
53
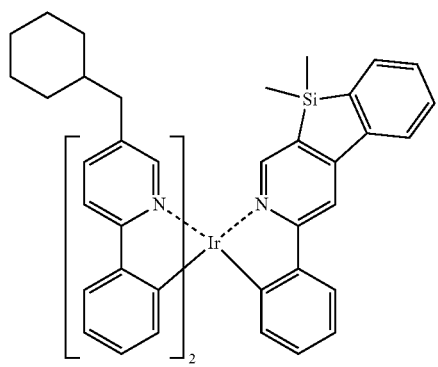
57
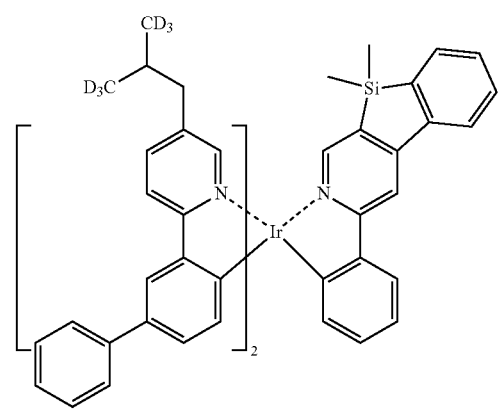
54
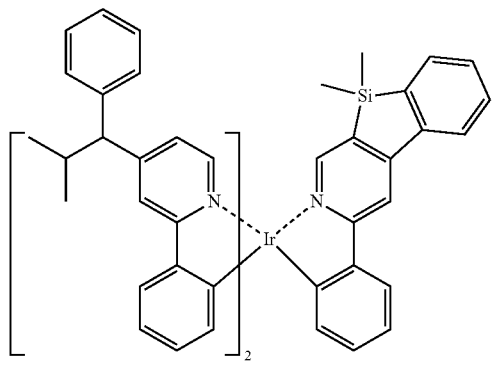
58
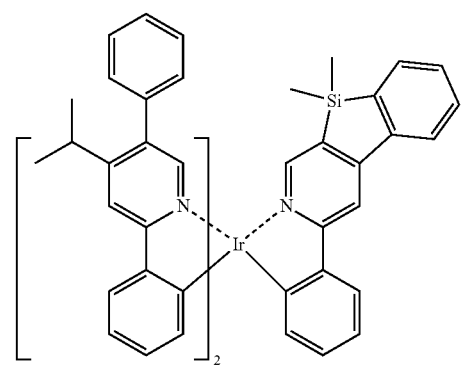

59
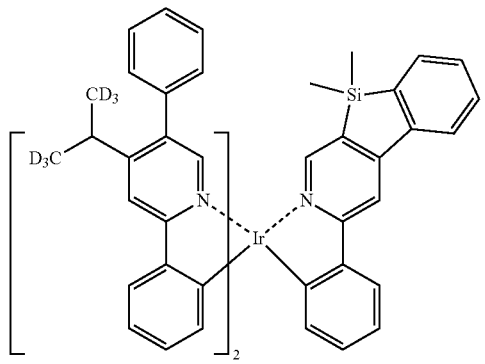
60
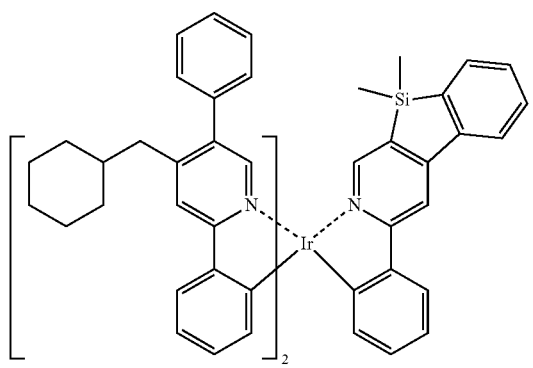
61
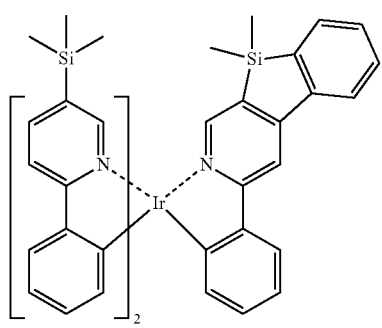
62
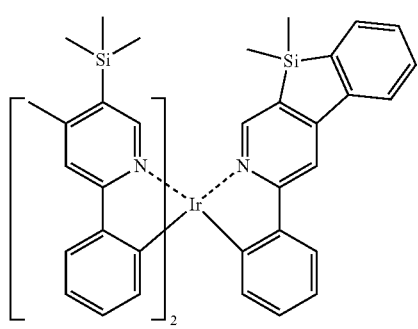
63
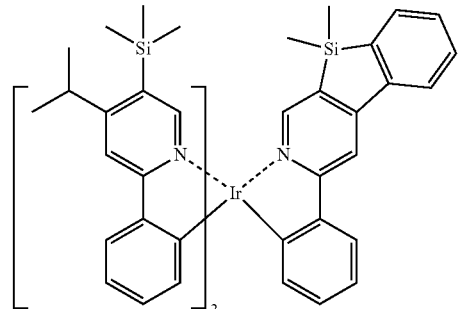
64
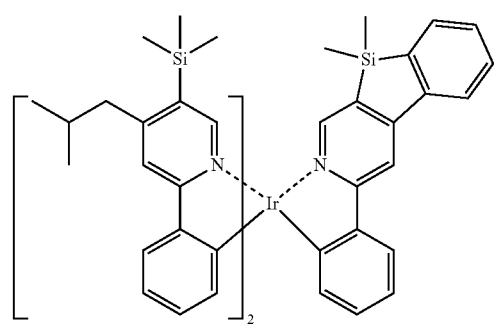
65
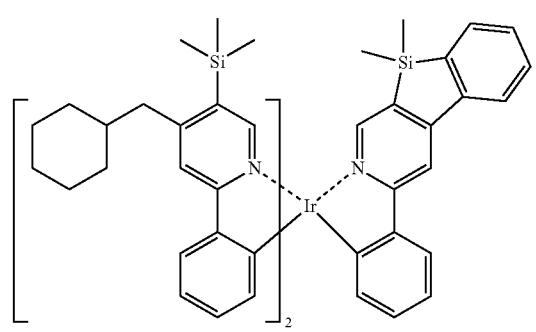
66
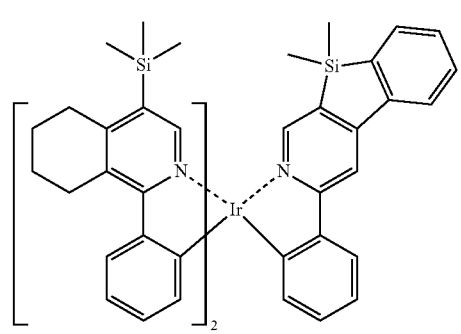
67
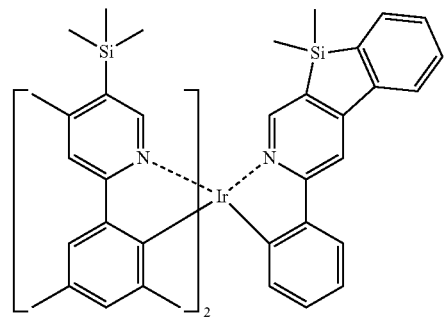

287
-continued
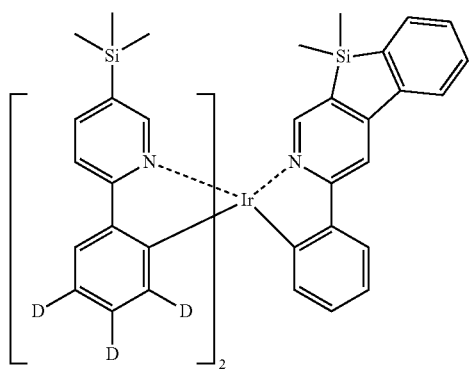
68
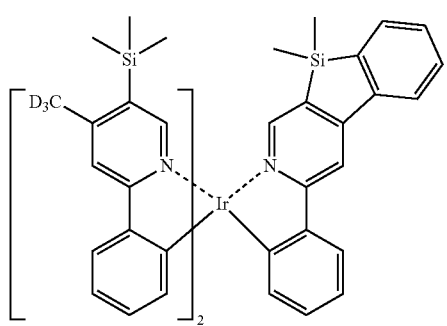
69
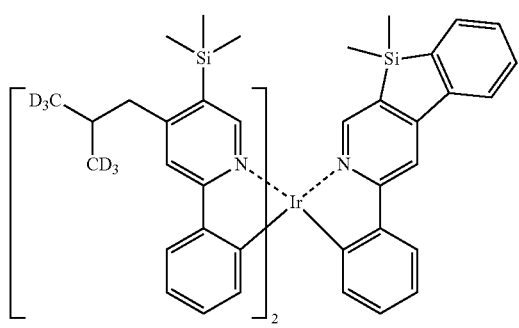
70
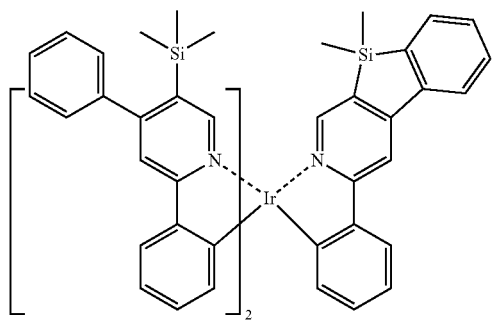
71
288
-continued
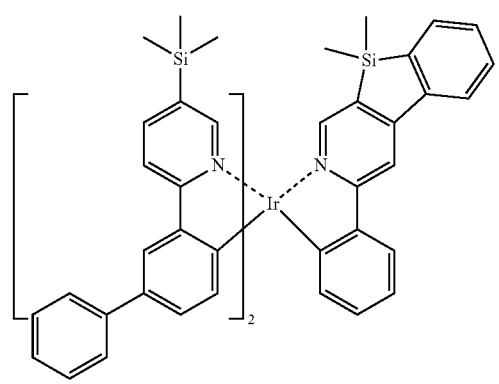
72
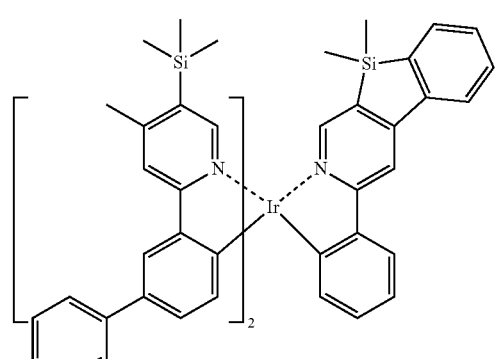
73
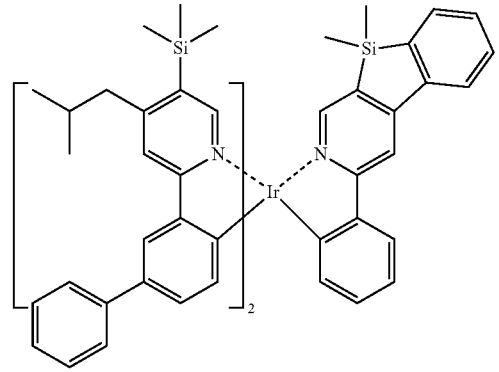
74
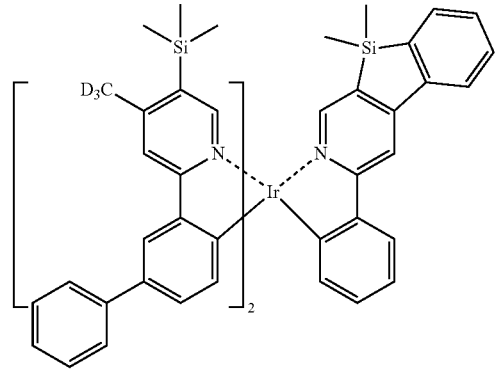
75

289
-continued
76
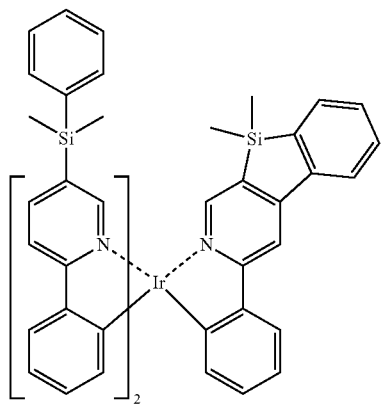
77
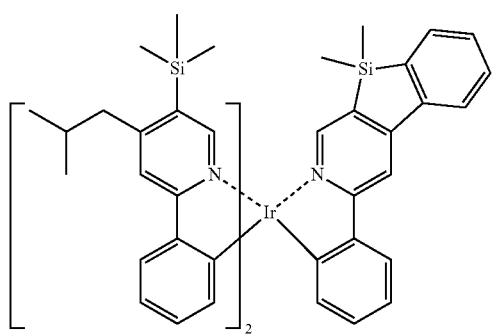
78
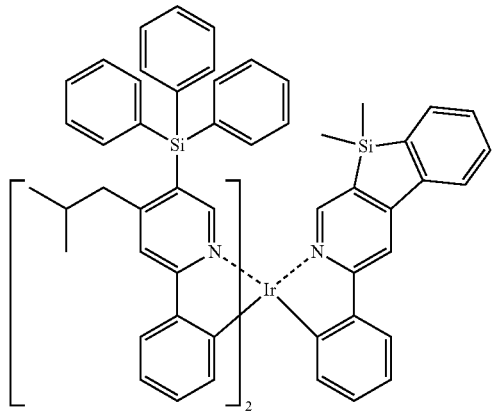
79
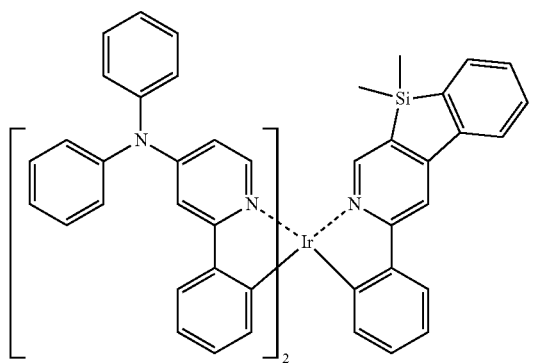
290
-continued
80
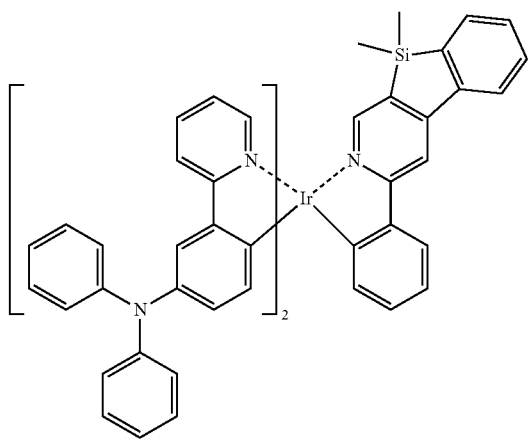
81
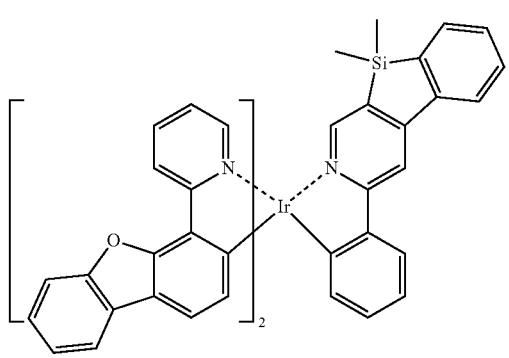
82
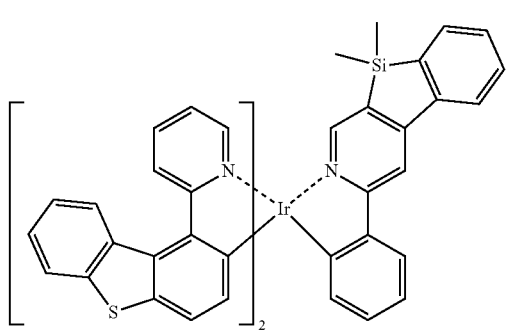
83
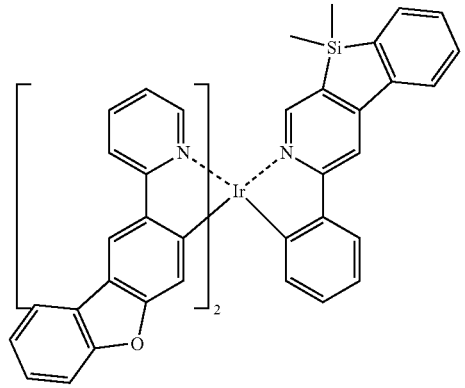

84
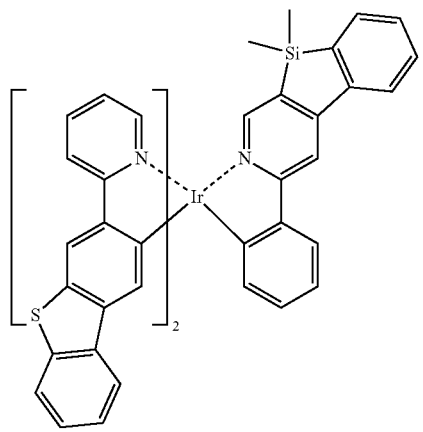
85
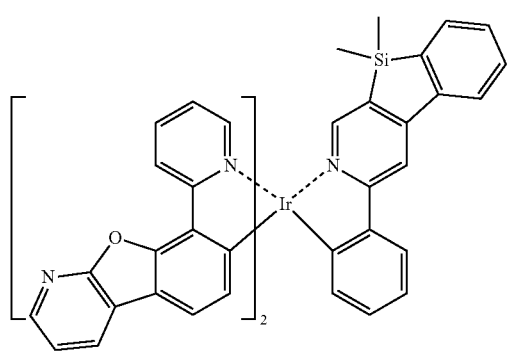
86
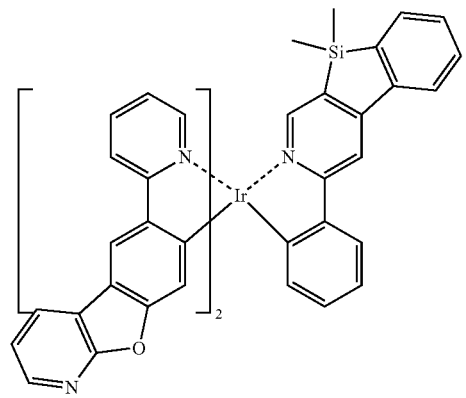
87
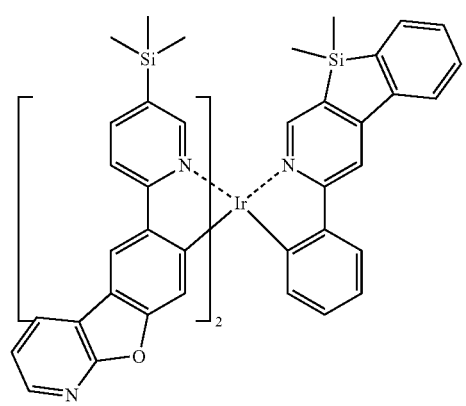
88
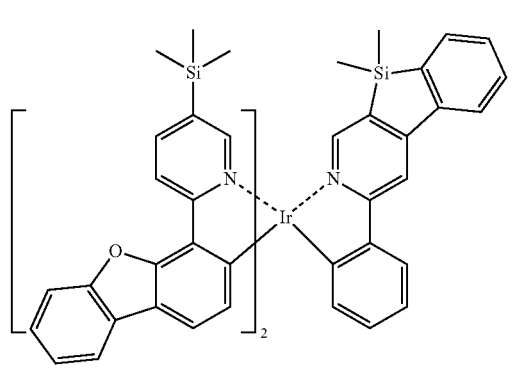
89
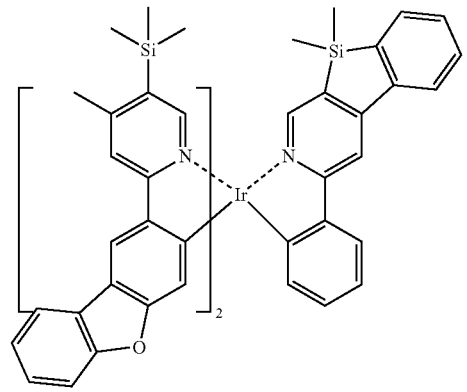
90
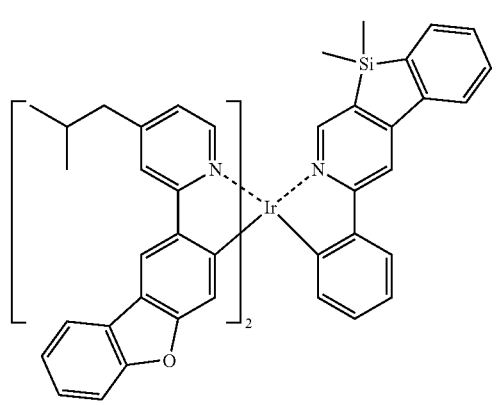
91
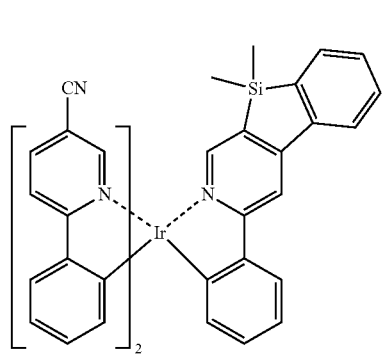

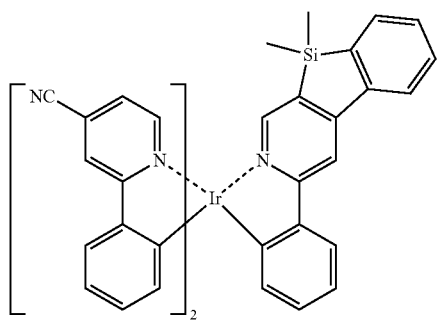
92
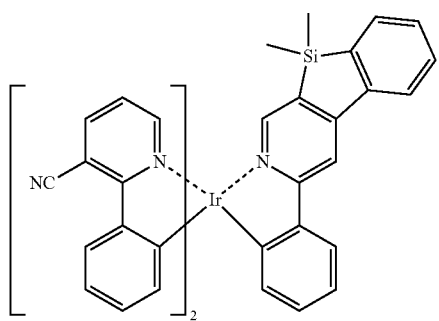
93
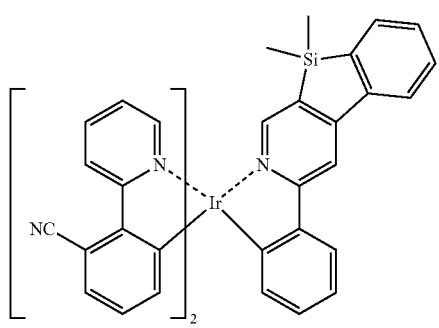
94
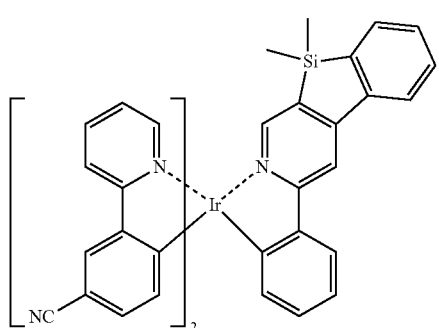
95
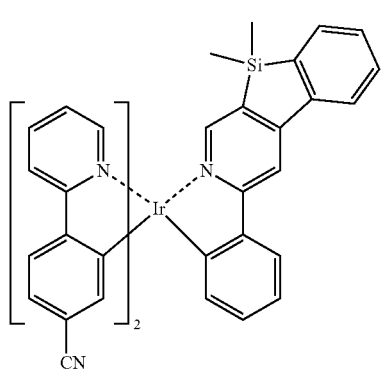
96
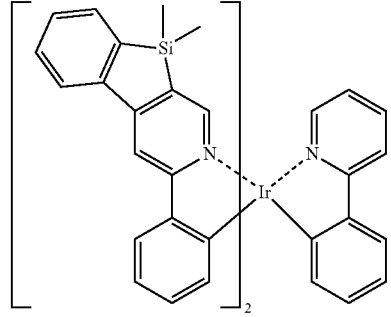
97
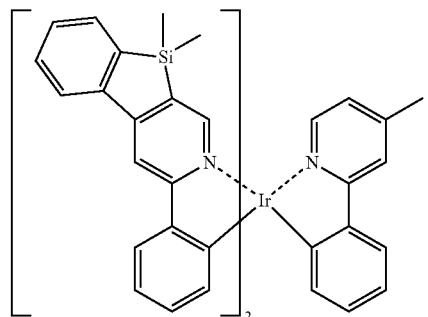
98
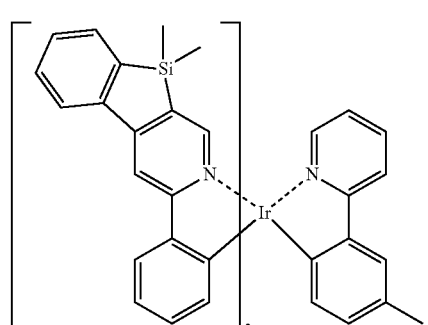
99
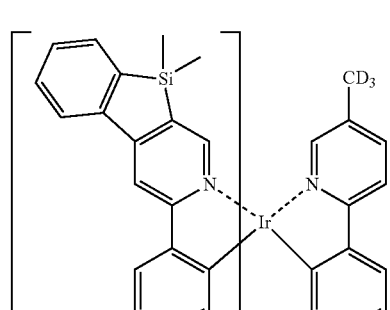
100
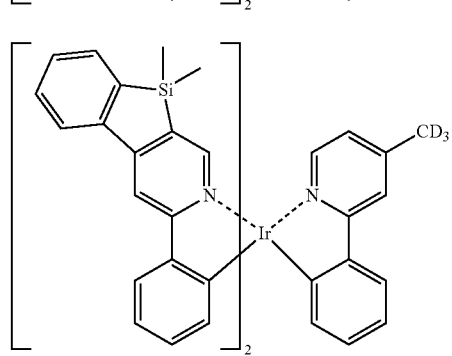
101

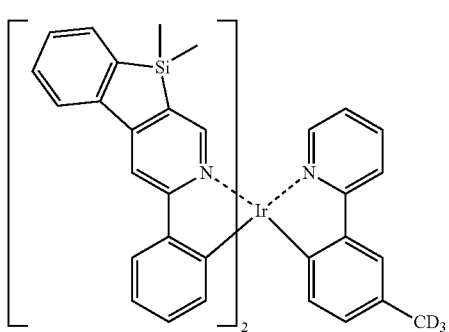
102
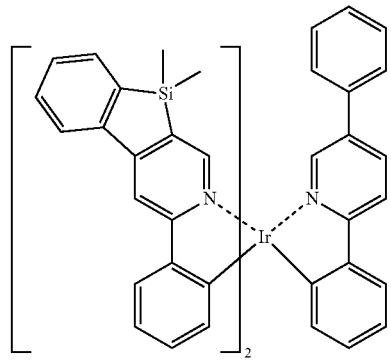
106
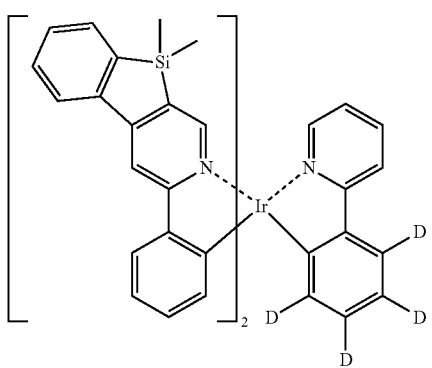
103
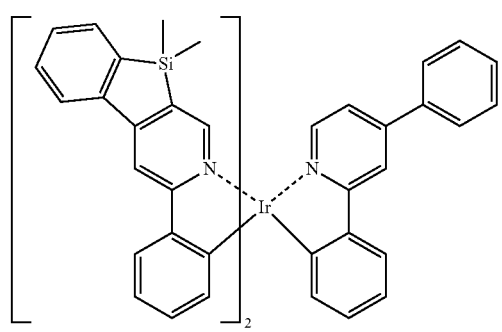
107
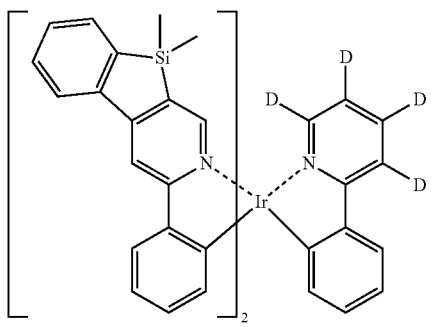
104
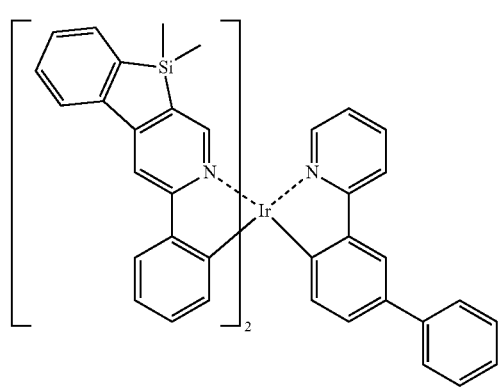
108
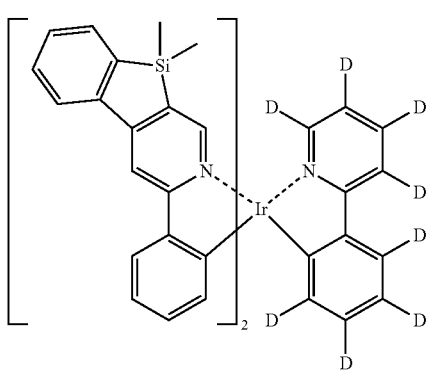
105
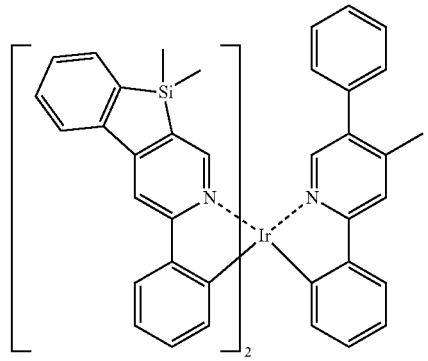
109

297
-continued
110
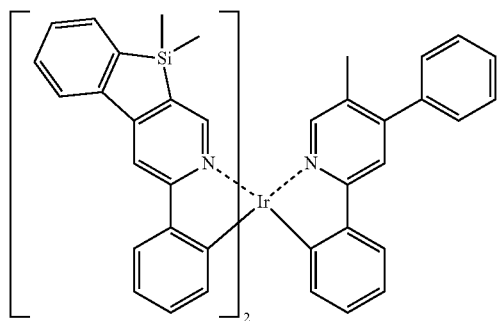
111
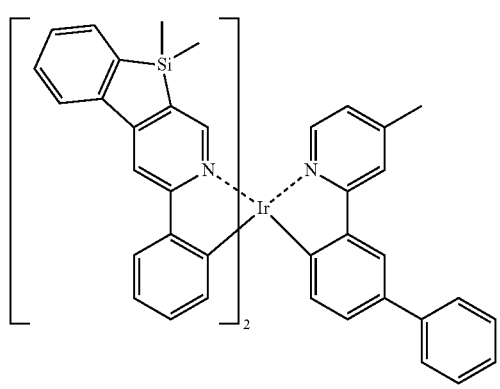
112
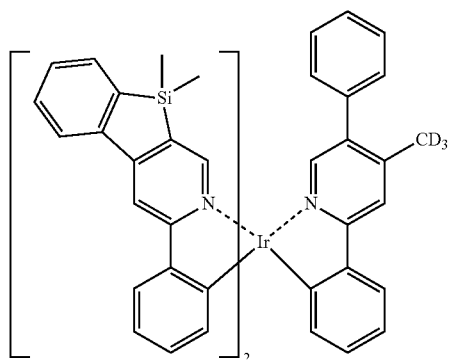
113
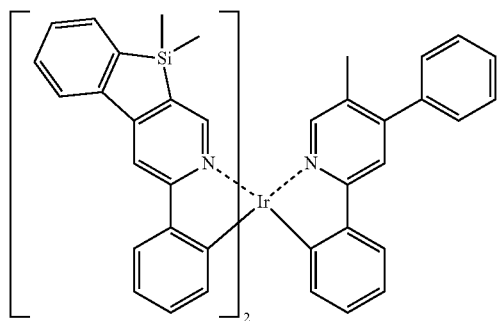
298
-continued
114
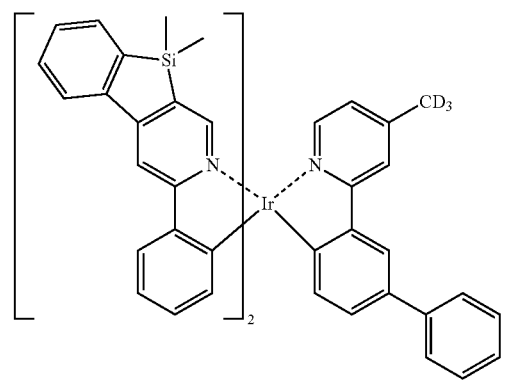
115
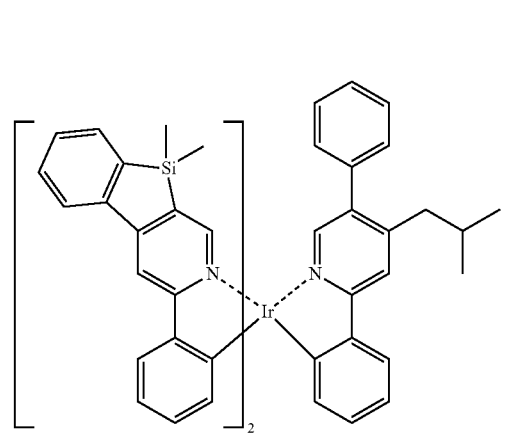
116
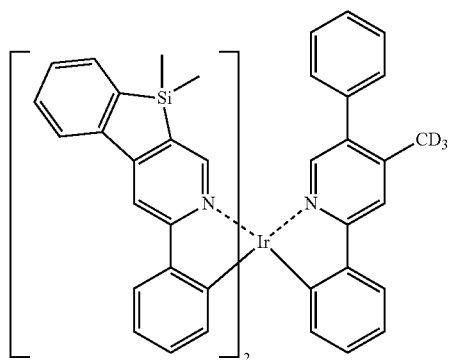
117
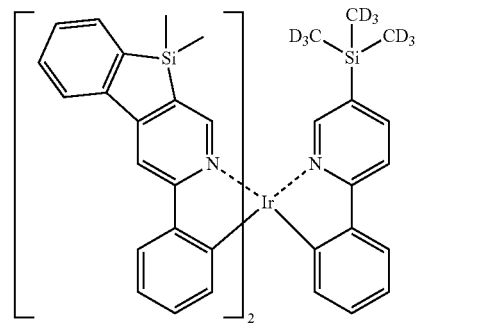

299
-continued
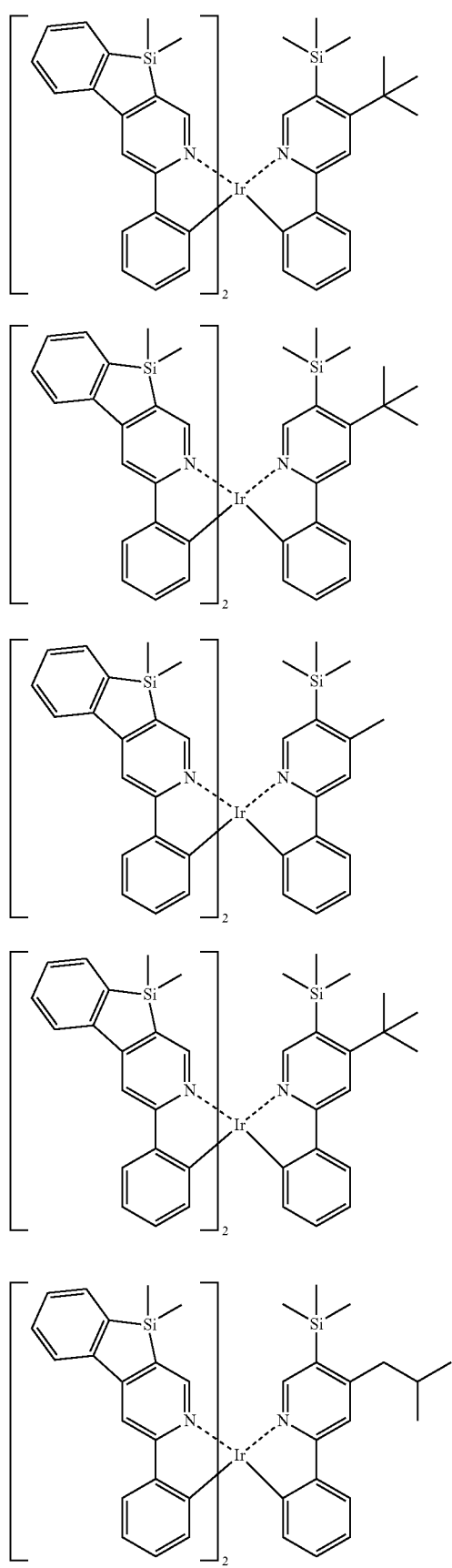
300
-continued
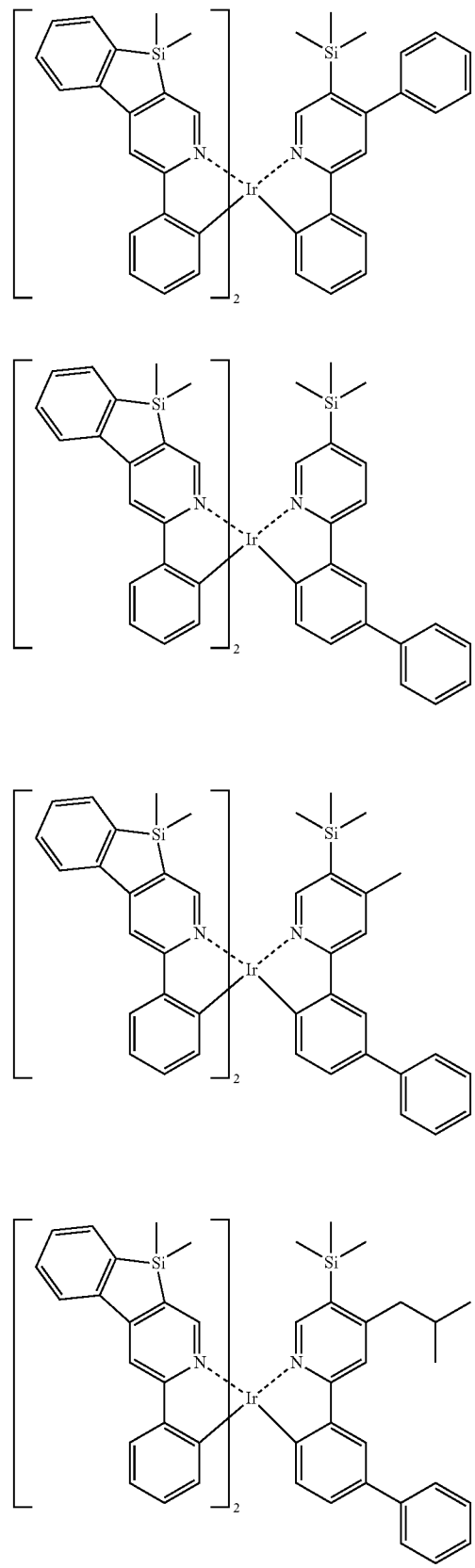

124
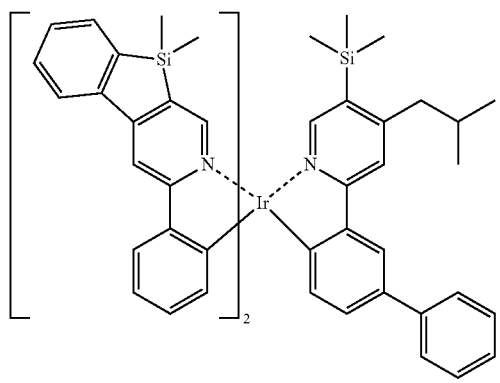
125
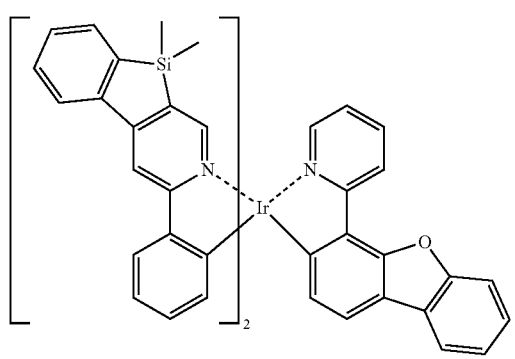
126
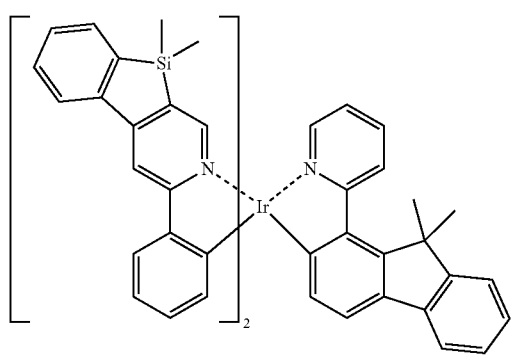
127
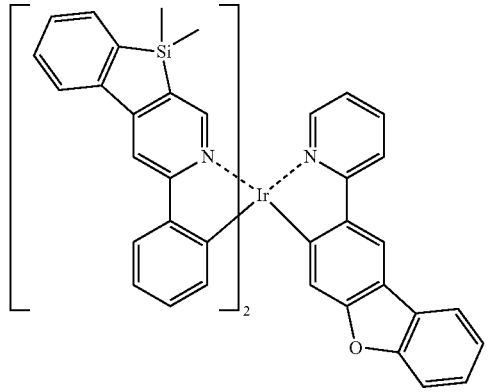
128
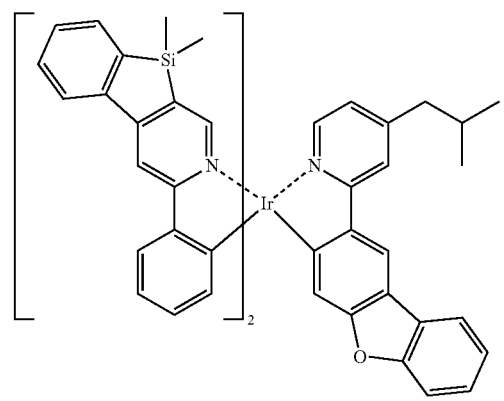
129
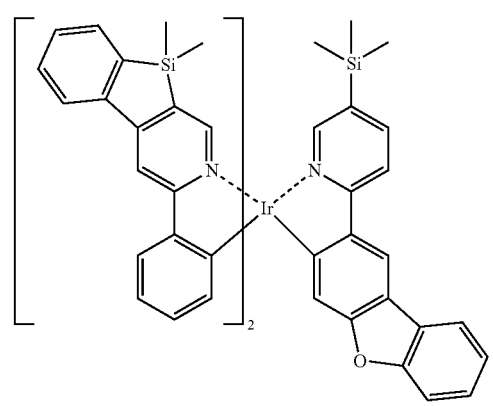
130
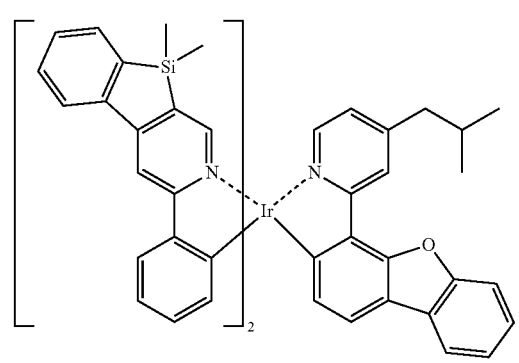
131
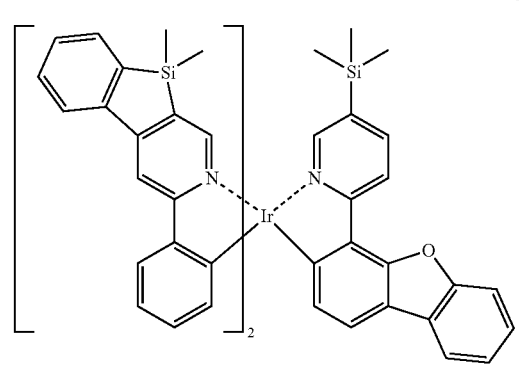

303
-continued
132
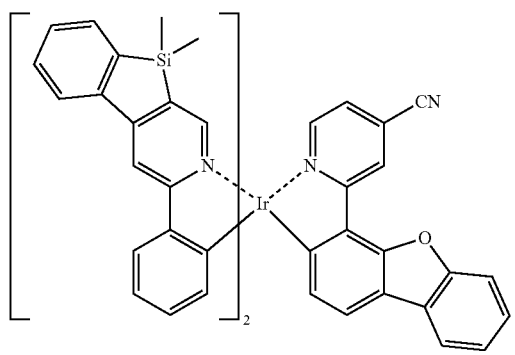
133
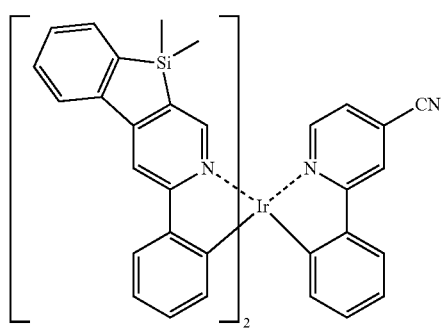
133
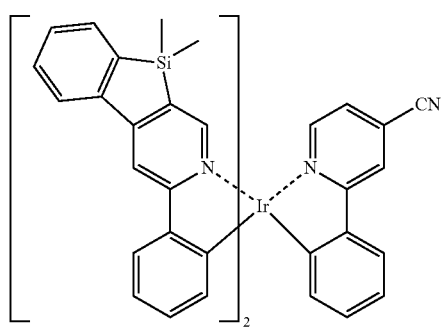
134
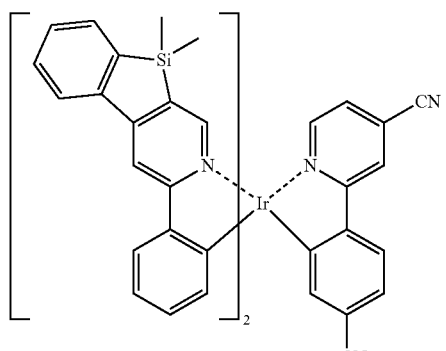
304
-continued
135
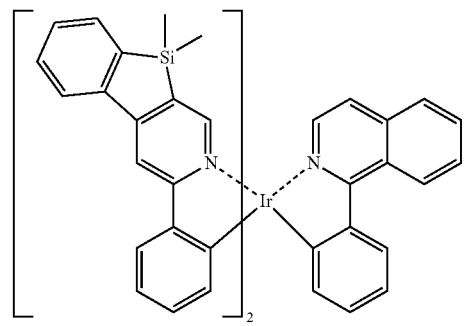
136
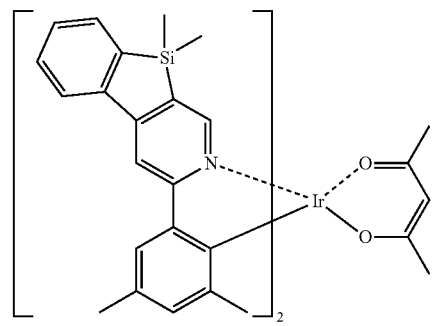
137
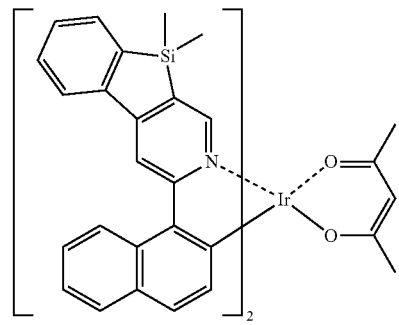
138
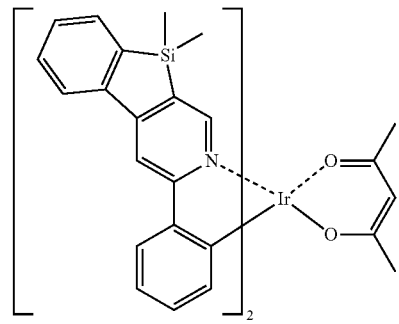
139
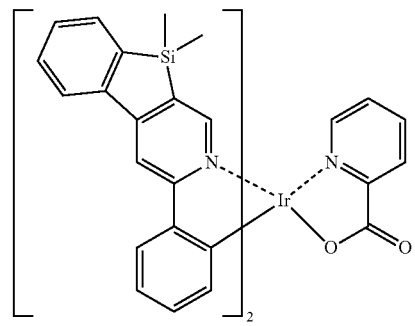

305
-continued
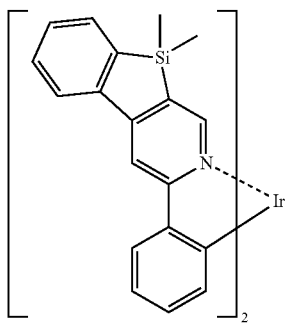
140
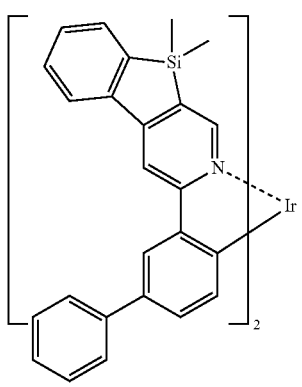
141
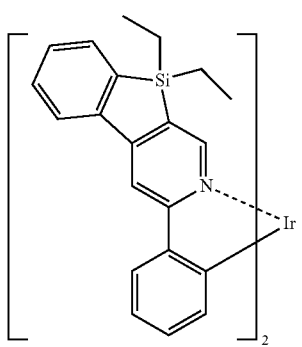
142
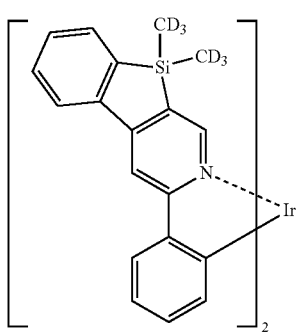
143
306
-continued
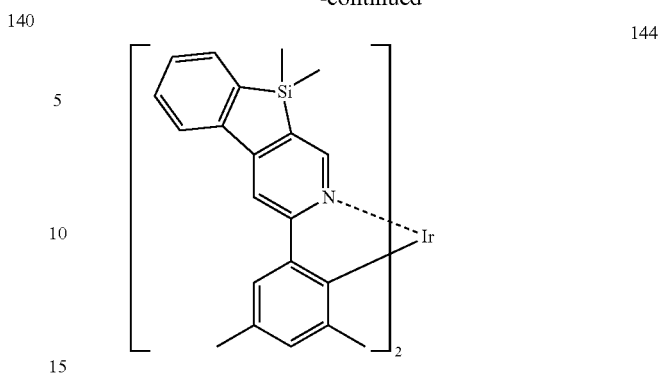
144
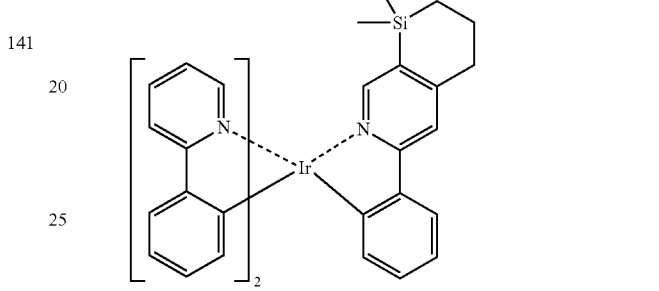
145
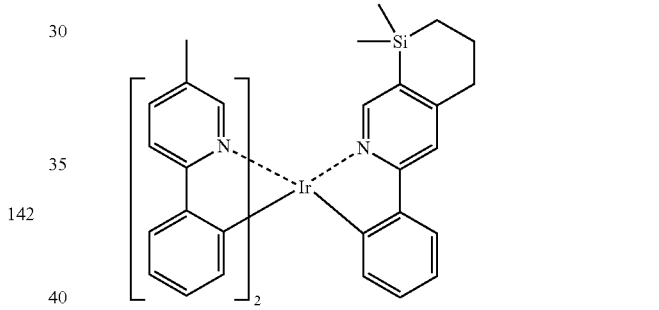
146
147
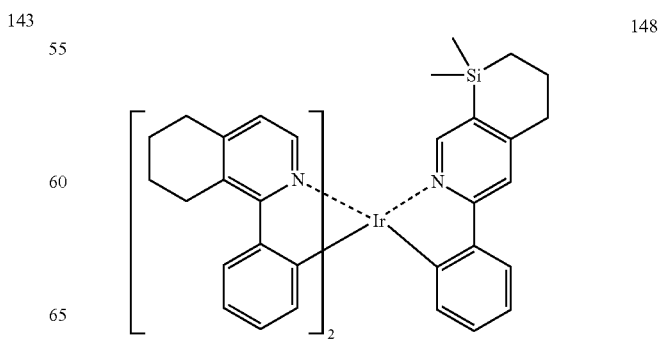
148

149
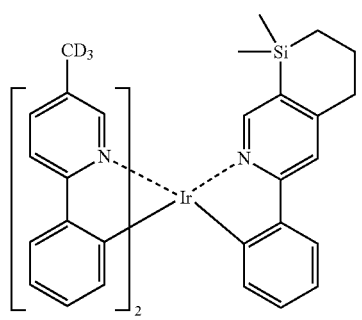
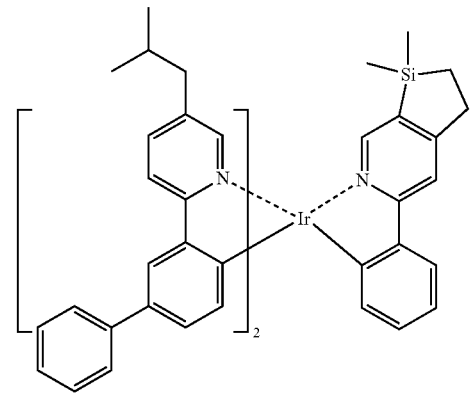
150
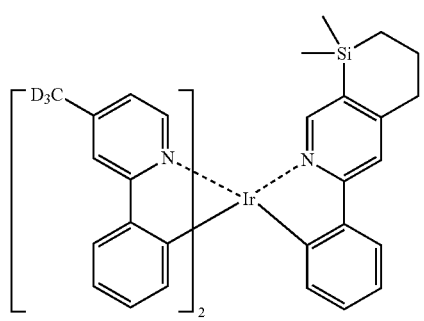
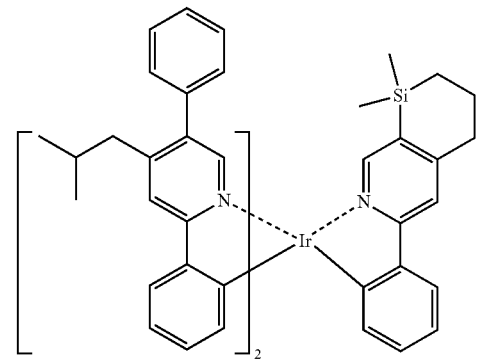
151
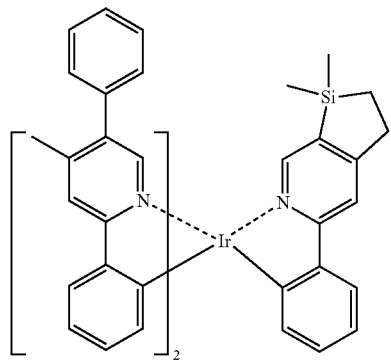
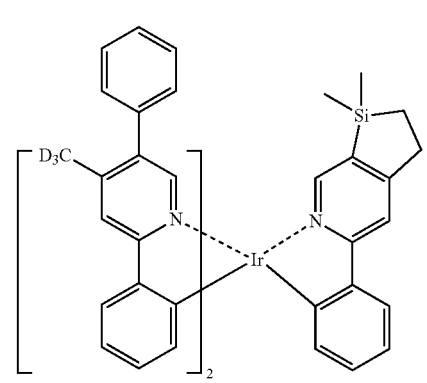
152
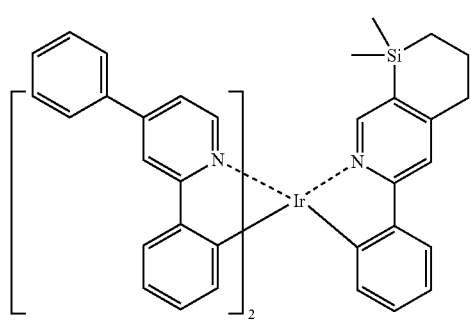
153
154
155
156
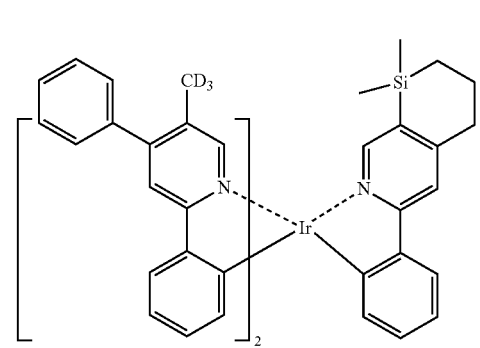

309 -continued
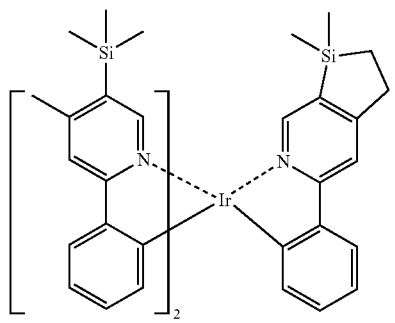
157
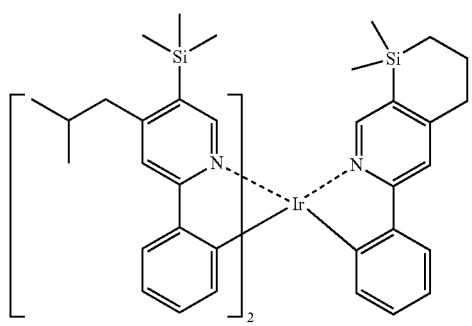
158
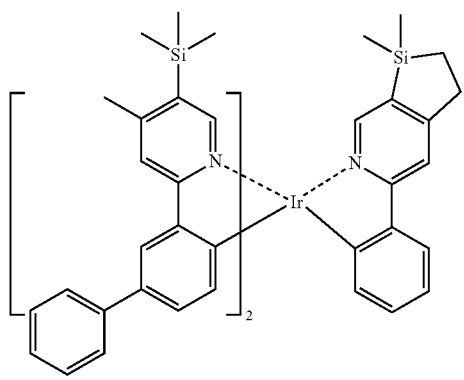
159
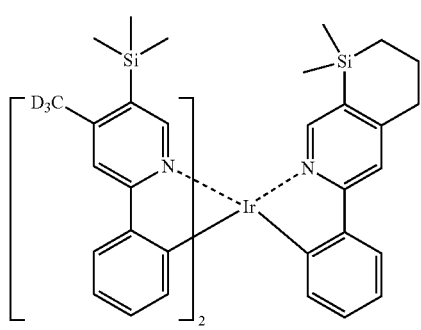
160
310 -continued
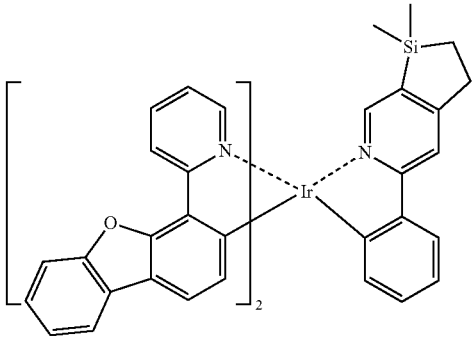
161
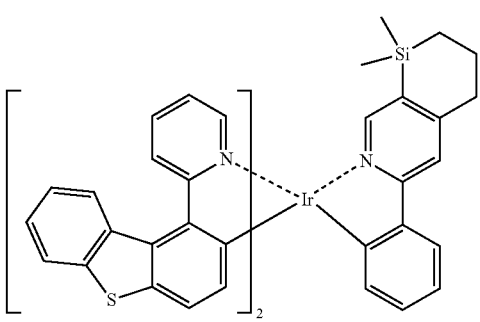
162
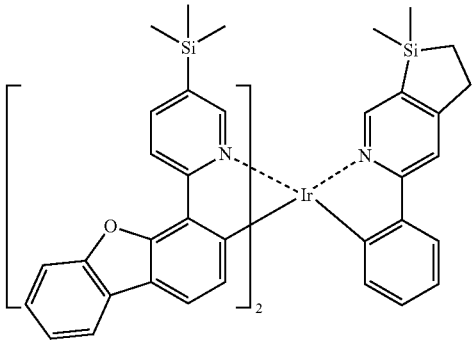
163
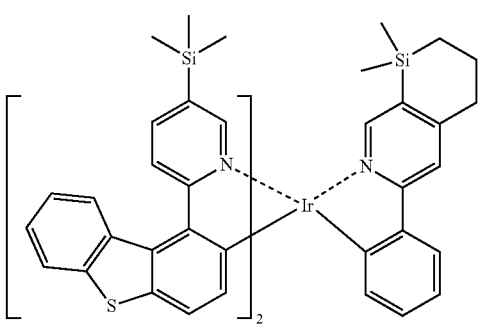
164

311
-continued
165 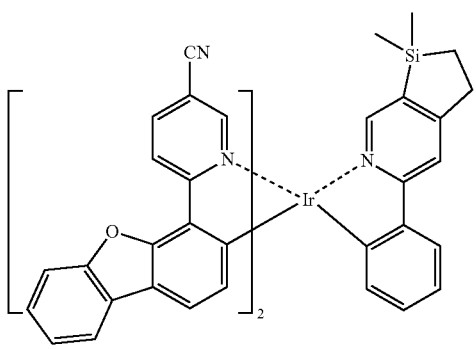
166 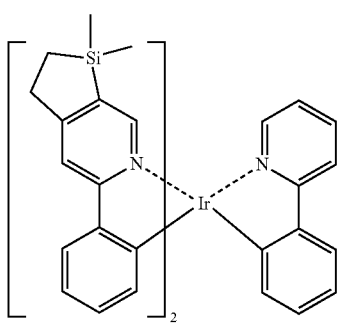
167 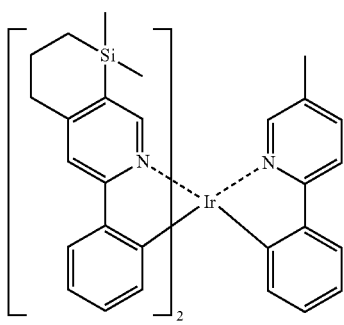
168 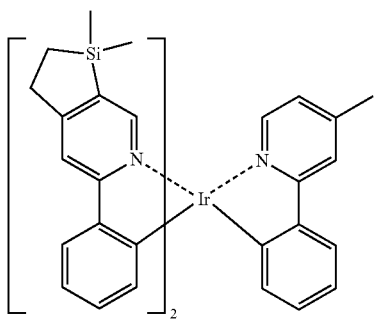
169 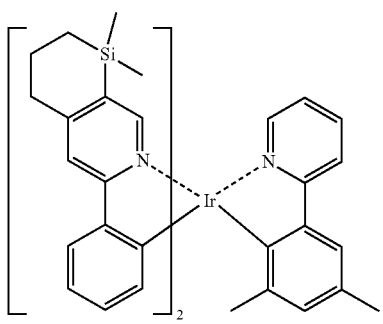
312
-continued
170 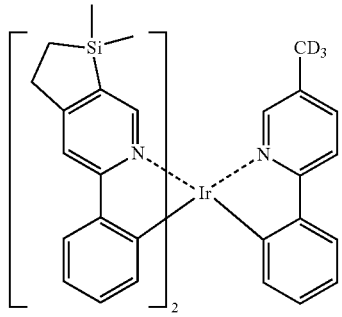
171 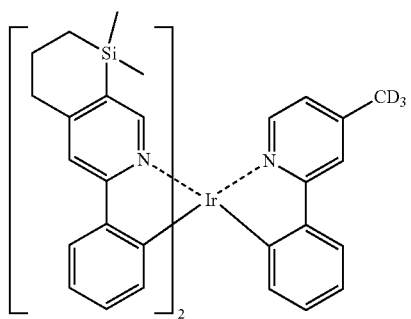
172 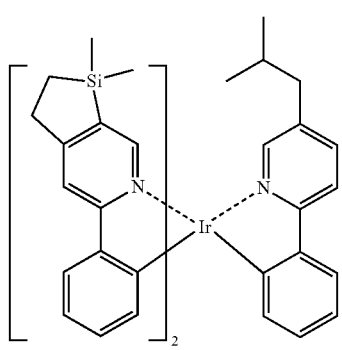
173 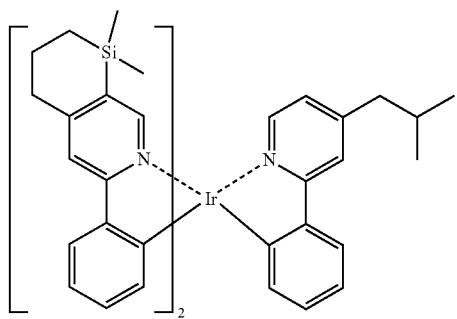

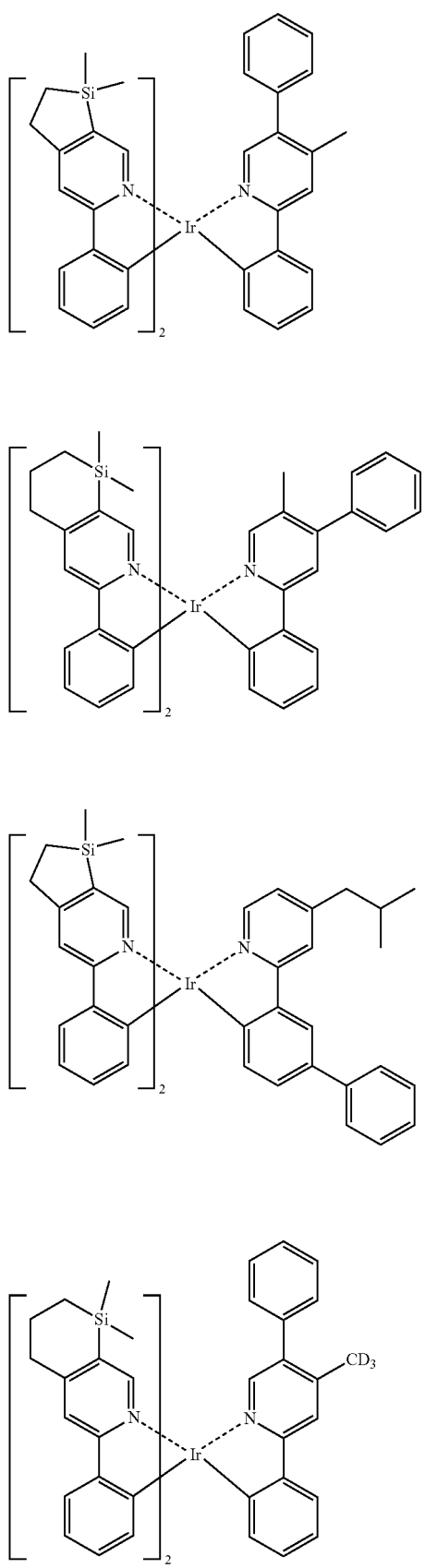
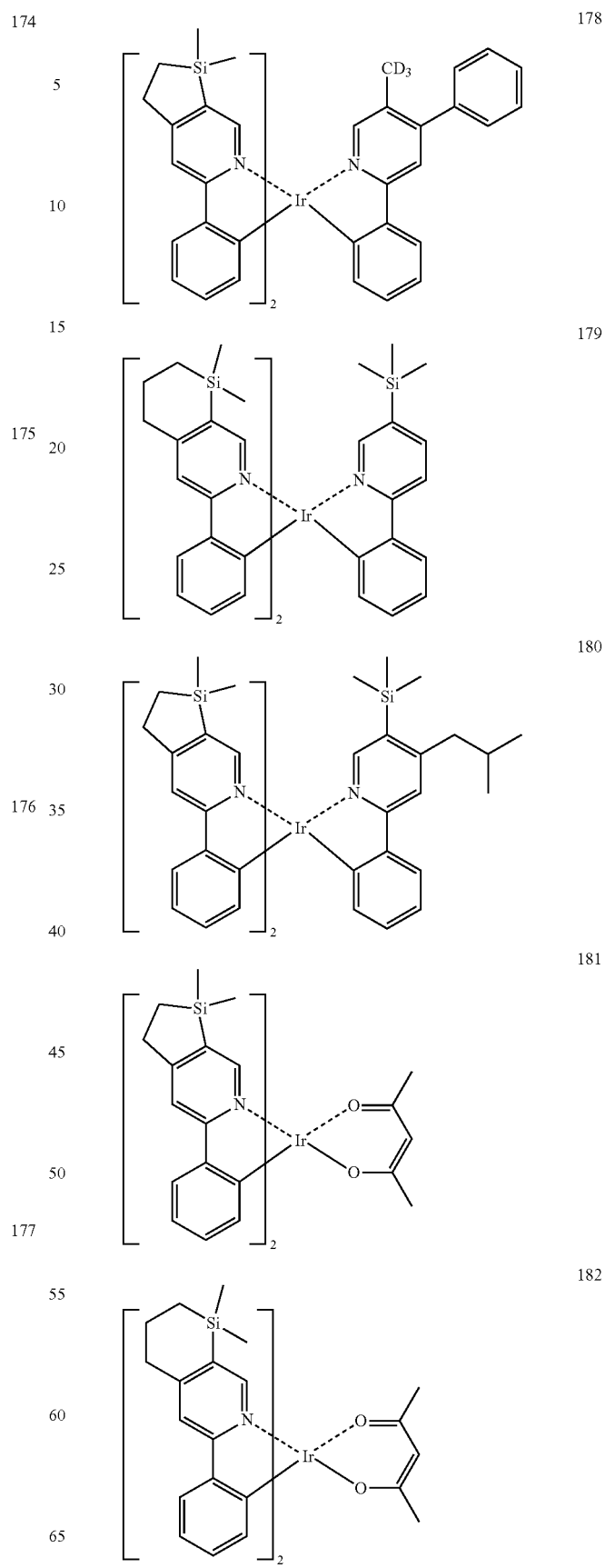

-continued
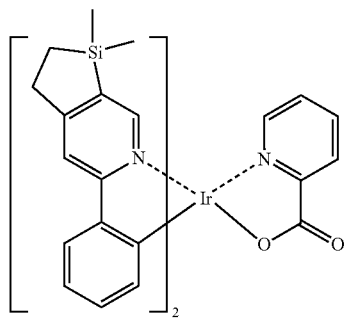
183
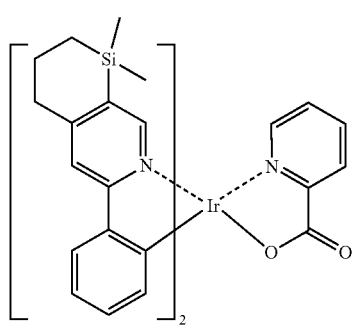
184
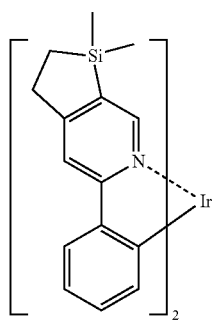
185
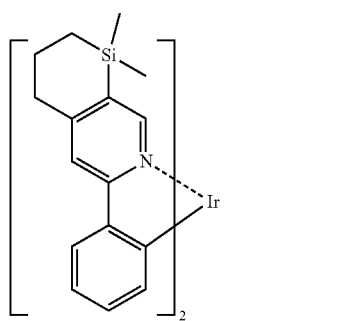
186
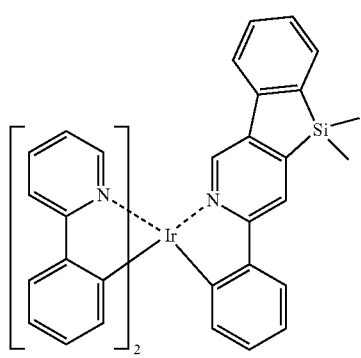
187
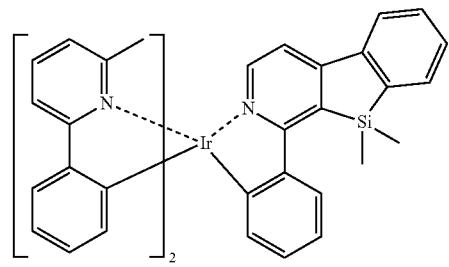
188
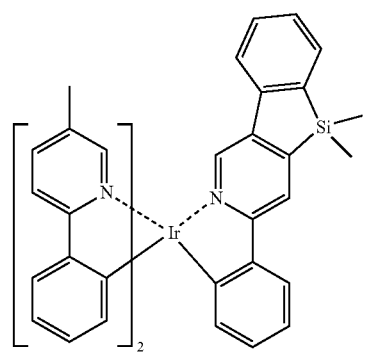
189
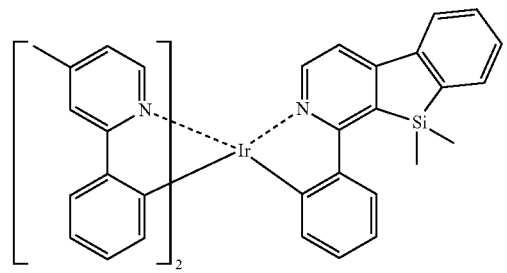
190
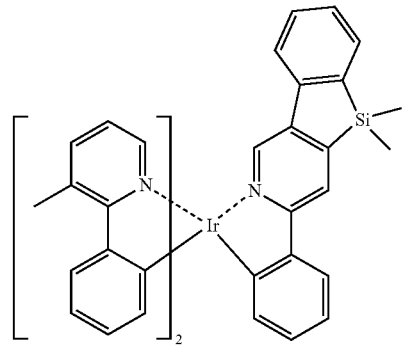
191
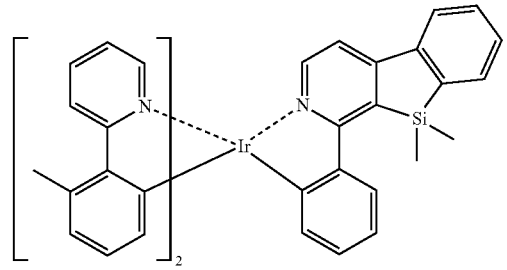
192

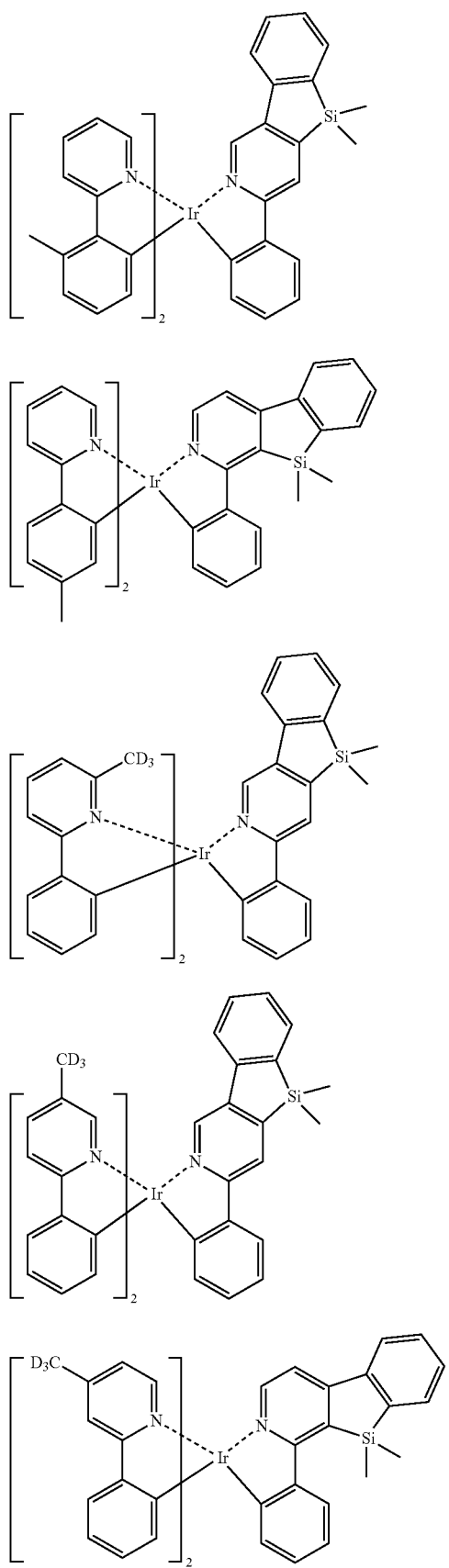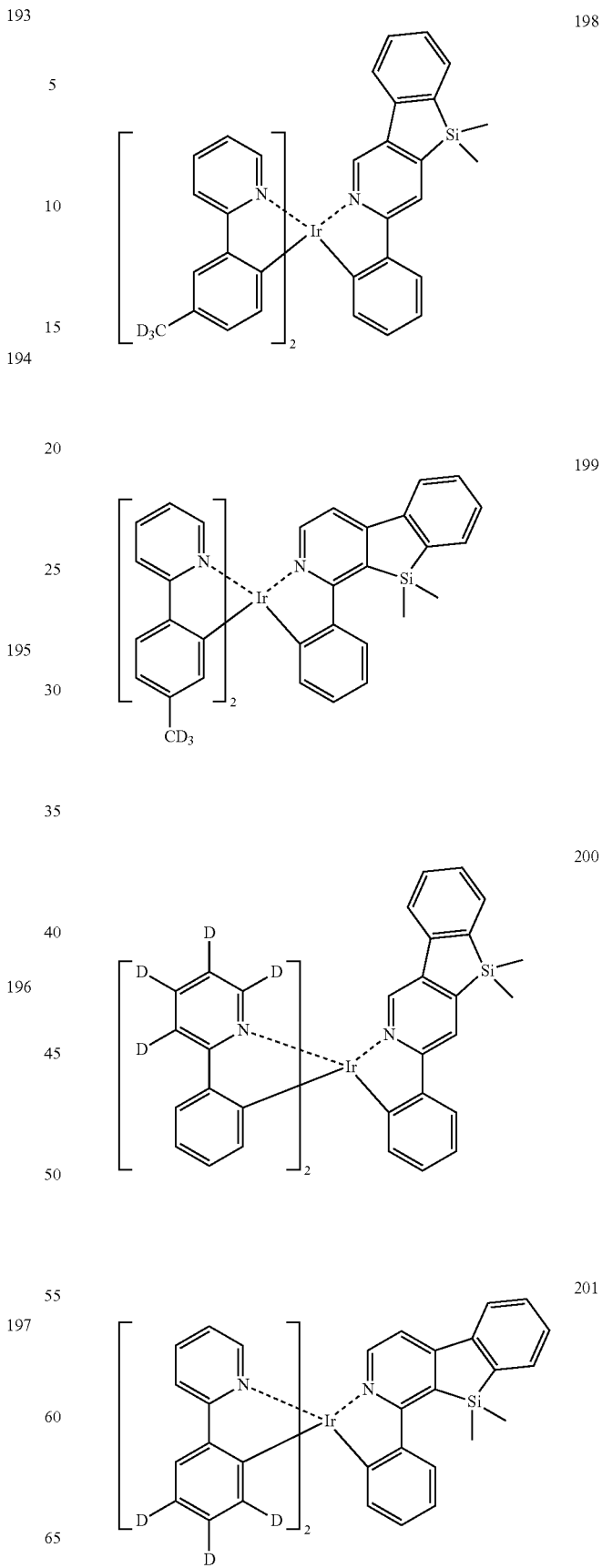

-continued
202
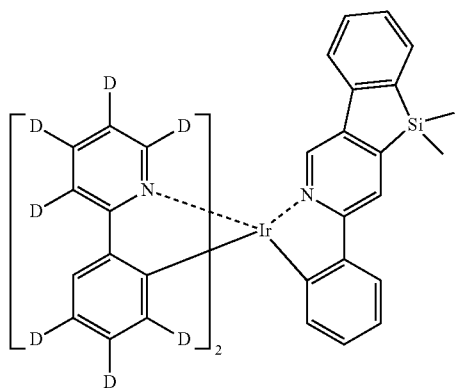
203
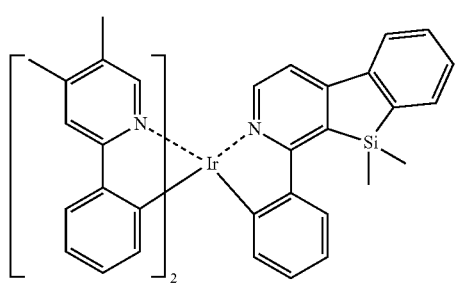
204
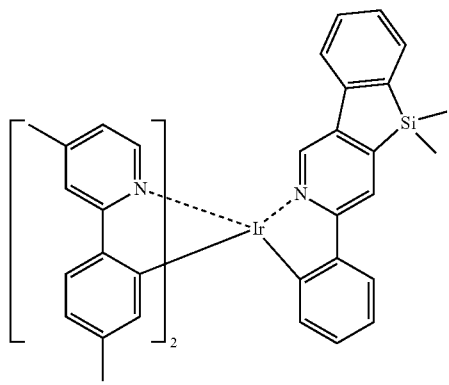
205
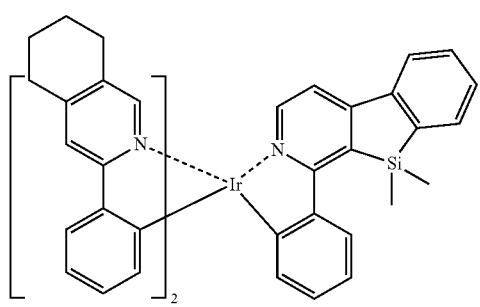
-continued
206
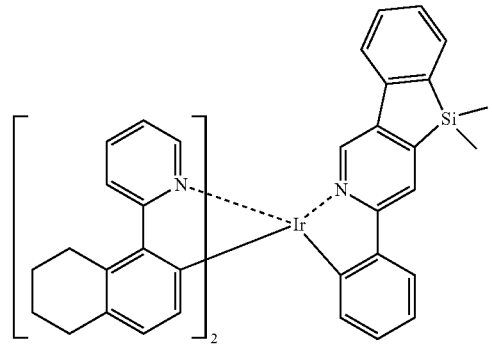
207
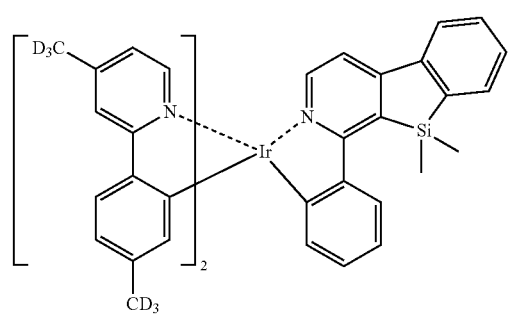
208
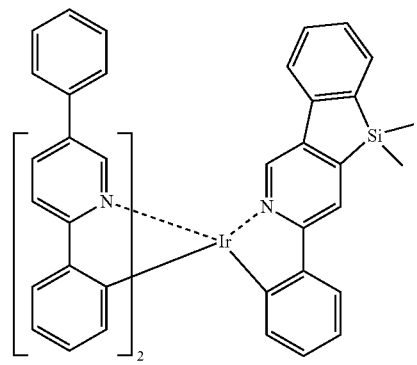
209
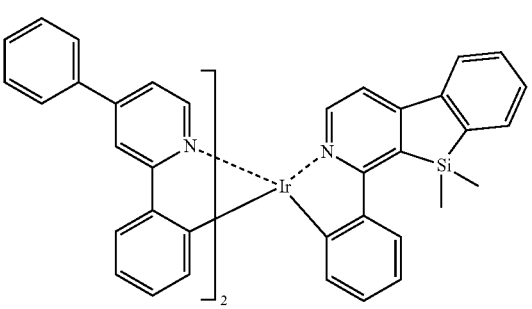

321
-continued
210
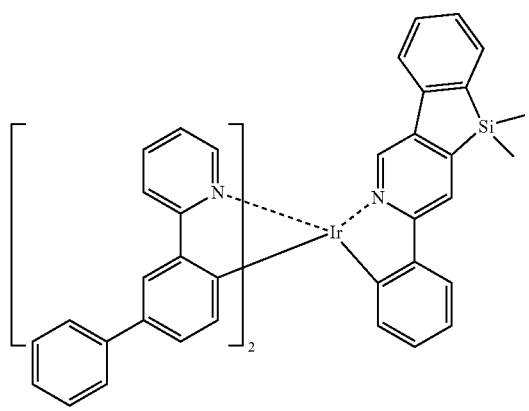
211
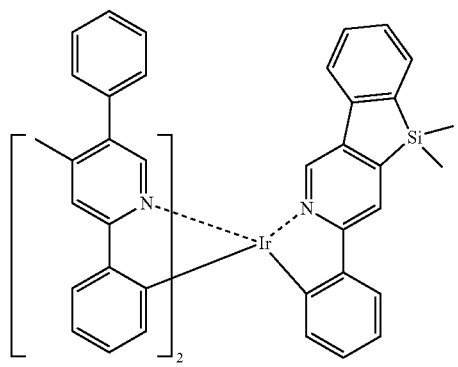
212
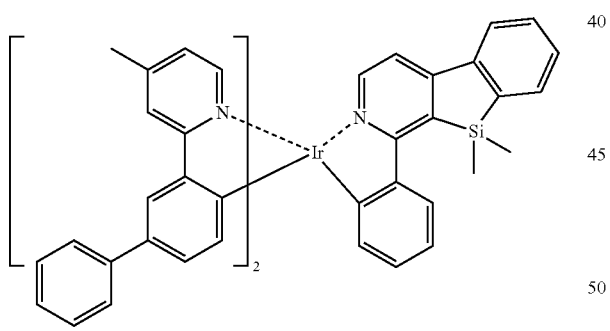
213
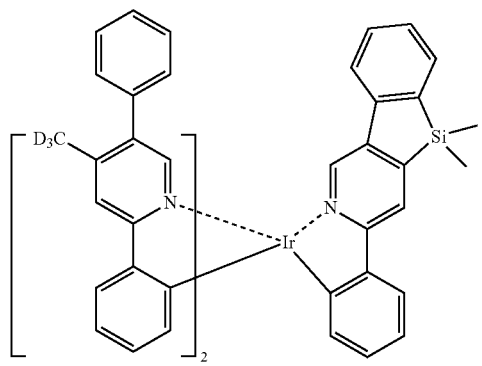
322
-continued
214
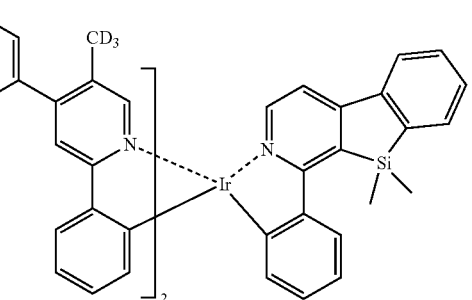
215
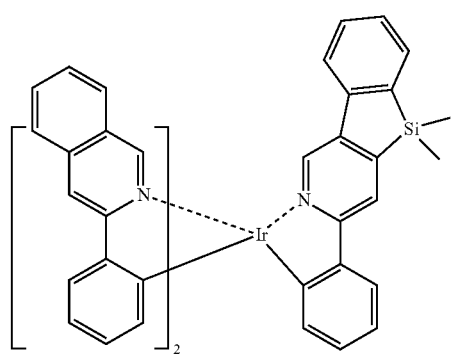
216
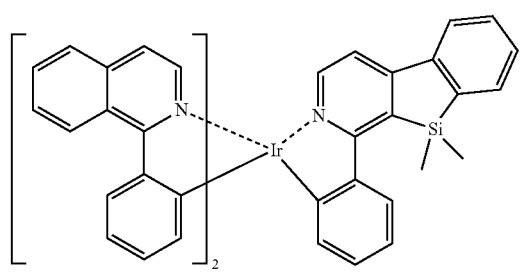
217
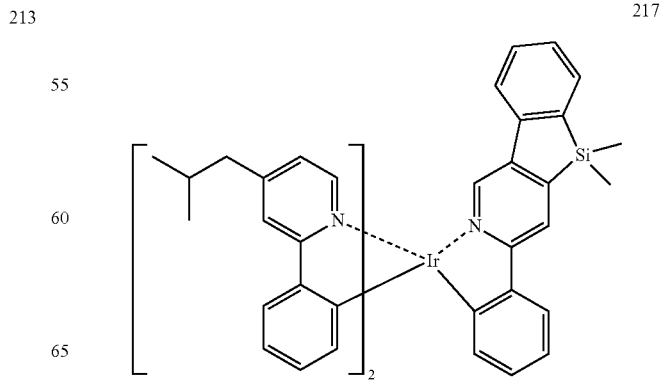

323
-continued
218
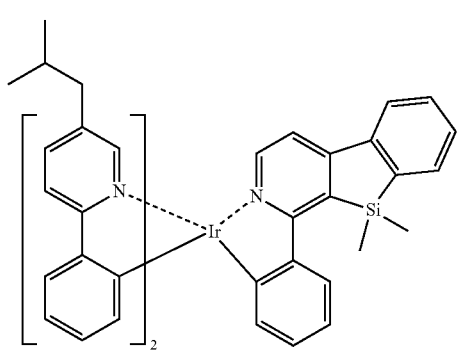
219
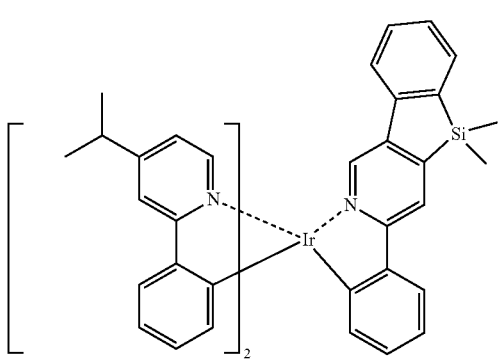
220
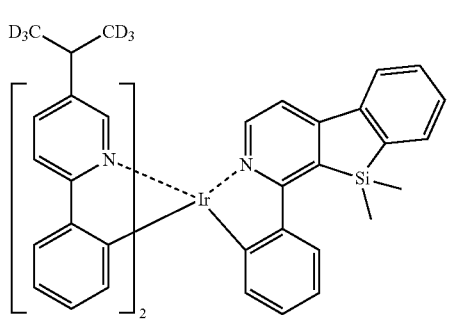
221
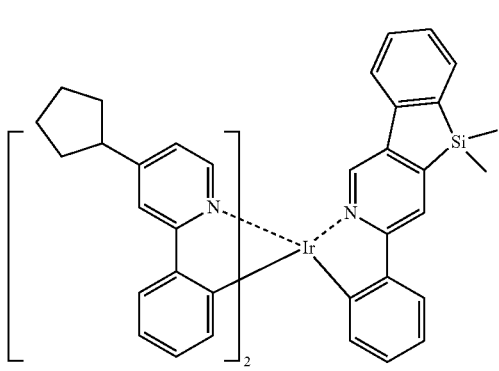
324
-continued
222
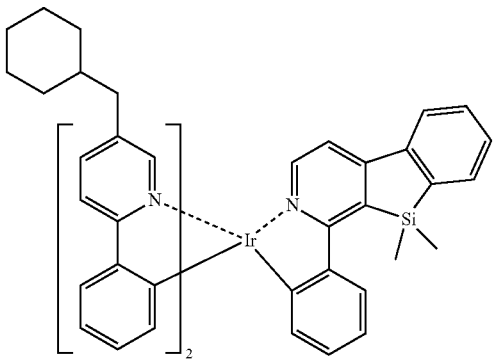
223
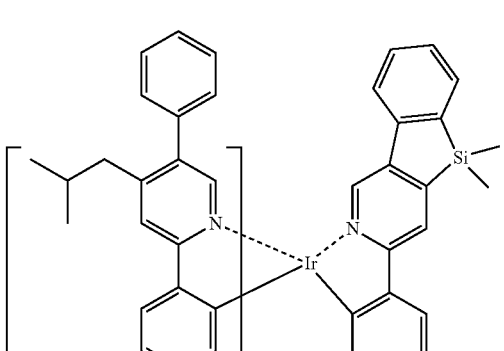
224
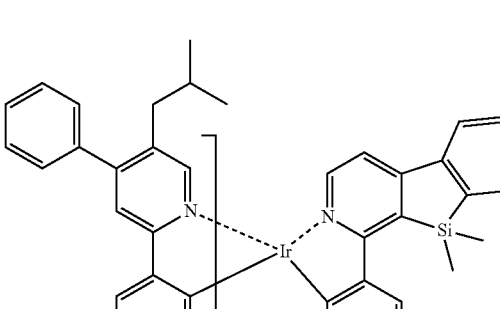
225
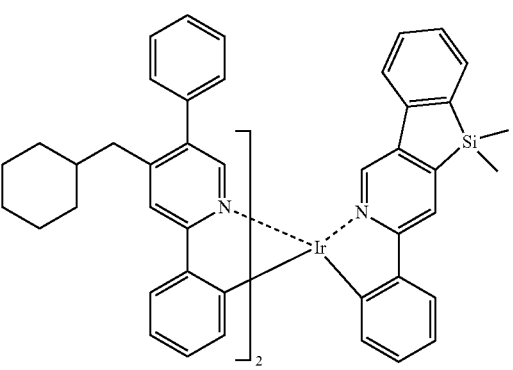

325
-continued
226
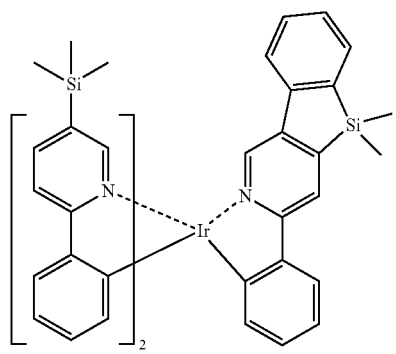
227
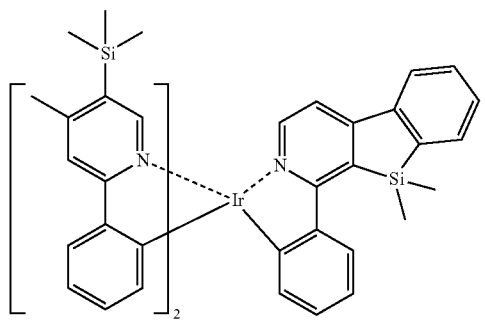
228
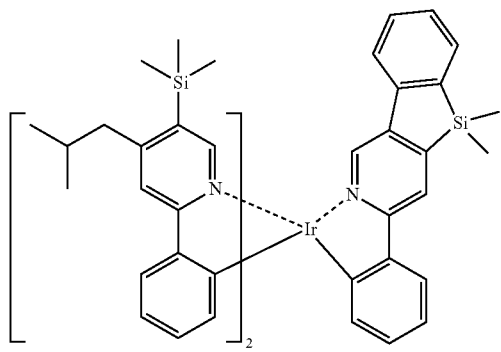
229
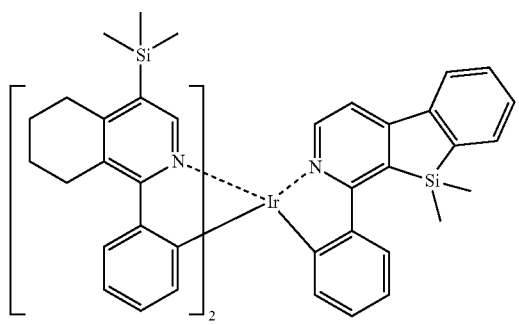
326
-continued
230
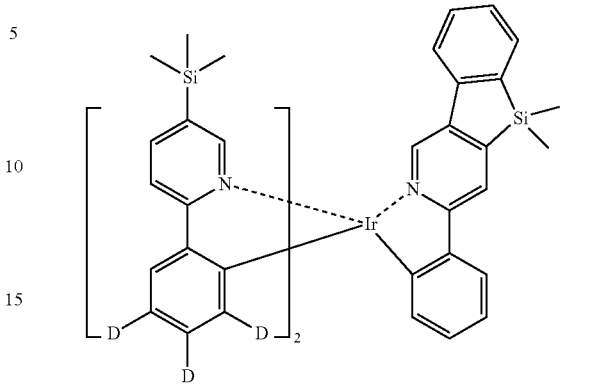
231
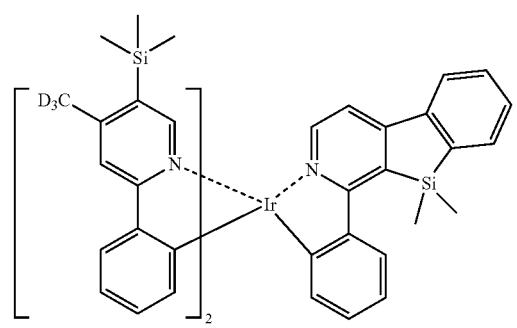
232
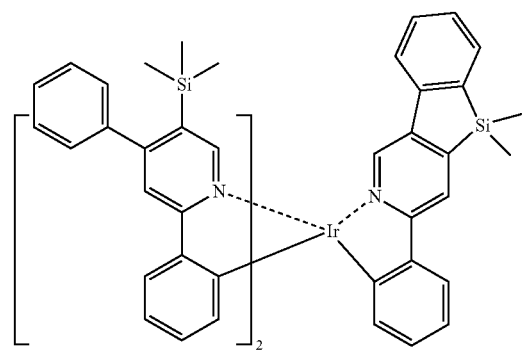
233
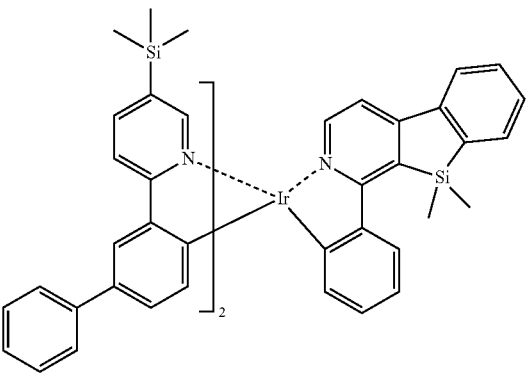

234
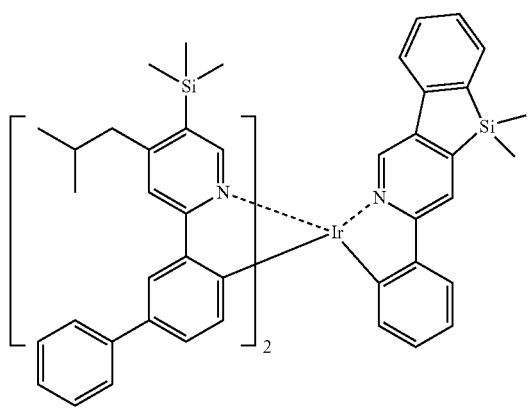
235
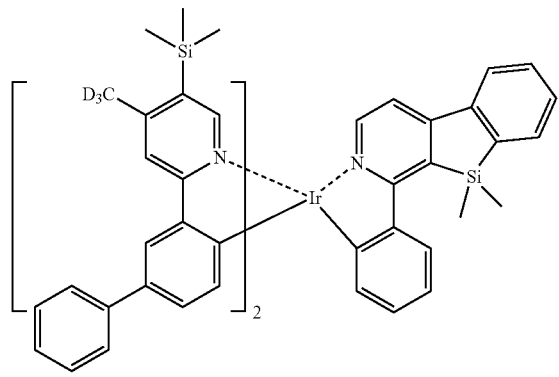
236
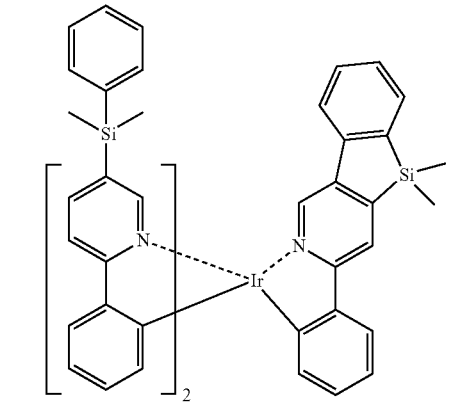
237
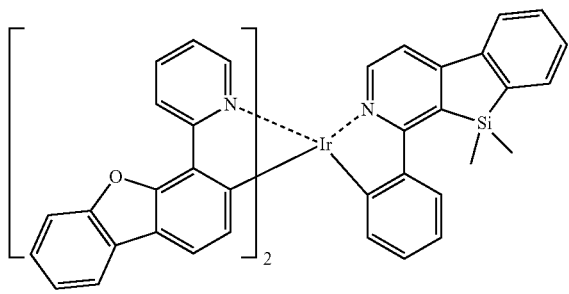
238
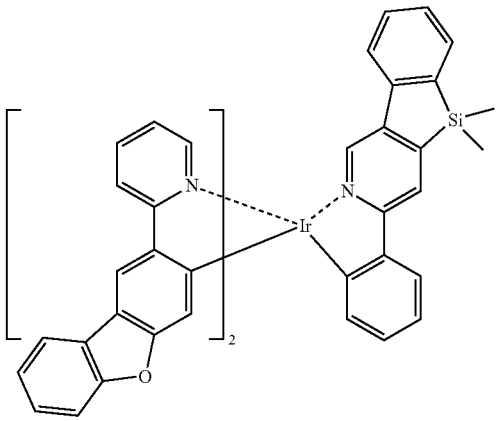
239
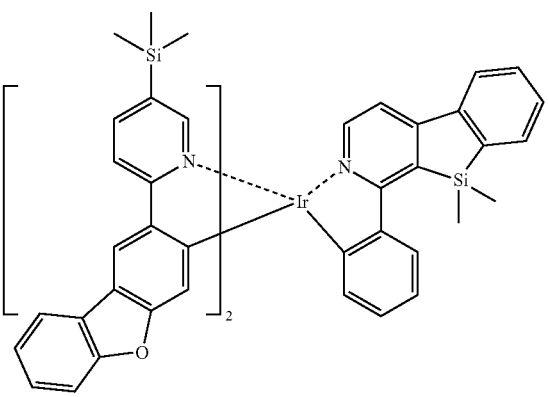
240
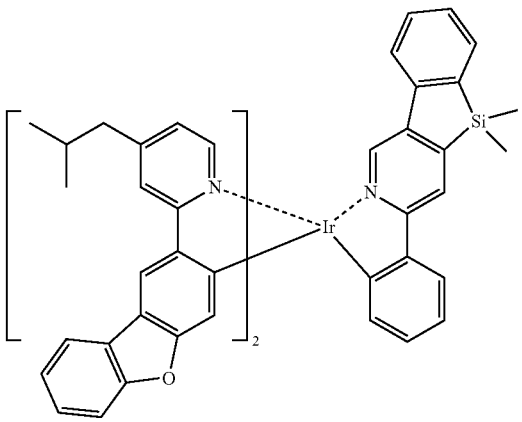
241
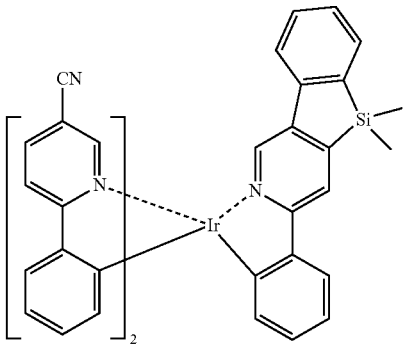

242
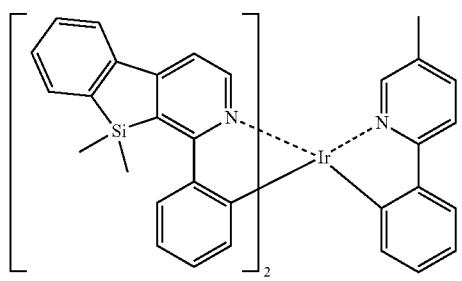
243
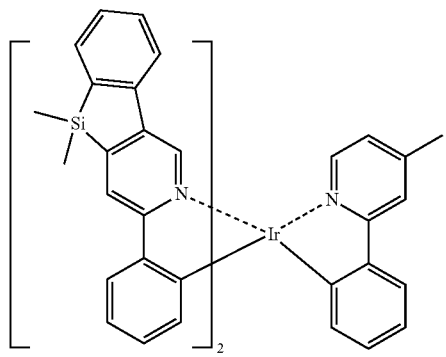
244
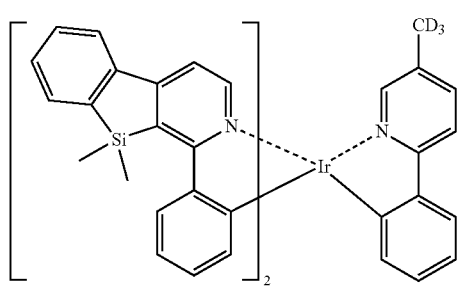
245
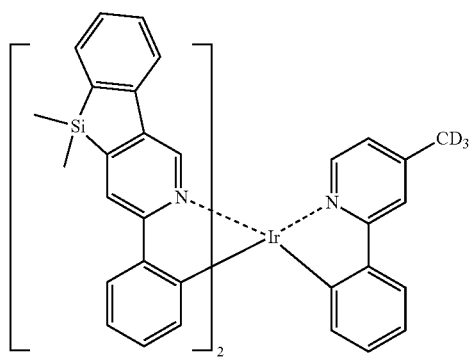
246
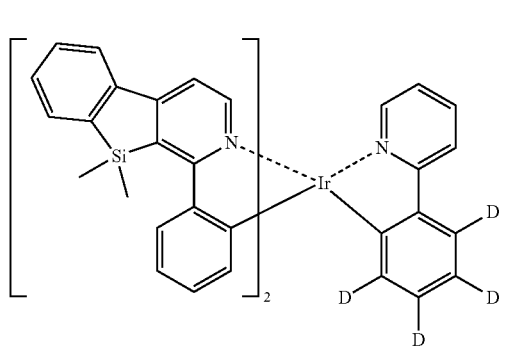
247
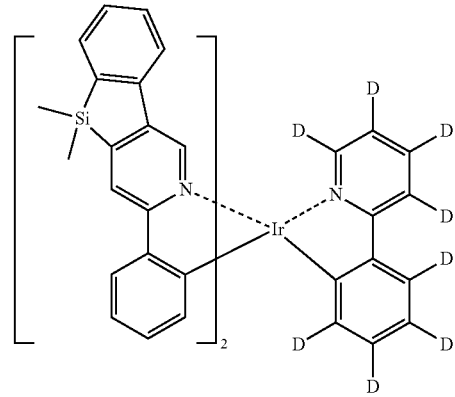
248
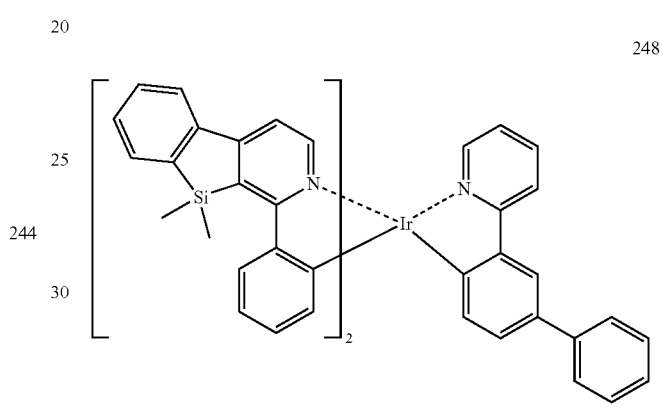
249
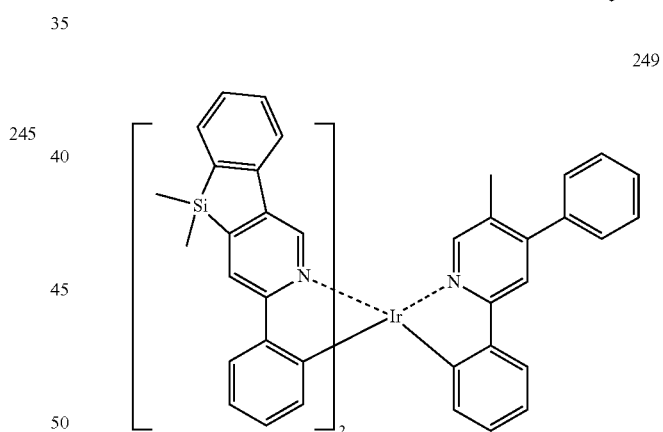
250
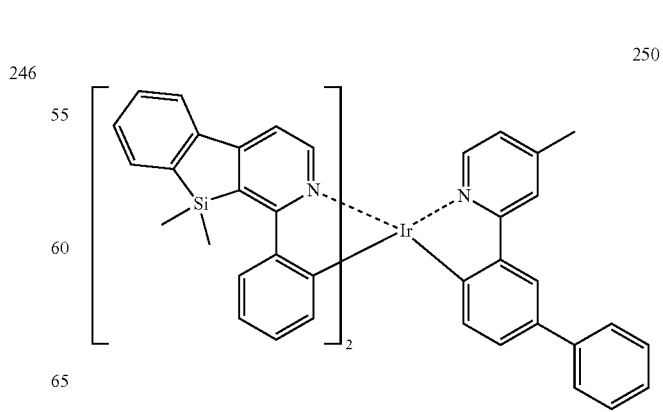

331
-continued
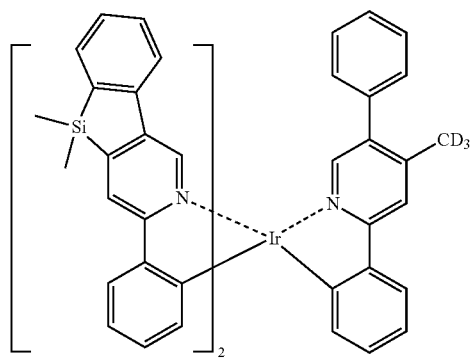
251
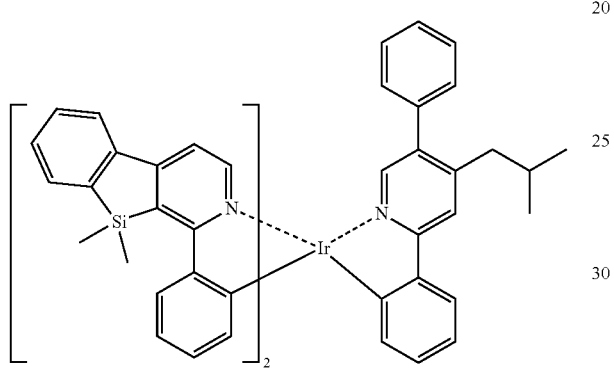
252
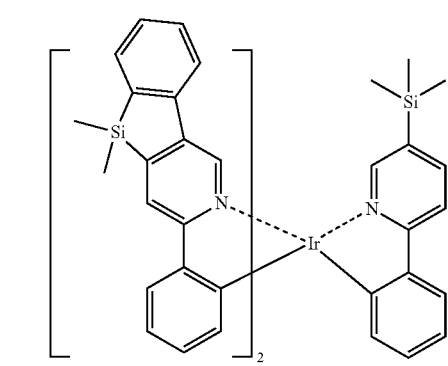
253
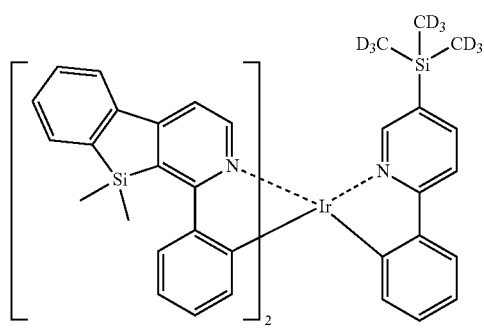
254
332
-continued
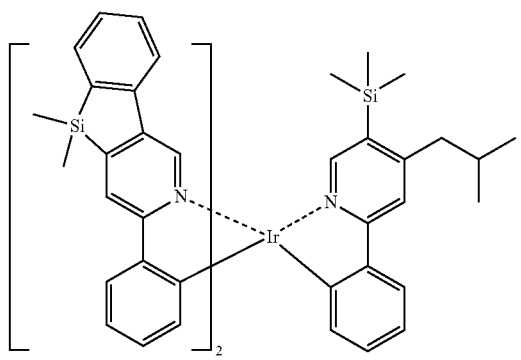
255
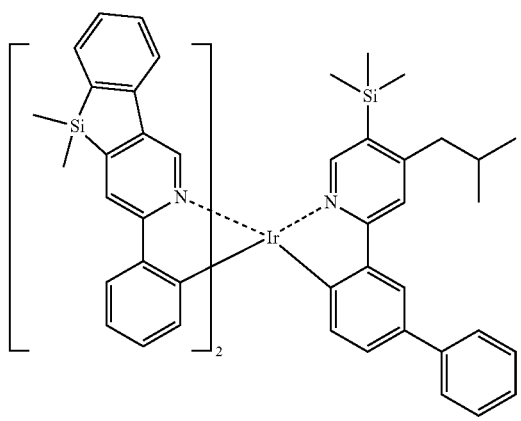
256
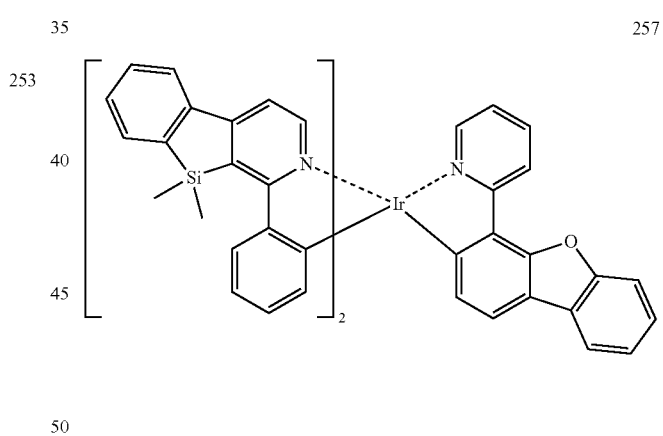
257
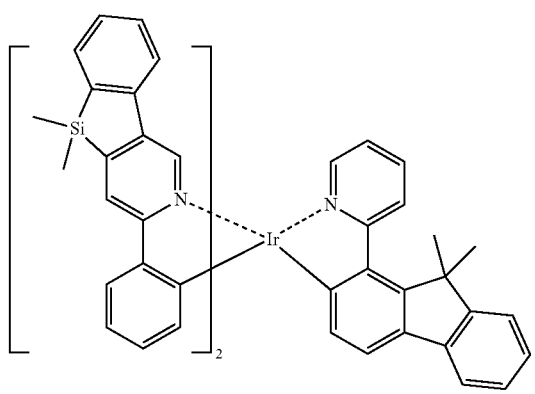
258

259
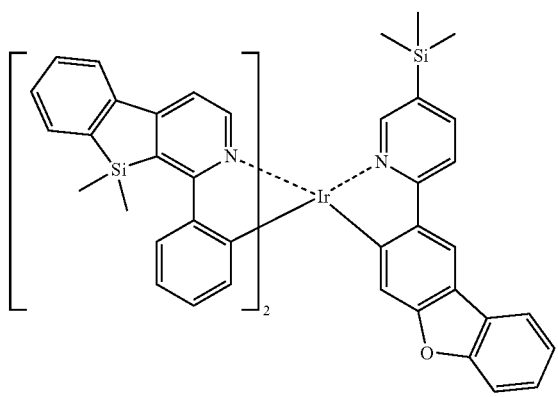
260
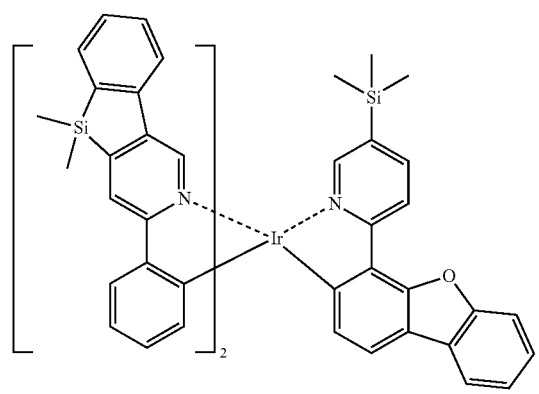
261
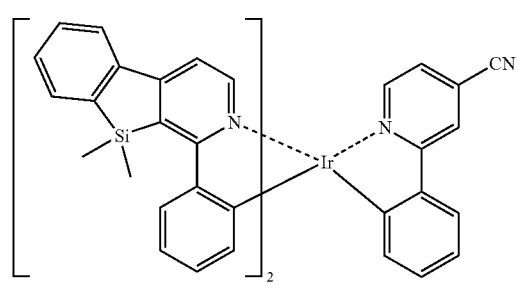
262
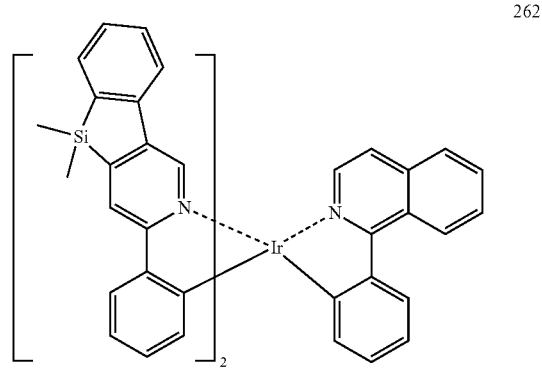
263
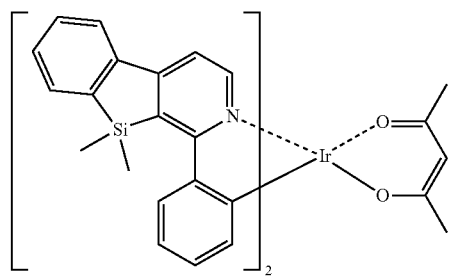
264
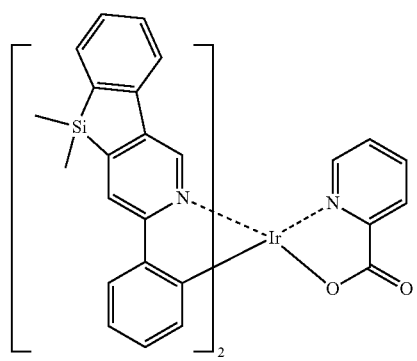
265
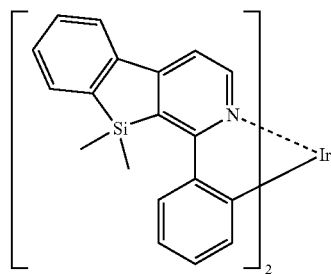
266
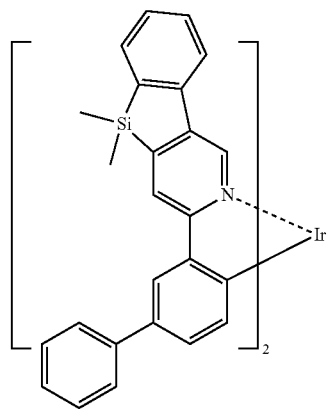

267 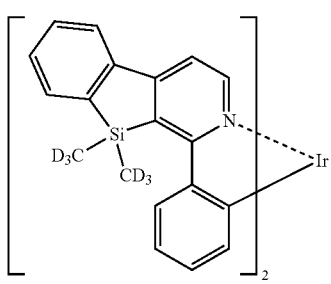

268 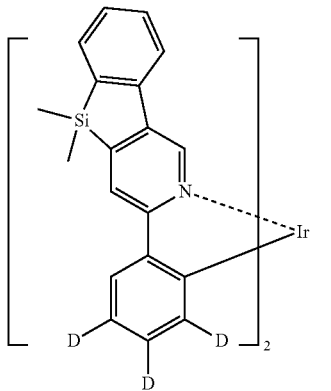

269 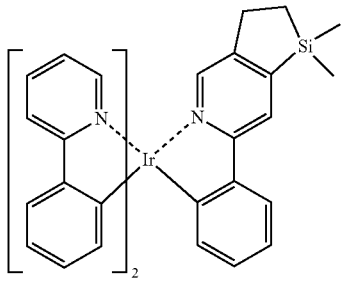

270 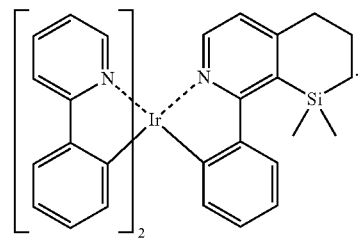

17. An organic light-emitting device comprising:
a first electrode;
a second electrode; and
an organic layer disposed between the first electrode and the second electrode,
wherein the organic layer comprises an emission layer and at least one organometallic compound of claim 1.

18. The organic light-emitting device of claim 17, wherein
the first electrode is an anode,
the second electrode is a cathode,
the organic layer comprises a hole transport region disposed between the first electrode and the emission layer and an electron transport region disposed between the emission layer and the second electrode,
wherein the hole transport region comprises at least one selected from a hole injection layer, a hole transport layer, and an electron blocking layer, and
wherein the electron transport region comprises at least one selected from a hole blocking layer, an electron transport layer, and an electron injection layer.

19. The organic light-emitting device of claim 17, wherein the emission layer comprises the at least one organometallic compound.

20. The organic light-emitting device of claim 19, wherein the emission layer further comprises a host, and an amount of the host is greater than an amount of the at least one organometallic compound.

* * * * *